US006331543B1

(12) United States Patent
Garvey et al.

(10) Patent No.: US 6,331,543 B1
(45) Date of Patent: Dec. 18, 2001

(54) NITROSATED AND NITROSYLATED PHOSPHODIESTERASE INHIBITORS, COMPOSITIONS AND METHODS OF USE

(75) Inventors: David S. Garvey, Dover, MA (US); Inigo Saenz de Tejada, Madrid (ES); Richard A. Earl, Westford; Subhash P. Khanapure, Clinton, both of MA (US)

(73) Assignee: NitroMed, Inc., Bedford, MA (US)

( * ) Notice: Subject to any disclaimer, the term of this patent is extended or adjusted under 35 U.S.C. 154(b) by 0 days.

(21) Appl. No.: 09/387,727

(22) Filed: Sep. 1, 1999

Related U.S. Application Data

(63) Continuation-in-part of application No. 09/145,142, filed on Sep. 1, 1998, now Pat. No. 5,958,926, which is a continuation-in-part of application No. 08/740,764, filed on Nov. 1, 1996, now Pat. No. 5,874,437, and a continuation-in-part of application No. PCT/US97/19870, filed on Oct. 31, 1997.

(51) Int. Cl.[7] ............... A61K 31/4985; C07D 471/14
(52) U.S. Cl. ............ 514/250; 514/246; 514/259; 514/267; 514/292; 514/307; 514/404; 514/619; 514/655; 514/676; 514/716; 514/728; 544/237; 544/251; 544/293; 544/343; 546/111; 546/149; 548/367.7; 568/306; 568/584; 568/588; 568/716; 568/744; 564/163; 564/384
(58) Field of Search .................. 544/343, 237, 544/251, 293; 514/250, 246, 259, 267, 292, 307, 404, 619, 655, 676, 716, 728; 546/111, 149; 548/367.7; 564/163, 384; 568/306, 584, 588, 716, 744

(56) References Cited

U.S. PATENT DOCUMENTS

| 4,308,278 | 12/1981 | Schneider et al. ........... 424/273 |
| 4,963,541 | 10/1990 | Brooks et al. ............... 514/183 |
| 5,171,217 | 12/1992 | March et al. .................. 604/53 |
| 5,190,967 | 3/1993 | Riley ........................... 514/411 |
| 5,196,426 | 3/1993 | Saccomano et al. ......... 514/258 |
| 5,223,504 | 6/1993 | Noverola et al. ............. 514/263 |
| 5,254,575 | 10/1993 | Pick et al. .................... 514/365 |
| 5,340,827 | 8/1994 | Beeley et al. ................. 514/352 |
| 5,380,758 | 1/1995 | Stamler et al. ............... 514/562 |
| 5,426,107 | 6/1995 | Bell et al. ................... 514/234.2 |

(List continued on next page.)

FOREIGN PATENT DOCUMENTS

| 0 252 721 | 1/1988 | (EP) . |
| 0 352 960 | 1/1990 | (EP) . |
| 0 442 204 | 8/1991 | (EP) . |
| 0 463 756 | 1/1992 | (EP) . |
| 0 506 194 | 9/1992 | (EP) . |
| 2547501 | 12/1984 | (FR) . |
| WO 93/07149 | 4/1993 | (WO) . |
| WO 93/12068 | 6/1993 | (WO) . |
| 9501338 | 1/1995 | (WO) . |
| WO 95/09636 | 4/1995 | (WO) . |
| WO 95/26725 | 10/1995 | (WO) . |
| WO 96/25184 | 8/1996 | (WO) . |
| 9703675 | 2/1997 | (WO) . |
| 9703985 | 2/1997 | (WO) . |
| WO 97/34871 | 9/1997 | (WO) . |
| WO 97/39760 | 10/1997 | (WO) . |
| 9743287 | 11/1997 | (WO) . |
| 9817668 | 4/1998 | (WO) . |
| 9819672 | 5/1998 | (WO) . |
| 9849166 | 11/1998 | (WO) . |
| 9852569 | 11/1998 | (WO) . |
| 9921558 | 5/1999 | (WO) . |
| 9921562 | 5/1999 | (WO) . |
| 9922731 | 5/1999 | (WO) . |
| 9930697 | 6/1999 | (WO) . |

OTHER PUBLICATIONS

International Preliminary Examination Report for PCT/US99/20024 dated Dec. 19, 2000.
Patnaik et al, Indian Journal of Pharmacology, 11 (2):139–142 (1979).
Agarwal et al, Indian Journal of Chemistry, 29B:80–84 (1990).

(List continued on next page.)

Primary Examiner—Richard L. Raymond
(74) Attorney, Agent, or Firm—Hale and Dorr LLP

(57) ABSTRACT

The present invention describes novel nitrosated and/or nitrosylated phosphodiesterase inhibitors, and novel compositions containing at least one nitrosated and/or nitrosylated phosphodiesterase inhibitor, and, optionally, one or more compounds that donate, transfer or release nitric oxide, elevate endogenous levels of endothelium-derived relaxing factor, stimulate endogenous synthesis of nitric oxide or is a substrate for nitric oxide synthase and/or one or more vasoactive agents. The present invention also provides novel compositions containing at least one phosphodiesterase inhibitor, and one or more compounds that donate, transfer or release nitric oxide, elevate endogenous levels of endothelium-derived relaxing factor, stimulate endogenous synthesis of nitric oxide or is a substrate for nitric oxide synthase and/or one or more vasoactive agents. The present invention also provides methods for treating or preventing sexual dysfunctions in males and females, for enhancing sexual responses in males and females, and for treating or preventing diseases induced by the increased metabolism of cyclic guanosine 3',5'-monophosphate (cGMP), such as hypertension, pulmonary hypertension, congestive heart failure, renal failure, myocardial infraction, stable, unstable and variant (Prinzmetal) angina, atherosclerosis, cardiac edema, renal insufficiency, nephrotic edema, hepatic edema, stroke, asthma, bronchitis, chronic obstructive pulmonary disease (COPD), cystic fibrosis, dementia, immunodeficiency, premature labor, dysmenorrhoea, benign prostatic hyperplasia (BPH), bladder outlet obstruction, incontinence, conditions of reduced blood vessel patency, e.g., postpercutaneous transluminal coronary angioplasty (post-PTCA), peripheral vascular disease, allergic rhinitis, glucoma, and diseases characterized by disorders of gut motility, e.g., irritable bowel syndrome (IBS).

94 Claims, 60 Drawing Sheets

U.S. PATENT DOCUMENTS

| | | | |
|---|---|---|---|
| 5,438,060 | 8/1995 | Miyazaki et al. | 514/258 |
| 5,439,938 | 8/1995 | Snyder et al. | 514/565 |
| 5,491,147 | 2/1996 | Boyd et al. | 514/247 |
| 5,492,911 | 2/1996 | Stief | 514/252 |
| 5,543,430 | 8/1996 | Kaesemeyer | 514/565 |
| 5,545,647 | 8/1996 | Tanaka et al. | 514/343 |
| 5,565,466 | 10/1996 | Gioco et al. | 514/280 |
| 5,583,101 | 12/1996 | Stamler et al. | 514/2 |
| 5,614,627 | 3/1997 | Takase et al. | 544/293 |
| 5,618,814 | 4/1997 | Heckel et al. | 514/234.2 |
| 5,645,839 | 7/1997 | Chobanian et al. | 424/400 |
| 5,646,181 | 7/1997 | Fung et al. | 514/506 |
| 5,698,589 | 12/1997 | Allen | 514/509 |
| 5,716,993 | 2/1998 | Ozaki et al. | 514/619 |
| 5,731,339 | 3/1998 | Lowrey | 514/400 |
| 5,767,160 | 6/1998 | Kaesemeyer | 514/565 |
| 5,824,669 | 10/1998 | Garvey et al. | 514/174 |
| 5,849,741 | 12/1998 | Watanabe et al. | 514/248 |
| 5,859,006 | 1/1999 | Daugan | 514/249 |
| 5,869,516 | 2/1999 | Arlt et al. | 514/404 |
| 5,877,216 | 3/1999 | Place et al. | 514/573 |
| 5,932,538 | 8/1999 | Garvey et al. | 514/2 |
| 5,958,926 | 9/1999 | Garvey et al. | 514/253 |
| 5,973,011 | 10/1999 | Noack et al. | 514/742 |
| 5,981,527 * | 11/1999 | Daugan et al. | 514/250 |
| 6,007,824 | 12/1999 | Duckett et al. | 424/195.1 |
| 6,037,346 | 3/2000 | Doherty, Jr. et al. | 514/258 |
| 6,143,746 * | 11/2000 | Daugan et al. | 514/249 |

OTHER PUBLICATIONS

Saxena et al, QSAR Strategies Des. Bioact. Compd., Proc. Eur. Symp. Quant. Struct. Act. Relat., 5th (1985), Meeting Date 1984, pp. 361–365.

Agarwal et al., Chemical Abstracts, vol. 112:235217, 1990.*

Saxena et al., Chemical Abstracts, vol. 104:62245, 1984.*

Patnaik et al., Chemical Abstracts, vol. 92:69309, 1980.*

Chemical Abstracts, vol. 120, No. 1, Abstract No. 5451d (1994).

Martel et al, Drugs of the Future, 22(2):138–143 (1997).

Boolell et al, British Journal of Urology, 78(2):257–261 (1996).

Chemical Abstracts, vol. 116, No. 1, Abstract No. 4477 (Jan. 6, 1992).

Chemical Abstracts, vol. 125, No. 15, Abstract No. 191382 (Oct. 7, 1996).

Chemical Abstracts, vol. 123, No. 1, Abstract No. 574 (Jul. 3, 1995).

Chemical Abstracts, vol. 120, No. 25, Abstract No. 315630 (Jun. 20, 1994).

Chemical Abstracts, vol. 121, No. 7, Abstract No. 73410 (Aug. 15, 1994).

Boolell et al, *International Journal of Impotence Research*, 8:47–52 (1996).

Krane et al, *New England Journal of Medicine*, 321(24):1648–1659 (1989).

Trigo–Rocha et al, *Neurourol. Urodyn.*, 13(1):71–80 (1994).

Sparwasser et al, *J. Urol.*, 152:6, Pt. 1, pp. 2159–2163 (1994).

Terrett et al, Bioorg. *Med. Chem. Lett.*, 6(15):1819–1824 (1996).

Park et al, *Biochem. Biophys. Res. Commun.*, 249(3):612–617 (1998).

Mathers et al, *European Urology*, 35(suppl 2):67 (abstract 266) (1999).

Zorgniotti et al, *Int. J. Impotence Res.*, 6:33–36 (1994).

* cited by examiner

US 6,331,543 B1

NITROSATED AND NITROSYLATED PHOSPHODIESTERASE INHIBITORS, COMPOSITIONS AND METHODS OF USE

RELATED APPLICATIONS

This is a continuation-in-part of U.S. application Ser. No. 09/145,142, filed Sep. 1, 1998, now U.S. Pat. No. 5,958,926, which is a continuation-in-part of U.S. application Ser. No. 08/740,764, filed Nov. 1, 1996, now U.S. Pat. No. 5,874,437; and is a continuation-in-part of PCT/US97/19870, filed Oct. 31, 1997.

FIELD OF THE INVENTION

The present invention describes novel nitrosated and/or nitrosylated phosphodiesterase inhibitors, and novel compositions comprising at least one nitrosated and/or nitrosylated phosphodiesterase inhibitor, and, optionally, at least one compound that donates, transfers or releases nitric oxide, elevates endogenous levels of endothelium-derived relaxing factor, stimulates endogenous synthesis of nitric oxide or is a substrate for nitric oxide synthase, and/or at least one vasoactive agent. The present invention also provides novel compositions comprising at least one phosphodiesterase inhibitor, and at least one compound that donates, transfers or releases nitric oxide, elevates endogenous levels of endothelium-derived relaxing factor, stimulates endogenous synthesis of nitric oxide or is a substrate for nitric oxide synthase, and/or at least one vasoactive agent. The present invention also provides methods for treating or preventing sexual dysfunctions in males and females, for enhancing sexual responses in males and females, and for treating or preventing diseases induced by the increased metabolism of cyclic guanosine 3',5'-monophosphate (cGMP), such as hypertension, pulmonary hypertension, congestive heart failure, renal failure, myocardial infraction, stable, unstable and variant (Prinzmetal) angina, atherosclerosis, cardiac edema, renal insufficiency, nephrotic edema, hepatic edema, stroke, asthma, bronchitis, chronic obstructive pulmonary disease (COPD), cystic fibrosis, dementia, immunodeficiency, premature labor, dysmenorrhoea, benign prostatic hyperplasis (BPH), bladder outlet obstruction, incontinence, conditions of reduced blood vessel patency, e.g., postpercutaneous transluminal coronary angioplasty (post-PTCA), peripheral vascular disease, allergic rhinitis, and glucoma, and diseases characterized by disorders of gut motility, such as irritable bowel syndrome (IBS).

BACKGROUND OF THE INVENTION

Adequate sexual function is a complex interaction of hormonal events and psychosocial relationships. There are four stages to sexual response as described in the *International Journal of Gynecology & Obstetrics*, 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, *J. Public Health Med.*, 19(4):387–391 (1997).

While there are obvious differences in the sexual response between males and females, one common aspect of the sexual response is the erectile response. The erectile response in both males and females is the result of engorgement of the erectile tissues of the genitalia with blood which is caused by the relaxation of smooth muscles in the arteries serving the genitalia.

In both pre-menopausal and menopausal females, sexual dysfunction can include, for example, sexual pain disorders, sexual desire disorders, sexual arousal dysfunction, orgasmic dysfunction, dyspareunia, and vaginismus. Sexual dysfunction can be caused, for example, by pregnancy, menopause, cancer, pelvic surgery, chronic medical illness or medications.

In males, some pharmacological methods of treating sexual dysfunctions are available, however, such methods have not proven to be highly satisfactory or without potentially severe side-effects. Papaverine now widely used to treat impotence, is generally effective in cases where the dysfunction is psychogenic or neurogenic and where severe atherosclerosis is not involved. Injection of papaverine, a smooth muscle relaxant, or phenoxybenzamine, a non-specific antagonist and hypotensive, into corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an α-adrenergic antagonist, is used. As an alternative or, in some cases, as an adjunct to α-adrenergic blockade, prostaglandin $E_1$ ($PGE_1$) has been administered via intracavernosal injection. A major side effect frequently associated with intracorparally delivered $PGE_1$ is penile pain and burning.

The use of phosphodiesterase inhibitors for the treatment and prevention of diseases induced by the increased metabolism of cyclic guanosine 3',5'-mono-phosphate (cGMP), such as hypertension, pulmonary hypertension, congestive heart failure, renal failure, myocardial infraction, stable, unstable and variant (Prinzmetal) angina, atherosclerosis, cardiac edema, renal insufficiency, nephrotic edema, hepatic edema, stroke, asthma, bronchitis, chronic obstructive pulmonary disease (COPD), cystic fibrosis, dementia, immunodeficiency, premature labor, dysmenorrhoea, benign prostatic hyperplasis (BPH), bladder outlet obstruction, incontinence, conditions of reduced blood vessel patency, e.g., postpercutaneous transluminal coronary angioplasty (post-PTCA), peripheral vascular disease, allergic rhinitis, and glucoma, and diseases characterized by disorders of gut motility, such as irritable bowel syndrome (IBS) have been previously described in, for example, U.S. Pat. Nos. 5,849,741 and 5,869,486, WO 98/49166 and WO 97/03985, the disclosures of each of which are incorporated herein by reference in their entirety.

There is a need in the art for new and improved treatments of sexual dysfunctions and other diseases. The present invention is directed to these, as well as other, important ends.

SUMMARY OF THE INVENTION

Nitric oxide (NO) has been shown to mediate a number of actions including the bactericidal and tumoricidal actions of macrophages and blood vessel relaxation of endothelial cells. NO and NO donors have also been implicated as mediators of nonvascular smooth muscle relaxation. As described herein, this effect includes the dilation of the corpus cavernosum smooth muscle, an event involved in the sexual response process in both males and females. However, the effects of modified phosphodiesterase inhibitors, which are directly or indirectly linked with a nitric oxide adduct, have not been previously investigated.

In arriving at the present invention it was recognized that the risk of toxicities and adverse effects that are associated with high doses of phosphodiesterase inhibitors can be avoided by the use of nitrosated and/or nitrosylated phosphodiesterase inhibitors or by the use of at least one phosphodiesterase inhibitor in combination with at least one nitric oxide donor. Such toxicities and adverse effects include hypotension, syncope, as well as priapism. The smooth muscle relaxant properties of phosphodiesterase inhibitors and of compounds that donate, release or transfer nitrogen monoxide or elevate levels of endogenous endothelium-derived relaxing factor (EDRF) or are substrates for nitric oxide synthase work together to permit the same efficacy with lower doses of the phosphodiesterase inhibitors or work synergistically to produce an effect that is greater than the additive effects of the phosphodiesterase inhibitor and the compound that donates, releases or transfers nitrogen monoxide or elevates levels of endogenous nitric oxide or EDRF or is a substrates for nitric oxide synthase.

One aspect of the present invention provides novel nitrosated and/or nitrosylated phosphodiesterase inhibitors. The phosphodiesterase inhibitors can be nitrosated and/or nitrosylated through one or more sites such as oxygen (hydroxyl condensation), sulfur (sulfhydryl condensation), carbon and/or nitrogen. The present invention also provides compositions comprising a therapeutically effective amount of such compounds in a pharmaceutically acceptable carrier.

Another aspect of the present invention provides compositions comprising a therapeutically effective amount of at least one phosphodiesterase inhibitor (PDE inhibitor), that is optionally substituted with at least one NO and/or $NO_2$ group (i.e., nitrosylated and/or nitrosated), and at least one compound that donates, transfers or releases nitrogen monoxide as a charged species, i.e., nitrosonium ($NO^+$) or nitroxyl (NO–), or as the neutral species, nitric oxide (NO•), and/or stimulates endogenous production of nitric oxide or EDRF in vivo and/or is a substrate for nitric oxide synthase. The present invention also provides for such compositions in a pharmaceutically acceptable carrier.

Yet another aspect of the present invention provides compositions comprising a therapeutically effective amount of at least one phosphodiesterase inhibitor, that is optionally substituted with at least one NO and/or $NO_2$ group (i.e., nitrosylated and/or nitrosated), at least one vasoactive drug, and, optionally, at least one compound that donates, transfers or releases nitrogen monoxide as a charged species, i.e., nitrosonium ($NO^+$) or nitroxyl (NO–), or as the neutral species, nitric oxide (NO•), and/or stimulates endogenous production of nitric oxide or EDRF in vivo and/or is a substrate for nitric oxide synthase. The invention also provides for such compositions in a pharmaceutically acceptable carrier.

Yet another aspect of the present invention provides methods for treating and/or preventing sexual dysfunctions and/or enhancing sexual responses in patients, including males and females, by administering to a patient in need thereof a therapeutically effective amount of at least one nitrosated and/or nitrosylated phosphodiesterase inhibitor and, optionally, at least one compound that donates, transfers or releases nitric oxide as a charged species, i.e., nitrosonium ($NO^+$) or nitroxyl (NO–), or as the neutral species, nitric oxide (NO•), and/or stimulates endogenous production of nitric oxide or EDRF in vivo and/or is a substrate for nitric oxide synthase. The methods can further comprise administering a therapeutically effective amount of at least one vasoactive agent. Alternatively, the methods for treating and/or preventing sexual dysfunctions and/or enhancing sexual responses in patients, including males and females, can comprise administering a therapeutically effective amount of at least one nitrosated and/or nitrosylated phosphodiesterase inhibitor, at least one vasoactive agent, and, optionally, at least one compound that donates, transfers or releases nitric oxide as a charged species, i.e., nitrosonium ($NO^+$) or nitroxyl (NO–), or as the neutral species, nitric oxide (NO•), and/or stimulates endogenous production of nitric oxide or EDRF in vivo and/or is a substrate for nitric oxide synthase. The nitrosated and/or nitrosylated phosphodiesterase inhibitors, nitric oxide donors, and/or vasoactive agents can be administered separately or as components of the same composition in one or more pharmaceutically acceptable carriers.

The present invention also provides methods for treating and/or preventing sexual dysfunctions and/or enhancing sexual responses in patients, including males and females, by administering to a patient in need thereof a therapeutically effective amount of at least one phosphodiesterase inhibitor and at least one compound that donates, transfers or releases nitric oxide as a charged species, i.e., nitrosonium ($NO^+$) or nitroxyl (NO–), or as the neutral species, nitric oxide (NO•), and/or stimulates endogenous production of nitric oxide or EDRF in vivo and/or is a substrate for nitric oxide synthase. The methods can further comprise administering a therapeutically effective amount of at least one vasoactive agent. Alternatively, the methods for treating and/or preventing sexual dysfunctions and/or enhancing sexual responses in patients, including males and females, can comprise administering a therapeutically effective amount of at least one phosphodiesterase inhibitor, at least one vasoactive agent, and, optionally, at least one compound that donates, transfers or releases nitric oxide as a charged species, i.e., nitrosonium ($NO^+$) or nitroxyl (NO–), or as the neutral species, nitric oxide (NO•), and/or stimulates endogenous production of nitric oxide or EDRF in vivo and/or is a substrate for nitric oxide synthase. The phosphodiesterase inhibitors, the nitric oxide donors, and the vasoactive agents can be administered separately or as components of the same composition in one or more pharmaceutically acceptable carriers.

The present invention also provides methods using the compounds and compositions described herein to prevent or treat diseases induced by the increased metabolism of cyclic guanosine 3',5'-monophosphate (cGMP), such as hypertension, pulmonary hypertension, congestive heart failure, myocardial infraction, stable, unstable and variant (Prinzmetal) angina, atherosclerosis, cardiac edema, renal insufficiency, nephrotic edema, hepatic edema, stroke, asthma, bronchitis, chronic obstructive pulmonary disease (COPD), dementia, immunodeficiency, premature labor, dysmenorrhoea, benign prostatic hyperplasia (BPH), bladder outlet obstruction, incontinence, conditions of reduced blood vessel patency, e.g., postpercutaneous transluminal coronary angioplasty (post-PTCA), peripheral vascular disease, allergic rhinitis, cystic fibrosis, and glucoma, and diseases characterized by disorders of gut motility, e.g., irritable bowel syndrome (IBS) by administering to a patient in need thereof a therapeutically effective amount of at least one of the compounds and/or compositions described herein. In these methods, the phosphodiesterase inhibitors that are optionally nitrosated and/or nitrosylated, nitric oxide donors and vasoactive agents can be administered separately or as components of the same composition in one or more pharmaceutically acceptable carriers.

These and other aspects of the present invention are described in detail herein.

DETAILED DESCRIPTION OF THE INVENTION

Figure 1:
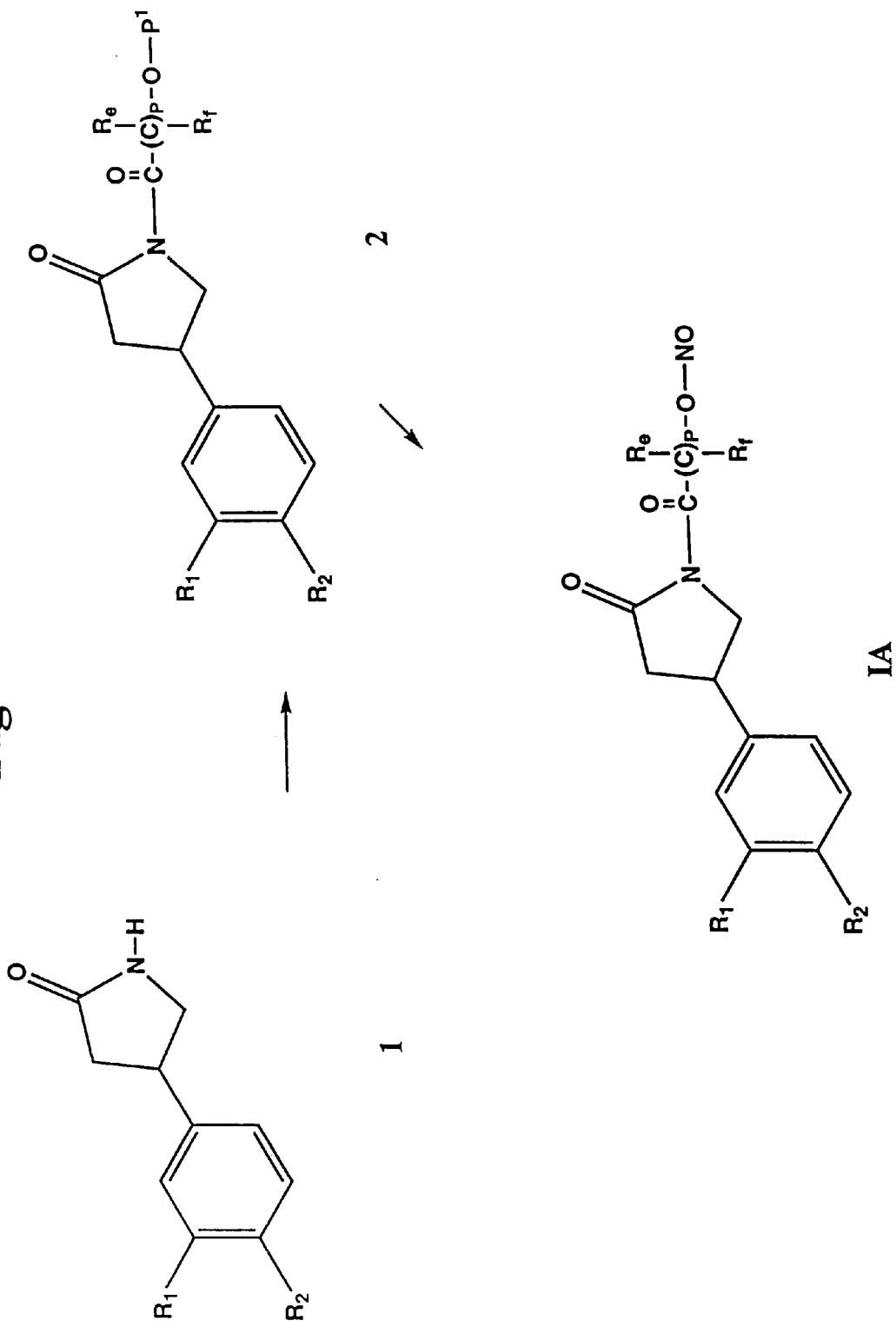
FIG. 1 shows a synthetic scheme for the preparation of nitrite containing substituted benzene derivatives.

The following definitions may be used throughout the specification.

"Phosphodiesterase inhibitor" or "PDE inhibitor" refers to any compound that inhibits the enzyme phosphodiesterase. The term refers to selective or non-selective inhibitors of cyclic guanosine 3',5'-monophosphate phosphodiesterases (cGMP-PDE) and cyclic adenosine 3',5'-monophosphate phosphodiesterases (cAMP-PDE).

"Patient" refers to animals, preferably mammals, more preferably humans.

"Transurethral" or "intraurethral" refers to delivery of a drug into the urethra, such that the drug contacts and passes through the wall of the urethra and enters into the blood stream.

"Transdermal" refers to the delivery of a drug by passage through the skin and into the blood stream.

"Transmucosal" refers to delivery of a drug by passage of the drug through the mucosal tissue and into the blood stream.

"Penetration enhancement" or "permeation enhancement" refers to an increase in the permeability of the skin or mucosal tissue to a selected pharmacologically active agent such that the rate at which the drug permeates through the skin or mucosal tissue is increased.

"Carriers" or "vehicles" refers to carrier materials suitable for drug administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO\bullet$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO-$, $NO\bullet$), such that the biological activity of the nitrogen monoxide species is expressed at the intended site of action.

"Nitric oxide donor" or "NO donor" refers to compounds that donate, release and/or directly or indirectly transfer a nitric oxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo[3.3.0]octane, 7-oxabycyclo[2.2.1]heptyl and the like.

"Cycloalkyl" refers to an alicyclic group comprising from about 3 to about 7 carbon atoms. Cycloalkyl groups can be unsubstituted or substituted with one, two or three substituents independently selected from alkyl, alkoxy, amino, alkylamino, dialkylamino, arylamino, diarylamino. alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, and the like.

"Heterocyclic ring or group" refers to a saturated or unsaturated cyclic hydrocarbon group having about 2 to about 10 carbon atoms (preferably about 4 to about 6 carbon atoms) where 1 to about 3 carbon atoms are replaced by one or more nitrogen, oxygen and/or sulfur atoms. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino. alkylarylamino, hydroxy, oxo, halo, carboxyl, alkylcarboxylic acid, alkylcarboxylic ester, aryl, amidyl, ester, carboxamido, alkylcarboxamido, arylcarboxamido, and nitro. Exemplary heterocyclic groups include pyrrolyl, pyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, amino, alkylamino, dialkylamino, arylamino, diarylamino. alkylarylamino, hydroxy, alkylcarboxylic acid, alkylcarboxylic ester, aryl, amidyl, ester, carboxamido, alkylcarboxamido and nitro. Exemplary substituted aryl groups include tetrafluorophenyl, pentafluorophenyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl refers to an alkoxy group, as defined herein, appended to a haloalkyl group, as defined herein. Exemplary alkoxyhaloalkyl groups include 4 methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo " refers to =O.

"Hydroxyalkyl" refers to a hydroxy group, as defined herein, appended to an alkyl group, as defined herein.

"Amino" refers to —$NH_2$.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N-$, wherein $R_{55}$ and $R_{60}$ are each independently an aryl group, as defined herein.

"Alkylarylamino" refers to $R_{52}R_{55}N-$, wherein $R_{52}$ is an alkyl group, as defined herein and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Sulfinyl" refers to $-S(O)-$.

"Sulfonyl" refers to $-S(O)_2-$.

"Sulfonic acid" refers to $-S(O)_2OH$

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to $-S(O)_2OR_{58}$, wherein $R_{58}$ is an alkyl group, an aryl group, an alkylaryl group or an aryl heterocyclic ring, as defined herein.

"Sulfonamido" refers to $-S(O)_2-N(R_{51})(R_{57})$, wherein $R_{51}$ and $R_{57}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S-$, wherein $R_{50}$ is an alkyl group, as defined herein.

"Arylthio" refers to $R_{55}S-$, wherein $R_{55}$ is an aryl group, as defined herein.

"Alkylsulfinyl" refers to $R_{50}-S(O)-$, wherein $R_{50}$ is an alkyl group, as defined herein.

"Alkylsulfonyl" refers to $R_{50}-S(O)_2-$, wherein $R_{50}$ is an alkyl group, as defined herein.

"Arylsulfinyl" refers to $R_{55}-S(O)-$, wherein $R_{55}$ is an aryl group, as defined herein.

"Arylsulfonyl" refers to $R_{55}-S(O)_2-$, wherein $R_{55}$ is an aryl group, as defined herein.

"Amidyl" refers to $R_{51}C(O)N(R_{57})-$ wherein $R_{51}$ and $R_{57}$ are each independently a hydrogen atom, an alkyl group, an aryl group, an alkylaryl group, or an arylheterocyclic ring, as defined herein.

"Ester" refers to $R_{51}C(O)O-$ wherein $R_{51}$ is a hydrogen atom, an alkyl group, an aryl group, an alkylaryl group, or an arylheterocyclic ring, as defined herein.

"Carbamoyl" refers to $-O-C(O)N(R_{51})(R_{57})$, wherein $R_{51}$ and $R_{57}$ are each independently a hydrogen atom, an alkyl group, an aryl group, an alkylaryl group or an aryl-heterocyclic ring, as defined herein, and $R_{51}$ and $R_{57}$ when taken together are a heterocyclic ring, a cycloalkyl group or a bridged cycloalkyl group, as defined herein.

"Carboxyl" refers to $-CO_2H$.

"Carbonyl" refers to $-C(O)-$.

"Methanthial" refers to $-C(S)-$.

"Carboxylic ester" refers to $-C(O)OR_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" refers to an aryl group, as defined herein, appended to a carboxylic ester group, as defined herein.

"Carboxamido" refers to $-C(O)N(R_{51})(R_{57})$, wherein $R_{51}$ and $R_{57}$ are each independently a hydrogen atom, an alkyl group, an aryl group, an alkylaryl group or an aryl-heterocyclic ring, as defined herein, and $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to $-N(R_{58})-C(O)N(R_{51})(R_{57})$ wherein $R_{51}$, $R_{57}$, and $R_{58}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Phosphoryl" refers to $-P(R_{70})(R_{71})(R_{72})$, wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

"Silyl" refers to $-Si(R_{73})(R_{74})$, wherein $R_{73}$ and $R_{74}$ are each independently a covalent bond, a lower alkyl, an alkoxy, an aryl or an arylalkoxy, as defined herein.

The term "sexual dysfunction" generally includes any sexual dysfunction in a patient, including an animal, preferably a mammal, more preferably a human. The patient can be male or female. Sexual dysfunctions can include, for example, sexual desire disorders, sexual arousal disorders, orgasmic disorders and sexual pain disorders. Female sexual dysfunction refers to any female sexual dysfunction including, for example, sexual desire disorders, sexual arousal dysfunctions, orgasmic dysfunctions, sexual pain disorders, dyspareunia, and vaginismus. The female can be pre-menopausal or menopausal. Male sexual dysfunction refers to any male sexual dysfunctions including, for example, male erectile dysfunction and impotence.

The present invention is directed to the treatment and/or prevention of sexual dysfunctions in patients, including males and females, by administering the compounds and compositions described herein. The present invention is also directed to improving and/or enhancing sexual responses in patients, including males and females, by administering the compounds and/or compositions described herein. The novel compounds and novel compositions of the present invention are described in more detail herein.

Phosphodiesterase inhibitors that may be used in the present invention include, for example, filaminast, piclamilast, rolipram, Org 20241, MCI-154, roflumilast, toborinone, posicar, lixazinone, zaprinast, sildenafil, pyrazolopyrimidinones (such as those disclosed in WO 98/49166), motapizone, pimobendan, zardaverine, siguazodan, CI 930, EMD 53998, imazodan, saterinone, loprinone hydrochloride, 3-pyridinecarbonitrile derivatives, denbufyllene, albifylline, torbafylline, doxofylline, theophylline, pentoxofylline, nanterinone, cilostazol, cilostamide, MS 857, piroximone, milrinone, amrinone, tolafentrine, dipyridamole, papaverine, E4021, thienopyrimidine derivatives (such as those disclosed in WO 98/17668), triflusal, ICOS-351, tetrahydropiperazino[1,2-b] beta-carboline-1,4-dione derivatives (such as those disclosed in U.S. Pat. No. 5,859,006, WO 97/03985 and WO 97/03675), carboline derivatives, (such as those disclosed in WO 97/43287), 2-pyrazolin-5-one derivatives (such as those disclosed in U.S. Pat. No. 5,869,516), fused pyridazine derivatives (such as those disclosed in U.S. Pat. No. 5,849,741), quinazoline derivatives (such as those disclosed in U.S. Pat. No. 5,614,627), anthranilic acid derivatives (such as those disclosed in U.S. Pat. No. 5,714,993), imidazoquinazoline derivatives (such as those disclosed in WO 96/26940), and the like. Also included are those phosphodiesterase inhibitors disclosed in WO 99/21562 and WO 99/30697. The disclosures of each of which are incorporated herein by reference in their entirety.

Sources of information for the above, and other, phosphodiesterase inhibitors include Goodman and Gilman, The Pharmacological Basis of Therapeutics (9th Ed.), McGraw-Hill, Inc. (1995), The Physician's Desk Reference (49th Ed.), Medical Economics (1995), Drug Facts and Comparisons (1993 Ed), Facts and Comparisons (1993), and The Merck Index (12th Ed.), Merck & Co., Inc. (1996), the disclosures of each of which are incorporated herein by reference in their entirety.

In one embodiment, the present invention describes nitrosated and/or nitrosylated PDE inhibitors of Formula (I):

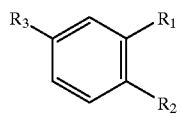

I wherein, $R_1$ is an alkoxy, a cycloalkoxy, a halogen, or

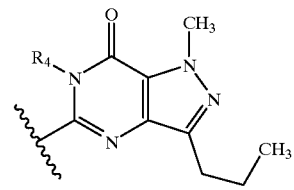

$R_2$ is a hydrogen, an alkoxy, or a haloalkoxy; and $R_3$ is:

(i)

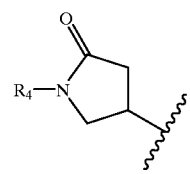

(ii)

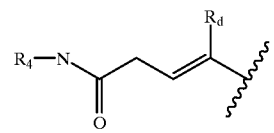

(iii)

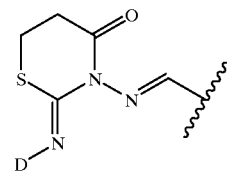

(iv)

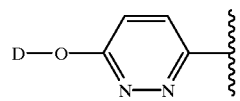

(v)

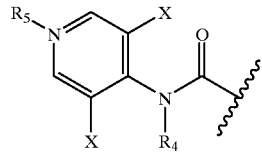

(vi)

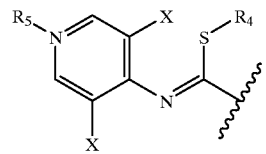

(vii)

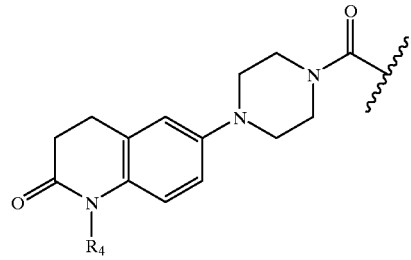

-continued (viii) [chemical structure with thiazole ring, N-D1, O-D, =N-D1]

(ix) [chemical structure with quinoline-piperazine-carbonyl, R4-S]

or (x) [imidazolidinone structure with R11, R12]

wherein,

D is
(i) —NO,
(ii) —NO$_2$,
(iii) —CH(R$_d$)—O—C(O)—Y—Z—(C(R$_e$)(R$_f$))$_p$—T—Q,
(iv) —C(O)—Y—Z—(G—(C(R$_e$)(R$_f$))$_b$—T—Q)$_p$;
(v) —P—Z—(G—(C(R$_e$)(R$_f$))$_b$—T—Q)$_p$;
(vi) —P$_1$—B$_1$—W—B$_t$—L$_r$—E$_s$—[C(R$_e$)(R$_f$)]$_w$—E$_c$—[C(R$_e$)(R$_f$)]$_x$—L$_d$—[C(R$_e$)(R$_f$)]$_y$—L$_i$—E$_j$—L$_g$—[C(R$_e$)(R$_f$)]$_z$—T—Q or
(vii) —P$_1$—F'$_n$—L$_r$—E$_s$—[C(R$_e$)(R$_f$)]$_w$—E$_{[C(R_e)}$(R$_f$)]$_x$—L$_d$—[C(R$_e$)(R$_f$)]$_y$—L$_i$—E$_j$—L$_g$—[C(R$_e$)(R$_f$)]$_z$—T—Q wherein, R$_d$ is a hydrogen, a lower alkyl, a cycloalkyl, an aryl or an arylalkyl;

Y is oxygen, S(O)$_o$, lower alkyl or NR$_1$;

o is an integer from 0 to 2;

R$_1$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, —CH$_2$—C(T—Q)(R$_e$)(R$_f$), or —(N$_2$O$_2$—)$^-$·M$^+$, wherein M$^+$ in an organic or inorganic cation;

R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, —T—Q , or [C(R$_e$)(R$_f$)]$_k$—T—Q, or R$_e$ and R$_f$ taken together are a carbonyl, a methanthial, a heterocyclic ring, a cycloalkyl group or a bridged cycloalkyl group;

k is an integer from 1 to 3;
p is an integer from 1 to 10;
T is independently a covalent bond, oxygen, S(O)$_o$ or NR$_1$;
Z is a covalent bond, an alkyl, an aryl, an arylalkyl, an alkylaryl, a heteroalkyl, or (C(R$_e$)(R$_f$))$_p$;
Q is —NO or —NO$_2$;
G is a covalent bond, —T—C(O)—, —C(O)—T—or T;
b is an integer from 0 to 5;
P is a carbonyl, a phosphoryl or a silyl;
l and t are each independently an integer from 1 to 3;
r, s, c, d, g, i and j are each independently an integer from 0 to 3;
w, x, y and z are each independently an integer from 0 to 10;
P$_1$ is a covalent bond or P;
B at each occurrence is independently an alkyl group, an aryl group, or [C(R$_e$)(R$_f$)]$_p$;
E at each occurrence is independently —T—, an alkyl group, an aryl group, or —(CH$_2$CH$_2$O)$_q$;
q is an integer of from 1 to 5;
L at each occurrence is independently —C(O)—, —C(S)—,—T—, a heterocyclic ring, an aryl group, an alkenyl group, an alkynyl group, an arylheterocyclic ring, or —(CH$_2$CH$_2$O)$_q$;
W is oxygen, S(O)$_o$, or NR$_1$;
F' at each occurrence is independently selected from B or carbonyl;
n is an integer from 2 to 5;
with the proviso that when R$_i$ is —CH$_2$—C(T—Q)(R$_e$)(R$_f$) or —(N$_2$O$_2$)$^{31}$ M$^+$, or R$_e$ or R$_f$are T—Q or [C(R$_e$)(R$_f$)]$_k$—T—Q, then the "—T—Q" subgroup designated in D can be a hydrogen, an alkyl, an alkoxy, an alkoxyalkyl, an aminoalkyl, a hydroxy, or an aryl.

In cases where multiple designations of variables which reside in sequence are chosen as a "covalent bond" or the integer chosen is 0, the intent is to denote a single covalent bond connecting one radical to another. For example, E$_0$ or [C(R$_e$)(R$_f$)]$_0$ would denote a covalent bond, while E$_2$ denotes (E—E) and [C(R$_e$)(R$_f$)—C(R$_e$)(R$_f$)]$_2$ denotes —C(R$_e$)(R$_f$)—C(R$_e$)(R$_f$)—.

R$_4$ is:
(i) hydrogen;
(ii) —CH(Rd)—O—C(O)—Y—Z—(C(R$_e$)(R$_f$))$_p$—T—Q;
(iii) —C(O)—T—(C(R$_e$)(R$_f$))$_p$—T—Q;
(iv) —C(O)—Z—(G—(C(R$_e$)(R$_f$))$_p$—T—Q)$_p$, or
(v) —W$_o$—L$_r$—E$_s$—[C(R$_e$)(R$_f$)]$_w$—E$_c$—[C(R$_e$) (R$_f$)]$_x$—L$_d$—[C(R$_e$)(R$_f$)]$_y$—L$_i$—E$_j$—L$_g$—[C(R$_e$)(R$_f$)]$_z$—T—Q wherein r,s,c,d,g,i,j,o,p,w,x,y,z, R$_d$, R$_e$ R$_f$, E, L, G, T, Q, W, Y, and Z areas defined herein;

R$_5$ is a lone pair of electrons or —CH(R$_d$)—O—C(O)—Y—Z—(C(R$_e$)(R$_f$))$_p$—T—Q;

R$_{11}$ and R$_{12}$ are independently selected from hydrogen or R$_4$; wherein R$_4$, R$_d$, R$_e$, R$_f$, p, T, Q, Y, and Z are as defined herein;

X is a halogen, and D$_1$ is D or hydrogen, wherein D is as defined herein; and with the proviso that if the structure does not contain D, then at least one of the variables R$_4$, R$_5$, R$_{11}$ or R$_{12}$ must contain the element "—T—Q";

Another embodiment of the present invention provides compounds of Formula (II):

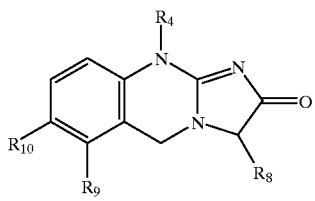

II wherein, $R_4$ is as defined herein; with the proviso that $R_4$ cannot be hydrogen;

$R_8$ is a hydrogen, a lower alkyl group or a haloalkyl group;

$R_9$ is a hydrogen or a halogen; and $R_{10}$ is:

(i) hydrogen, (ii)

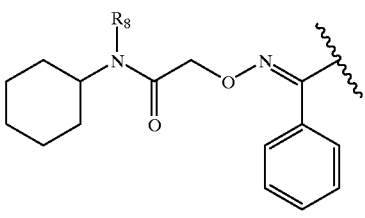

or (iii)

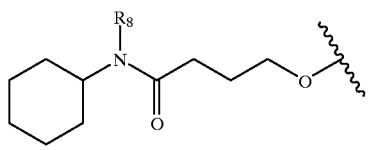

wherein $R_8$ is as defined herein.

Another embodiment of the present invention provides compounds of Formula (III):

III

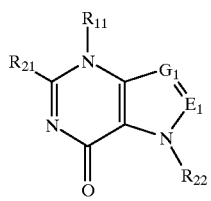

wherein, $E_1$ is nitrogen or —CH—;

$G_1$ is nitrogen or —C($R_8$)—;

$R_{21}$ is:

(i)

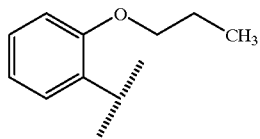

(ii)

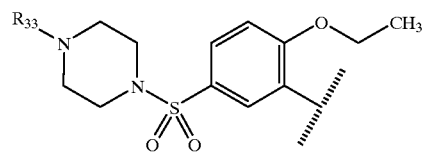

$R_{22}$ is $R_{12}$ or a lower alkyl;

$R_{33}$ is a lower alkyl or $[C(R_e)(R_f)]_p$—T—Q; and p, $R_e$, $R_f$, $R_{11}$, $R_{12}$, T and Q are as defined herein; with the proviso that at least one of the variables $R_{11}$, $R_{12}$, $R_{22}$ or $R_{33}$ must contain the element "T—Q".

Another embodiment of the present invention provides compounds of Formula (IV):

IV

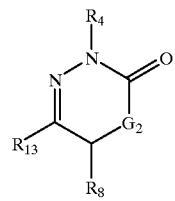

wherein, $G_2$ is —CH$_2$— or sulfur;

$R_4$ and $R_8$ are each as defined herein; and $R_{13}$ is:

(i)

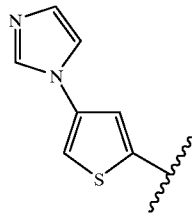

(ii)

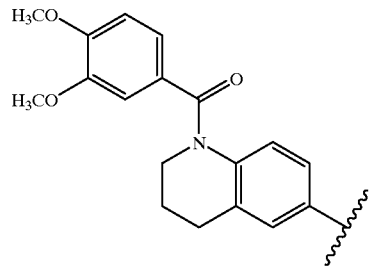

(iii)

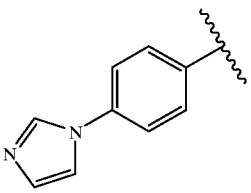

-continued (iv)

[structure: H3CO-phenyl-benzimidazole with R6]

(v)

[structure: pyridine-vinyl]

(vi)

[structure: 4-oxo-pyridinyl-phenyl]

or (vii)

[structure: guanidine with R6, R7, CH3, CN, phenyl]

wherein,

R$_6$ and R$_7$ are independently selected from R$_4$, wherein R$_4$ is as defined herein; with the proviso that at least one of the variables R$_4$, R$_6$ or R$_7$ must contain the element "T—Q".

Another embodiment of the present invention provides compounds of Formula (V):

V

[structure: pyridinone with H3C, R4, R14, CN]

wherein,

R$_4$ is as defined herein; and

R$_{14}$ is:

(i)

[structure: quinoline]

(ii)

[structure: imidazopyridine]

-continued (iii)

[structure: pyridine]

or (iv)

[structure: piperazine-phenyl ether with OCH3, O-R6]

wherein R$_6$ is as defined herein; with the proviso that at least one of the variables R$_4$, or R$_6$ must contain the element "T—Q".

Another embodiment of the present invention provides compounds of Formula (VI):

VI

[structure: xanthine with R15, R16, R17]

wherein,

R$_{15}$ is a hydrogen, a lower alkyl, R$_4$, or —(CH$_2$)$_4$—C(CH$_3$)$_2$—O—D$_1$; wherein R$_4$ is as defined herein;

R$_{16}$ is a lower alkyl; and

R$_{17}$ is a hydrogen, a lower alkyl, CH$_3$—C(O)—CH$_2$—; CH$_3$—O—CH$_2$, or D with the proviso that either R$_{15}$ or R$_{17}$ must contain D, wherein D and D$_1$ are as defined herein.

Another embodiment of the present invention provides compounds of Formula (VII):

VII

[structure: quinolinone with R8, R4, R18]

wherein,

R$_4$ and R$_8$ are as defined herein; and

R$_{18}$ is:

(i)

[structure: dimethylpyrrole]

-continued (ii)

and wherein $R_8$ is as defined herein; with the proviso that $R_4$ cannot be hydrogen.

Another embodiment of the present invention provides compounds of Formula (VIII):

VIII wherein, $R_{19}$ is:

(i)

(ii)

(iii)

(iv)

(v)

or (vi)

and wherein $R_4$, $R_{11}$, and $R_{12}$ are as defined herein; with the proviso that at least one of the variables $R_4$, $R_{11}$ or $R_{12}$ must contain the element "T—Q".

Another embodiment of the present invention provides compounds of Formula (IX):

IX wherein, $R_{20}$ is:

(i)

(ii)

or (iii) —D;

wherein $R_4$ is as defined herein; with the proviso that when $R_{20}$ is not D, then $R_4$ cannot be hydrogen.

Another embodiment of the present invention provides compounds of Formula (X):

X

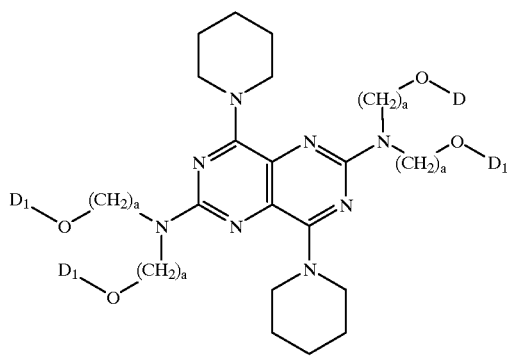

wherein,
a is an integer from 2 to 3 and D and $D_1$ are as defined herein.

Another embodiment of the present invention provides compounds of Formula (XI):

XI

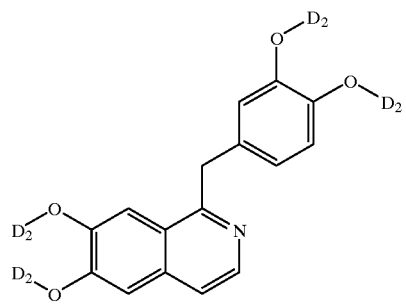

wherein,
$D_2$ is hydrogen, a lower alkyl or D; wherein D is as defined herein; with the proviso that at least one $D_2$ must be D.

Another embodiment of the present invention provides compounds of Formula (XII):

XII

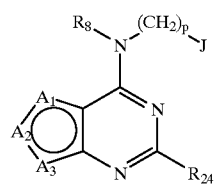

wherein,
$R_8$ is as defined herein;
J is:

(i)

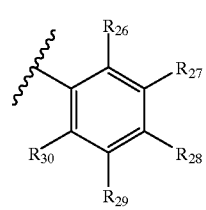

(ii)

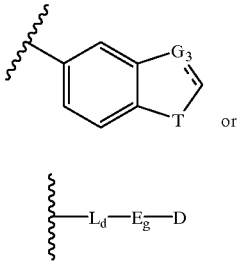

or (iii)

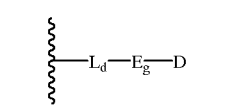

$R_{24}$ is hydrogen or K—G—D;
wherein,
K is:

(i)

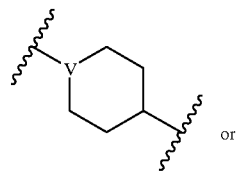

or (ii)

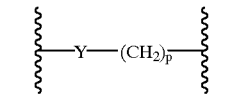

$G_3$ is (CH), (CH$_2$), oxygen, sulfur or nitrogen;
V is carbon or nitrogen;
$A_1$, $A_2$ and $A_3$ comprise the other subunits of a 5- or 6-membered monocyclic aromatic ring and each is independently (i) C—$R_{23}$ wherein $R_{23}$ at each occurrence is independently D, a hydrogen, a halogen, an alkoxy, a nitrile, an alkyl, an arylalkyl, an alkylaryl, a carboxamido, a carboxyl, a haloalkyl, an alkoxyalkyl, an alkoxyaryl or a nitro; (ii) sulfur; (iii) oxygen; and (iv) $B_a$=$B_b$ wherein $B_a$ and $B_b$ are each independently nitrogen or C—$R_{23}$ wherein at each occurrence $R_{23}$ is as defined herein; and wherein $R_{26}$, $R_{27}$, $R_{28}$, $R_{29}$, and $R_{30}$ are independently a hydrogen, a halogen, a hydroxy, a haloalkyl, an alkoxy, an alkoxyalkyl, an alkoxyaryl, an alkoxyhaloalkyl, a nitrile, a nitro, an alkyl, an alkylaryl, an arylalkyl, a hydroxy alkyl, a carboxamido, or a carboxyl; and
wherein d, g, p, E, L, G, T, Y and D are as defined herein; with the proviso that at least one of the variables $A_1$, $A_2$, $A_3$, J or $R_{24}$ must contain the element "—T—Q" or "D".

Another embodiment of the present invention provides compounds of Formula (XIII):

XIII

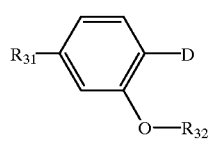

wherein,
$R_{31}$ is an alkyl, a halogen, a haloalkyl, or a haloalkoxy;
$R_{32}$ is $D_1$ or —C(O)—$R_8$; and D, $D_1$ and $R_8$ are as defined herein.

Another embodiment of the present invention provides compounds of Formula (XIV):

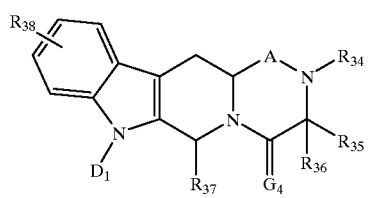

XIV

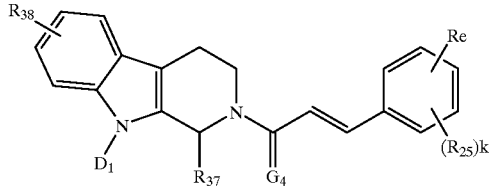

XV wherein,

A is CH$_2$, a carbonyl or a methanethial;

G$_4$ is oxygen or sulfur;

R$_{34}$ is hydrogen, lower alkyl, alkenyl, alkynyl or L$_r$—E$_s$—[C(R$_e$)(R$_f$)]$_w$E$_c$—[C(R$_e$)(R$_f$)]$_x$—L$_d$—[C(R$_e$)(R$_f$)]$_y$—L$_i$—E$_j$—L$_g$—[C(R$_e$)(R$_f$)]$_z$—T—Q;

R$_{35}$ and R$_{36}$ are independently a hydrogen, a lower alkyl, an arylalkyl, an alkylaryl, a cycloalkylalkyl, a heterocyclicalkyl, T—Q or [C(R$_e$)(R$_f$)]$_k$—T—Q;

R$_{35}$ and R$_{36}$ taken together are a carbonyl group, a methanethial group, a heterocyclic group or a cycloalkyl group;

R$_{34}$ and R$_{35}$ taken together are [C(R$_g$)(R$_h$)]$_u$ or —C(R$_g$)(R$_h$)—C(R$_g$)=C(R$_g$)—[C(R$_g$)(R$_h$)]$_v$ wherein u is an integer of 3 or 4, v is an integer of 1 or 2 and R$_g$ and R$_h$ at each occurrence is independently a hydrogen, an alkyl, T—Q or [C(R$_e$)(R$_f$)]$_k$—T—Q;

R$_{38}$ is a hydrogen, a halogen or a lower alkyl; and

R$_{37}$ is:

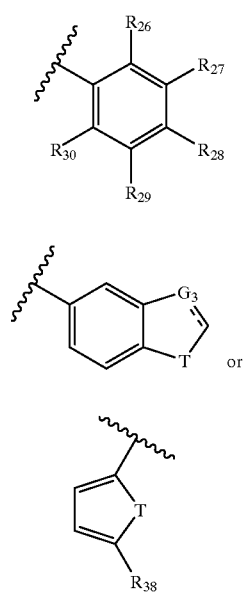

(i)

(ii)

(iii)

wherein, c, d, g, i, j, k, r, s, w, x, y, z, D$_1$, E, L, G$_3$, T, Q, R$_e$, R$_f$, R$_{26}$, R$_{27}$, R$_{28}$, R$_{29}$, R$_{30}$ and R$_{38}$ are as defined herein; with the proviso that D$_1$ must be D if R$_{34}$, R$_{35}$ R$_{36}$ or R$_{37}$ do not contain the element "T—Q".

Another embodiment of the present invention provides compounds of Formula (XV):

wherein,

R$_{25}$ at each occurrence is a hydrogen, an alkyl, a cycloalkoxy, a halogen, a hydroxy, an hydroxyalkyl, an alkoxyalkyl, an arylheterocyclic ring, an alkylaryl, an arylalkoxy, an alkylthio, an arylthio, a cyano, an aminoalkyl, an amino an alkoxy, an aryl, an arylalkyl, a carboxamido, a alkyl carboxamido, an aryl carboxamido, a carboxyl, a carbamoyl, an alkylcarboxylic acid, an arylcarboxylic acid, a carboxylic ester, an alkylcarboxylic ester, an arylcarboxylic ester, a carboxamido, an alkylcarboxamido, an arylcarboxamido, a haloalkoxy, a sulfonamido, a urea, a nitro, or L$_r$—E$_s$—[C(R$_e$)(R$_f$)]$_w$—E$_c$—[C(R$_e$)(R$_f$)]$_x$—L$_d$—[C(R$_e$)(R$_f$)]$_y$—L$_i$—E$_j$—L$_g$[C(R$_e$)(R$_f$)]$_z$—T—Q; and wherein c, d, g, i, j, k, r, s, w, x, y, z, G$_4$, D$_1$, E, L, T, Q, R$_e$, R$_f$, R$_{37}$ and R$_{38}$ are as defined herein; with the proviso that D$_1$ must be D if R$_e$ or R$_{25}$ do not-contain the element "T—Q".

Another embodiment of the present invention provides compounds of the Formula (XVI):

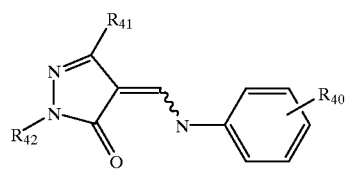

XVI wherein,

R$_{40}$ is a hydrogen, a lower alkyl, a haloalkyl, a halogen, an alkoxy, an alkenyl, an alkynyl, a carbamoyl, a sulfonamido or L$_r$—E$_s$—[C(R$_e$)(R$_f$)]$_w$—E$_c$—[C(R$_e$)(R$_f$)]$_x$—L$_d$—[C(R$_e$)(R$_f$)]$_y$—L$_i$—E$_j$—L$_g$—[C(R$_e$)(R$_f$)]$_z$—T—Q; and wherein c, d, g, i, j, k, r, , w, x, y, z, E, L, T, Q, R$_e$ and R$_f$ are as defined herein;

R$_{41}$ is a lower alkyl, a hydroxyalkyl, an alkylcarboxylic acid, an alkylcarboxylic ester an alkylcarboxamido or L$_r$—E$_s$—[C(R$_e$)(R$_f$)]$_w$—E$_c$—[C(R$_e$)(R$_f$)]$_x$—L$_d$—[C(R$_e$)(R$_f$)]$_y$—L$_i$—E$_j$—L$_g$—[C(R$_e$)(R$_f$)]$_z$—T—Q; and wherein c, d, g, i, j, k, r, s, w, x, y, z, E, L, T, Q, R$_e$ and R$_f$ are as defined herein;

R$_{42}$ is:

(i)

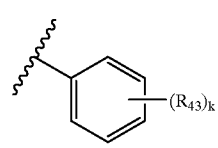

-continued (ii)

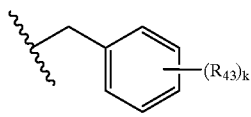

or (iii)

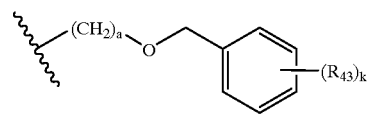

wherein, $R_{43}$ at each occurrence is independently an amino, a cyano, a halogen, a nitro group, a carboxyl, a carbamoyl, a sulfonic acid, a sulfonic ester, a sulfonamido, a heterocyclic ring, a carboxamido, a carboxylic ester, an ester, an amidyl, a phosphoryl or $L_r$—$E_s$—$[C(R_e)(R_f)]_w$—$E_c$—$[C(R_e)(R_f)]_x$—$L_d$—$[C(R_e)(R_f)]_y$—$L_i$—$E_j$—$L_g$—$[C(R_e)(R_f)]_z$—T—Q; and c, d, g, i, j, k, r, s, w, x, y, z, E, L, T, Q, $R_e$, and $R_f$ are as defined herein; with the proviso that at least one of $R_{40}$, $R_{41}$, or $R_{43}$ must contain the element "T—Q".

Another embodiment of the present invention provides compounds of the Formula (XVII):

XVII

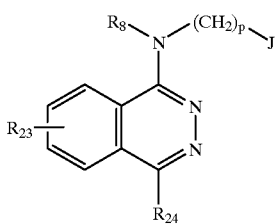

wherein $R_8$, $R_{23}$, $R_{24}$, p and J are as defined herein; with the proviso that at least one $R_{24}$ or J must contain the element "—T—Q" or "—D".

Another embodiment of the present invention provides compounds of the Formula (XVIII):

XVIII

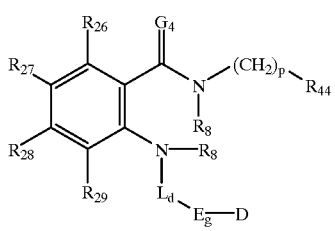

wherein,
$R_{44}$ is:

(i)

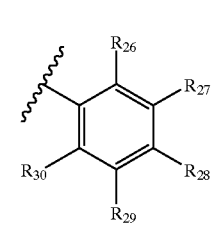

(ii)

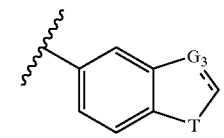

or (iii)

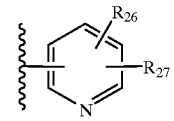

wherein d, g, p, D, E, L, $G_3$, $G_4$, T, $R_8$, $R_{26}$, $R_{27}$, $R_{28}$, $R_{29}$, and $R_{30}$ are as defined herein.

Another embodiment of the present invention provides compounds of the Formula (XIX):

XIX

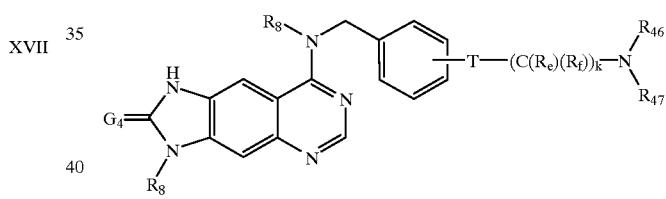

wherein,
$R_{46}$ and $R_{47}$ are independently selected from lower alkyl, hydroxyalkyl or D, or $R_{46}$ and $R_{47}$ taken together are a heterocyclic ring, wherein $G_4$, T, $R_8$, and k are defined herein; with the proviso that at least one of the variables $R_{46}$ or $R_{47}$ must be D or when the variables taken together are a heterocyclic ring, the ring must contain $NR_i$, wherein $R_i$ must contain the element "T—Q".

Compounds of the present invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. The present invention includes within its scope all such isomers and mixtures thereof.

Another aspect of the present invention provides processes for making the novel compounds of the invention and to the intermediates useful in such processes. The compounds of the present invention may be synthesized following the reaction schemes shown in FIGS. 1–57, in which $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, $R_{46}$, $R_{47}$, $R_e$, $R_f$, a, p, A, $A_1$, $A_2$, $A_3$, D, $D_1$, $D_2$, $E_1$, $G_1$, $G_2$, $G_3$, $G_4$, J, K, T and X are as defined herein or as depicted in the reaction schemes for formulas I–XIX; $P^1$ is an oxygen protecting group and $P^2$ is a sulfur protecting group. The reactions are performed in solvents appropriate to the reagents, and materials used are suitable for the transformations being effected. One skilled in the art of organic synthesis will understand that the functionality present in the molecule must be consistent with the chemical transformation proposed. This will, on occasion, necessitate judgment by the routine as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to the skilled practitioner in the art. The use of sulfur and oxygen protecting groups is well known in the art for protecting thiol and alcohol groups against undesirable reactions during a synthetic procedure and many such protecting groups are known, as described, for example, by T. H. Greene and P. G. M. Wuts, *Protective Groups in Organic Synthesis,* John Wiley & Sons, New York (1991), the disclosure of which is incorporated by reference herein in its entirety.

Nitroso compounds of structure (I), wherein $R_1$, $R_2$, $R_e$, $R_f$, and p are as defined herein, and a nitrite containing imide is representative of the $R_3$ group, as defined herein, may be prepared as shown in FIG. 1. The amide group of structure 1 is converted to the imide of structure 2, wherein p, $R_e$ and $R_f$ are as defined herein, by reaction with an appropriate protected alcohol containing activated acylating agent, wherein $P^1$ is as defined herein. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst, such as sulfuric acid. Preferred protecting groups for the alcohol moiety are silyl ethers, such as a trimethylsilyl ether, a tert-butyldimethylsilyl ether, or a tert-butyldiphenylsilyl ether. Deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloro-methane, THF, DMF, or acetonitrile, with or without an amine base, such as pyridine or triethylamine affords the compound of structure IA.

Figure 2:
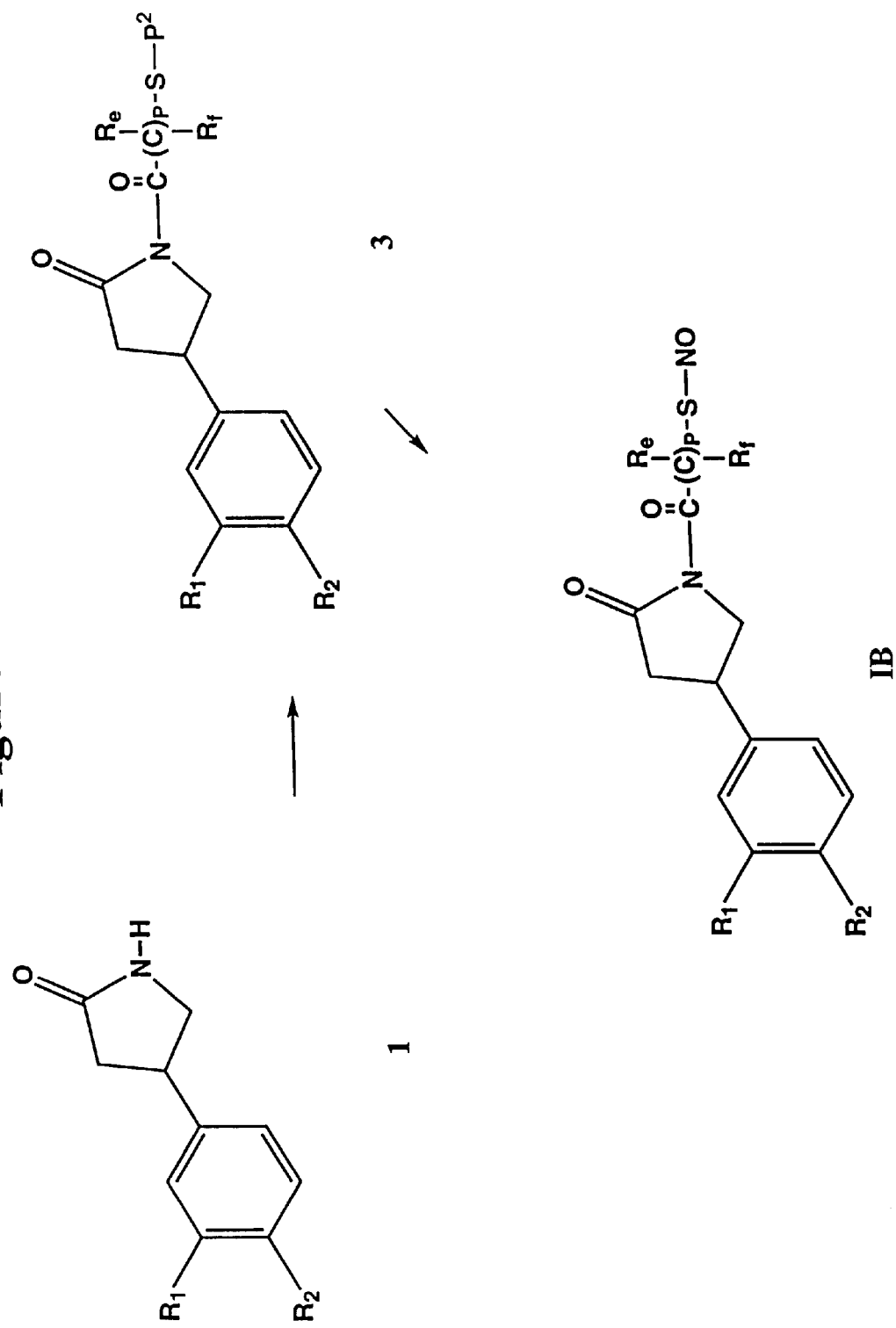
FIG. 2 shows a synthetic scheme for the preparation of nitrosothiol containing substituted benzene derivatives.

Nitroso compounds of structure (I), wherein $R_1$, $R_2$, $R_e$, $R_f$, and p are as defined herein, and a nitrosothiol containing imide is representative of the $R_3$ group, as defined herein, may be prepared as shown in FIG. 2. The amide group of structure 1 is converted to the imide of structure 3, wherein p, $R_e$ and $R_f$ are as defined herein, by reaction with an appropriate protected thiol containing activated acylating agent, wherein $P^2$ is as defined herein. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst, such as sulfuric acid. Preferred protecting groups for the thiol moiety are as a thioester, such as a thioacetate or thiobenzoate, as a disulfide, as a thiocarbamate, such as N-methoxymethyl thiocarbamate, or as a thioether, such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids, such as trifluoroacetic or hydrochloric acid, and heat are used to remove a paramethoxy-benzyl thioether, a tetrahydropyranyl thioether, or a 2,4,6-trimethoxybenzyl thioether group) followed by reaction a suitable nitrosylating agent, such as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of structure IB. Alternatively, treatment of the deprotected thiol derived from compound 3 with a stoichiometric quantity of sodium nitrite in an acidic aqueous or alcoholic solution affords the compound of structure IB.

Figure 3:
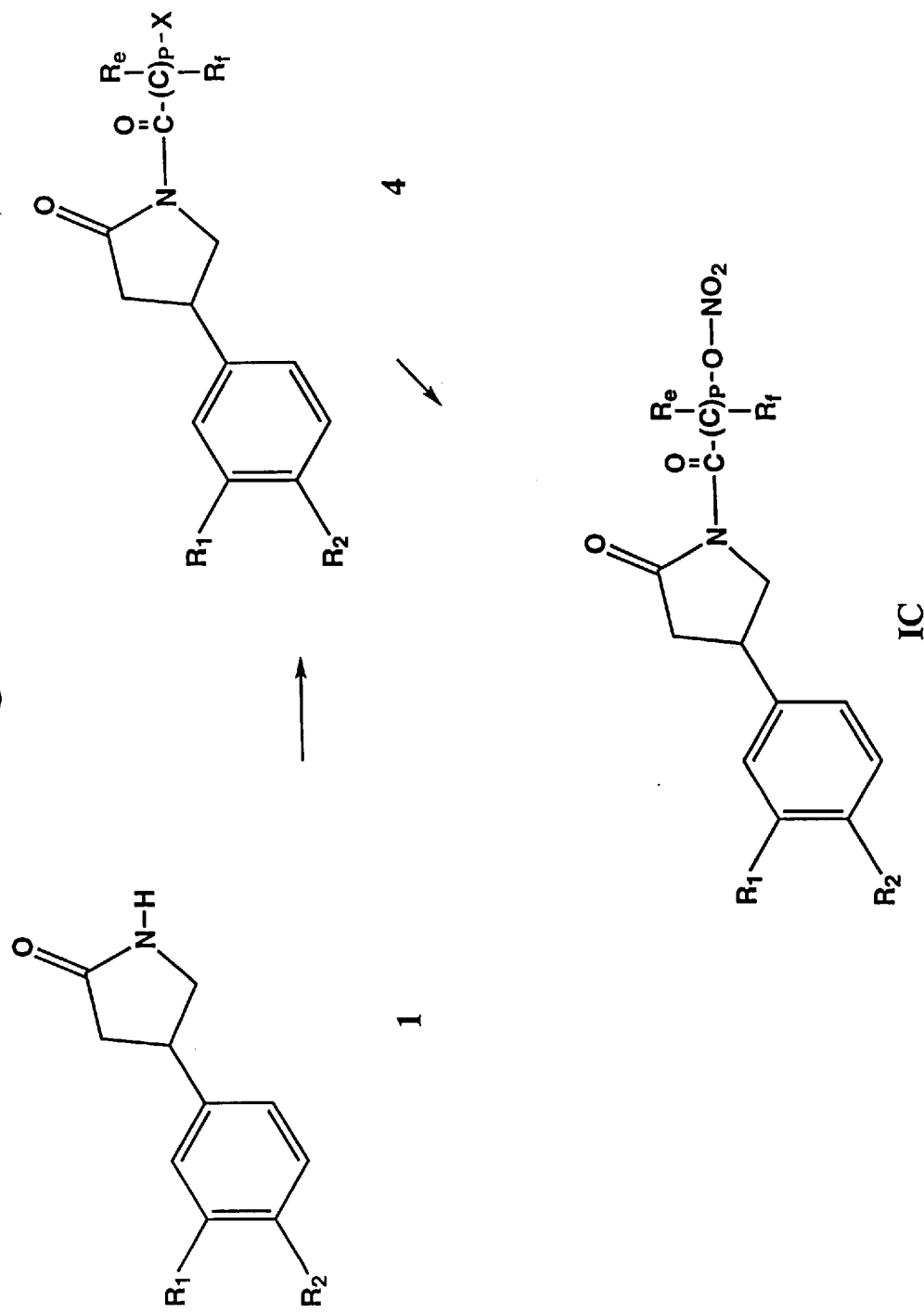
FIG. 3 shows a synthetic scheme for the preparation of nitrate containing substituted benzene derivatives.

Nitro compounds of structure (I), wherein $R_1$, $R_2$, $R_e$, $R_f$, and p are as defined herein, and a nitrate containing imide is representative of the $R_3$ group, as defined herein, may be prepared as shown in FIG. 3. The amide group of structure 1 is converted to the imide of structure 4, wherein p, $R_e$ and $R_f$ are as defined herein, and X is a halogen, by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst, such as sulfuric acid. Preferred halides are bromide and iodide. Reaction of the imide of structure 4 with a suitable nitrating agent, such as silver nitrate, in an inert solvent, such as acetonitrile, affords the compound of structure IC.

Figure 4:
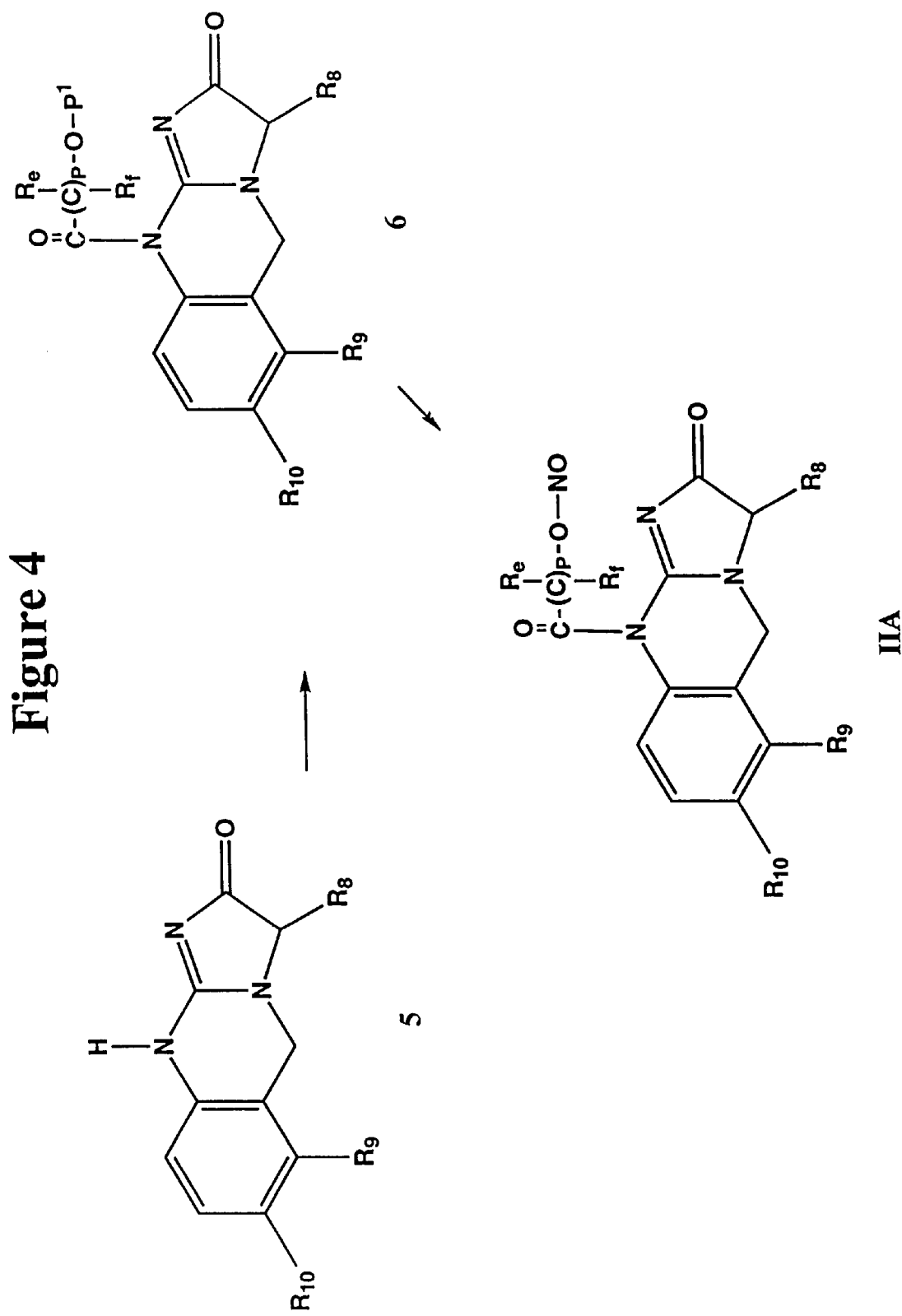
FIG. 4 shows a synthetic scheme for the preparation of nitrite containing imidazo[2,1-b]quinazoline derivatives.

Nitroso compounds of structure (II), wherein $R_8$, $R_9$, $R_{10}$, $R_e$, $R_f$, and p are as defined herein, and a nitrite containing amide is representative of the $R_4$ group, as defined herein, may be prepared as shown in FIG. 4. The imidazo[2,1-b]quinazoline of structure 5 is converted to the acylimidazo[2,1-b]quinazoline of structure 6, wherein p, $R_e$ and $R_f$ are as defined herein, by reaction with an appropriate protected alcohol containing activated acylating agent, wherein $P^1$ is as defined herein. Preferred methods for the formation of acylimidazo[2,1-b]quinazolines are reacting the imidazo[2,1-b]quinazoline with the preformed acid chloride or symmetrical anhydride of the protected alcohol containing acid or condensing the imidazo[2,1-b]quinazoline and protected alcohol containing acid in the presence of a dehydrating agent, such as dicyclohexylcarbodiimide (DCC) or 1-ethyl-3 (3-dimethylaminopropyl) carbodiimide hydrochloride (EDAC.HCl) with or without a catalyst such as 4-dimethylamino-pyridine (DMAP) or 1-hydroxybenzotriazole (HOBt). Preferred protecting groups for the alcohol moiety are silyl ethers, such as a trimethylsilyl or tertbutyldimethylsilyl ether. Deprotection of the hydroxyl moiety (fluoride ion is the preferred method for removing silyl ether protecting groups) followed by reaction a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure IIA.

Figure 5:
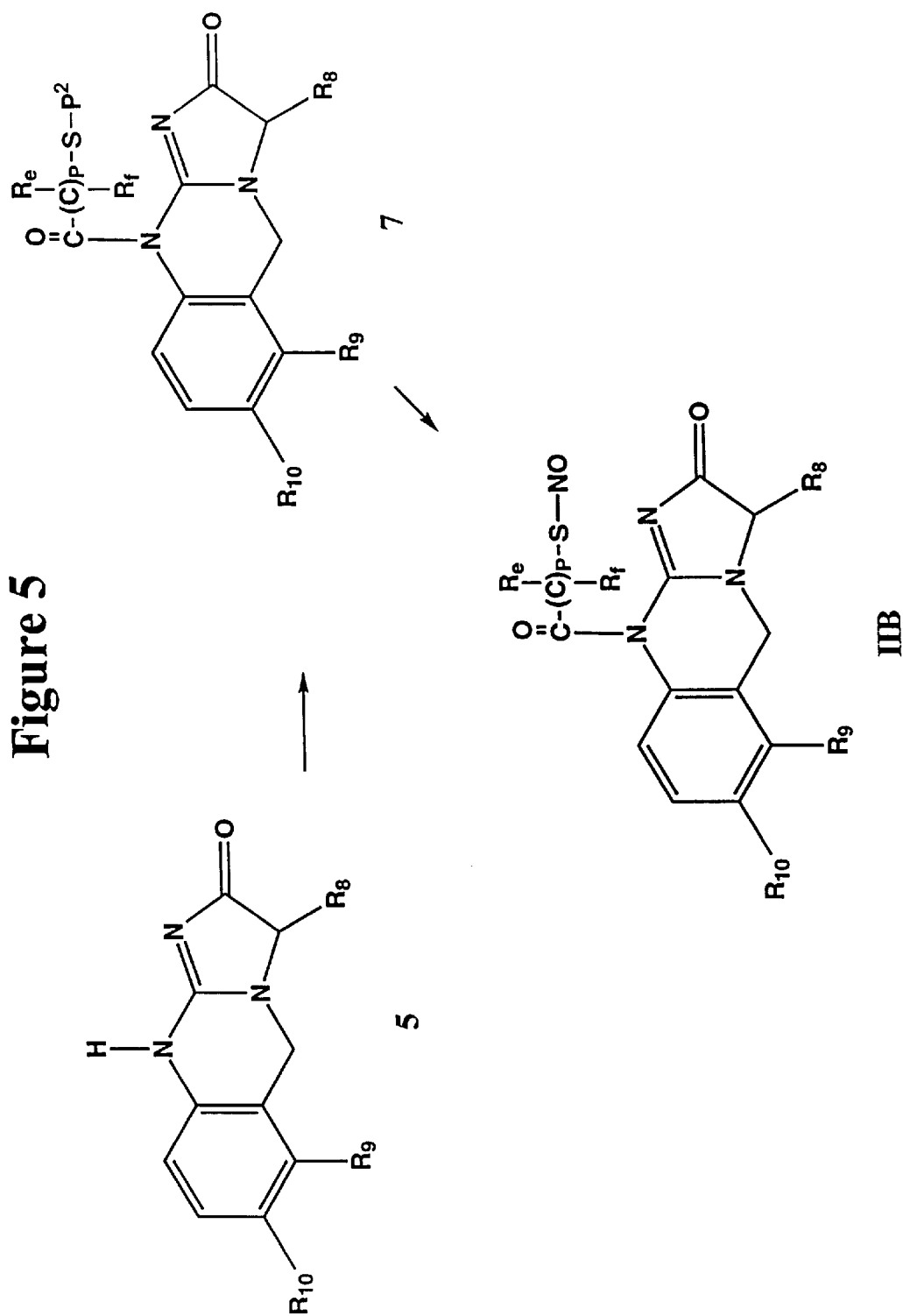
FIG. 5 shows a synthetic scheme for the preparation of nitrosothiol containing imidazo[2,1-b]quinazoline derivatives.

Nitroso compounds of structure (II), wherein $R_8$, $R_9$, $R_{10}$, $R_e$, $R_f$, and p are as defined herein, and a nitrosothiol containing amide is representative of the $R_4$ group, as defined herein, may be prepared as shown in FIG. 5. The imidazo[2,1-b]quinazoline of structure 5 is converted to the acylimidazo[2,1-b]quinazoline of structure 7, wherein p, $R_e$ and $R_f$ are as defined herein, by reaction with an appropriate protected thiol containing activated acylating agent, wherein $P^2$ is as defined herein. Preferred methods for the formation of acylated imidazo[2,1-b]quinazolines are reacting the imidazo[2,1-b]-quinazoline with the preformed acid chloride or symmetrical anhydride of the protected thiol containing acid or condensing the imidazo[2,1-b]-quinazoline and protected thiol containing acid in the presence of a dehydrating agent, such as DCC or EDAC.HCl with or without a catalyst, such as DMAP or HOBt. Preferred protecting groups for the thiol moiety are a thioester, such as a thioacetate or thiobenzoate, a disulfide, a thiocarbamate, such as N-methoxymethyi thiocarbamate, or a thioether, such as a paramethoxybenzyl thioether, a tetrahydropyranyl thioether or a 2,4,6-trimethoxybenzyl thioether. Deprotection of the thiol moiety (zinc in dilute aqueous acid, triphenyiphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids, such as trifluoroacetic or hydrochloric acid, and heat are used to remove a paramethoxybenzyl thioether, a tetrahydropyranyl thioether, or a 2,4,6-trimethoxybenzyl thioether group) followed by reaction with a suitable nitrosylating agent, such as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of structure IIB. Alternatively, treatment of the deprotected thiol derived from compound 7 with a stoichiometric quantity of sodium nitrite in an acidic aqueous or alcoholic solution affords the compound of structure IIB.

Figure 6:
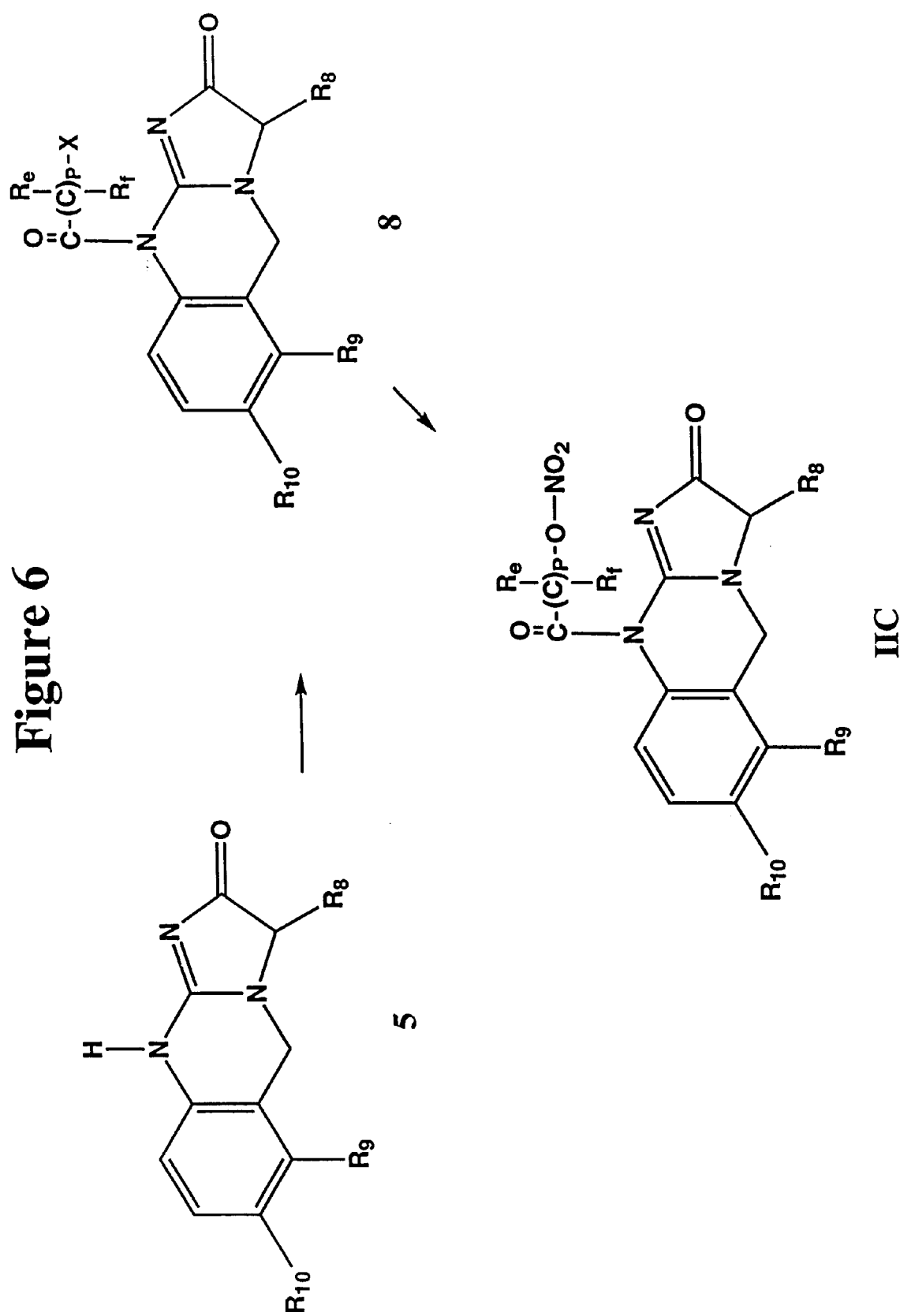
FIG. 6 shows a synthetic scheme for the preparation of nitrate containing imidazo [2,1-b]quinazoline derivatives.

Nitro compounds of structure (II), wherein $R_8$, $R_9$, $R_{10}$, $R_e$, $R_f$, and p are as defined herein, and a nitrate containing amide is representative of the $R_4$ group, as defined herein, may be prepared as shown in FIG. 6. The imidazo[2,1-b]quinazoline of structure 5 is converted to the acylimidazo[2,1-b]quinazoline of structure 8, wherein p, $R_e$ and $R_f$ are as defined herein, and X is halogen, by reaction with an appropriate halide containing activated acylating agent. Preferred methods for the formation of the acylimidazo-[2,1-b]quinazolines are reacting the imidazo[2,1-b]quinazoline with the preformed acid chloride or symmetrical anhydride of the halide containing acid or condensing the alcohol and halide containing acid in the presence of a dehydrating agent, such as DCC or EDAC.HCl, with or without a catalyst, such as DMAP or HOBt. Preferred halides are bromide and iodide. Reaction of the acylimidazo[2,1-b]quinazoline of structure 8 with a suitable nitrating agent, such as silver nitrate, in an inert solvent, such as acetonitrile, affords the compound of structure IIC.

Figure 7:
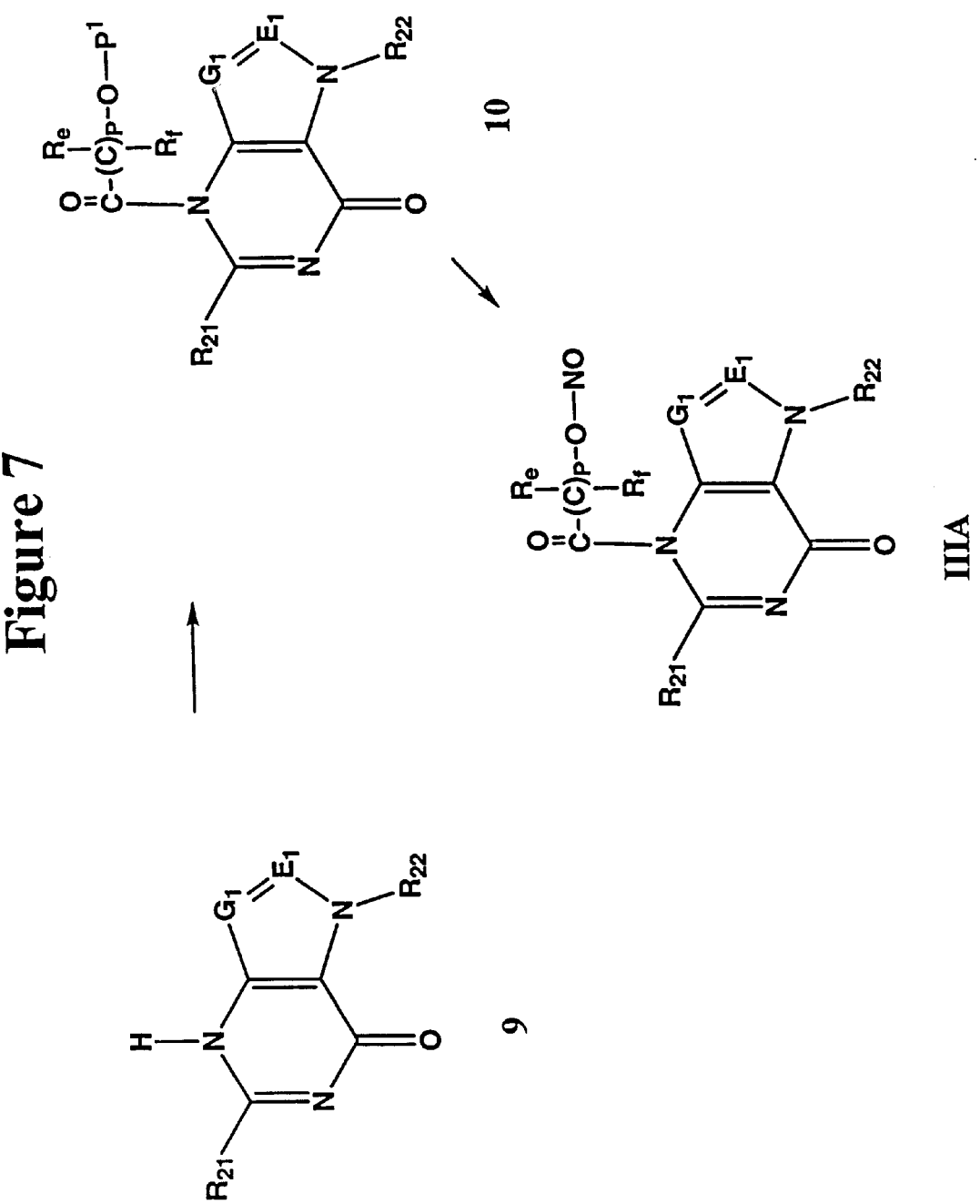
FIG. 7 shows a synthetic scheme for the preparation of nitrite containing purine-6-one derivatives.

Nitroso compounds of structure (III), wherein $E_1$, $G_1$, $R_{21}$, $R_{22}$, $R_e$, $R_f$, and p are as defined herein, and a nitrite containing amide is representative of the $R_{11}$ group, as defined herein, may be prepared as shown in FIG. 7. The purine-6-one group of structure 9 is converted to the acylated purine-6-one of structure 10, wherein p, $R_e$ and $R_f$ are as defined herein, by reaction with an appropriate protected alcohol containing activated acylating agent, wherein $P^1$ is as defined herein. Preferred methods for the formation of acylated purine-6-ones are reacting the purine-6-one with the preformed acid chloride or symmetrical anhydride of the protected alcohol containing acid. Preferred protecting groups for the alcohol moiety are silyl ethers, such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure IIIA.

Figure 8:
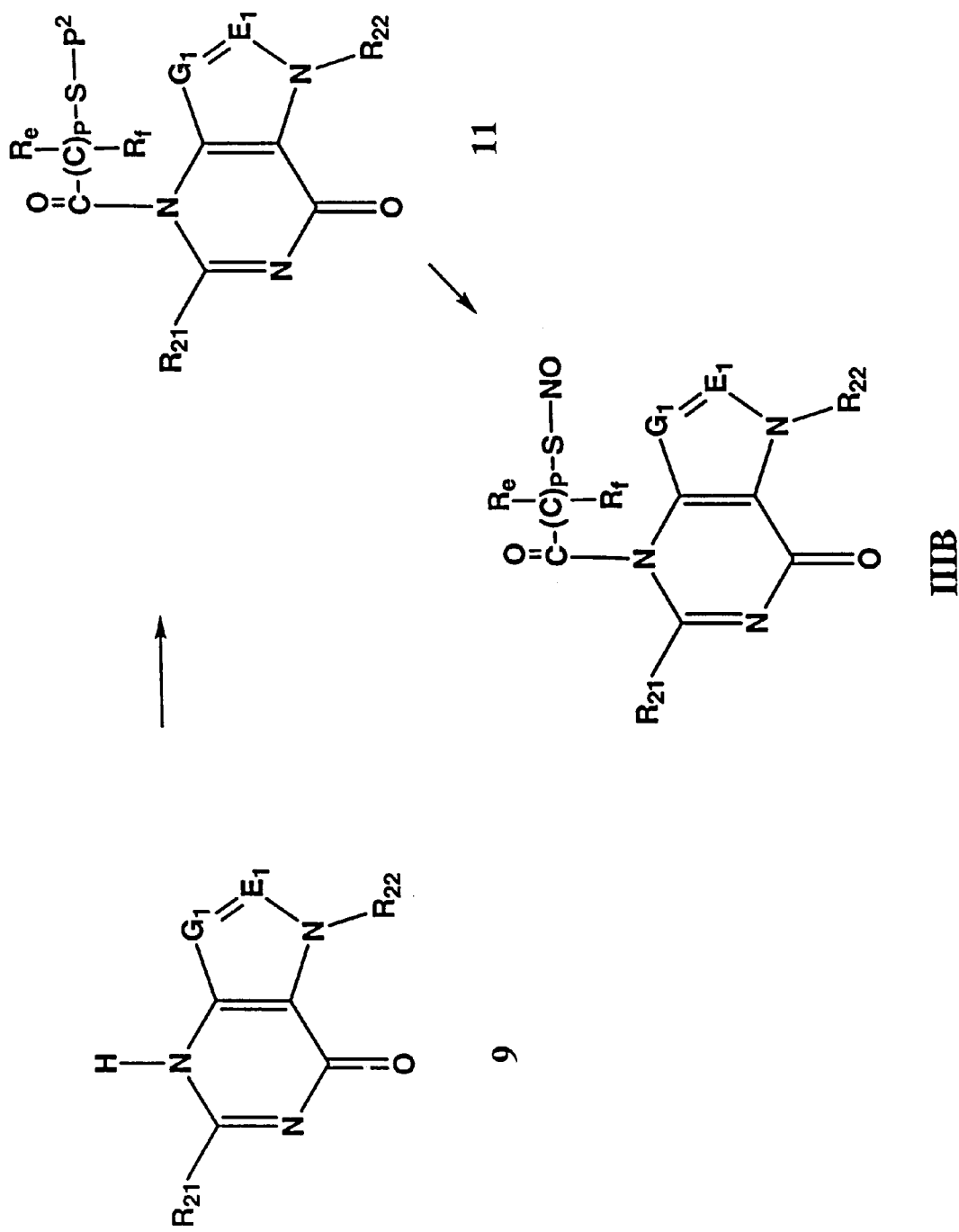
FIG. 8 shows a synthetic scheme for the preparation of nitrosothiol containing purine-6-one derivatives.

Nitroso compounds of structure (III), wherein $E_1$, $G_1$, $R_{21}$, $R_{22}$, $R_e$, $R_f$, and p are as defined herein, and an nitrosothiol containing amide is representative of the $R_{11}$ group, as defined herein, may be prepared as shown in FIG. 8. The purine-6-one group of structure 9 is converted to the acylated purine-6-one of structure 11, wherein p, $R_e$ and $R_f$ are as defined herein, by reaction with an appropriate protected thiol containing activated acylating agent, wherein $P^2$ is as defined herein. Preferred methods for the formation of acylated purine-6-ones are reacting the purine-6-one with the preformed acid chloride or symmetrical anhydride of the protected alcohol containing acid. Preferred protecting groups for the thiol moiety are a thioester, such as a thioacetate, or thiobenzoate, a disulfide, a thiocarbamate, such as N-methoxymethyl thiocarbamate, or a thioether, such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids, such as trifluoroacetic or hydrochloric acid, and heat are used to remove a paramethoxy- benzyl thioether, a tetrahydropyranyl thioether, or a 2,4,6-trimethoxybenzyl thioether group) followed by reaction a suitable nitrosylating agent, such as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of structure IIIB. Alternatively, treatment of the deprotected thiol derived from compound 11 with a stoichiometric quantity of sodium nitrite in an acidic aqueous or alcoholic solution affords the compound of structure IIIB.

Figure 9:
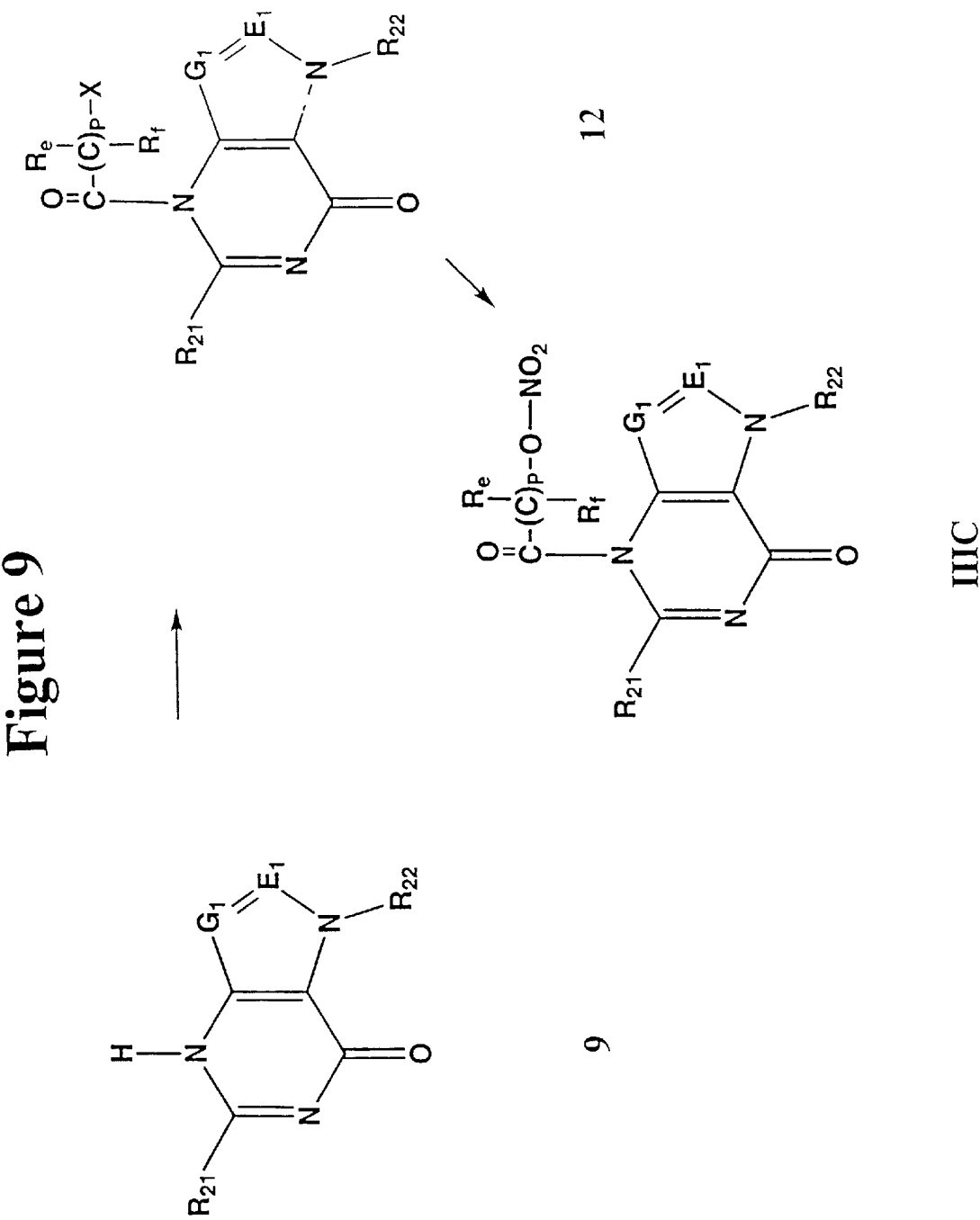
FIG. 9 shows a synthetic scheme for the preparation of nitrate containing purine-6-one derivatives.

Nitro compounds of structure (III), wherein $E_1$, $G_1$, $R_{21}$, $R_{22}$, $R_e$, $R_f$, and p are as defined herein, and a nitrate containing amide is representative of the $R_{11}$ group, as defined herein, may be prepared as shown in FIG. 9. The purine-6-one of structure 9 is converted to the acylated purine-6-one of structure 12, wherein p, $R_e$ and $R_f$ are as defined herein and X is halogen. Preferred methods for the formation of acylated purine-6-ones are reacting the purine-6-one with the preformed acid chloride or symmetrical anhydride of the halide containing acid. Preferred halides are bromide and iodide. Reaction of the of the acylated purine-6-one of structure 12 with a suitable nitrating agent, such as silver nitrate, in an inert solvent, such as acetonitrile, affords the compound of structure IIIC.

Figure 10:
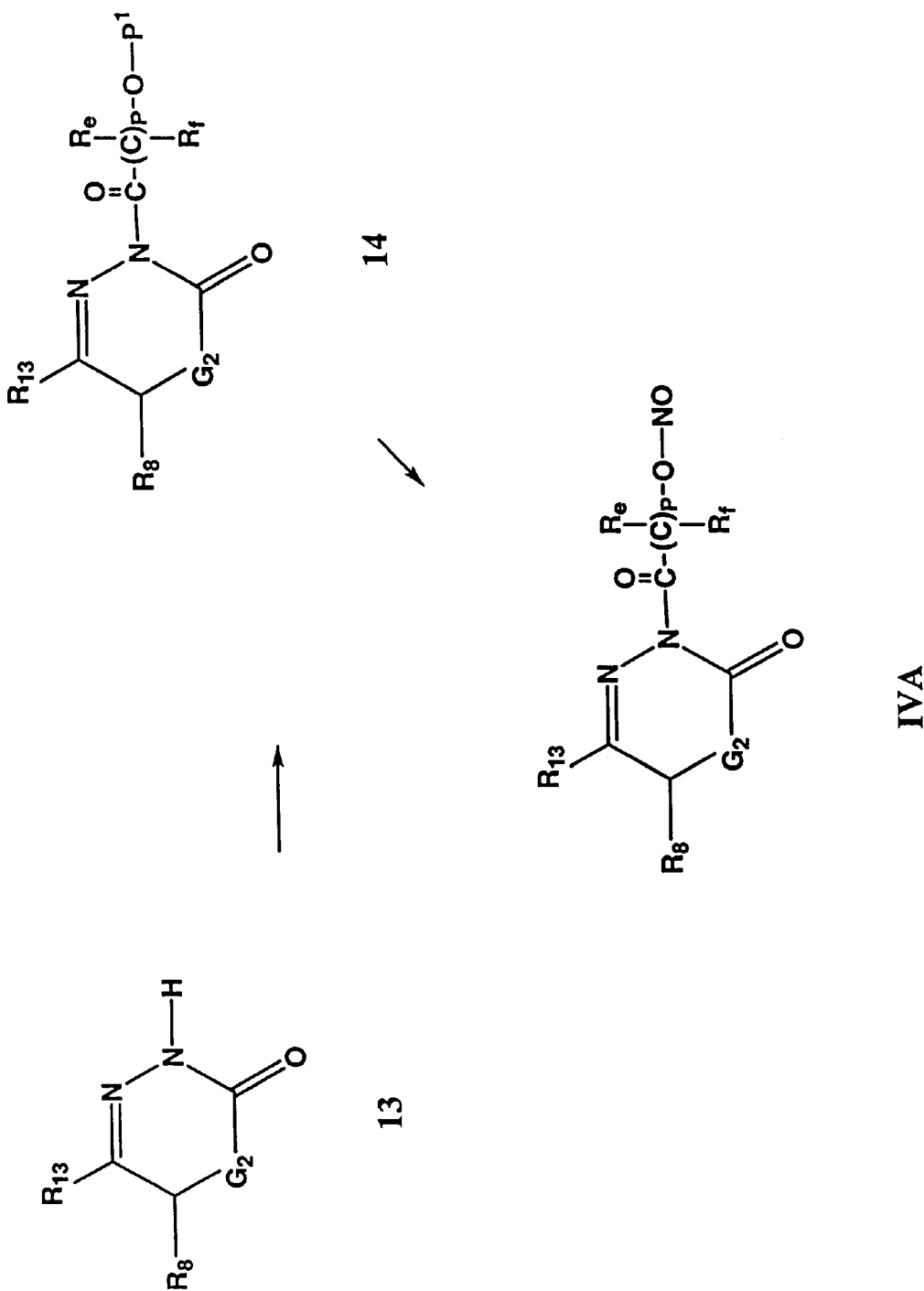
FIG. 10 shows a synthetic scheme for the preparation of nitrite containing pyrimidin-4-one derivatives.

Nitroso compounds of structure (IV), wherein $G_2$, $R_8$ $R_{13}$, $R_e$, $R_f$, and p are as defined herein, and a nitrite containing acyl hydrazide is representative of the $R_4$ group, as defined herein, may be prepared as shown in FIG. 10. The 3 (2-H)-pyridazinone or 2H-1,2,3,4-thiadiazine of structure 13 is converted to the 3 (2-acyl)-pyridazinone or 2-acyl-1,2,3,4-thiadiazine of structure 14, wherein p, $R_e$ and $R_f$ are as defined herein, by reaction with an appropriate protected alcohol containing activated acylating agent, wherein $P^1$ is as defined herein. Preferred methods for the formation of 3 (2-acyl)-pyridazinone or 2-acyl-1,2,3,4-thiadiazine are reacting the 3 (2H)-pyridazinone or 2H-1,2,3,4-thiadiazine with the preformed acid chloride or symmetrical anhydride of the protected alcohol containing acid or condensing the 3 (2-H)-pyridazinone or 2H-1,2,3,4-thiadiazine and protected alcohol containing acid in the presence of a dehydrating agent, such as DCC or EDAC.HCl with a catalyst, such as DMAP or HOBt. Preferred protecting groups for the alcohol moiety are silyl ethers, such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure IVA.

Figure 11:
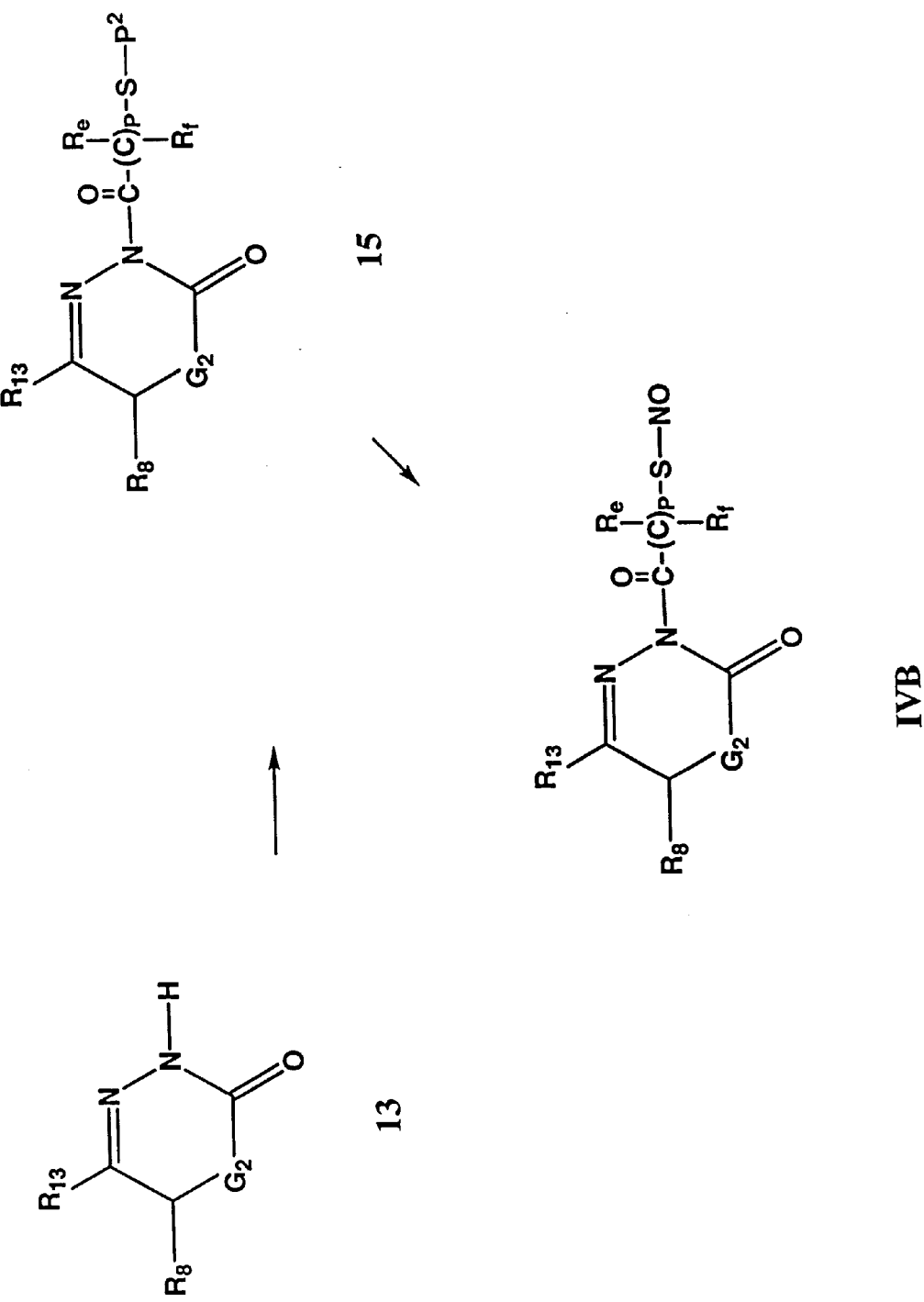
FIG. 11 shows a synthetic scheme for the preparation of nitrosothiol containing pyrimidin-4-one derivatives.

Nitroso compounds of structure (IV), wherein $G_2$, $R_8$, $R_{13}$, $R_e$, $R_f$, and p are as defined herein, and a nitrosothiol containing acyl hydrazide is representative of the $R_4$ group, as defined herein, may be prepared as shown in FIG. 11. The 3 (2-H)-pyridazinone or 2H-1,2,3,4-thiadiazine of structure 13 is converted to the 3 (2-acyl)-pyridazinone or 2-acyl-1,2,3,4-thiadiazine of structure 15, wherein p, $R_e$ and $R_f$ are as defined herein, by reaction with an appropriate protected thiol containing activated acylating agent, wherein $P^2$ is as defined herein. Preferred methods for the formation of 3 (2-acyl)-pyridazinones or 2-acyl-1,2,3,4-thiadiazines are reacting the 3 (2-H)-pyridazinone or 2H-1,2,3,4-thiadiazine with the preformed acid chloride or symmetrical anhydride of the protected thiol containing acid or condensing the 3 (2-H)-pyridazinone or 2H-1,2,3,4-thiadiazine and protected thiol containing acid in the presence of a dehydrating agent, such as DCC or EDAC.HCl with a catalyst, such as DMAP or HOBt. Preferred protecting groups for the thiol moiety are a thioester, such as thioacetate, or thiobenzoate, a disulfide, or a thioether, such as paramethoxybenzyl thioether, tetrahydropyranyl thioether or 2,4,6-trimethoxybenzyl thioether. Deprotection of the thiol moiety (zinc in dilute aqueous acid, triphenylphosphine in water and sodium borohydride are preferred methods for reducing disulfide groups while mercuric trifluoroacetate, silver nitrate, or strong acids, such as trifluoroacetic or hydrochloric acid, and heat are used to remove a paramethoxybenzyl thioether, a tetrahydropyranyl thioether, or a 2,4,6-trimethoxybenzyl thioether group) followed by reaction a suitable nitrosylating agent, such as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of structure IVB. Alternatively, treatment of the deprotected thiol derived from compound 15 with a stoichiometric quantity of sodium nitrite in an acidic aqueous or alcoholic solution affords the compound of structure IVB.

Figure 12:
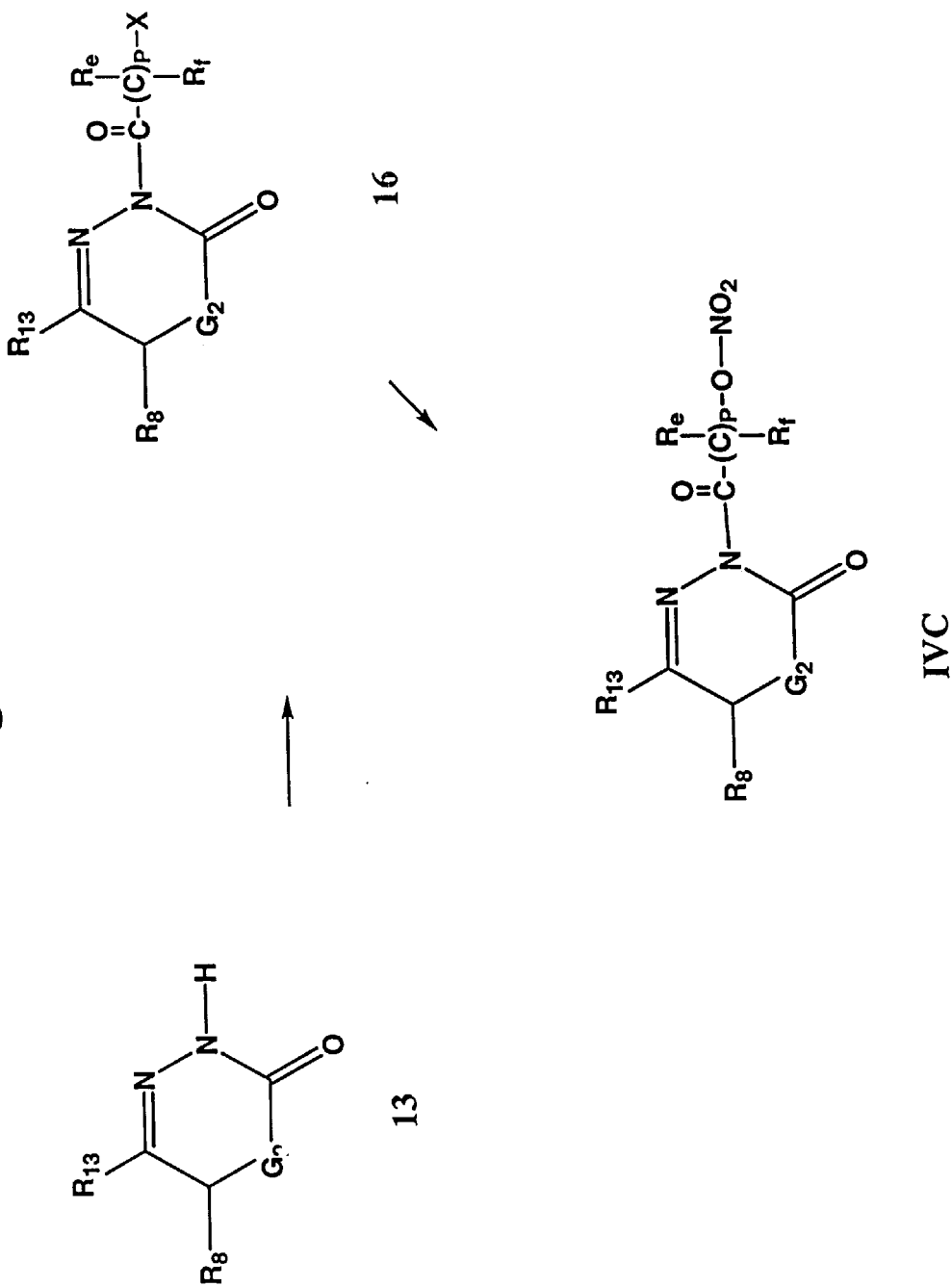
FIG. 12 shows a synthetic scheme for the preparation of nitrate containing pyrimidin-4-one derivatives.

Nitro compounds of structure (IV), wherein $G_2$, $R_8$, $R_{13}$, $R_e$, $R_f$, and p are as defined herein, and an nitrate containing acyl hydrazide is representative of the $R_4$ group, as defined herein, may be prepared as outlined in FIG. 12. The 3 (2-H)-pyridazinone or 2H-1,2,3,4-thiadiazine of structure 13 is converted to the 3 (2-acyl)-pyridazinone or 2-acyl-1,2,3,4-thiadiazine of structure 16, wherein p, $R_e$ and $R_f$ are as defined herein, and X is halogen. Preferred methods for the formation of 3 (2-acyl)-pyridazinones or 2-acyl-1,2,3,4-thiadiazines are reacting the 3 (2-H)-pyridazinone or 2H-1,2,3,4-thiadiazine with the preformed acid chloride or symmetrical anhydride of the halide containing acid or condensing the 3 (2-H)-pyridazinone or 2H-1,2,3,4-thiadiazine and halide containing acid in the presence of a dehydrating agent such as DCC or EDAC.HCl with a catalyst such as DMAP or HOBt. Preferred halides are bromide and iodide. Reaction of the 3 (2-acyl)-pyridazinone or 2-acyl-1,2,3,4-thiadiazine of structure 16 with a suitable nitrating agent such as silver nitrate in an inert solvent such as acetonitrile affords the compound of structure IVC.

Figure 13:
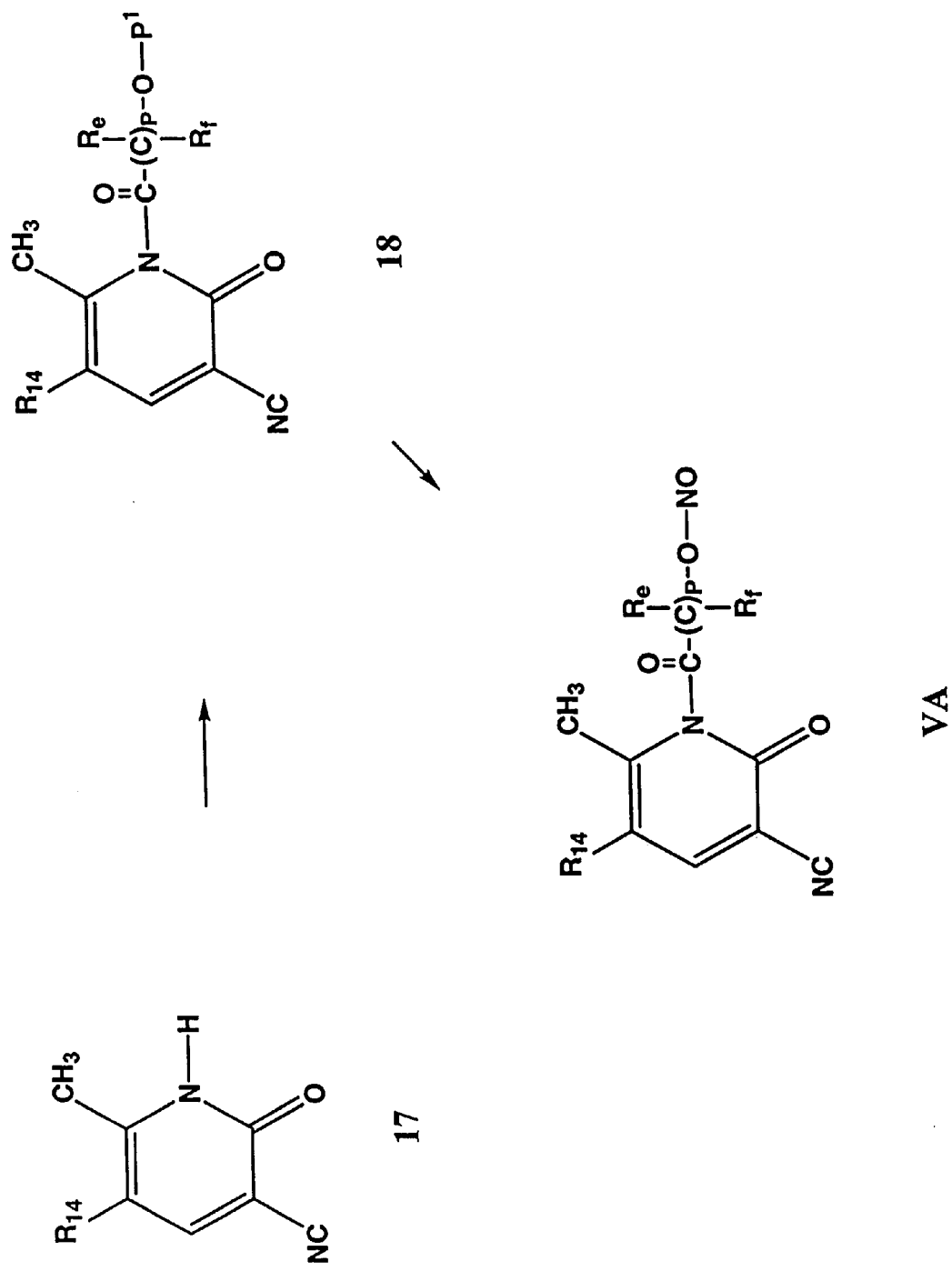
FIG. 13 shows a synthetic scheme for the preparation of nitrite containing 2-pyridone derivatives.

Nitroso compounds of structure (V), wherein $R_{14}$, $R_e$, $R_f$, and p are as defined herein, and an nitrite containing imide is representative of the $R_4$ group, as defined herein, may be prepared as outlined in FIG. 13. The amide group of structure 17 is converted to the imide of structure 18, wherein p, $R_e$, and $R_f$ are as defined herein, by reaction with an appropriate protected alcohol containing activated acylating agent, wherein $P^1$ is as defined herein. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of structure VA.

Figure 14:
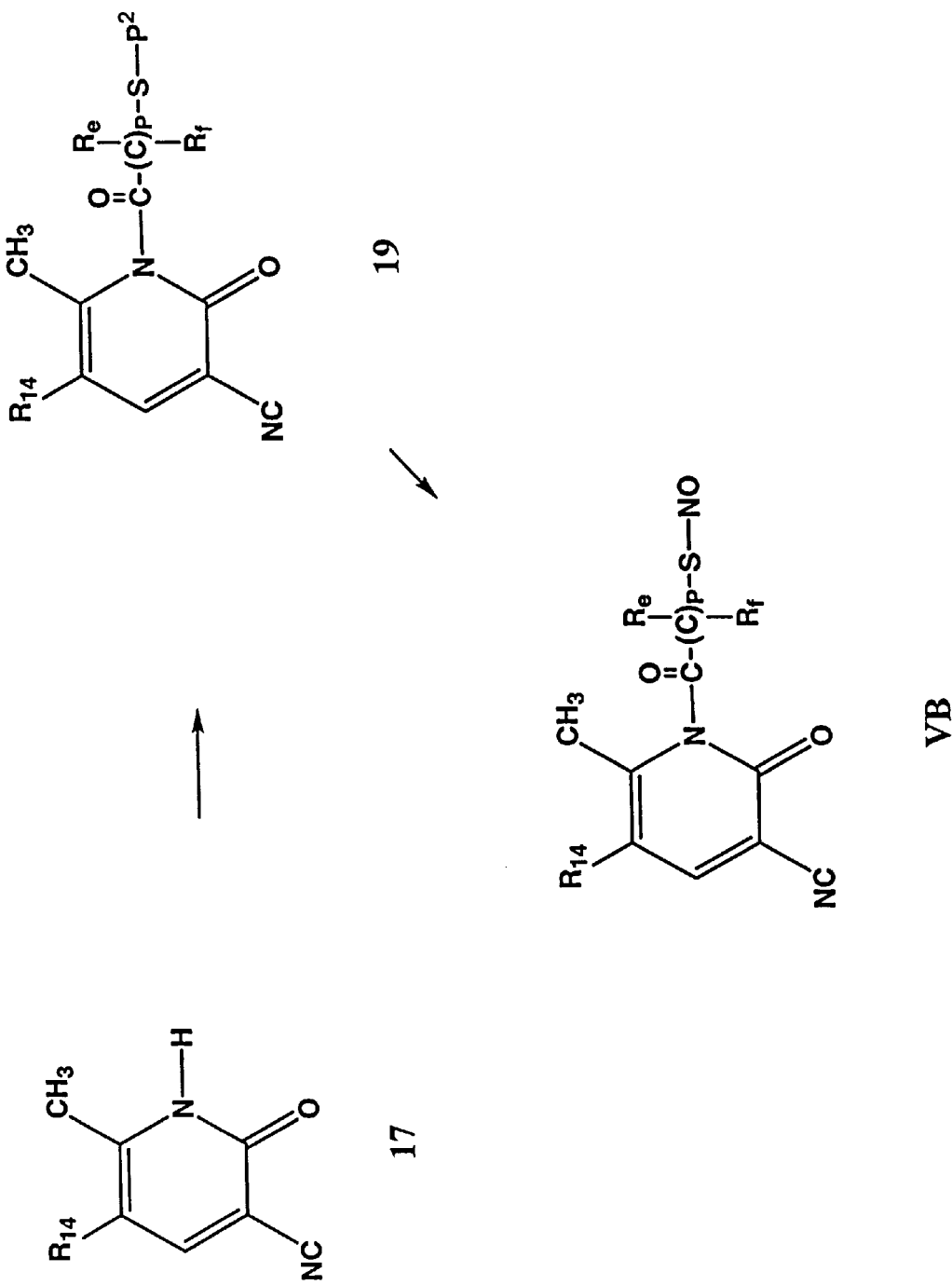
FIG. 14 shows a synthetic scheme for the preparation of nitrosothiol containing 2-pyridone derivatives.

Nitroso compounds of structure (V), wherein $R_{14}$, $R_e$, $R_f$, and p are as defined herein, and a nitrosothiol containing imide is representative of the $R_4$ group, as defined herein, may be prepared as outlined in FIG. 14. The amide group of structure 17 is converted to the imide of structure 19, wherein p, $R_e$ and $R_f$ are as defined herein, by reaction with an appropriate protected thiol containing activated acylating agent, wherein $P^2$ is as defined herein. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure VB. Alternatively, treatment of the deprotected thiol derived from compound 19 with a stoichiometric quantity of sodium nitrite in an acidic aqueous or alcoholic solution affords the compound of structure VB.

Figure 15:
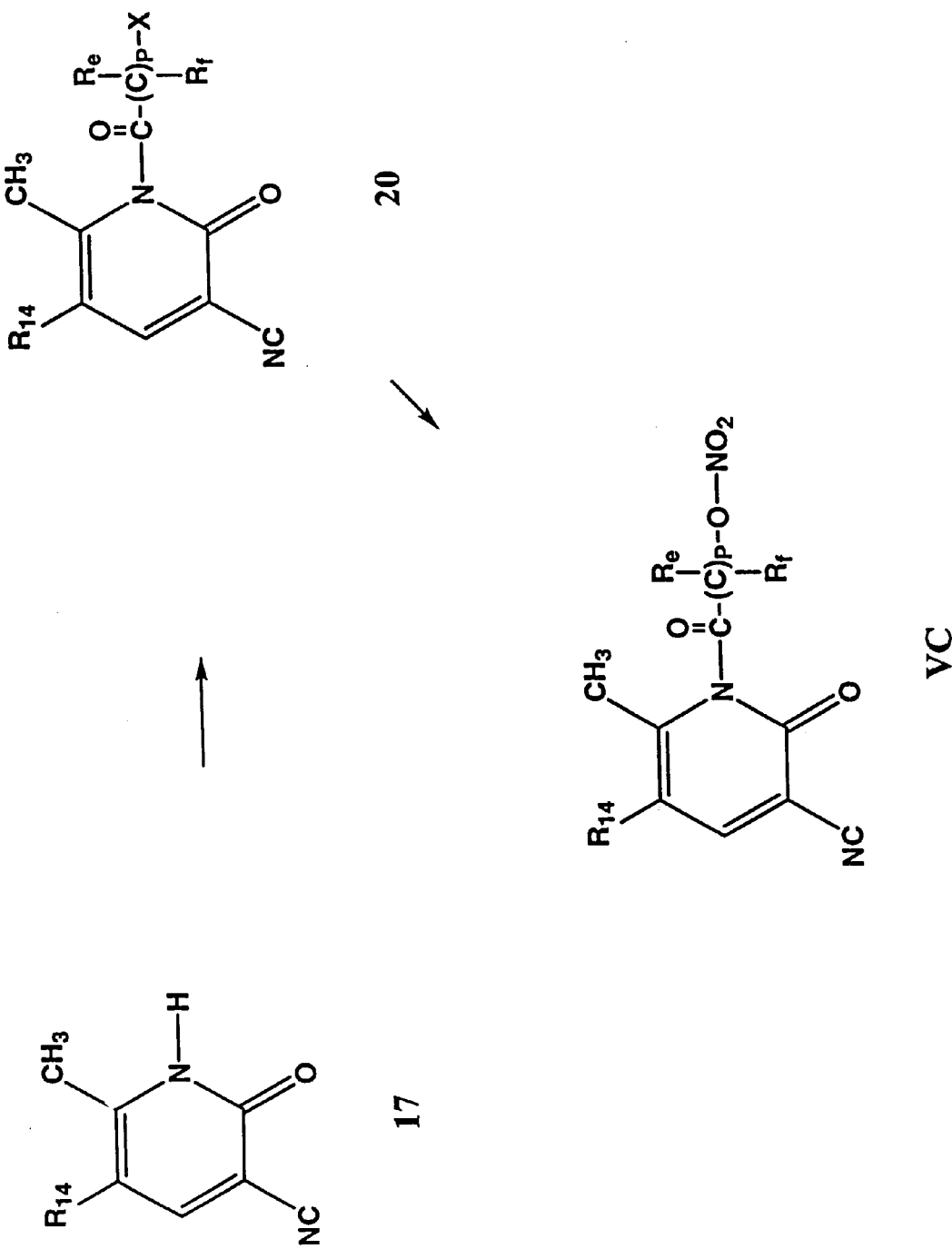
FIG. 15 shows a synthetic scheme for the preparation of nitrate containing 2-pyridone derivatives.

Nitro compounds of structure (V), wherein $R_{14}$, $R_e$, $R_f$, and p are as defined herein, and a nitrate containing imide is representative of the $R_4$ group, as defined herein, may be prepared as outlined in FIG. 15. The amide group of the formula 17 is converted to the imide of the formula 20, wherein p, $R_e$ and $R_f$ are as defined herein, and X is a halogen by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 20 with a suitable nitrating agent such as silver nitrate in an inert solvent such as acetonitrile affords the compound of structure VC.

Figure 16:
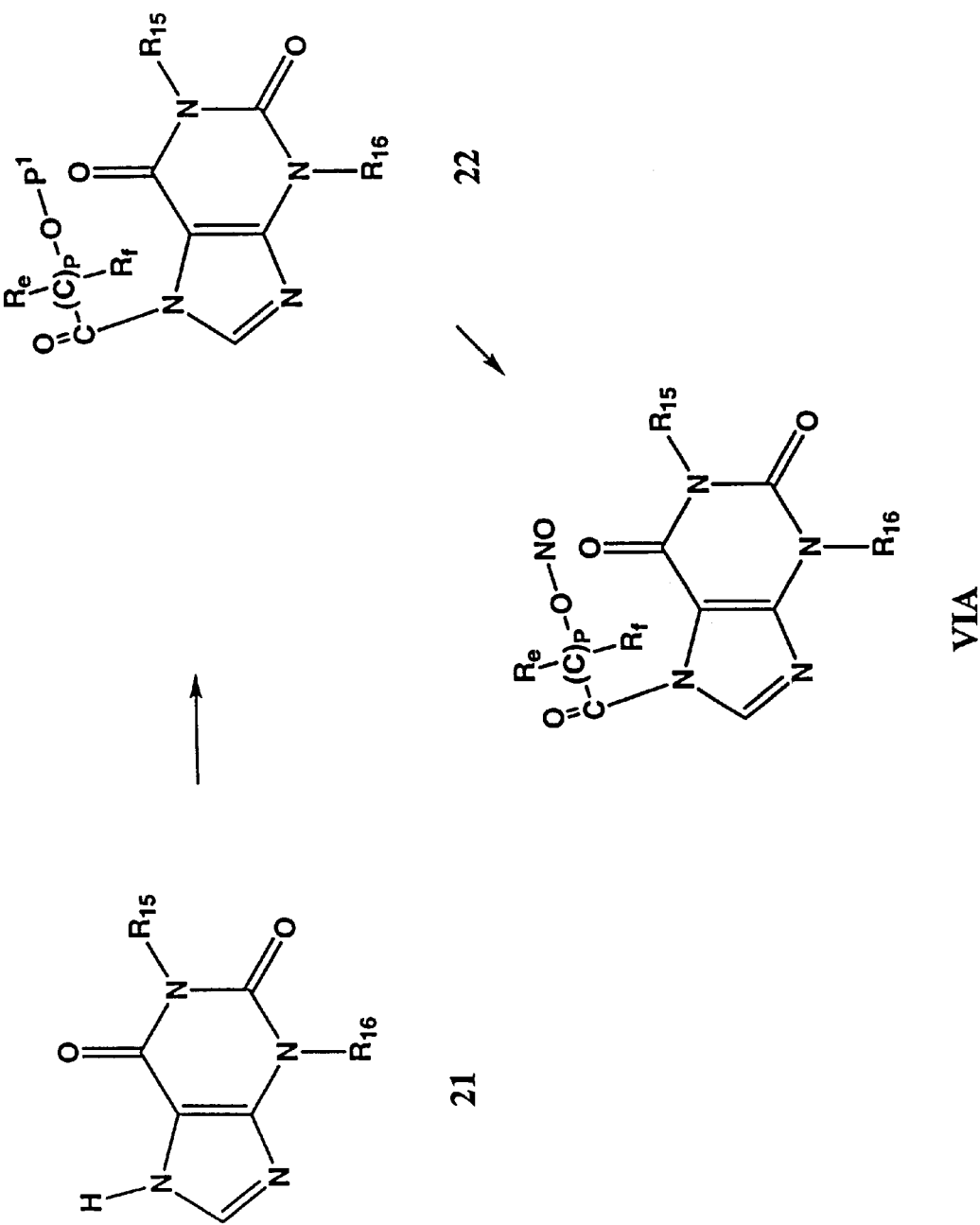
FIG. 16 shows a synthetic scheme for the preparation of nitrite containing purine-2,6-dione derivatives.

Nitroso compounds of structure (VI), wherein $R_{15}$, $R_{16}$, $R_e$, $R_f$ and p are as defined herein, and a nitrite containing acyl imidazolide is representative of the $R_{17}$ group, as defined herein, may be prepared as outlined in FIG. 16. The 1H-purine-2,6-dione of structure 21 is converted to the acylated derivative of the formula 22, wherein p, $R_e$ and $R_f$ are as defined herein, by reaction with an appropriate protected alcohol containing activated acylating agent, wherein $P^1$ is as defined herein. Preferred methods for the formation of acylated 1H-purine-2,6-diones are reacting the 1H-purine-2,6-dione with the preformed acid chloride or symmetrical anhydride of the protected alcohol containing acid or condensing the 1H-purine-2,6-dione and protected alcohol containing acid in the presence of a dehydrating agent such as DCC or EDAC.HCl with a catalyst such as DMAP or HOBt. Preferred protecting groups for the alcohol moiety are silyl ethers such as a tert-butyldimethylsilyl ether or a tert-butyldimethyl-silyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of structure VIA.

Figure 17:
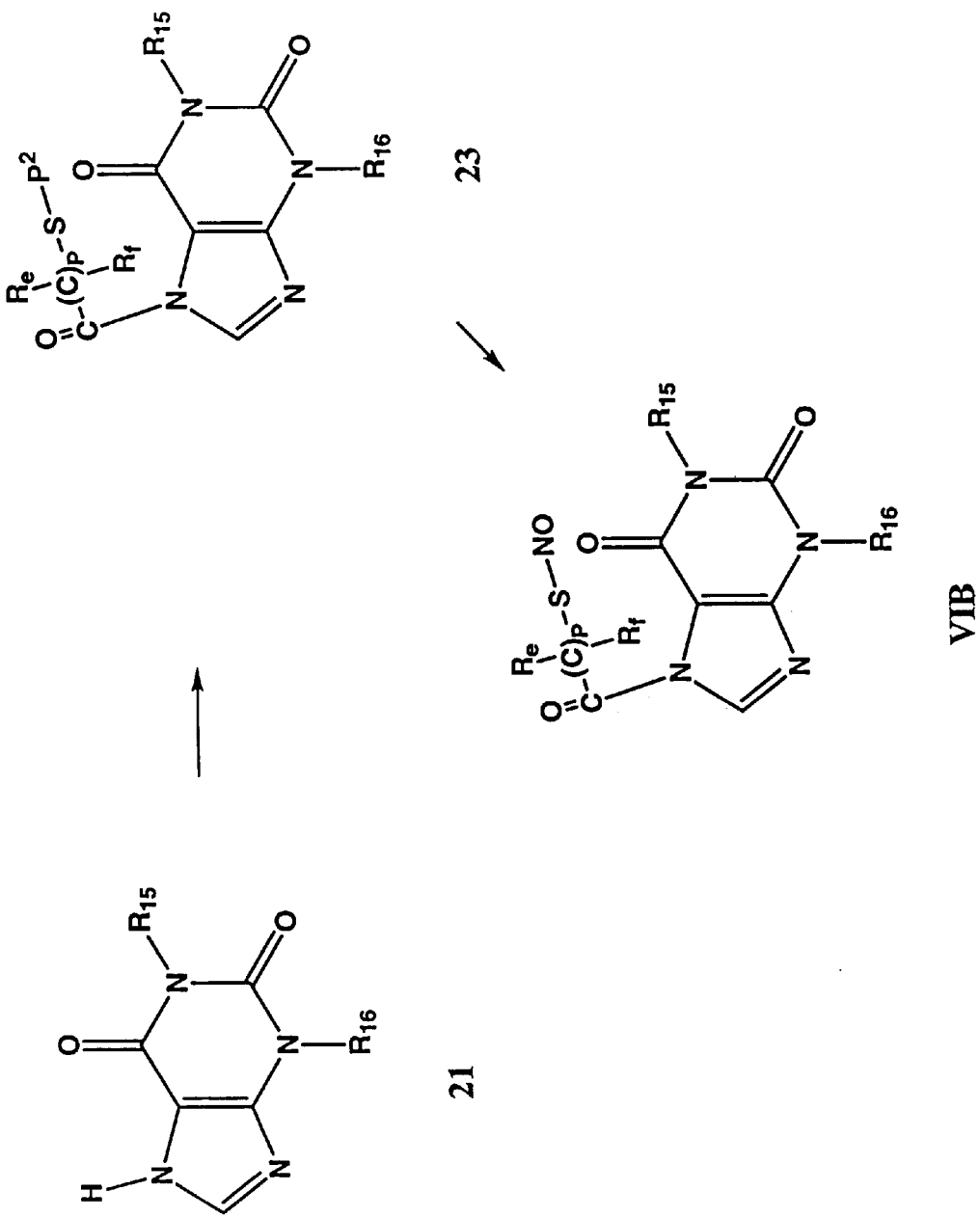
FIG. 17 shows a synthetic scheme for the preparation of nitrosothiol containing purine-2,6-dione derivatives.

Nitroso compounds of structure (VI), wherein $R_{15}$, $R_{16}$, $R_e$, $R_f$, and p are as defined herein, and a nitrosothiol containing acyl imidazolide is representative of the $R_{17}$ group, as defined herein, may be prepared as outlined in FIG. 17. The 1H-purine-2,6-dione of structure 21 is converted to the acylated derivative of the formula 23, wherein p, $R_e$ and $R_f$ are as defined herein, by reaction with an appropriate protected thiol containing activated acylating agent, wherein $P^2$ is as defined herein. Preferred methods for the formation of acylated 1H-purine-2,6-diones are reacting the 1H-purine-2,6-dione with the preformed acid chloride or symmetrical anhydride of the protected thiol containing acid or condensing the 1H-purine-2,6-dione and protected thiol containing acid in the presence of a dehydrating agent such as DCC or EDAC.HCl with a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure VIB. Alternatively, treatment of the deprotected thiol derived from compound 23 with a stoichiometric quantity of sodium nitrite in an acidic aqueous or alcoholic solution affords the compound of structure VIB.

Figure 18:
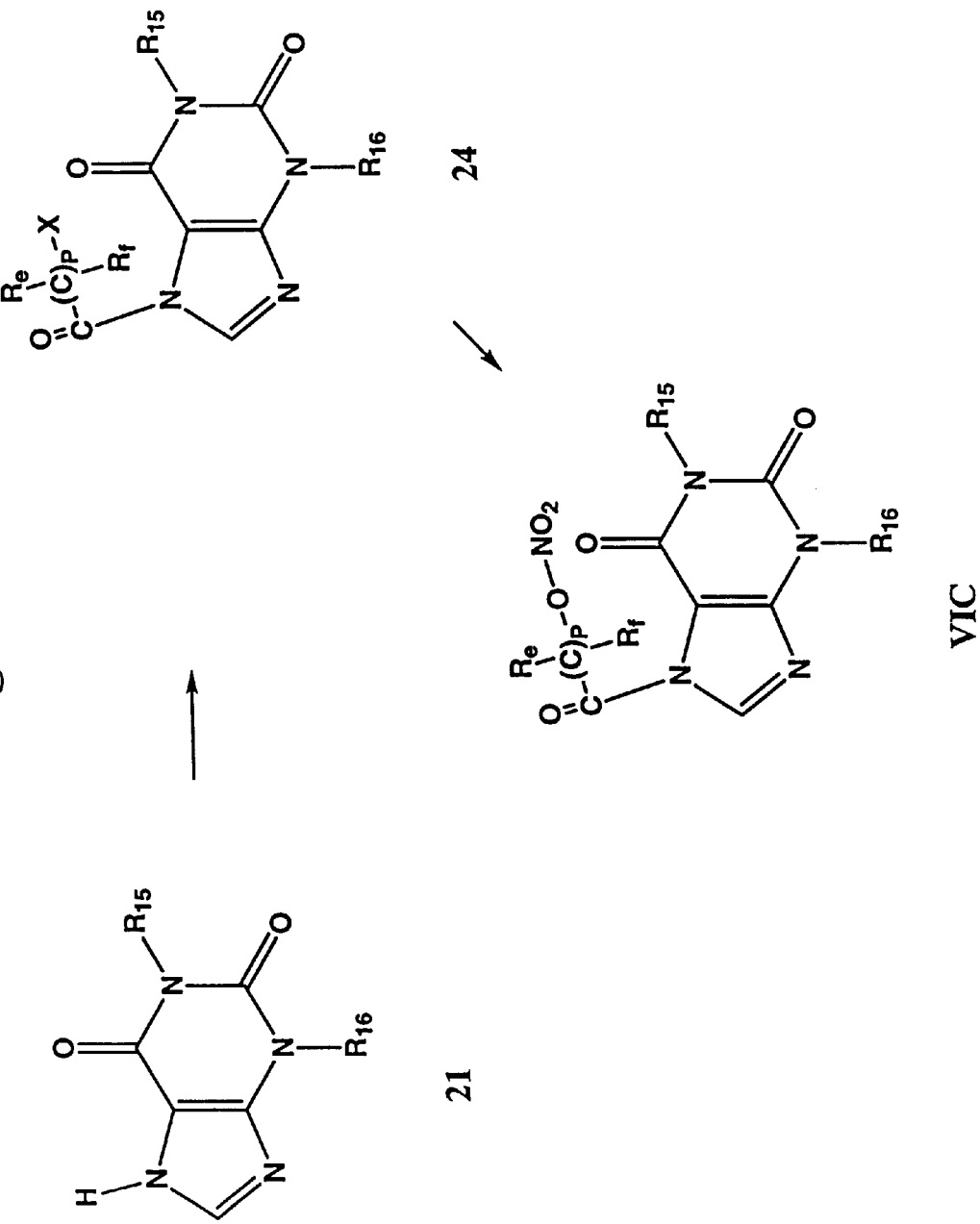
FIG. 18 shows a synthetic scheme for the preparation of nitrate containing purine-2,6-dione derivatives.

Nitro compounds of structure (VI), wherein $R_{15}$, $R_{16}$, $R_e$, $R_f$, and p are as defined herein, and an nitrate containing acylated 1H-purine-2,6-dione is representative of the $R_{17}$ group, as defined herein, may be prepared as outlined in FIG. 18. The 1H-purine-2,6- dione of the formula 21 is converted to the acylated derivative of the formula 24, wherein p, $R_e$ and $R_f$ are as defined herein, and X is a halogen, by reaction with an appropriate halide containing activated acylating agent. Preferred methods for the formation of acylated 1H-purine-2,6-diones are reacting the 1H-purine-2,6-dione with the preformed acid chloride or symmetrical anhydride of the halide containing acid or condensing the 1H-purine-2,6-dione and halide containing acid in the presence of a dehydrating agent such as DCC or EDAC.HCl with a catalyst such as DMAP or HOBt. Preferred halides are bromide and iodide. Reaction of the acylated 1H-purine-2,6-dione of the formula 24 with a suitable nitrating agent such as silver nitrate in an inert solvent such as acetonitrile affords the compound of structure VIC.

Figure 19:
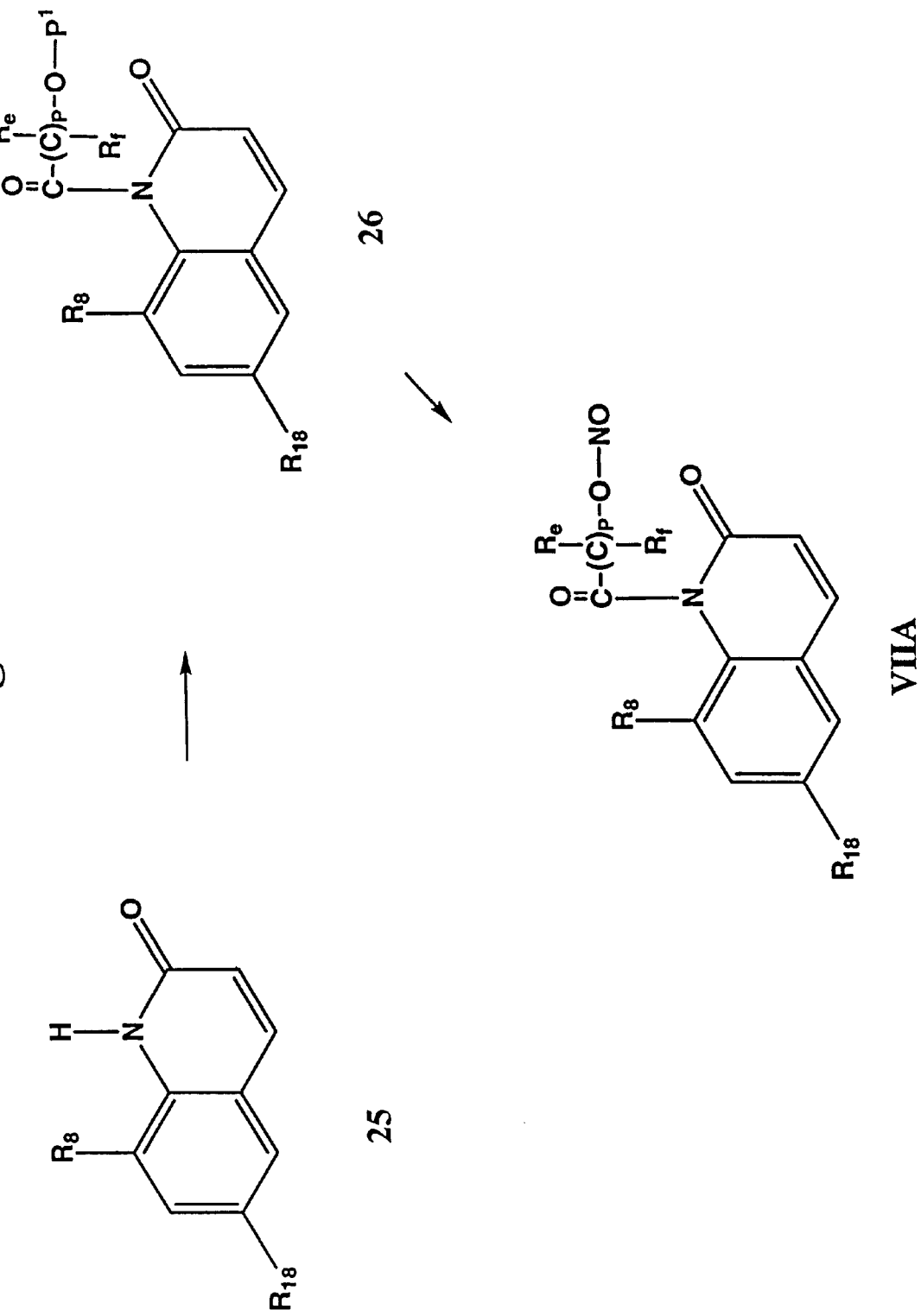
FIG. 19 shows a synthetic scheme for the preparation of nitrite containing quinoline derivatives.

Nitroso compounds of structure (VII), wherein $R_8$, $R_{18}$, $R_e$, $R_f$, and p are as defined herein, and a nitrite containing imide is representative of the $R_4$ group, as defined herein, may be prepared as outlined in FIG. 19. The amide nitrogen of structure 25 is converted to the imide of structure 26, wherein p, $R_e$ and $R_f$ are as defined herein, by reaction with an appropriate protected alcohol containing activated acylating agent, wherein $P^1$ is as defined herein. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst such as sulfuric acid. Preferred protecting groups for the alcohol moiety are silyl ethers such as a tert-butyldimethylsilyl ether or a tertbutyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of structure VIIA.

Figure 20:
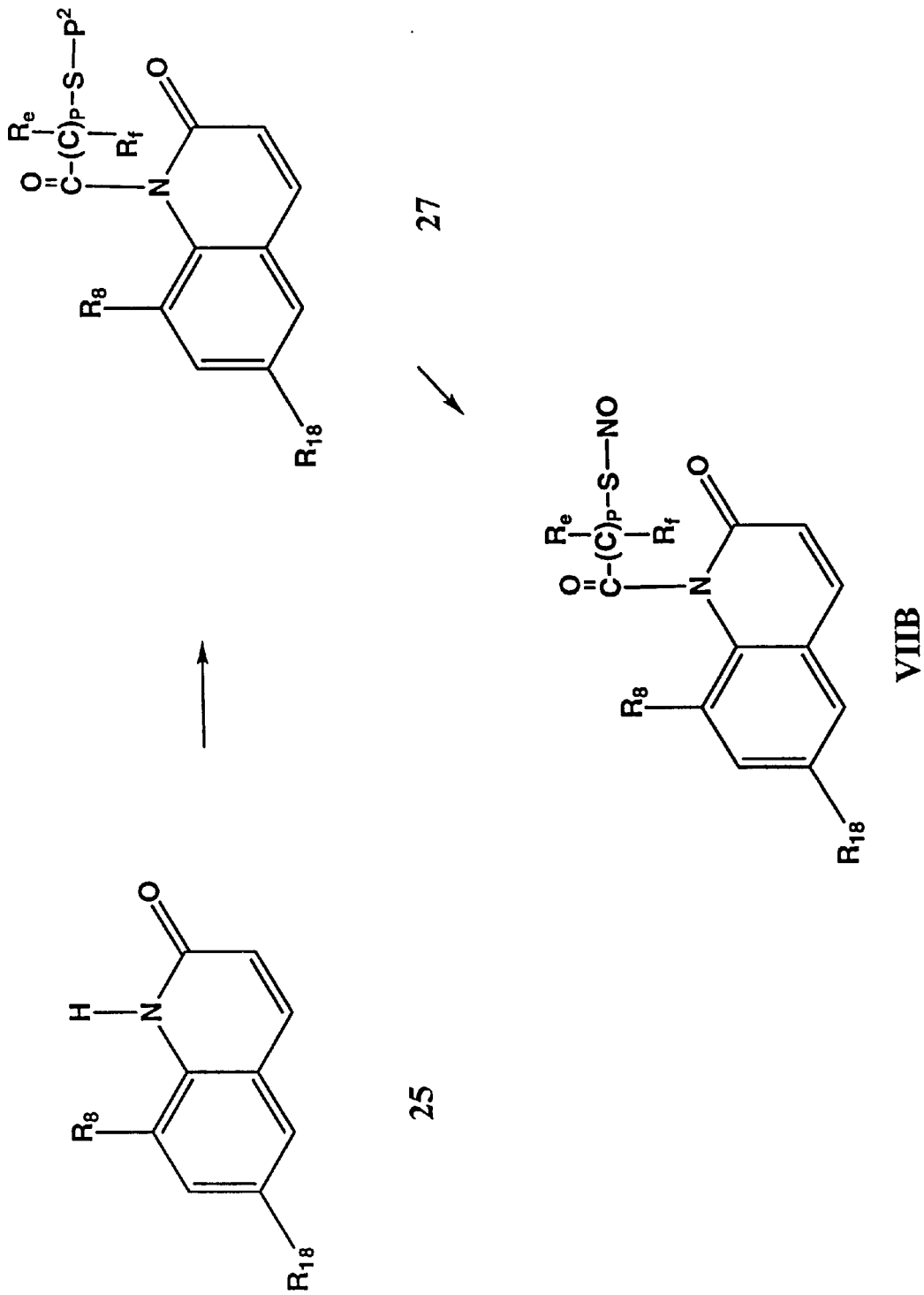
FIG. 20 shows a synthetic scheme for the preparation of nitrosothiol containing quinoline derivatives.

Nitroso compounds of structure (VII), wherein $R_8$, $R_{18}$, $R_e$, $R_f$, and p are as defined herein, and a nitrosothiol containing imide is representative of the $R_4$ group, as defined herein, may be prepared as outlined in FIG. 20. The amide nitrogen of structure 25 is converted to the imide of structure 27, wherein p, $R_e$ and $R_f$ are as defined herein, by reaction with an appropriate protected thiol containing activated acylating agent, wherein $P^2$ is as defined herein. Preferred methods for the formation of imides are reacting the amide with the preformed acid chloride of the protected thiol containing acid in the presence of pyridine at low temperature or condensing the amide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure VIIB. Alternatively, treatment of the deprotected thiol derived from compound 27 with a stoichiometric quantity of sodium nitrite in an acidic aqueous or alcoholic solution affords the compound of structure VIIB.

Figure 21:
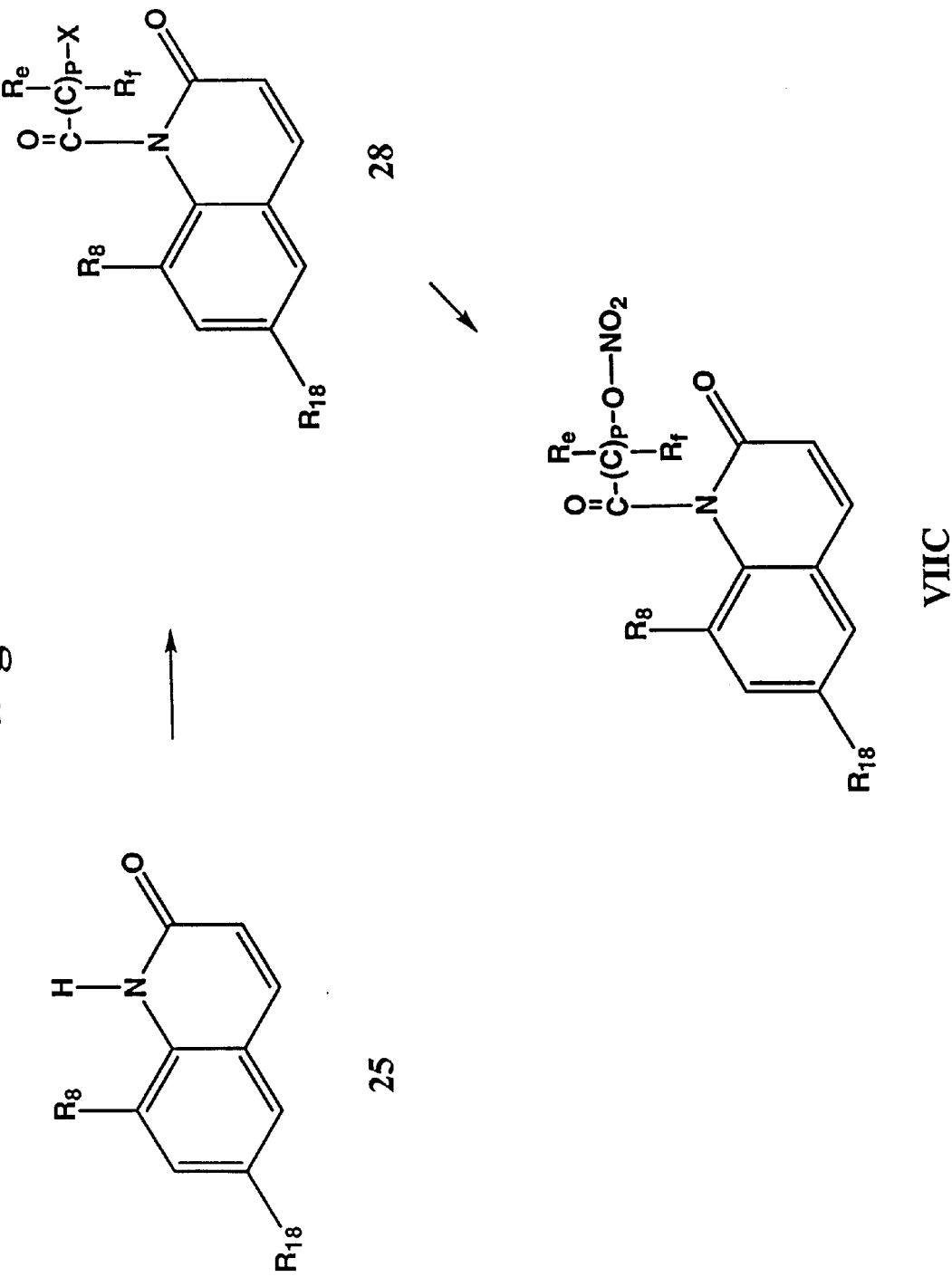
FIG. 21 shows a synthetic scheme for the preparation of nitrate containing quinoline derivatives.

Nitro compounds of structure (VII), wherein $R_8$, $R_{18}$, $R_e$, $R_f$, and p are as defined herein, and a nitrate containing imide is representative of the $R_4$ group, as defined herein, may be prepared as outlined in FIG. 21. The amide group of the formula 25 is converted to the imide of the formula 28, wherein p, $R_e$ and $R_f$ are as defined herein, and X is a halogen, by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 28 with a suitable nitrating agent such as silver nitrate in an inert solvent such as acetonitrile affords the compound of structure VIIC.

Figure 22:
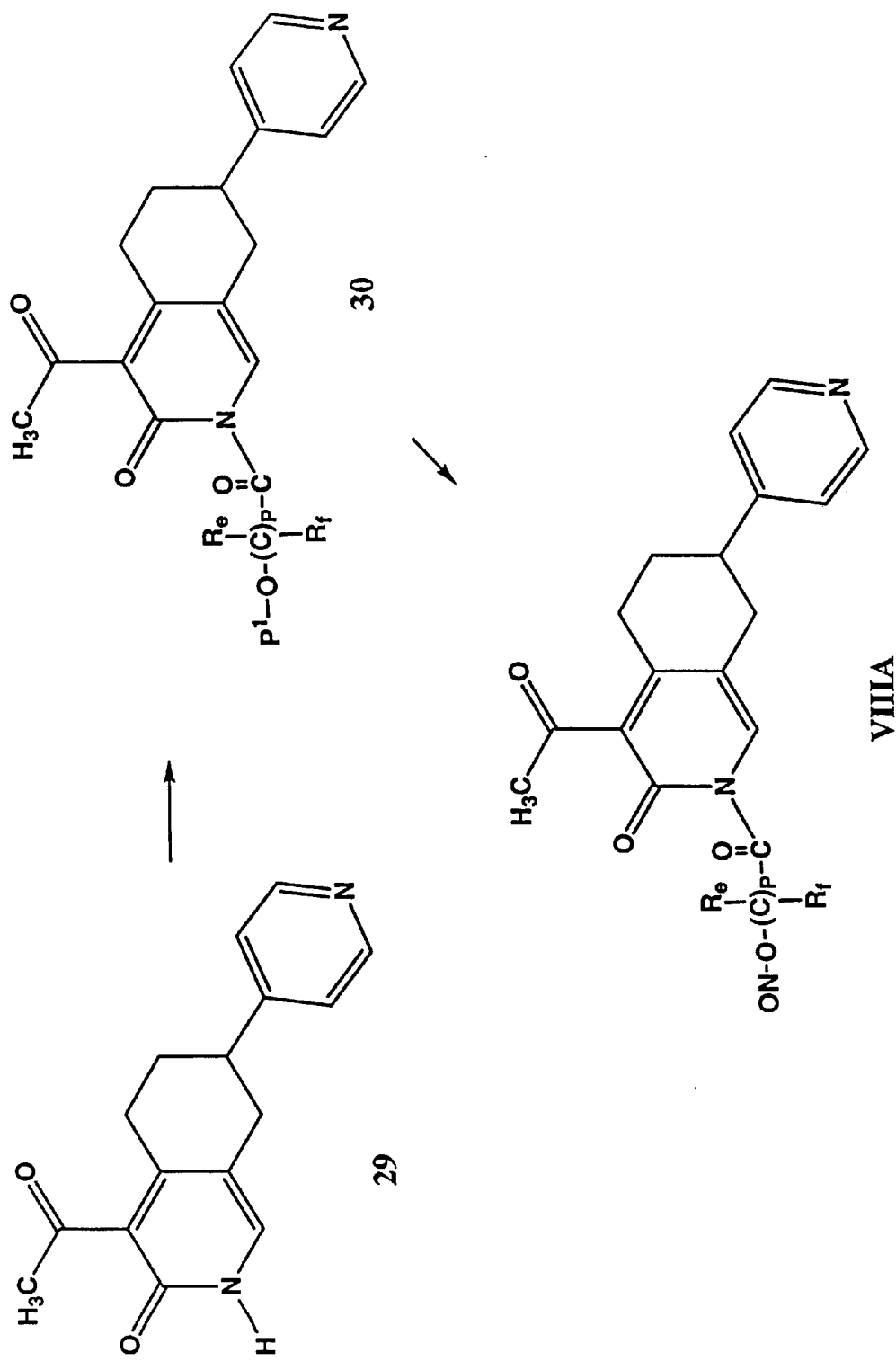
FIG. 22 shows a synthetic scheme for the preparation of nitrite containing substituted pyridine derivatives.

Nitroso compounds of structure (VIII), wherein $R_e$ $R_f$, and p are as defined herein, and a nitrite containing imide is representative of the $R_{19}$ group, as defined herein, may be prepared as outlined in FIG. 22. The amide nitrogen of structure 29 is converted to the imide of structure 30, wherein p, $R_e$ and $R_f$ are as defined herein, by reaction with an appropriate protected alcohol containing activated acylating agent, wherein $P^1$ is as defined herein. Preferred methods for the formation of imides are reacting the amide with the preformed acid chloride of the protected alcohol containing acid in the presence of pyridine at low temperature or condensing the amide and protected alcohol containing symmetrical anhydride in the presence of a catalyst, such as sulfuric acid. Preferred protecting groups for the alcohol moiety are silyl ethers such as a tert-butyldimethylsilyl ether or a tert-butyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile, with or without an amine base, such as pyridine or triethylamine, affords the compound of structure VIIIA.

Figure 23:
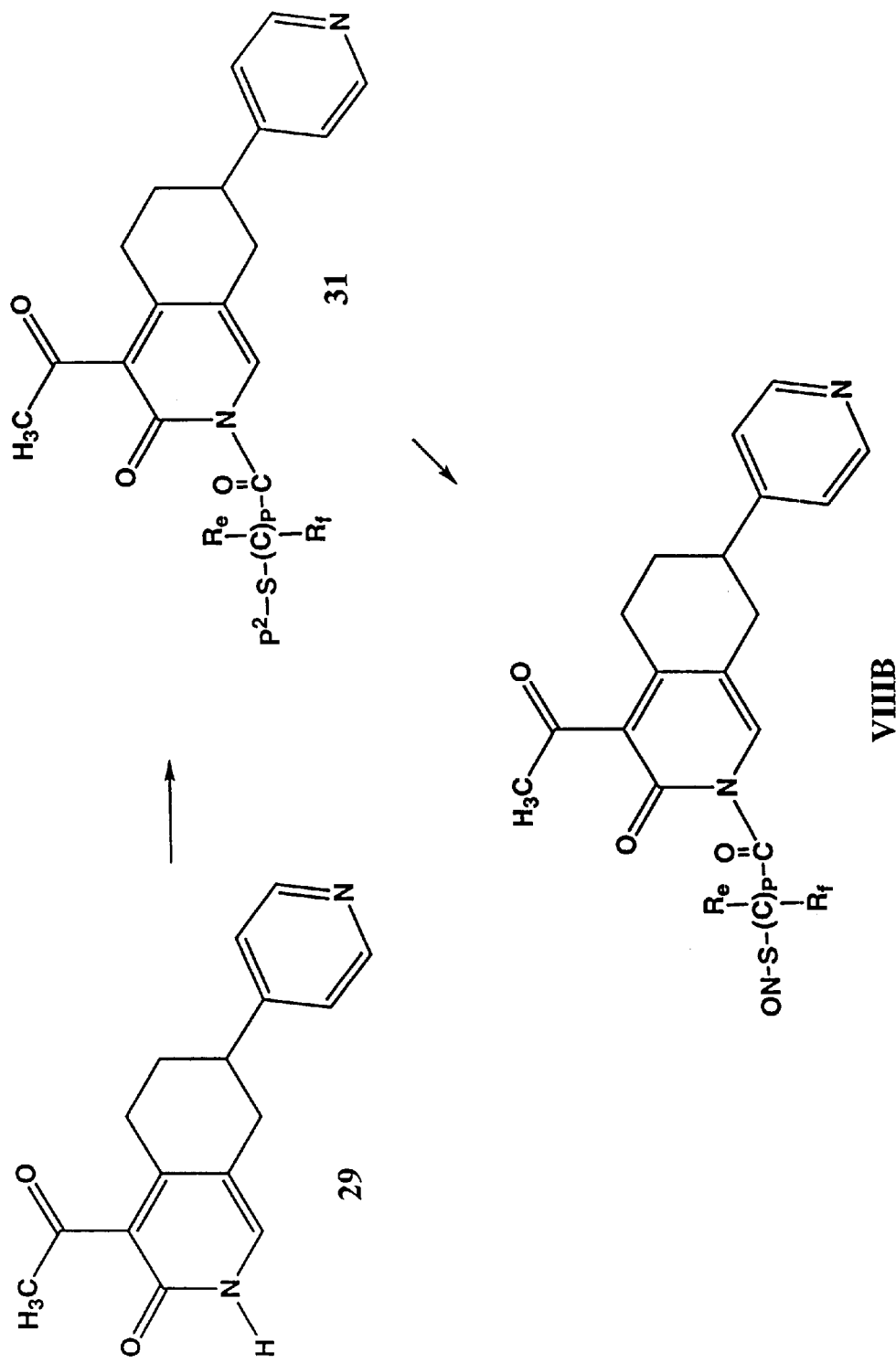
FIG. 23 shows a synthetic scheme for the preparation of nitrosothiol containing substituted pyridine derivatives.

Nitroso compounds of structure (VIII), wherein $R_e$, $R_f$, and p are as defined herein, and a nitrosothiol containing imide is representative of the $R_{19}$ group, as defined herein, may be prepared as outlined in FIG. 23. The amide nitrogen of structure 29 is converted to the imide of structure 31, wherein p, $R_e$ and $R_f$ are as defined herein, by reaction with an appropriate protected thiol containing activated acylating agent, wherein $P^2$ is as defined herein. Preferred methods for the formation of imides are reacting the amide with the preformed acid chloride of the protected thiol containing acid in the presence of pyridine at low temperature or condensing the amide and protected alcohol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure VIIB. Alternatively, treatment of the deprotected thiol derived from compound 31 with a stoichiometric quantity of sodium nitrite in an acidic aqueous or alcoholic solution affords the compound of structure VIIIB.

Figure 24:
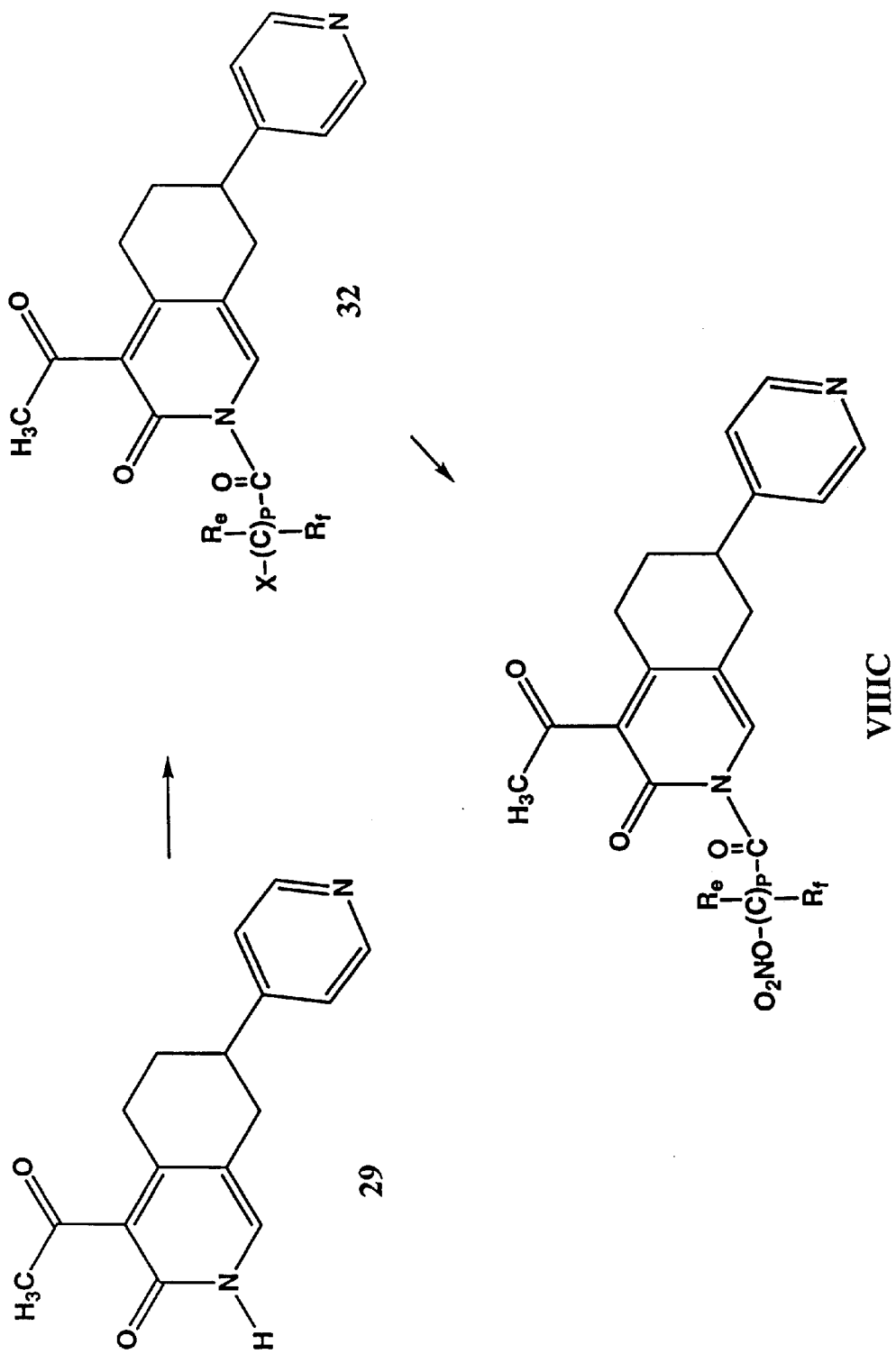
FIG. 24 shows a synthetic scheme for the preparation of nitrate containing substituted pyridine derivatives.

Nitro compounds of structure (VIII), wherein $R_e$ $R_f$, and p are as defined herein, and a nitrate containing imide is representative of the $R_{19}$ group, as defined herein, may be prepared as outlined in FIG. 24. The amide group of the formula 29 is converted to the imide of the formula 32, wherein p, $R_e$ and $R_f$ are as defined herein, and X is a halogen, by reaction with an appropriate halide containing activated acylating agent. Preferred methods for the formation of imides are reacting the amide with the preformed acid chloride of the halide containing acid in the presence of pyridine at low temperature or condensing the amide and halide containing symmetrical anhydride in the presence of a catalyst such as sulfuric acid. Preferred halides are bromide and iodide. Reaction of the imide of the formula 32 with a suitable nitrating agent such as silver nitrate in an inert solvent such as acetonitrile affords the compound of structure VIIIC.

Figure 25:
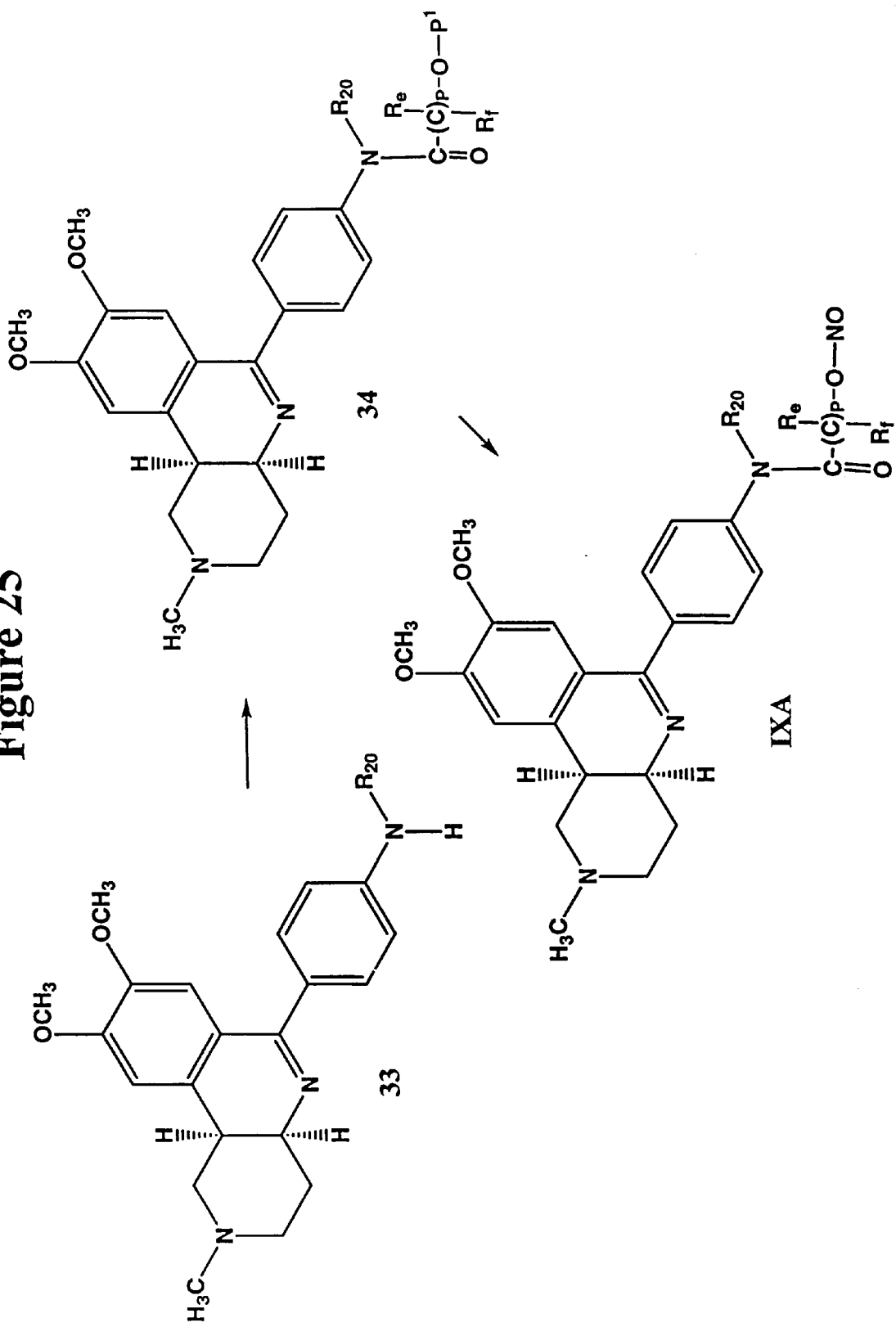
FIG. 25 shows a synthetic scheme for the preparation of nitrite containing benzo [c][1,6] naphthyridine derivatives.

Nitroso compounds of structure (IX), wherein $R_{20}$, $R_e$, $R_f$, and p are as defined herein, and an nitrite containing acylated amide or sulfonamide is representative of the $R_4$ group, as defined herein, may be prepared as outlined in FIG. 25. The amide or sulfonamide nitrogen of structure 33 is converted to the N-acylated derivative of structure 34, wherein p, $R_e$ and $R_f$ are as defined herein, by reaction with an appropriate protected alcohol containing activated acylating agent, wherein $P^1$ is as defined herein. Preferred methods for the formation of acylated amides or sulfonamides are reacting the amide or sulfonamide with the preformed acid chloride of the protected alcohol containing acid in the presence of pyridine at low temperature or condensing the amide or sulfonamide and protected alcohol containing symmetrical anhydride in the presence of a catalyst such as sulfuric acid. Preferred protecting groups for the alcohol moiety are silyl ethers such as a tert-butyldimethylsilyl ether or a tertbutyldiphenylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of structure IXA.

Figure 26:
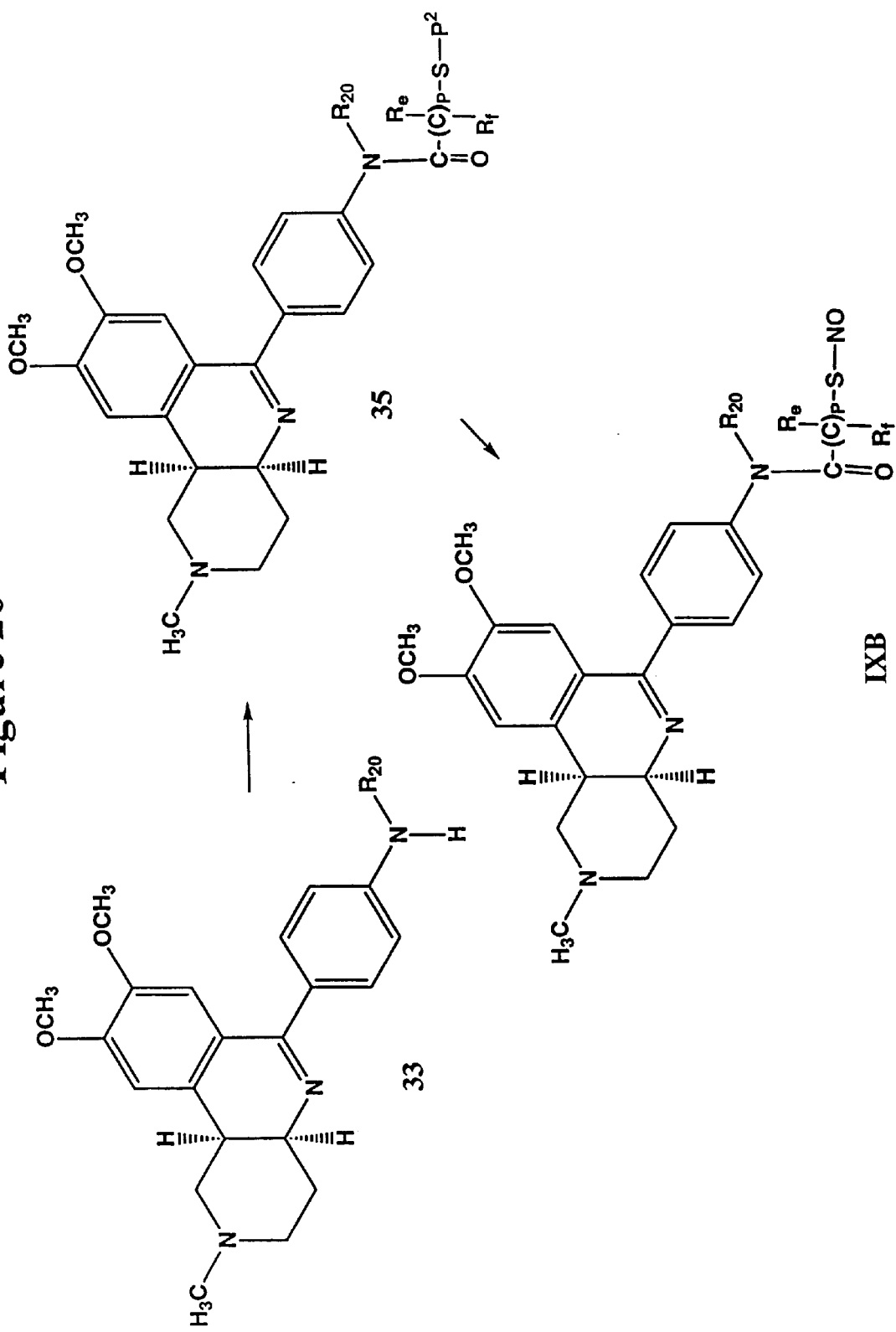
FIG. 26 shows a synthetic scheme for the preparation of nitrosothiol containing benzo[c][1,6] naphthyridine derivatives.

Nitroso compounds of structure (IX), wherein $R_{20}$, $R_e$, $R_f$, and p are as defined herein, and an nitrosothiol containing acylated amide or sulfonamide is representative of the $R_4$ group, as defined herein, may be prepared as outlined in FIG. 26. The amide or sulfonamide nitrogen of structure 33 is converted to the N-acylated derivative of structure 35, wherein p, $R_e$ and $R_f$ are as defined herein, by reaction with an appropriate protected thiol containing activated acylating agent, wherein $P^2$ is as defined herein. Preferred methods for the formation of acylated amides or sulfonamides are reacting the amide or sulfonamide with the preformed acid chloride of the protected thiol containing acid in the presence of pyridine at low temperature or condensing the amide or sulfonamide and protected thiol containing symmetrical anhydride in the presence of a catalyst such as sulfuric acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure IXB. Alternatively, treatment of the deprotected thiol derived from compound 35 with a stoichiometric quantity of sodium nitrite in an acidic aqueous or alcoholic solution affords the compound of structure IXB.

Figure 27:
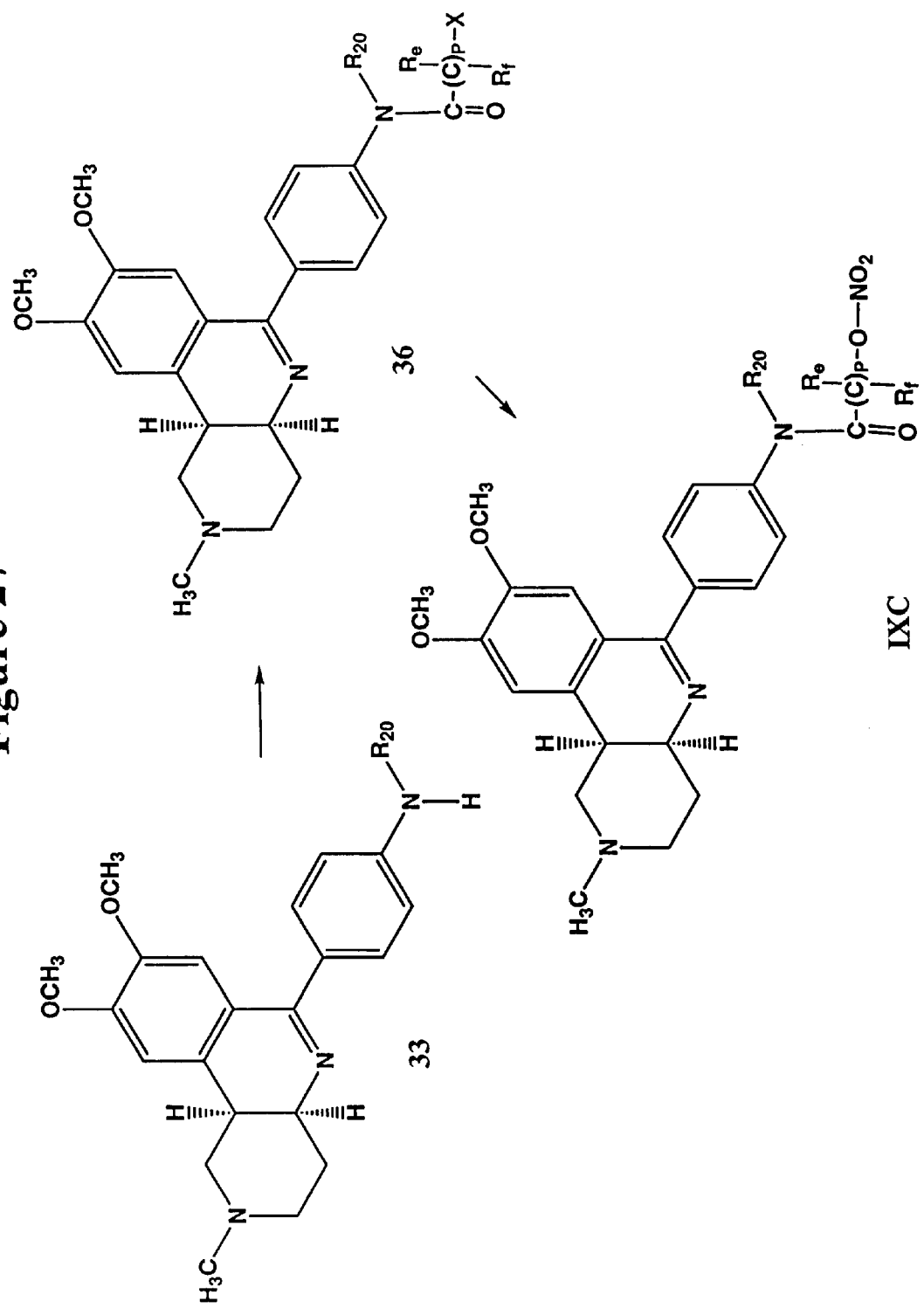
FIG. 27 shows a synthetic scheme for the preparation of nitrate containing benzo[c][1,6] naphthyridine derivatives.

Nitro compounds of structure (IX), wherein $R_{20}$, $R_e$ $R_f$, and p are as defined herein, and a nitrate containing acylated amide or sulfonamide is representative of the $R_4$ group, as defined herein, may be prepared as outlined in FIG. 27. The amide or sulfonamide group of the formula 33 is converted to the N-acylated derivative of the formula 36, wherein p, $R_e$ and $R_f$ are as defined herein, and X is a halogen, by reaction with an appropriate halide containing activated acylating agent. Preferred methods for the formation of acylated amides or sulfonamides are reacting the amide or sulfonamide with the preformed acid chloride of the halide containing acid in the presence of pyridine at low temperature or condensing the amide or sulfonamide and halide containing symmetrical anhydride in the presence of a catalyst such as sulfuric acid. Preferred halides are bromide and iodide. Reaction of the imide or sulfonamide of the formula 36 with a suitable nitrating agent such as silver nitrate in an inert solvent such as acetonitrile affords the compound of structure IXC.

Figure 28:
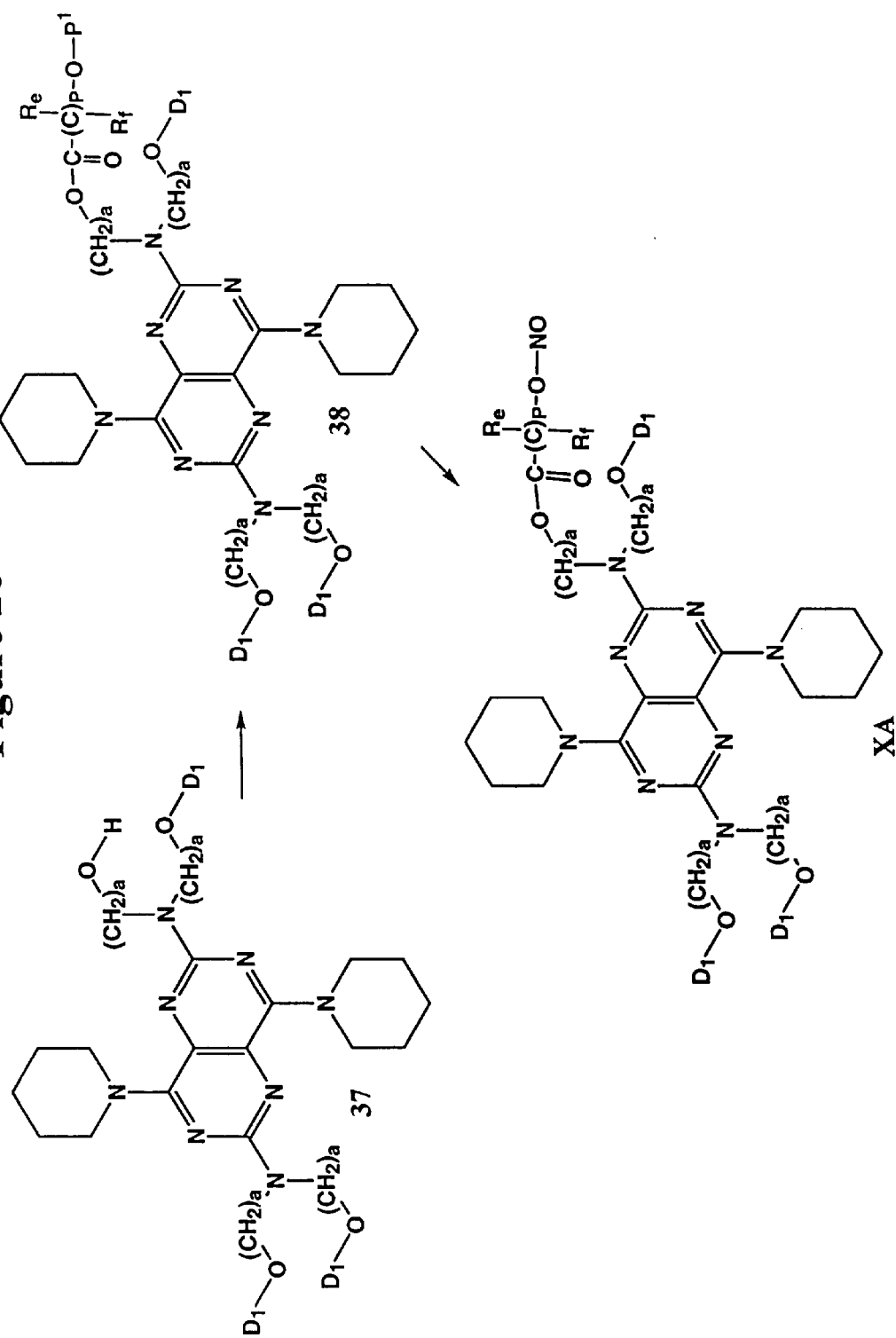
FIG. 28 shows a synthetic scheme for the preparation of nitrite containing 2,6-dihydroxyalkylamino-4,8-dipiperidino pyrimido [5,4-d] pyrimidine derivatives.

Nitroso compounds of structure (X), wherein $D_1$, $R_e$, $R_f$, and p are as defined herein, and a nitrite containing ester is representative of the D group, as defined herein, may be prepared according to FIG. 28. The alcohol group of structure 37 is converted to the ester of structure 38, wherein p, $R_e$ and R are as defined herein, by reaction with an appropriate protected alcohol containing activated acylating agent, wherein $P^1$ is as defined herein. Preferred methods for the formation of esters are reacting the alcohol with the preformed acid chloride or symmetrical anhydride of the protected alcohol containing acid or condensing the alcohol and protected alcohol containing acid with a dehydrating agent such as DCC or EDAC.HCl in the presence of a catalyst such as DMAP or HOBt. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosonium tetrafluoroborate in a suitable anhydrous solvent such as dichloromethane, THF, DMF, or acetonitrile with or without an amine base such as pyridine or triethylamine affords the compound of structure XA.

Figure 29:
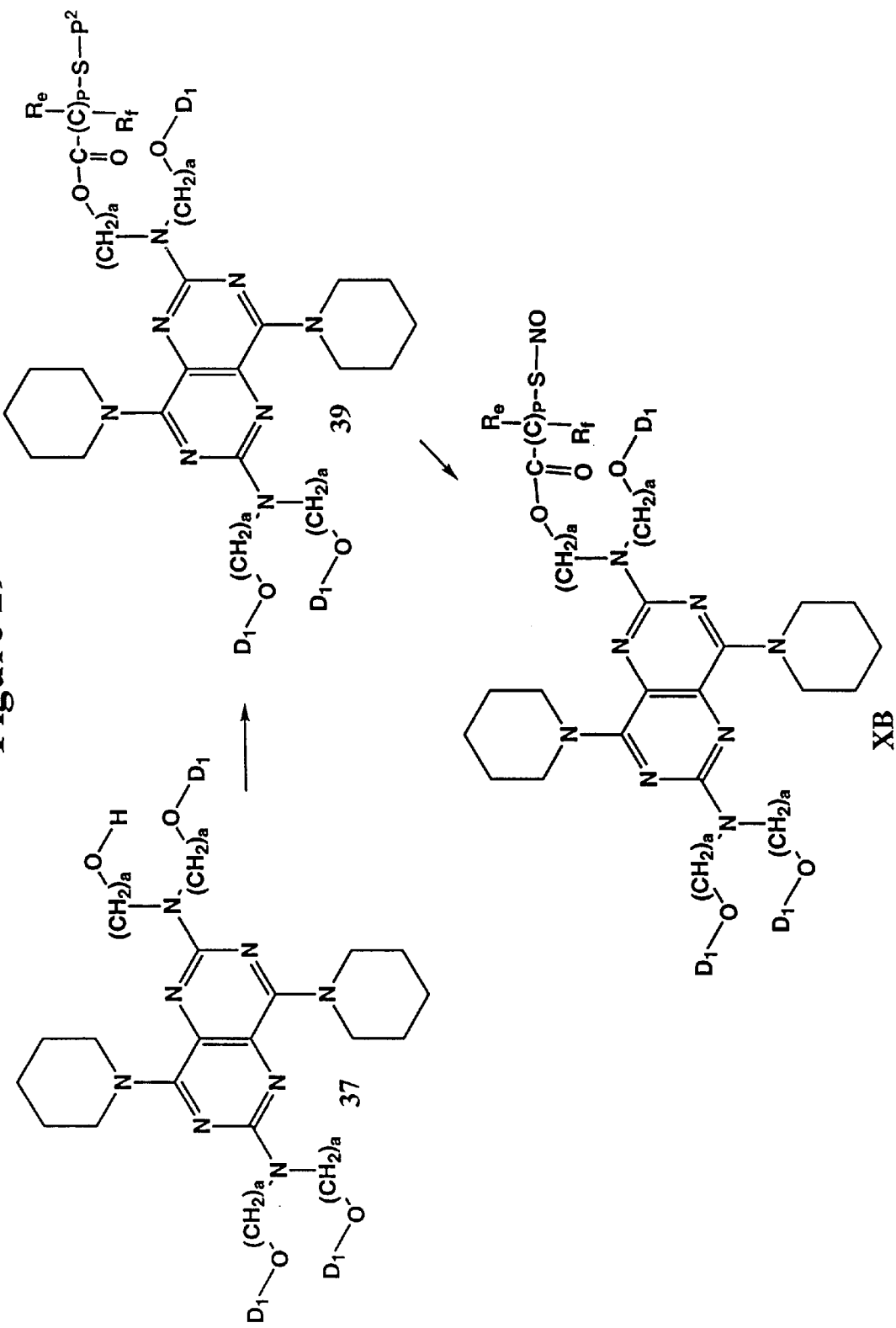
FIG. 29 shows a synthetic scheme for the preparation of nitrosothiol containing 2,6-dihydroxyalkylamino-4,8-dipiperidino pyrimido [5,4-d] pyrimidine derivatives.

Nitroso compounds of structure (X), wherein $D_1$, $R_e$ $R_f$, and p are as defined herein, and a nitrosothiol containing ester is representative of the D group, as defined herein, may be prepared as shown in FIG. 29. The alcohol group of structure 37 is converted to the ester of structure 39, wherein p, $R_e$ and $R_f$ are as defined herein, by reaction with an appropriate protected thiol containing activated acylating agent, wherein $P^2$ is as defined herein. Preferred methods for the formation of esters are reacting the alcohol with the preformed acid chloride or symmetrical anhydride of the protected thiol containing acid or condensing the alcohol and protected thiol containing acid with a dehydrating agent such as DCC or EDAC.HCl in the presence of a catalyst such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of structure XB. Alternatively, treatment of the deprotected thiol derived from compound 39 with a stoichiometric quantity of sodium nitrite in aqueous or alcoholic acid affords the compound of structure XB.

Figure 30:
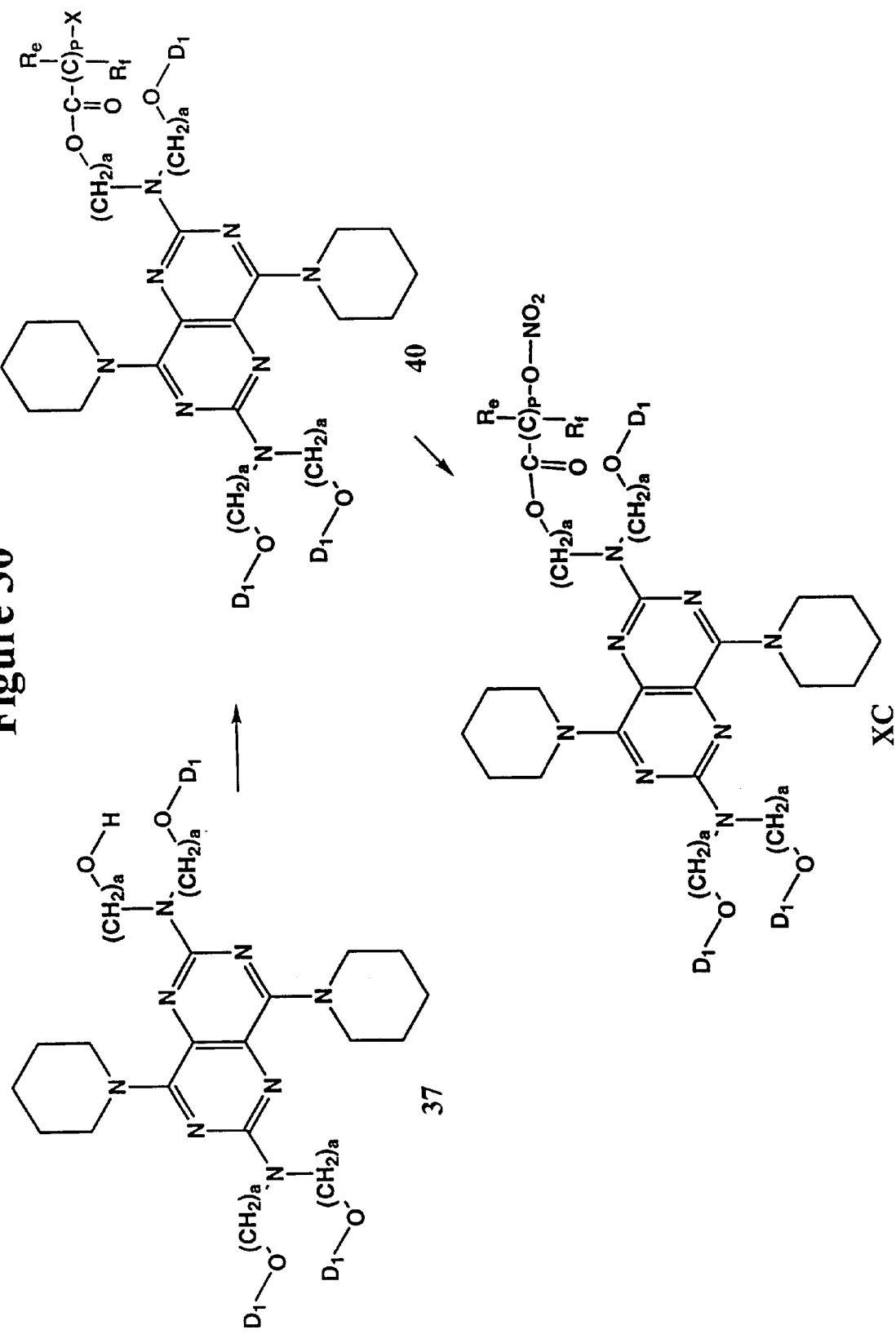
FIG. 30 shows a synthetic scheme for the preparation of nitrate containing 2,6-dihydroxyalkylamino-4,8-dipiperidino pyrimido [5,4-d] pyrimidine derivatives.

Nitro compounds of structure (X), wherein $D_1$, $R_e$, $R_f$, and p are as defined herein, and a nitrate containing ester is representative of the D group, as defined herein, may be prepared according to FIG. 30. The alcohol group of the formula 37 is converted to the ester of the formula 40, wherein p, $R_e$ and $R_f$ are as defined herein, and X is a halogen, by reaction with an appropriate halide containing activated acylating agent. Preferred methods for the formation of esters are reacting the alcohol with the preformed acid chloride or symmetrical anhydride of the halide containing acid or condensing the alcohol and halide containing acid with a dehydrating agent such as DCC or EDAC.HCl in the presence of a catalyst such as DMAP or HOBt. Preferred halides are bromide and iodide. Reaction of the ester of the formula 40 with a suitable nitrating agent such as silver nitrate in an inert solvent such as acetonitrile affords the compound of structure XC.

Figure 31:
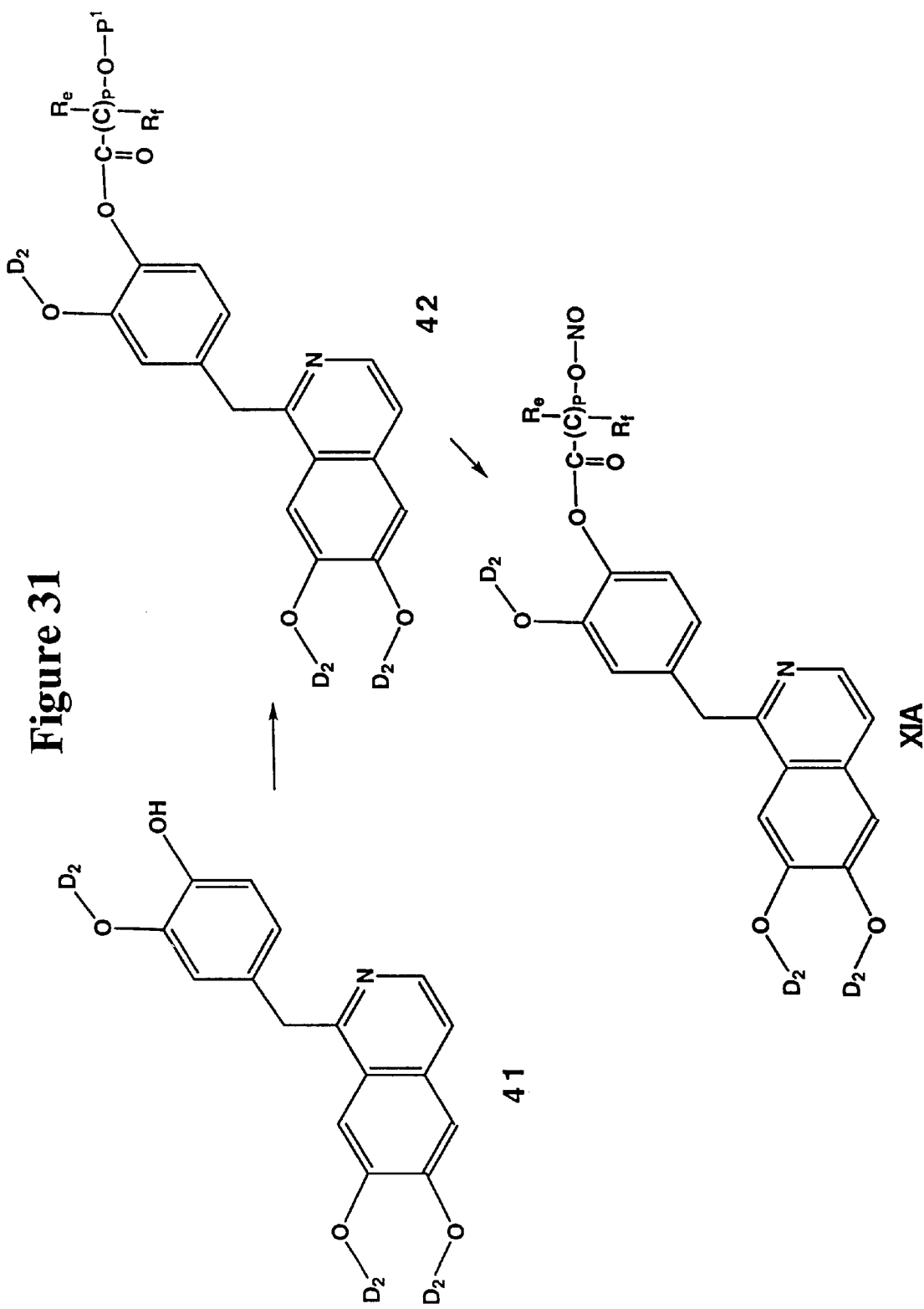
FIG. 31 shows a synthetic scheme for the preparation of nitrite containing 1-((3,4-dihydroxyphenyl)methyl)-6,7-isoquinoline derivatives.

Nitroso compounds of structure (XI), wherein $D_2$, $R_e$, $R_f$, and p are as defined herein, and a nitrite containing ester is representative of the D group, as defined herein, may be prepared according to FIG. 31. The alcohol group of structure 41 is converted to the ester of structure 42, wherein p, $R_e$ and $R_f$ are as defined herein, by reaction with an appropriate protected alcohol containing activated acylating agent, wherein $P^1$ is as defined herein. Preferred methods for the formation of esters are reacting the alcohol with the preformed acid chloride or symmetrical anhydride of the protected alcohol containing acid or condensing the alcohol and protected alcohol containing acid with a dehydrating agent, such as DCC or EDAC.HCl, in the presence of a catalyst, such as DMAP or HOBt. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XIA.

Figure 32:
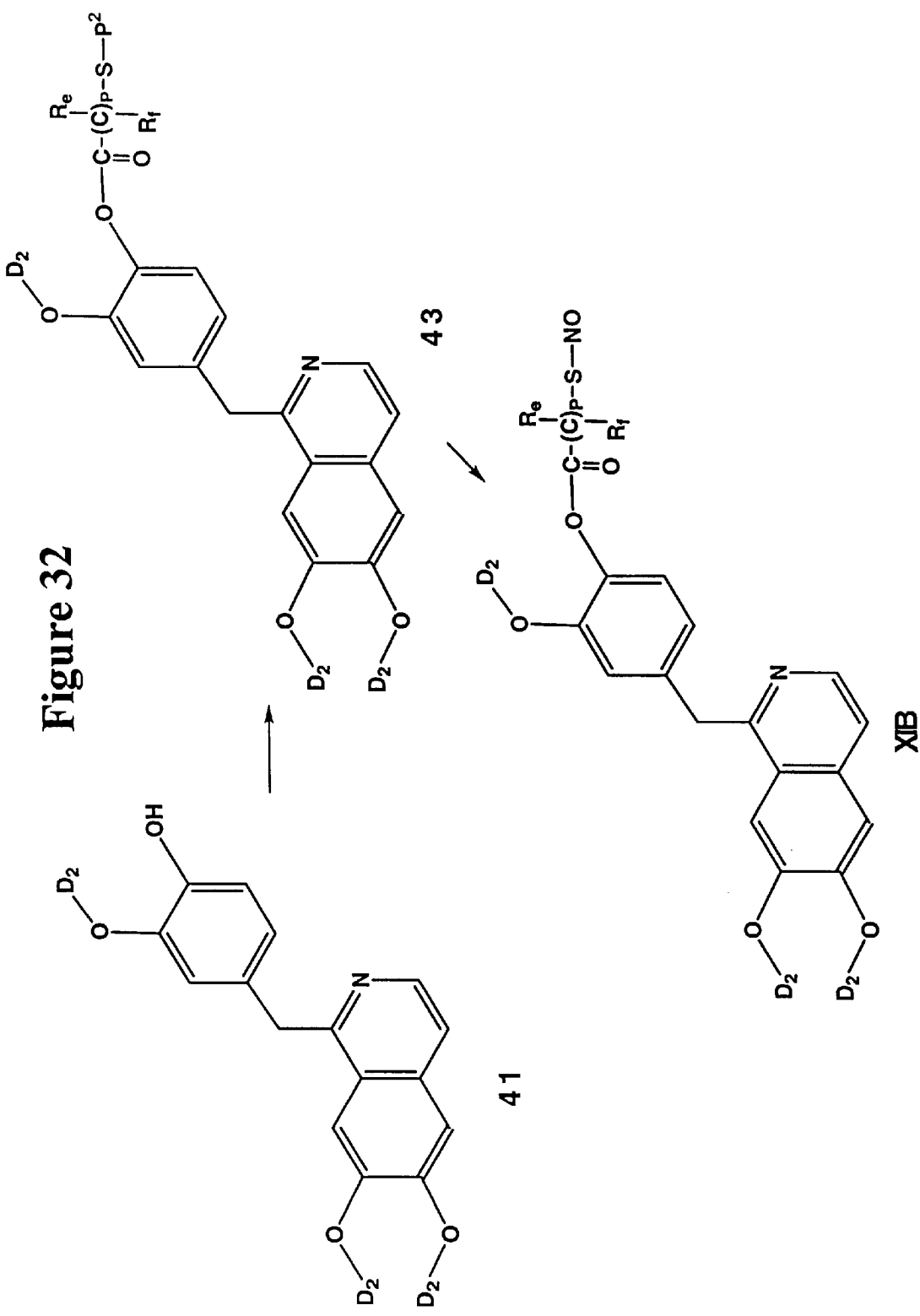
FIG. 32 shows a synthetic scheme for the preparation of nitrosothiol containing 1-((3,4-dihydroxyphenyl)methyl)-6, 7-isoquinoline derivatives.

Nitroso compounds of structure (XI), wherein $D_2$, $R_e$ $R_f$, and p are as defined herein, and a nitrosothiol containing ester is representative of the D group, as defined herein, may be prepared according to FIG. 32. The alcohol group of structure 41 is converted to the ester of structure 43, wherein p, $R_e$ and $R_f$ are as defined herein, by reaction with an appropriate protected thiol containing activated acylating agent, wherein $P^2$ is as defined herein. Preferred methods for the formation of esters are reacting the alcohol with the preformed acid chloride or symmetrical anhydride of the protected thiol containing acid or condensing the alcohol and protected thiol containing acid with a dehydrating agent, such as DCC or EDAC.HCl, in the presence of a catalyst, such as DMAP or HOBt. Preferred protecting groups for the thiol moiety are as a thioester, such as a thioacetate or thiobenzoate, as a disulfide, as a thiocarbamate, such as N-methoxymethyl thiocarbamate, or as a thioether, such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids, such as trifluoroacetic or hydrochloric acid, and heat are used to remove a paramethoxybenzyl thioether, a tetrahydropyranyl thioether or a S-triphenylmethyl thioether group) followed by reaction a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF, or acetonitrile, with or without an amine base, such as pyridine or triethylamine, affords the compound of structure XIB. Alternatively, treatment of the deprotected thiol derived from compound 43 with a stoichiometric quantity of sodium nitrite in aqueous or alcoholic acid affords the compound of structure XIB.

Figure 33:
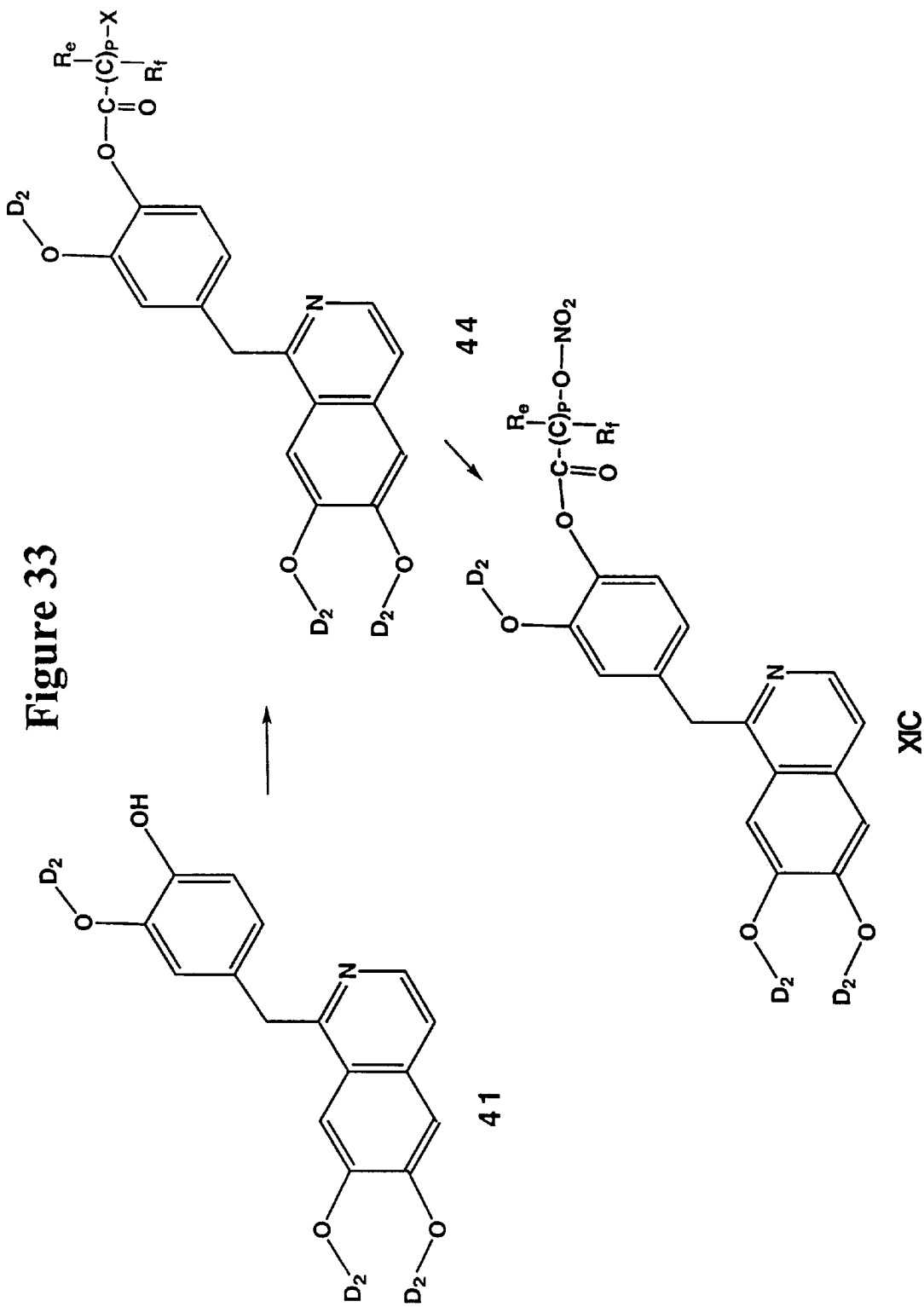
FIG. 33 shows a synthetic scheme for the preparation of nitrate containing 1-((3,4-dihydroxyphenyl)methyl)-6,7-isoquinoline derivatives.

Nitro compounds of structure (XI), wherein $D_2$, $R_e$, $R_f$, and p are as defined herein, and a nitrate containing ester is representative of the D group, as defined herein, may be prepared according to FIG. 33. The alcohol group of the formula 41 is converted to the ester of the formula 44, wherein p, $R_e$ and $R_f$ are as defined herein, and X is a halogen, by reaction with an appropriate halide containing activated acylating agent. Preferred methods for the formation of esters are reacting the alcohol with the preformed acid chloride or symmetrical anhydride of the halide containing acid or condensing the alcohol and halide containing acid with a dehydrating agent, such as DCC or EDAC.HCl, in the presence of a catalyst, such as DMAP or HOBt. Preferred halides are bromide and iodide. Reaction of the ester of the formula 44 with a suitable nitrating agent, such as silver nitrate, in an inert solvent, such as acetonitrile, affords the compound of structure XIC.

Figure 34:
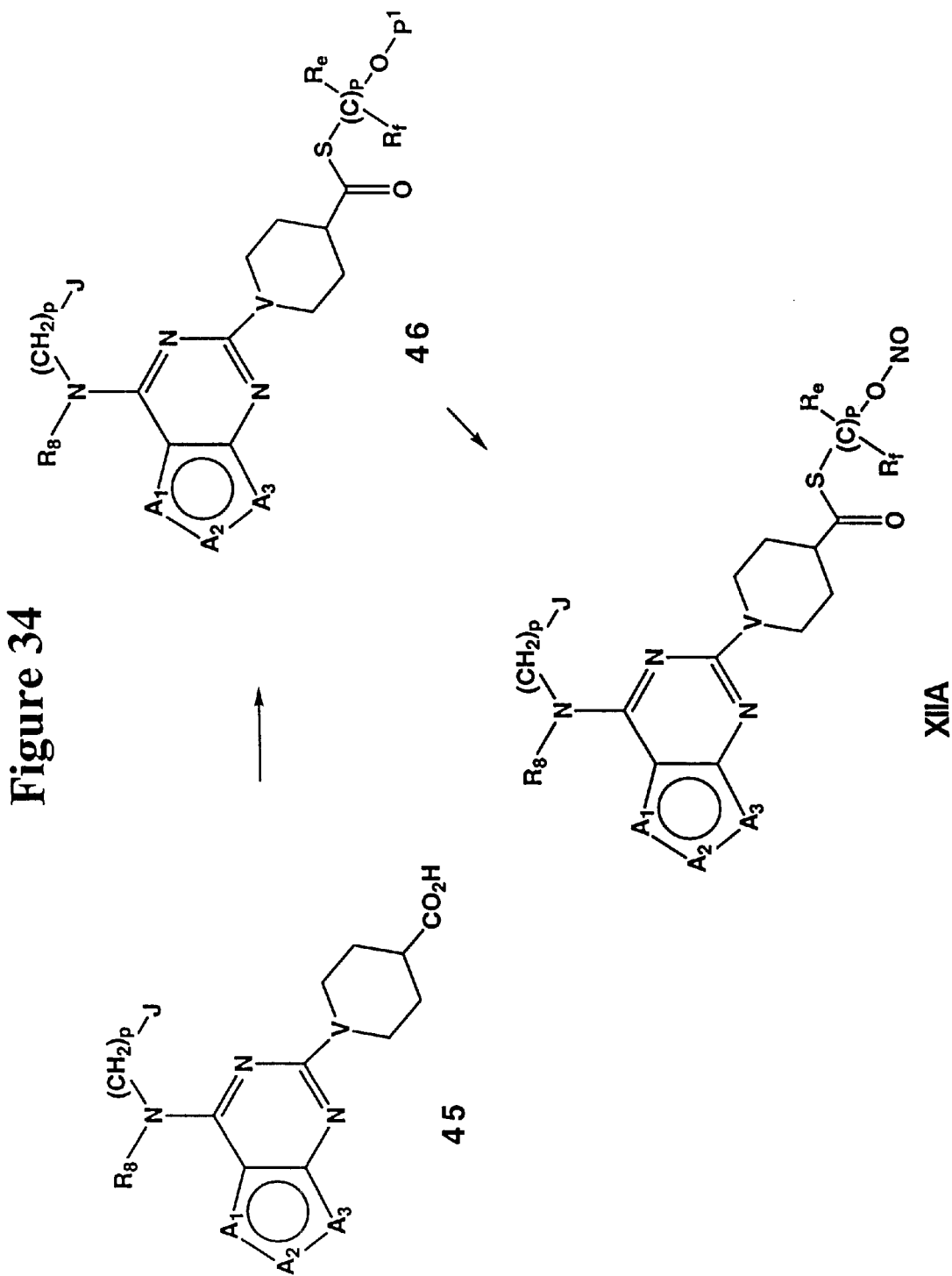
FIG. 34 shows a synthetic scheme for the preparation of nitrite containing substituted quinazoline derivatives.

Nitroso compounds of structure (XII), wherein $R_e$, $R_f$, $A_1$, $A_2$, $A_3$, J, V and p are as defined herein, and a nitrite containing thioester is representative of the $R_{24}$ group, as defined herein, may be prepared according to FIG. 34. The carboxylic acid group of structure 45 is converted to the thioester of structure 46, wherein p, $R_e$ and $R_f$ are as defined herein, by reaction with an appropriate protected alcohol containing thiol agent, wherein $p^1$ is as defined herein. Preferred methods for the formation of thioesters are reacting the thiol with the preformed acid chloride or symmetrical anhydride of the carboxylic acid or condensing the thiol and carboxylic acid with a dehydrating agent, such as DCC or EDAC.HCl, in the presence of a catalyst, such as DMAP or HOBt. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XIIA.

Figure 35:
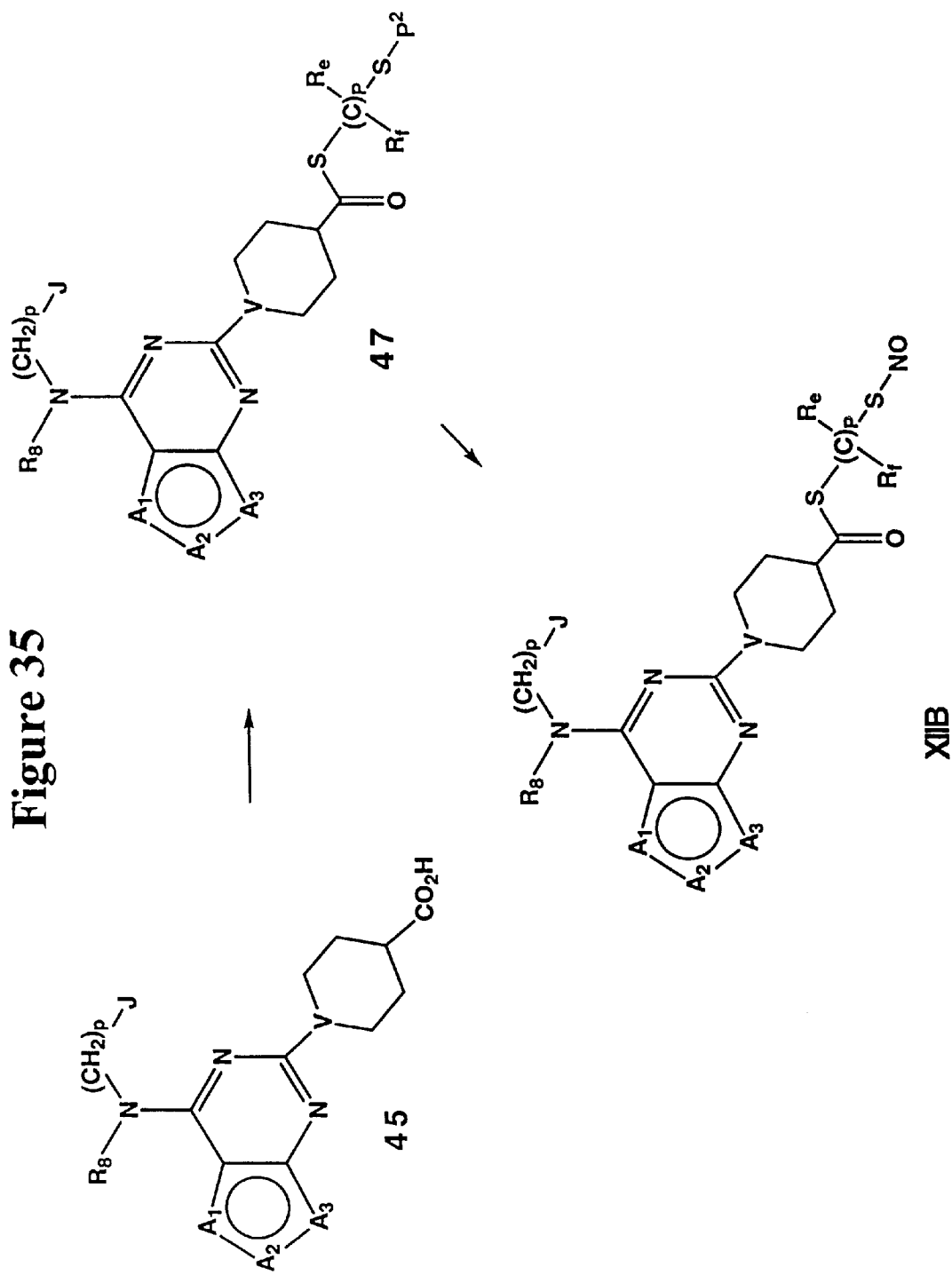
FIG. 35 shows a synthetic scheme for the preparation of nitrosothiol containing substituted quinazoline derivatives.

Nitroso compounds of structure (XII), wherein $R_e$, $R_f$, $A_1$, $A_2$, $A_3$, J, V and p are as defined herein, and a nitrosothiol containing thioester is representative of the $R_{24}$ group, as defined herein, may be prepared according to FIG. 35. The carboxylic acid group of structure 45 is converted to the thioester of structure 47, wherein p, $R_e$ and $R_f$ are as defined herein, by reaction with an appropriate mono protected dithiol. Preferred methods for the formation of thioesters are reacting the free thiol with the preformed acid chloride or symmetrical anhydride of the carboxylic acid or condensing the free thiol and carboxylic acid with a dehydrating agent, such as DCC or EDAC.HCl, in the presence of a catalyst, such as DMAP or HOBt. Preferred protecting groups for the thiol moiety are as a thioester, such as a thioacetate or thiobenzoate, as a disulfide, as a thiocarbamate, such as N-methoxymethyl thiocarbamate, or as a thioether, such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids, such as trifluoroacetic or hydrochloric acid, and heat are used to remove a paramethoxybenzyl thioether, a tetrahydropyranyl thioether or a S-triphenylmethyl thioether group). Reaction of the free thiol with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF, or acetonitrile, with or without an amine base, such as pyridine or triethylamine, affords the compound of structure XIIB. Alternatively, treatment of the deprotected thiol derived from compound 47 with a stoichiometric quantity of sodium nitrite in aqueous or alcoholic acid affords the compound of structure XIIB.

Figure 36:
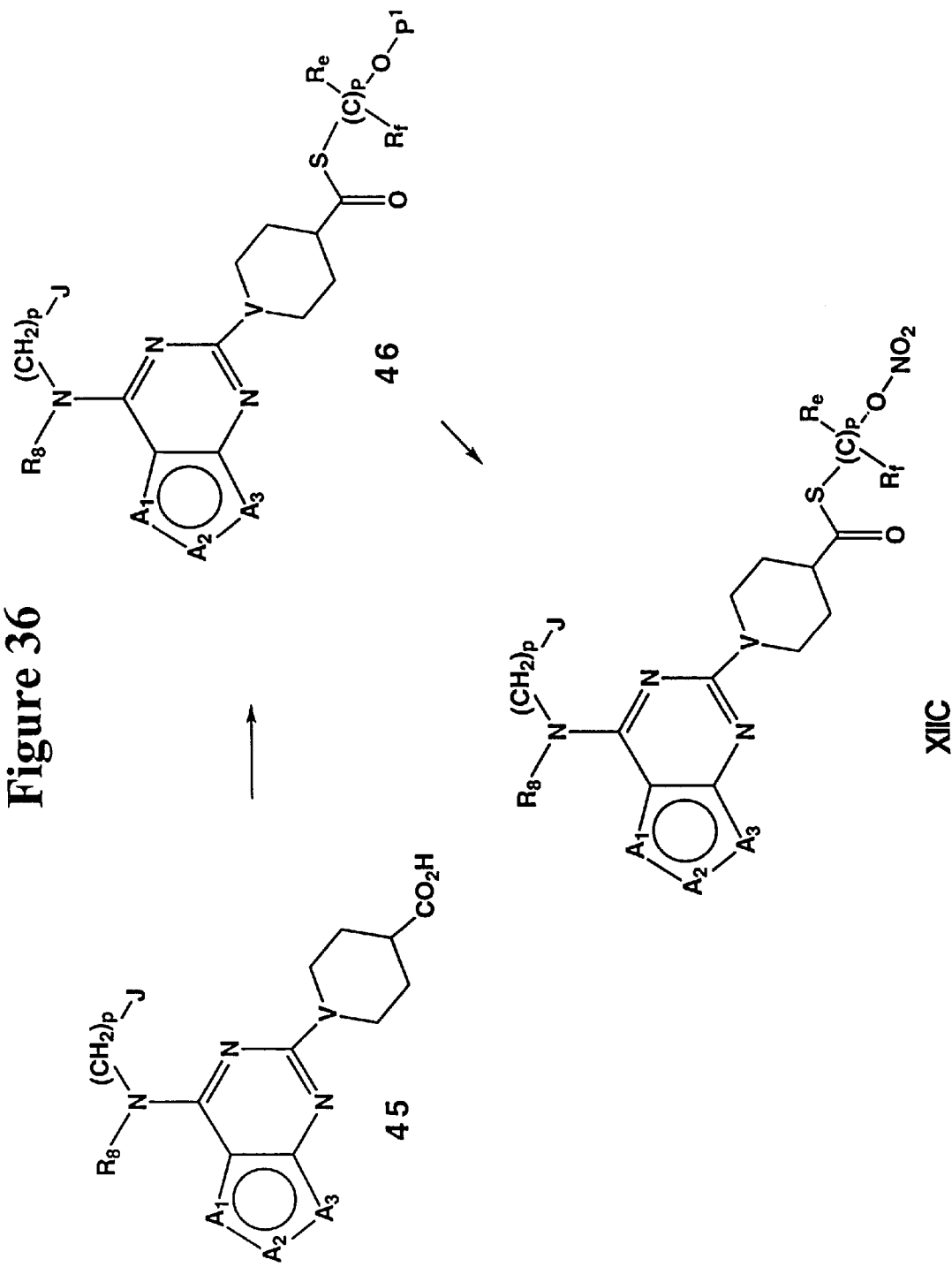
FIG. 36 shows a synthetic scheme for the preparation of nitrate containing substituted quinazoline derivatives.

Nitro compounds of structure (XII), wherein $R_e$, $R_f$, $A_1$, $A_2$, $A_3$, J, V and p are as defined herein, and a nitrate containing thioester is representative of the $R_{24}$ group, as defined herein, may be prepared according to FIG. 36. The carboxylic acid group of the formula 45 is converted to the thioester of structure 46, wherein p, $R_e$ and $R_f$ are as defined herein, by reaction with an appropriate protected alcohol containing thiol agent, wherein $P^1$ is as defined herein. Preferred methods for the formation of thioesters are reacting the thiol with the preformed acid chloride or symmetrical anhydride of the carboxylic acid or condensing the thiol and carboxylic acid with a dehydrating agent, such as DCC or EDAC.HCl, in the presence of a catalyst, such as DMAP or HOBt. Preferred protecting groups for the alcohol moiety are silyl ether, such as trimethylsilyl or a tert-butyldimethylsilyl ether. Deprotection of the hydroxyl moiety (fluoride ion is the preferred method for removing silyl ether protecting groups) followed by reaction of the alcohol with a suitable nitrating agent, such as nitric acid and acetic anhydride in ethyl acetate/acetic acid affords the compound of structure XIIC. Alternatively, the carboxylic acid group of structure 45 is converted to the thioester of structure 48, wherein p, $R_e$ and $R_f$ are as defined herein, and X is halogen, by reaction with an appropriate halide containing thiol. Preferred methods for the formation of thioesters are reacting the thiol with the preformed acid chloride or symmetrical anhydride of the carboxylic acid or condensing the thiol and carboxylic acid with a dehydrating agent, such as DCC or EDAC.HCl, in the presence of a catalyst, such as DMAP or HOBt. Preferred halides are bromide and iodide. Reaction of the ester of structure 48 with a suitable nitrating agent, such as silver nitrate in an inert solvent, such as acetonitrile, affords the compound of structure XIIC.

Figure 37:
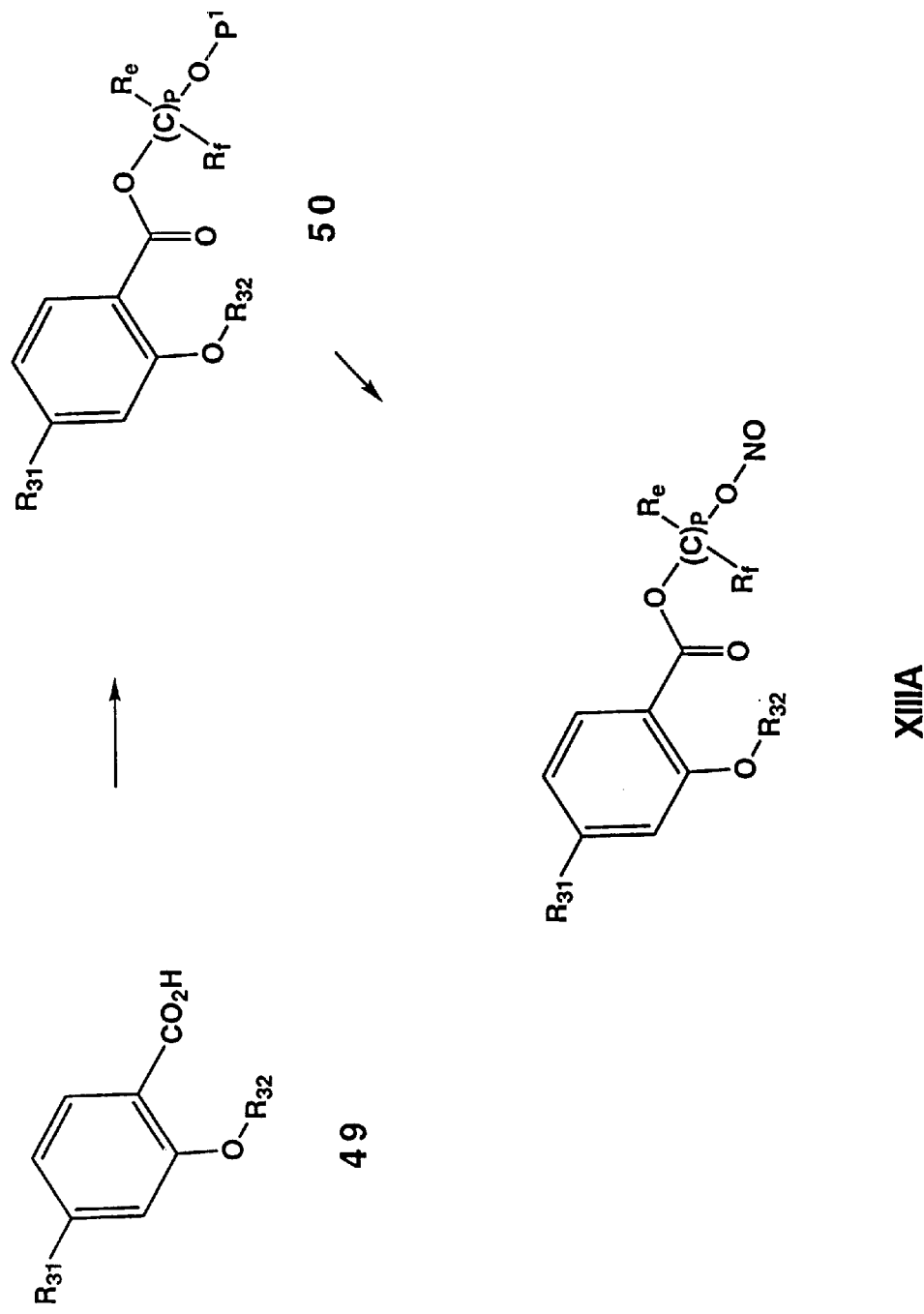
FIG. 37 shows a synthetic scheme for the preparation of nitrate containing substituted phenol derivatives.

Nitroso compounds of structure (XIII), wherein $R_e$, $R_f$, $R_{31}$, $R_{32}$, and p are as defined herein, and a nitrite containing ester is representative of the D group, as defined herein, may be prepared according to FIG. 37. The carboxylic acid group of structure 49 is converted to the ester of structure 50, wherein p, $R_e$ and R are as defined herein, by reaction with a monoprotected diol, wherein $P^1$ is as defined herein. Preferred methods for the formation of esters are reacting the alcohol with the preformed acid chloride or symmetrical anhydride of the carboxylic acid or condensing the alcohol and carboxylic acid with a dehydrating agent, such as DCC or EDAC.HCl, in the presence of a catalyst, such as DMAP or HOBt. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XIIIA.

Figure 38:
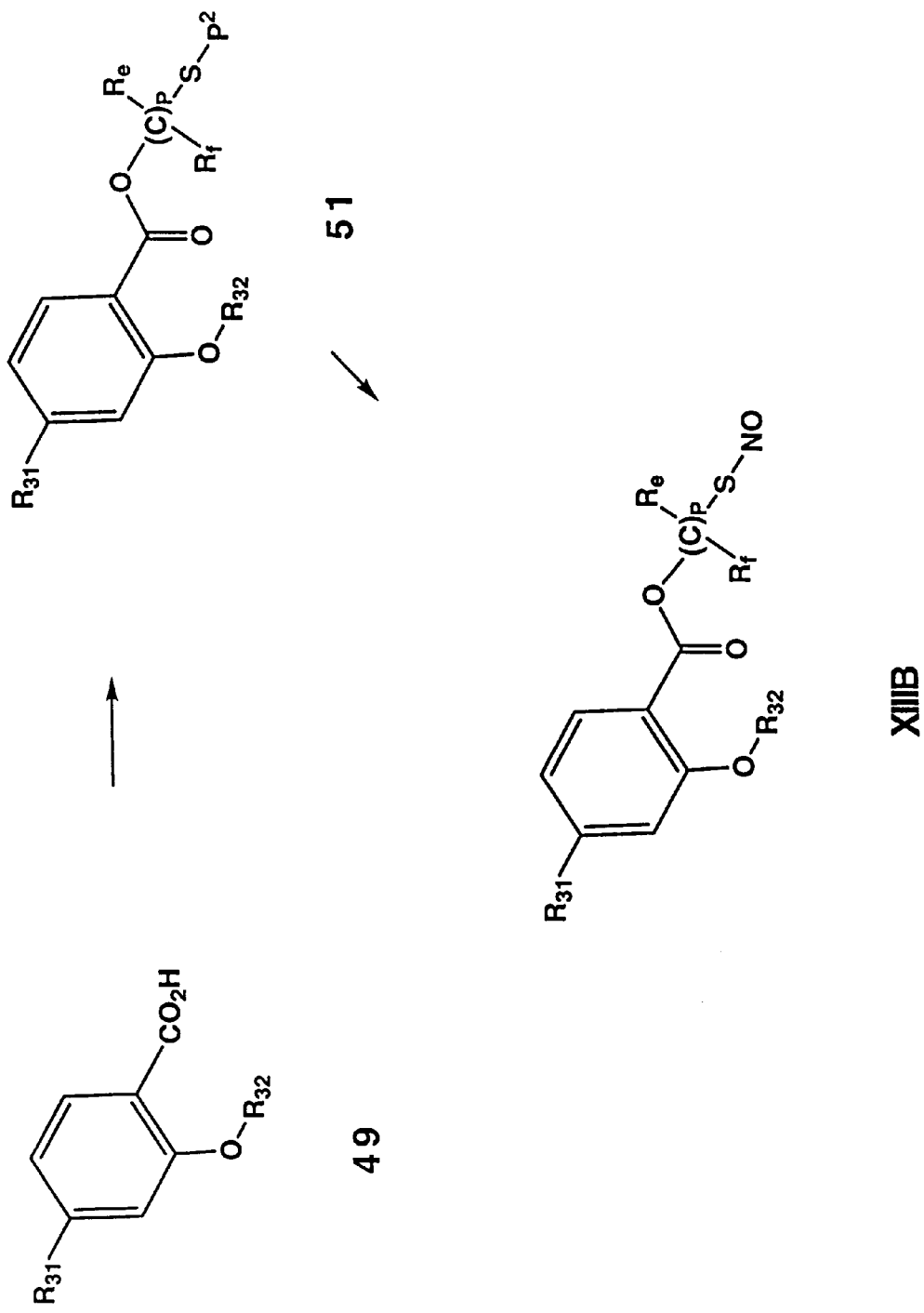
FIG. 38 shows a synthetic scheme for the preparation of nitrosothiol containing substituted phenol derivatives.

Nitroso compounds of structure (XIII), wherein $R_e$, $R_f$, $R_{31}$, $R_{32}$, and p are as defined herein, and a nitrosothiol containing ester is representative of the D group, as defined herein, may be prepared according to FIG. 38. The carboxylic acid group of structure 49 is converted to the ester of structure 51, wherein p, $R_e$ and $R_f$ are as defined herein, by reaction with an appropriate protected thiol containing alcohol. Preferred methods for the formation of esters are reacting the alcohol with the preformed acid chloride or symmetrical anhydride of the carboxylic acid or condensing the primary thiol and carboxylic acid with a dehydrating agent, such as DCC or EDAC.HCl, in the presence of a catalyst, such as DMAP or HOBt. Preferred protecting groups for the thiol moiety are as a thioester, such as a thioacetate or thiobenzoate, as a disulfide, as a thiocarbamate, such as N-methoxymethyl thiocarbamate, or as a thioether, such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids, such as trifluoroacetic or hydrochloric acid, and heat are used to remove a paramethoxybenzyl thioether, a tetrahydropyranyl thioether or a S-triphenylmethyl thioether group) Reaction of the free thiol with a suitable nitrosylating agent, such as thionyl chloride nitrite, thionyl dinitrite, a lower alkyl nitrite, such as tert-butyl nitrite, or nitrosium tetrafluoroborate, in a suitable anhydrous solvent, such as methylene chloride, THF, DMF, or acetonitrile, with or without an amine base, such as pyridine or triethylamine, affords the compound of structure XIIIB. Alternatively, treatment of the deprotected thiol derived from compound 51 with a stoichiometric quantity of sodium nitrite in aqueous or alcoholic acid affords the compound of structure XIIIB.

Figure 39:
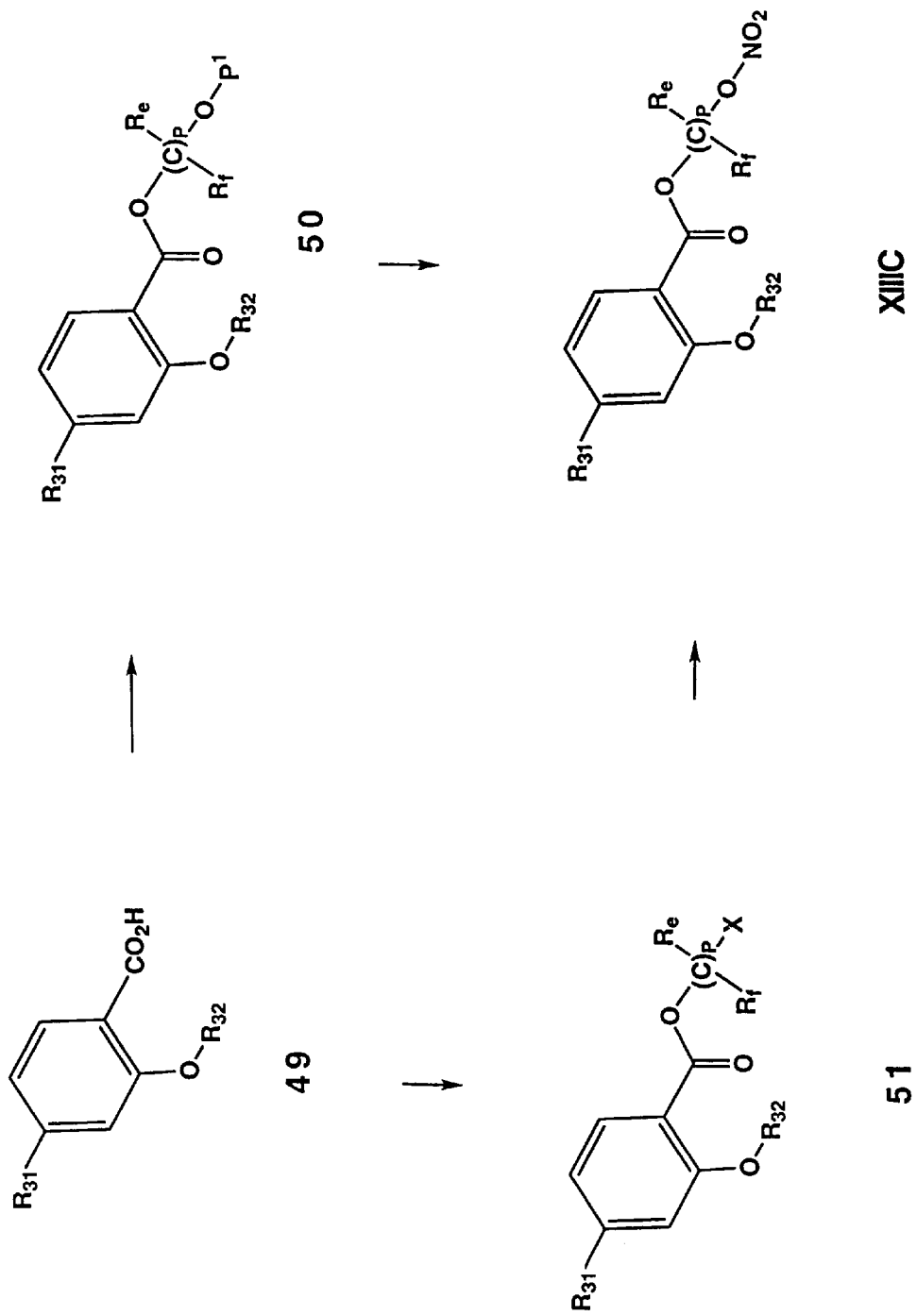
FIG. 39 shows a synthetic scheme for the preparation of nitrate containing substituted phenol derivatives.

Nitro compounds of structure (XIII), wherein $R_e$, $R_f$, $R_{31}$, $R_{32}$ and p are as defined herein, and a nitrate containing ester is representative of the D group, as defined herein, may be prepared according to FIG. 39. The carboxylic acid group of the formula 49 is converted to the ester of structure 50, wherein p, $R_e$ and $R_f$ are as defined herein, by reaction with an appropriate mono-protected diol, wherein $p^1$ is as defined herein. Preferred methods for the formation of esters are reacting the alcohol with the preformed acid chloride or symmetrical anhydride of the carboxylic acid or condensing the alcohol and carboxylic acid with a dehydrating agent, such as DCC or EDAC.HCl, in the presence of a catalyst, such as DMAP or HOBt. Preferred protecting groups for the alcohol moiety are silyl ether, such as trimethylsilyl or a tert-butyldimethylsilyl ether. Deprotection of the hydroxyl moiety (fluoride ion is the preferred method for removing silyl ether protecting groups) followed by reaction of the alcohol with a suitable nitrating agent, such as nitric acid and acetic anhydride in ethyl acetate/acetic acid affords the compound of structure XIIIC. Alternatively, the carboxylic acid group of structure 49 is converted to the ester of structure 52, wherein p, $R_e$ and $R_f$ are as defined herein, and X is halogen, by reaction with an appropriate halide containing alcohol. Preferred methods for the formation of esters are reacting the alcohol with the preformed acid chloride or symmetrical anhydride of the halide containing acid or condensing the alcohol and halide containing alcohol with a dehydrating agent, such as DCC or EDAC.HCl in the presence of a catalyst, such as DMAP or HOBt. Preferred halides are bromide and iodide. Reaction of the ester of structure 52 with a suitable nitrating agent, such as silver nitrate in an inert solvent, such as acetonitrile, affords the compound of structure XIIIC.

Figure 40:
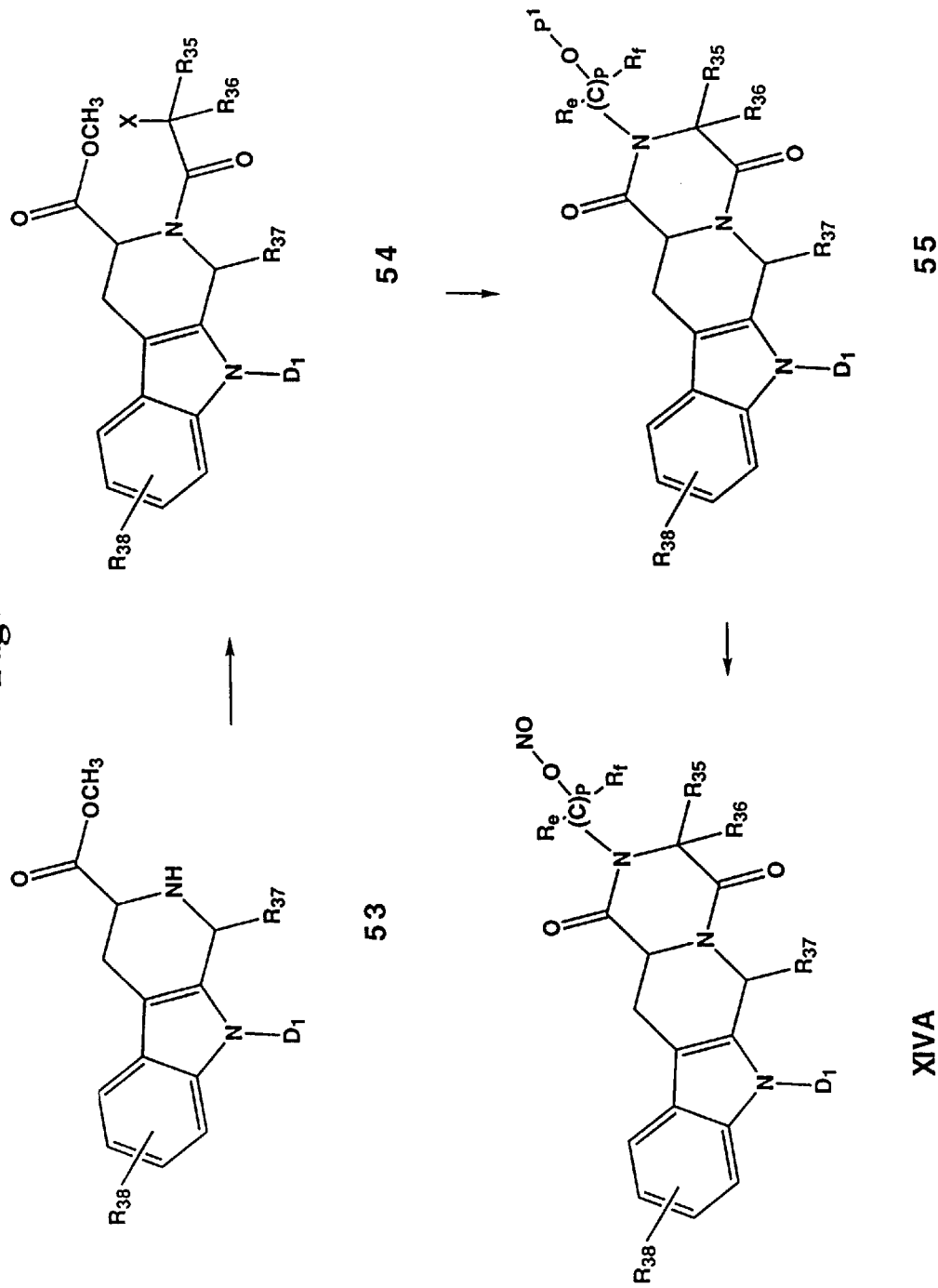
FIG. 40 shows a synthetic scheme for the preparation of nitrate containing substituted 5,11,11a,4a-tetrahydropiperazino[1,2-b]beta-carboline-1 ,4-dione derivatives.

Nitroso compounds of structure (XIV), wherein $R_e$, $R_f$, $R_{35}$, $R_{36}$, $R_{37}$, $R_{38}$, $D_1$ and p are as defined herein, a carbonyl group is representative of the A group, as defined herein, and a nitrite containing substituent is representative of the $R_{34}$ group, as defined herein, may be prepared according to FIG. 40. The methyl 9a-methyl-1,2,3,4,4a,9a-hexahydrobeta-carboline-3-carboxylate of structure 53 is converted to the acylated derivative of the formula 54, wherein p, $R_{35}$ and $R_{36}$ are as defined herein, oxygen is representative of $G_4$, as defined herein, by reaction with an appropriate α-halo containing activated acylating agent, wherein X is preferably chlorine or bromine. Preferred methods for the formation of N-acylated 1,2,3,4,4a,9a-hexahydrobeta-carboline-3-carboxylate esters are reacting the 1,2,3,4,4a,9a-hexahydrobeta-carboline-3-carboxylate ester with the preformed acid chloride or symmetrical anhydride of the α-halo containing acid or condensing the 5 1,2,3,4,4a,9a-hexahydrobeta-carboline-3-carboxylate ester and α-halo containing acid in the presence of a dehydrating agent such as DCC or EDAC.HCl with a catalyst such as DMAP or HOBt. Hydrolysis of the ester affords the carboxylic acid followed by subsequent reaction with a hydroxy protected primary amino containing alcohol, wherein $P^1$ is as defined herein, affords the compound of structure 55. Preferred methods for the formation of amides are reacting the amine with the preformed acid chloride or symmetrical anhydride of the carboxylic acid or condensing the amine and carboxylic acid with a dehydrating agent, such as DCC or EDAC.HCl, in the presence of a catalyst, such as DMAP or HOBt. Preferred protecting groups for the alcohol moiety are silyl ethers, such as a trimethylsilyl or a tert-butyidimethylsilyl ether. A preferred method for facilitating the cyclization to the afford the 3,6,17-triaza-1-methyltetracyclo[8.7.0.0<3,8>.0<11,16>]heptadeca-11(16),12,14-triene-4,7-dione is to heat the α-halo diamide intermediate in an inert solvent such as methanol. Deprotection of the hydroxyl moiety (fluoride ion is the preferred method for removing silyl ether protecting groups) followed by reaction with a stoichometric quantity of a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XIVA.

Figure 41:
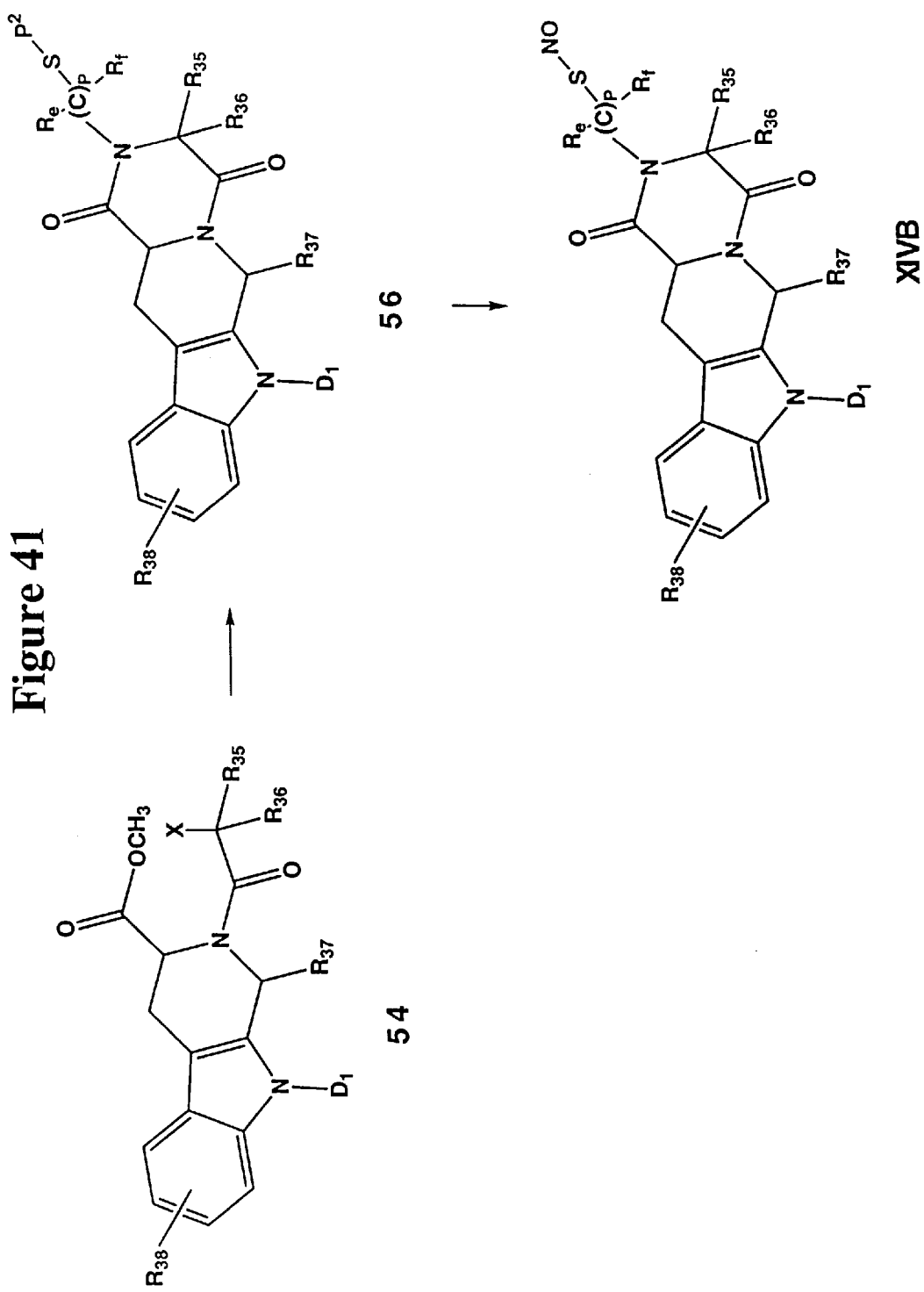
FIG. 41 shows a synthetic scheme for the preparation of nitrosothiol containing substituted 5,11,11a,4a-tetrahydropiperazino[1,2-b]beta-carboline-1,4-dione derivatives.

Nitroso compounds of structure (XIV), wherein $R_e$, $R_f$, $R_{35}$, $R_{36}$, $R_{37}$, $R_{38}$, $D_1$ and p are as defined herein, a carbonyl group is representative of the A group, as defined herein, oxygen is representative of $G_4$, as defined herein, and a nitrosothiol containing substituent is representative of the $R_{34}$ group, as defined herein, may be prepared according to FIG. 41. Hydrolysis of the ester of the compound of structure 54 affords the carboxylic acid which is reacted with a sulfanyl protected primary amino containing thiol, wherein $P^2$ is as defined herein, to afford the compound of structure 56. Preferred methods for the formation of amides are reacting the amine with the preformed acid chloride or symmetrical anhydride of the carboxylic acid or condensing the amine and carboxylic acid with a dehydrating agent, such as DCC or EDAC.HCl, in the presence of a catalyst, such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxy-benzyl thioether, a tetrahydropyranyl thioether or a 2,4,6-trimethoxybenzyl thioether. A preferred method for facilitating the cyclization to the afford the 3,6,17-triaza-1-methyltetracyclo[8.7.0.0<3,8>.0<11,16>]heptadeca-11(16),12,14-triene-4,7-dione is to heat the α-halo diamide intermediate wherein X is preferably chlorine or bromine in an inert solvent such as methanol. Deprotection of the sulfanyl moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction with a stoichometric quantity of a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure XIVB. Alternatively, treatment of the deprotected thiol derived from compound 55 with a stoichiometric quantity of sodium nitrite in an acidic aqueous or alcoholic solution affords the compound of structure XIVB.

Figure 42:
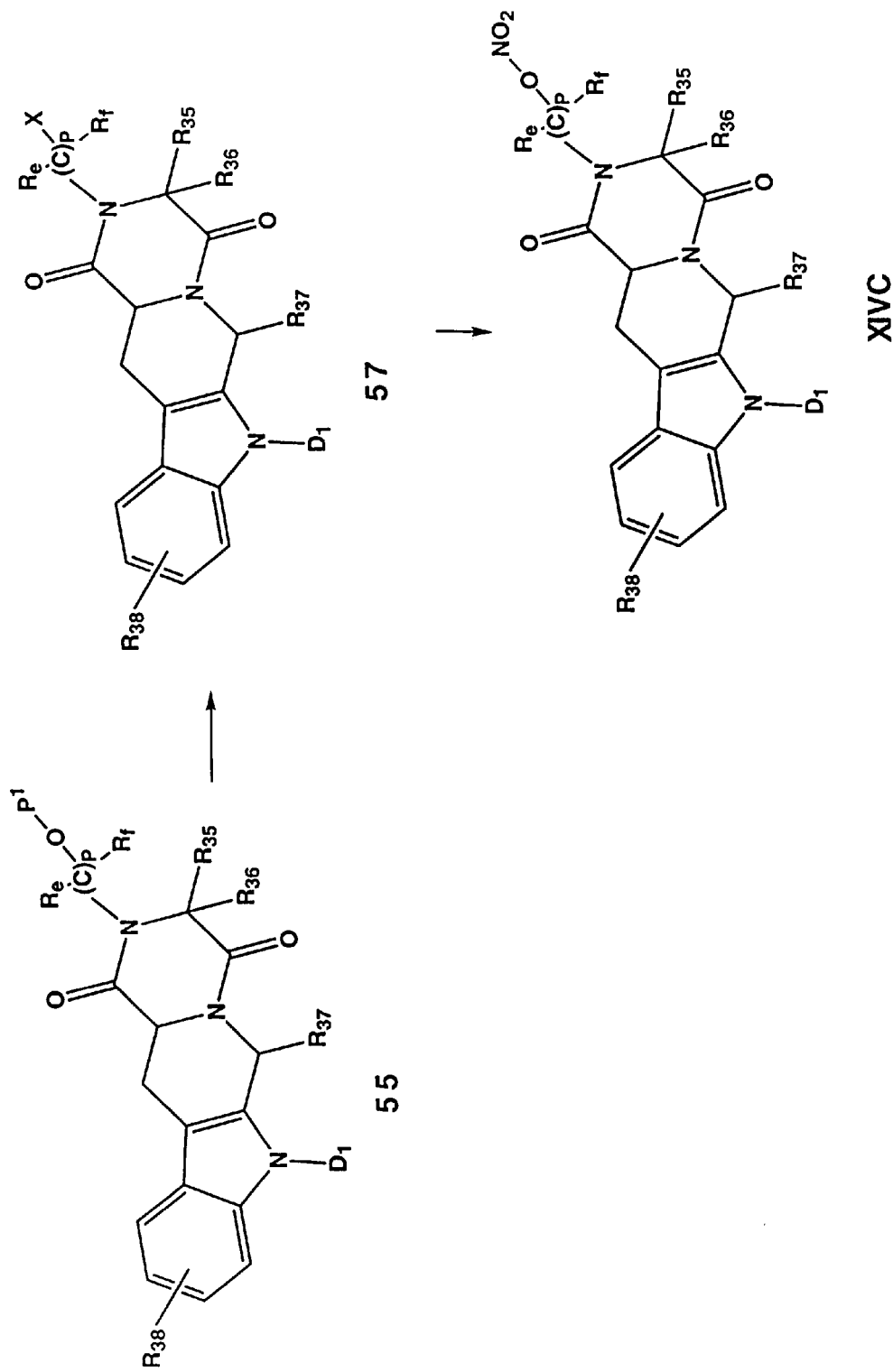
FIG. 42 shows a synthetic scheme for the preparation of nitrate containing substituted 5,11,11a,4a-tetrahydropiperazino[1,2-b]beta-carboline-1,4-dione derivatives.

Nitro compounds of structure (XIV), wherein $R_e$, $R_f$, $R_{35}$, $R_{36}$, $R_{37}$, $R_{38}$, $D_1$ and p are as defined herein, a carbonyl group is representative of the A group, as defined herein, oxygen is representative of $G_4$, as defined herein, and a nitrate containing substituent is representative of the $R_{34}$ group, as defined herein, may be prepared according to FIG. 42. Deprotection of the hydroxyl moiety of the compound of structure 54 (fluoride ion is the preferred method for removing silyl ether protecting groups) followed by activation and nucleophilic displacement of the hydroxyl by a halogen affords the compound of structure 57, wherein X is preferably a bromine or an iodine. Preferred methods for converting a hydroxyl group to a halogen moiety are to first activate it as the mesylate or tosylate by reacting it with methansulfonyl chloride or p-toluesulfonyl chloride in an inert solvent such as methylene chloride or THF in the presence of a base such as triethylamine followed by nucleophilic displacement of the sulfonate moiety with iodide or bromide by reaction with sodium iodide or sodium bromide in refluxing acetone. Reaction of the compound of structure 57 with a suitable nitrating agent such as silver nitrate in an inert solvent such as acetonitrile affords the compound of structure XIVC.

Figure 43:
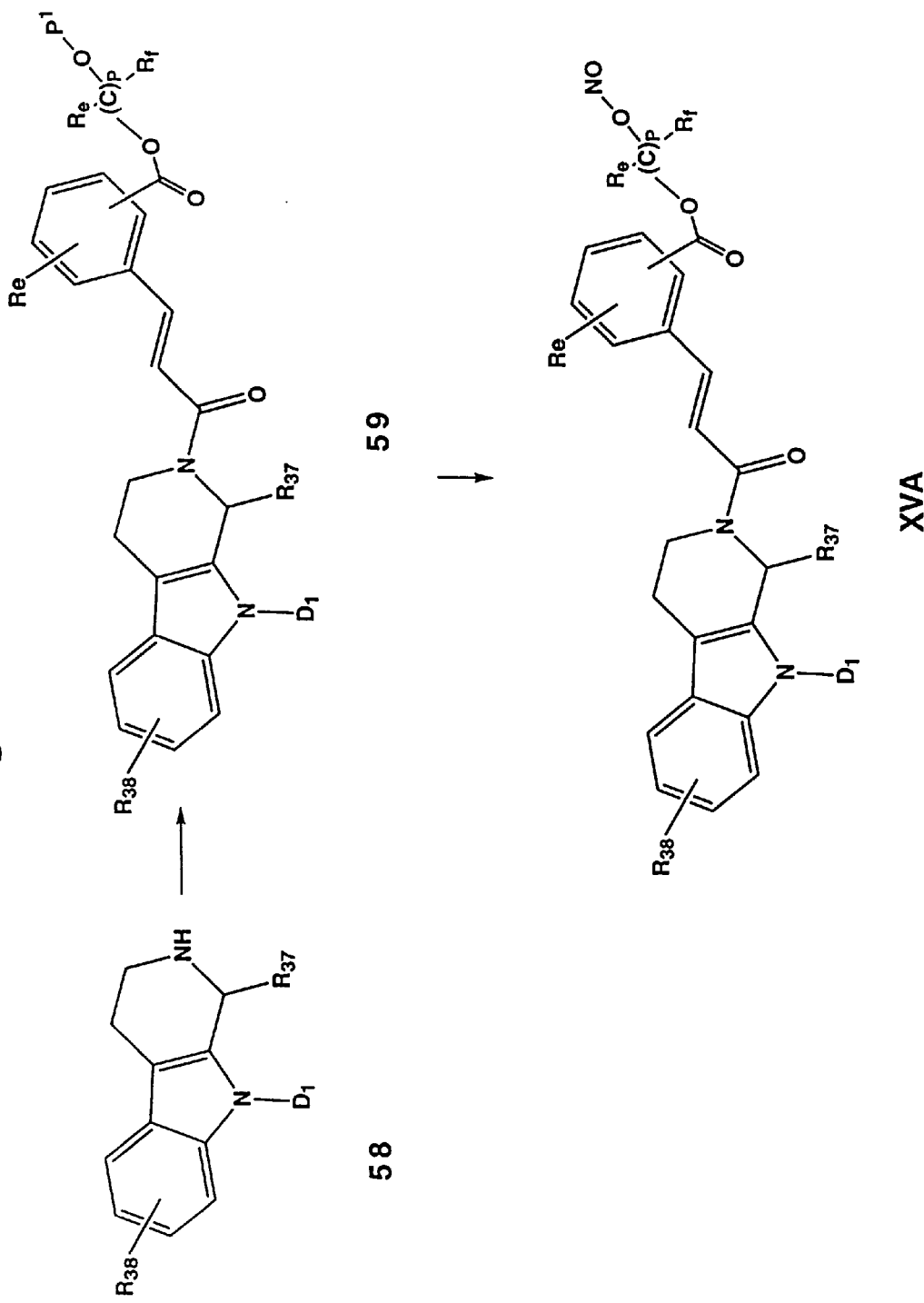
FIG. 43 shows a synthetic scheme for the preparation of nitrite containing substituted 2-acyl -1,2,3,4-tetrahydrobeta-carboline derivatives.

Nitroso compounds of structure (XV), wherein $R_e$, $R_f$, $R_{37}$, $R_{38}$, $D_1$ and p are as defined herein, and a nitrite containing ester substituent is representative of the $R_{25}$ group, as defined herein, may be prepared according to FIG. 43. 1,2,3,4-Tetrahydrobeta-carboline of the formula 58 is converted to the N-acylated compound of the formula 59, wherein $P^1$ is as defined herein, and oxygen is representative of $G_4$, as defined herein, by reaction with a hydroxy protected carboxylic ester substituted cinnamic acid derivative. Preferred methods for the formation of amides are reacting the amine with the preformed acid chloride or symmetrical anhydride of the carboxylic acid or condensing the amine and carboxylic acid with a dehydrating agent, such as DCC or EDAC.HCl, in the presence of a catalyst, such as DMAP or HOBt. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a stoichometric quantity of a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XVA.

Figure 44:
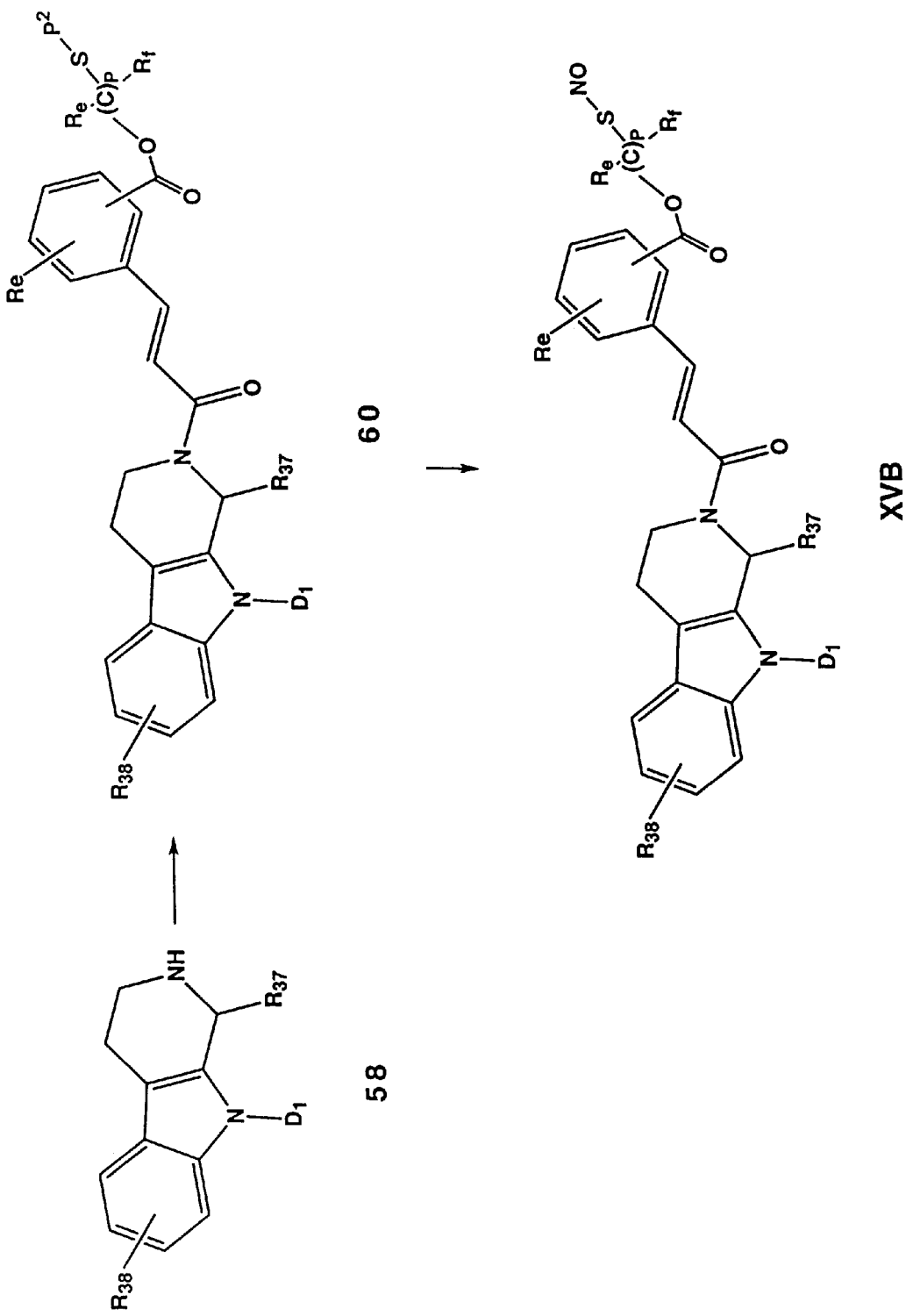
FIG. 44 shows a synthetic scheme for the preparation of nitrosothiol containing substituted 2-acyl -1,2,3,4-tetrahydrobeta-carboline derivatives.

Nitroso compounds of structure (XV), wherein $R_e$, $R_f$, $R_{37}$, $R_{38}$, $D_1$ and p are as defined herein, and a nitrosothiol containing ester substituent is representative of the $R_{25}$ group, as defined herein, may be prepared according to FIG. 44. 1,2,3,4-Tetrahydrobeta-carboline of the formula 58 is converted to the N-acylated compound of the formula 60, wherein $P^2$ is as defined herein, and oxygen is representative of $G_4$, as defined herein, by reaction with a sulfanyl protected carboxylic ester substituted cinnamic acid derivative. Preferred methods for the formation of amides are reacting the amine with the preformed acid chloride or symmetrical anhydride of the carboxylic acid or condensing the amine and carboxylic acid with a dehydrating agent, such as DCC or EDAC.HCl, in the presence of a catalyst, such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the sulfanyl moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction with a stoichometric quantity of a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure XVB. Alternatively, treatment of the deprotected thiol derived from compound 60 with a stoichiometric quantity of sodium nitrite in an acidic aqueous or alcoholic solution affords the compound of structure XVB.

Figure 45:
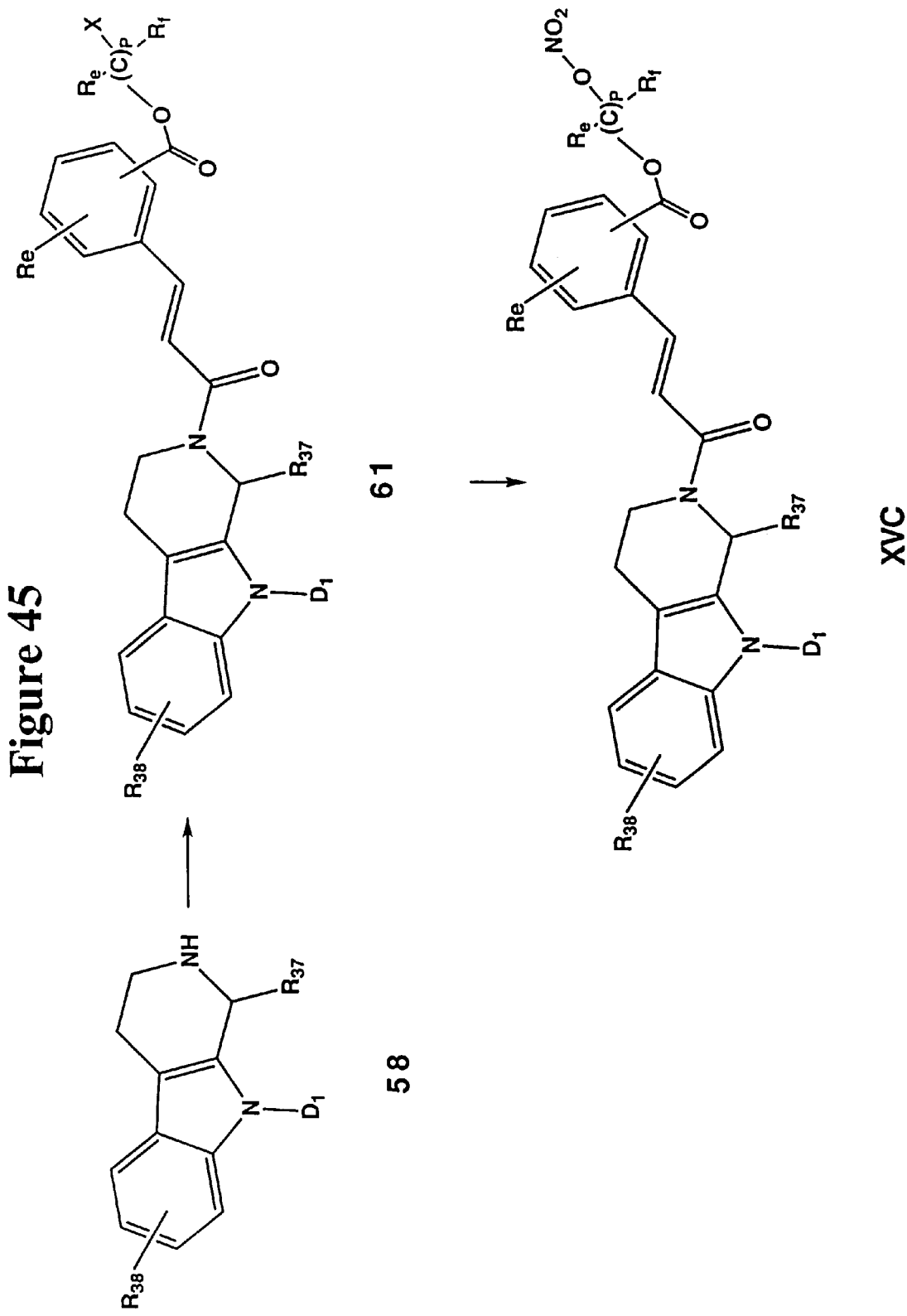
FIG. 45 shows a synthetic scheme for the preparation of nitrate containing substituted 2-acyl -1,2,3,4-tetrahydrobeta-carboline derivatives.

Nitro compounds of structure (XV), wherein $R_e$, $R_f$, $R_{37}$, $R_{38}$, $D_1$ and p are as defined herein, and a nitrate containing ester substituent is representative of the $R_{25}$ group, as defined herein, may be prepared according to FIG. 45. 1,2,3,4-Tetrahydrobeta-carboline of the formula 58 is converted to the N-acylated compound of the formula 61, wherein X is as defined herein, and oxygen is representative of $G_4$, as defined herein, by reaction with a halogen containing carboxylic ester substituted cinnamic acid derivative. Preferred methods for the formation of amides are reacting the amine with the preformed acid chloride or symmetrical anhydride of the halide containing acid or condensing the amine and halide containing acid with a dehydrating agent, such as DCC or EDAC.HCl in the presence of a catalyst, such as DMAP or HOBt. Preferred halides are bromide and iodide. Reaction of the amide of structure 61 with a suitable nitrating agent, such as silver nitrate in an inert solvent, such as acetonitrile, affords the compound of structure XVC.

Figure 46:
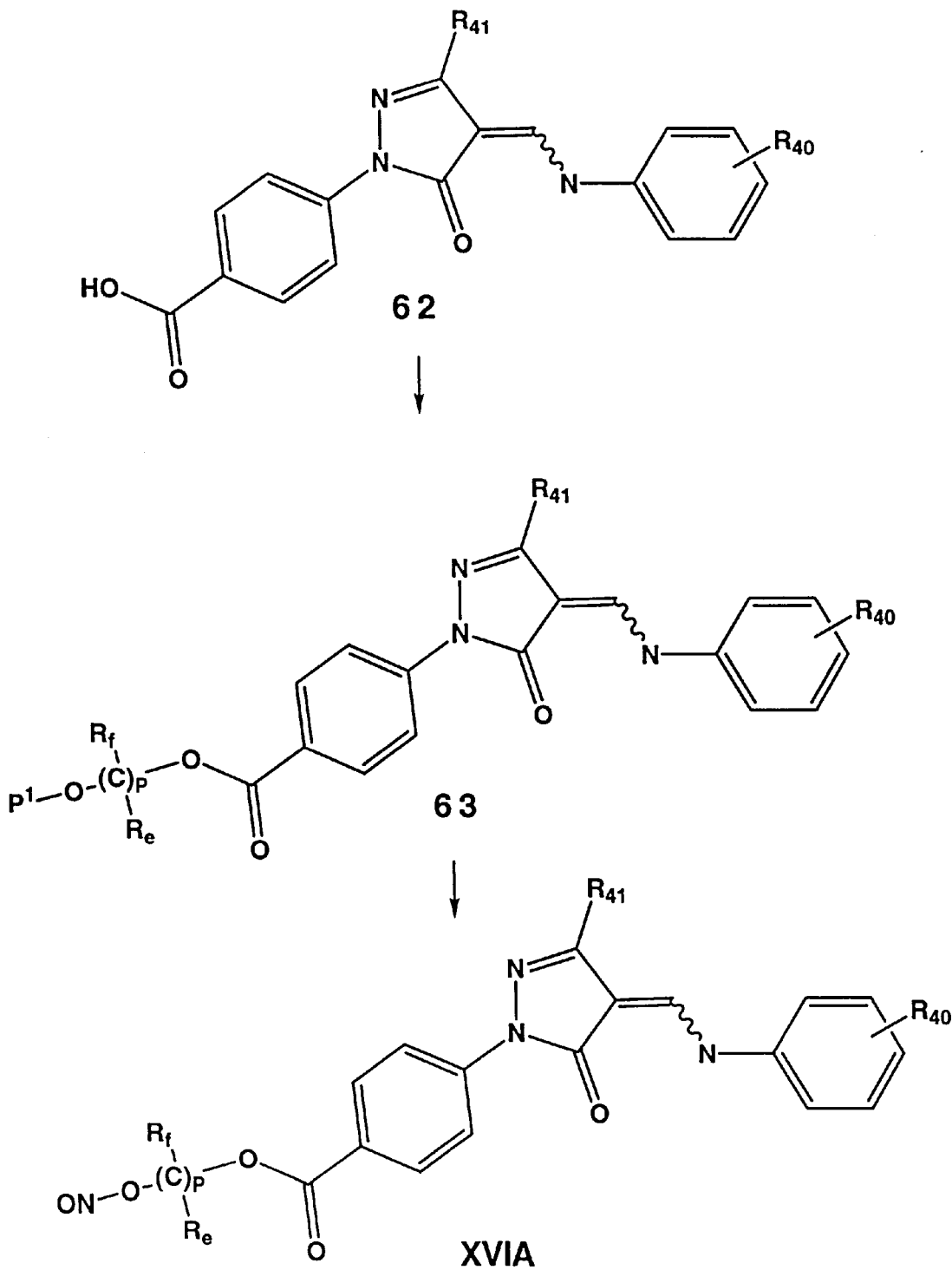
FIG. 46 shows a synthetic scheme for the preparation of nitrite containing substituted 2-pyrazolin-5-one derivatives.

Nitroso compounds of structure (XVI), wherein $R_e$, $R_f$, $R_{40}$, $R_{41}$ and p are as defined herein, and a nitrite containing benzoic ester substituent is representative of the $R_{42}$ group, as defined herein, may be prepared according to FIG. 46. 2-Pyrazolin-5-one of the formula 62 is converted to the ester of the formula 63, wherein $P^1$ is as defined herein, by reaction with a monoprotected diol. Preferred methods for the formation of esters are reacting the alcohol with the preformed acid chloride or symmetrical anhydride of the carboxylic acid or condensing the alcohol and carboxylic acid with a dehydrating agent, such as DCC or EDAC.HCl, in the presence of a catalyst, such as DMAP or HOBt. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a stoichometric quantity of a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XVIA.

Figure 47:
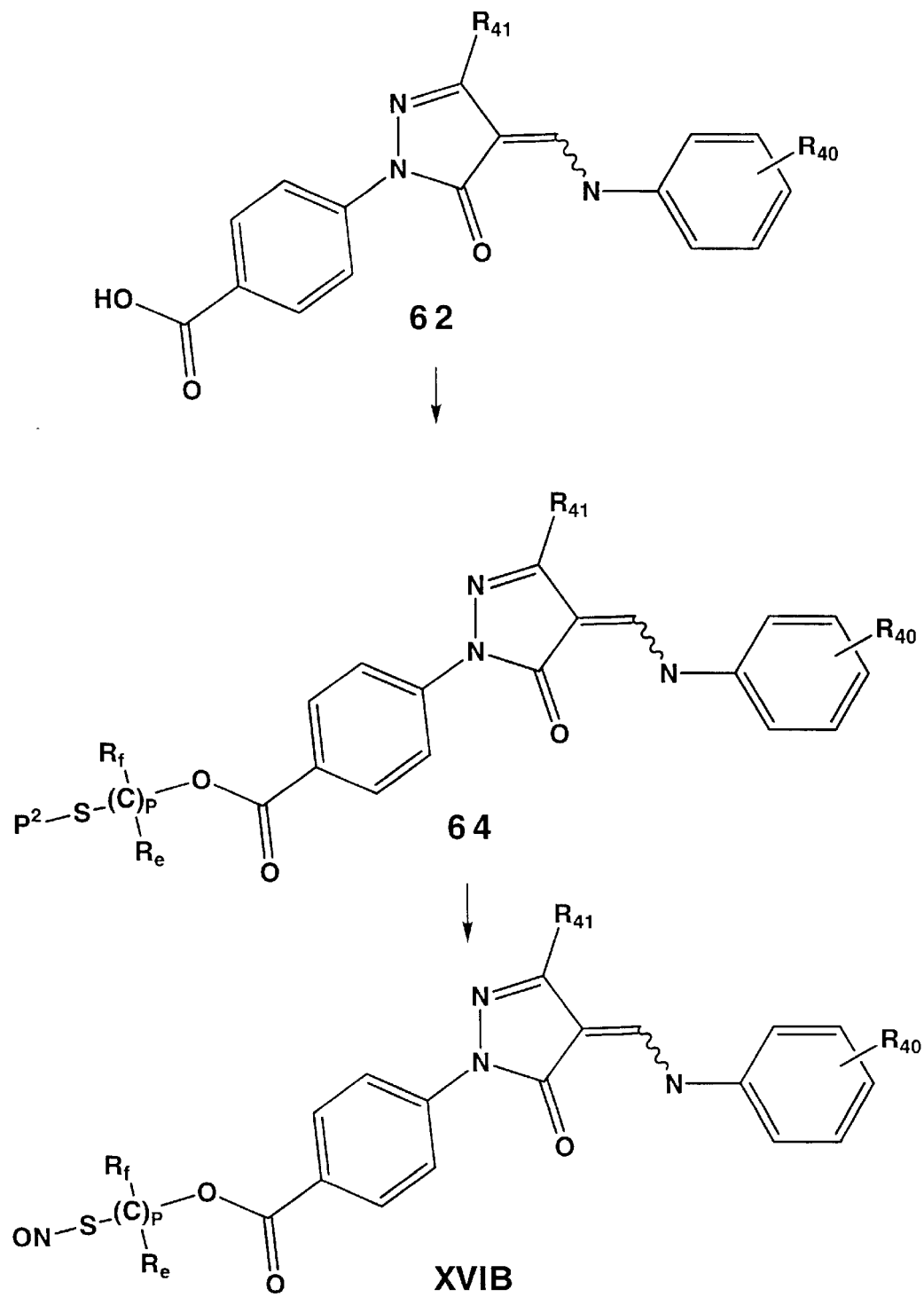
FIG. 47 shows a synthetic scheme for the preparation of nitrosothiol containing substituted 2-pyrazolin-5-one derivatives.

Nitroso compounds of structure (XVI), wherein $R_e$, $R_f$, $R_{40}$, $R_{41}$ and p are as defined herein, and a nitrosothiol containing benzoic ester substituent is representative of the $R_{42}$ group, as defined herein, may be prepared according to FIG. 47. 2-Pyrazolin-5-one of the formula 62 is converted to the ester of the formula 64, wherein $P^2$ is as defined herein, by reaction with a sulfanyl protected alcohol. Preferred methods for the formation of esters are reacting the alcohol with the preformed acid chloride or symmetrical anhydride of the carboxylic acid or condensing the alcohol and carboxylic acid with a dehydrating agent, such as DCC or EDAC.HCl, in the presence of a catalyst, such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the sulfanyl moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction with a stoichometric quantity of a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure XVIB. Alternatively, treatment of the deprotected thiol derived from compound 64 with a stoichiometric quantity of sodium nitrite in an acidic aqueous or alcoholic solution affords the compound of structure XVIB.

Figure 48:
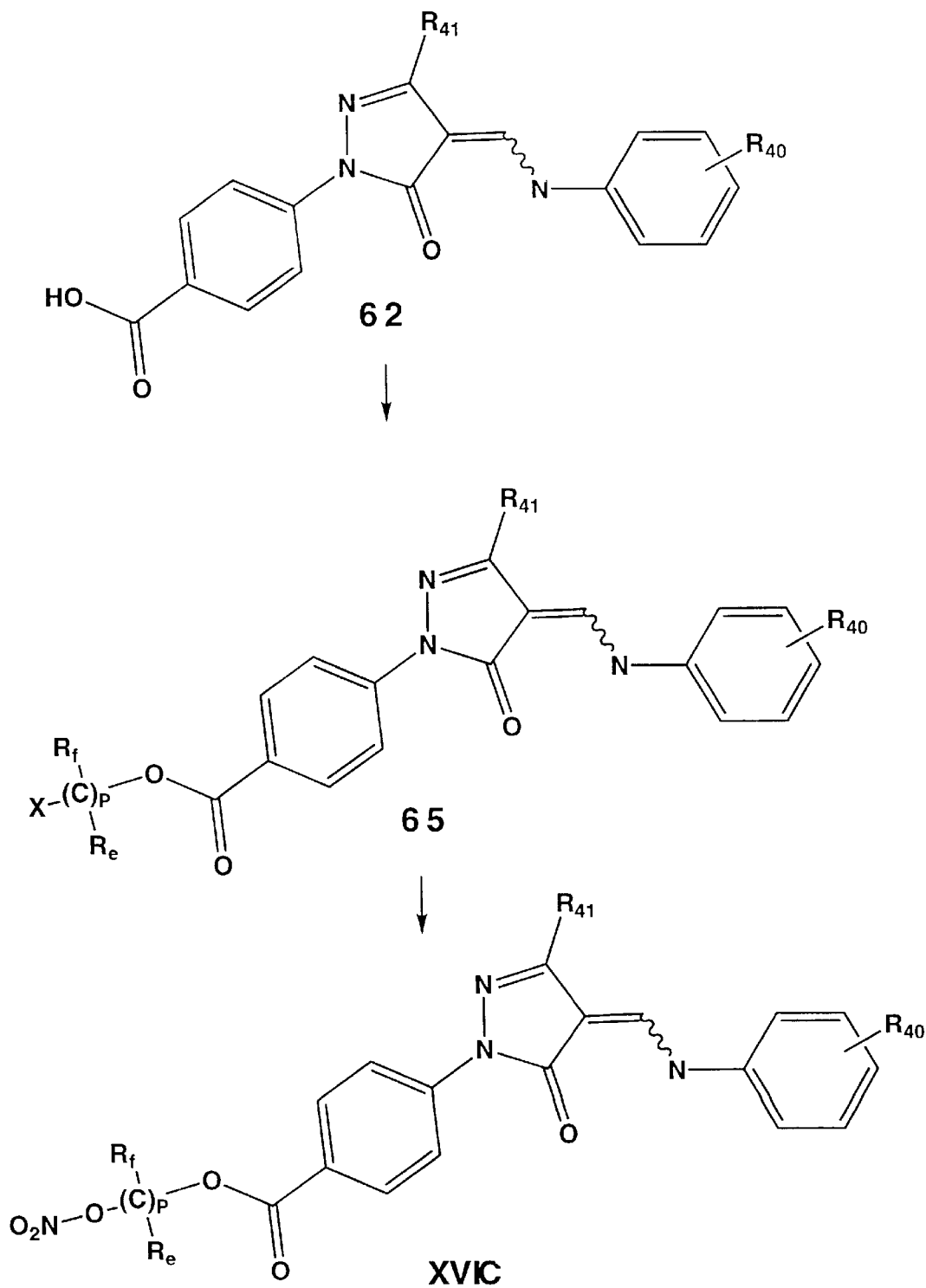
FIG. 48 shows a synthetic scheme for the preparation of nitrate containing substituted 2-pyrazolin-5-one derivatives.

Nitro compounds of structure (XVI), wherein $R_e$, $R_f$, $R_{40}$, $R_{41}$ and p are as defined herein, and a nitrate containing benzoic ester substituent is representative of the $R_{42}$ group, as defined herein, may be prepared according to FIG. 48. 2-Pyrazolin-5-one of the formula 62 is converted to the ester of the formula 65, wherein X is as defined herein, by reaction with a halogen containing alcohol. Preferred methods for the formation of esters are reacting the alcohol with the preformed acid chloride or symmetrical anhydride of the carboxylic acid or condensing the alcohol and carboxylic acid with a dehydrating agent, such as DCC or EDAC.HCl, in the presence of a catalyst, such as DMAP or HOBt. Preferred halides are bromide and iodide. Reaction of the amide of structure 64 with a suitable nitrating agent, such as silver nitrate in an inert solvent, such as acetonitrile, affords the compound of structure XVIC.

Figure 49:
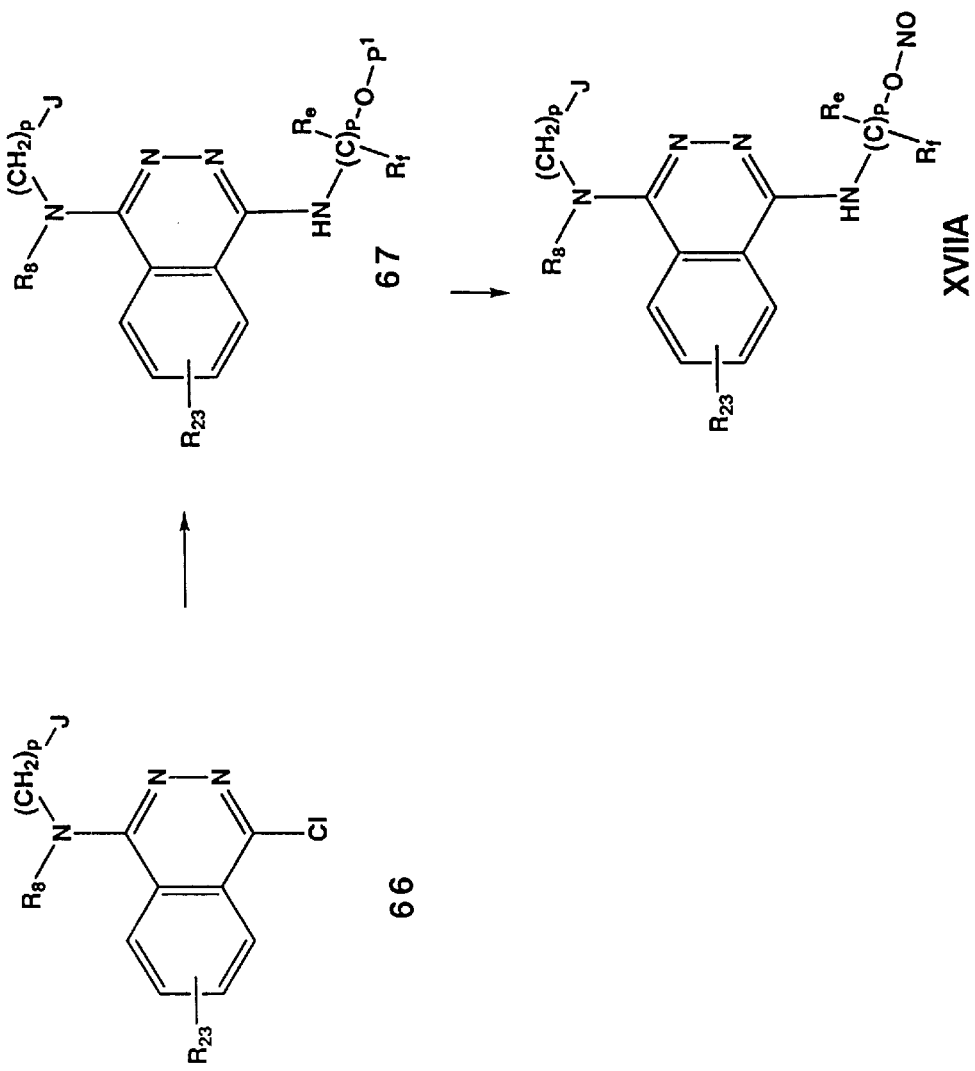
FIG. 49 shows a synthetic scheme for the preparation of nitrite containing substituted phthalazine derivatives.

Nitroso compounds of structure (XVII), wherein $R_e$, $R_f$, $R_8$, $R_{23}$, J and p are as defined herein, and a nitrite containing amino containing substituent is representative of the $R_{24}$ group, as defined herein, may be prepared according to FIG. 49. Chlorophthalazine of the formula 66 is converted to the compound of structure 67 by reaction with an amine containing a protected hydroxyl group, wherein $P^1$ is as defined herein. Preferred conditions for the formation of the compound of structure 67 are to heat the amine and the compound of structure 65 at 170° C. for several hours in a high boiling inert solvent such as 2-methylpyrrolidone in the presence of an amine base such as diisopropylethylamine. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a stoichometric quantity of a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XVIIA.

Figure 50:
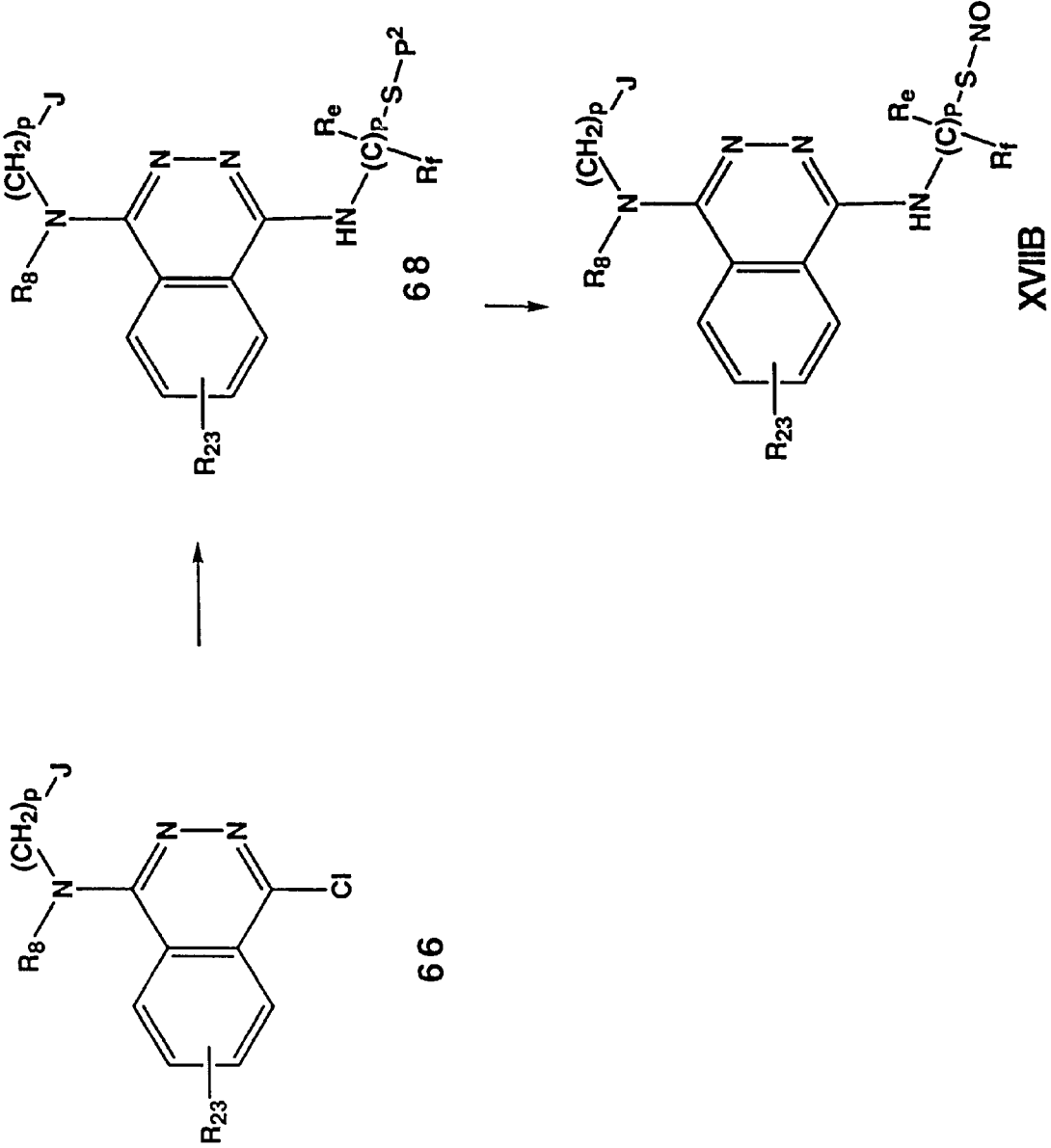
FIG. 50 shows a synthetic scheme for the preparation of nitrosothiol containing substituted phthalazine derivatives.

Nitroso compounds of structure (XVII), wherein $R_e$, $R_f$, $R_8$, $R_{23}$, J and p are as defined herein, and a nitrosothiol containing amino containing substituent is representative of the $R_{24}$ group, as defined herein, may be prepared according to FIG. 50. Chlorophthalazine of the formula 66 is converted to the compound of structure 68 by reaction with an amine containing a protected thiol group, wherein $P^2$ is as defined herein. Preferred conditions for the formation of the compound of structure 68 are to heat the amine and the compound of structure 65 at 170° C. for several hours in a high boiling inert solvent such as 2-methylpyrrolidone in the presence of an amine base such as diisopropylethylamine. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the sulfanyl moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction with a stoichometric quantity of a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure XVIIB. Alternatively, treatment of the deprotected thiol derived from compound 68 with a stoichiometric quantity of sodium nitrite in an acidic aqueous or alcoholic solution affords the compound of structure XVIIB.

Figure 51:
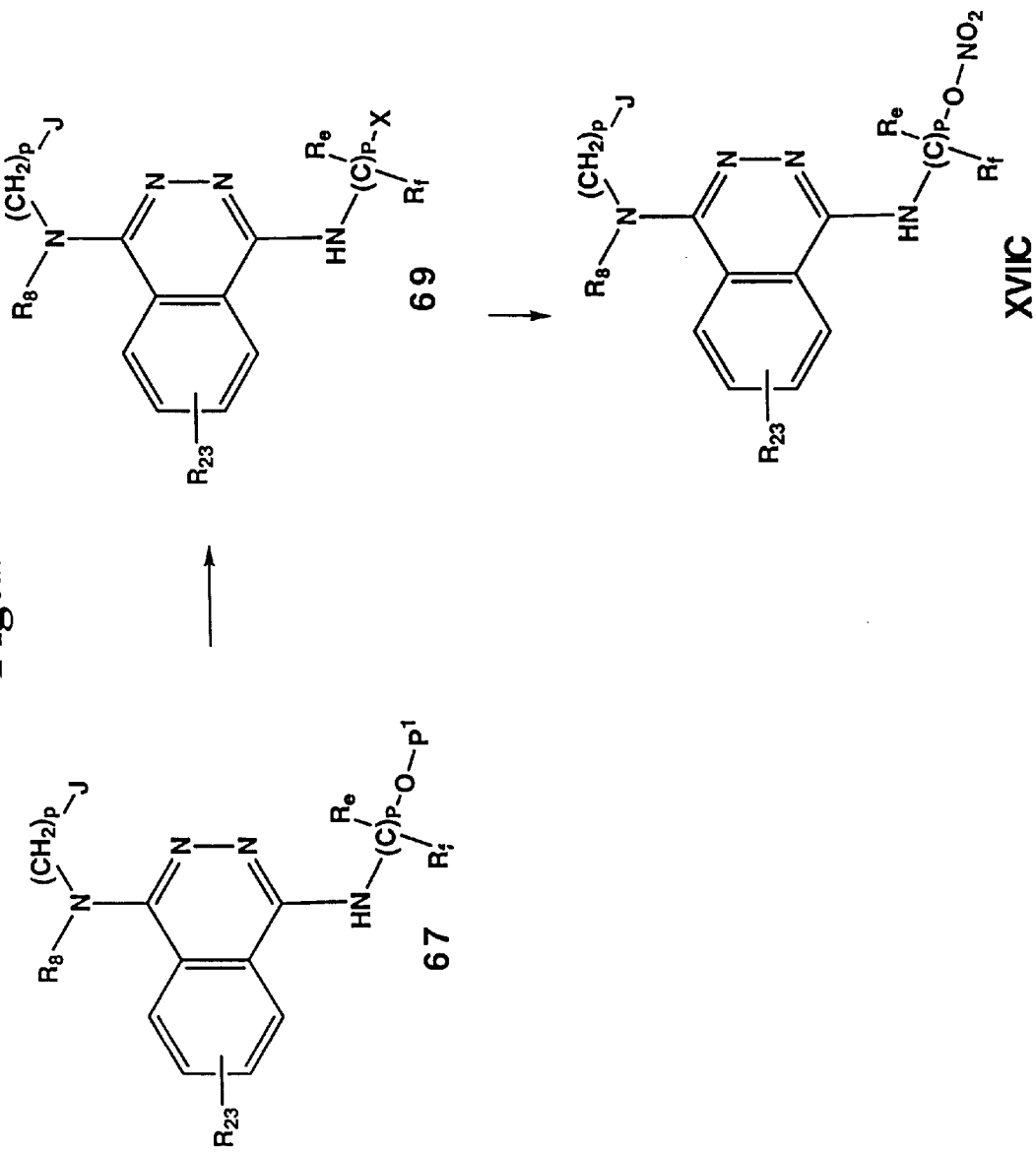
FIG. 51 shows a synthetic scheme for the preparation of nitrate containing substituted phthalazine derivatives.

Nitro compounds of structure (XVII), wherein $R_e$, $R_f$, $R_8$, $R_{23}$, J and p are as defined herein, and a nitrate containing substituent is representative of the $R_{24}$ group, as defined herein, may be prepared according to FIG. 51. Deprotection of the hydroxyl moiety of the compound of structure 67 (fluoride ion is the preferred method for removing silyl ether protecting groups) followed by activation and nucleophilic displacement of the hydroxyl by a halogen affords the compound of structure 69, wherein X is preferably a bromine or an iodine. Preferred methods for converting a hydroxyl group to a halogen moiety are to first activate it as the mesylate or tosylate by reacting it with methansulfonyl chloride or p-toluesulfonyl chloride in an inert solvent such as methylene chloride or THF in the presence of a base such as triethylamine followed by nucleophilic displacement of the sulfonate moiety with iodide or bromide by reaction with sodium iodide or sodium bromide in refluxing acetone. Reaction of the compound of structure 69 with a suitable nitrating agent such as silver nitrate in an inert solvent such as acetonitrile affords the compound of structure XVIIC.

Figure 52:
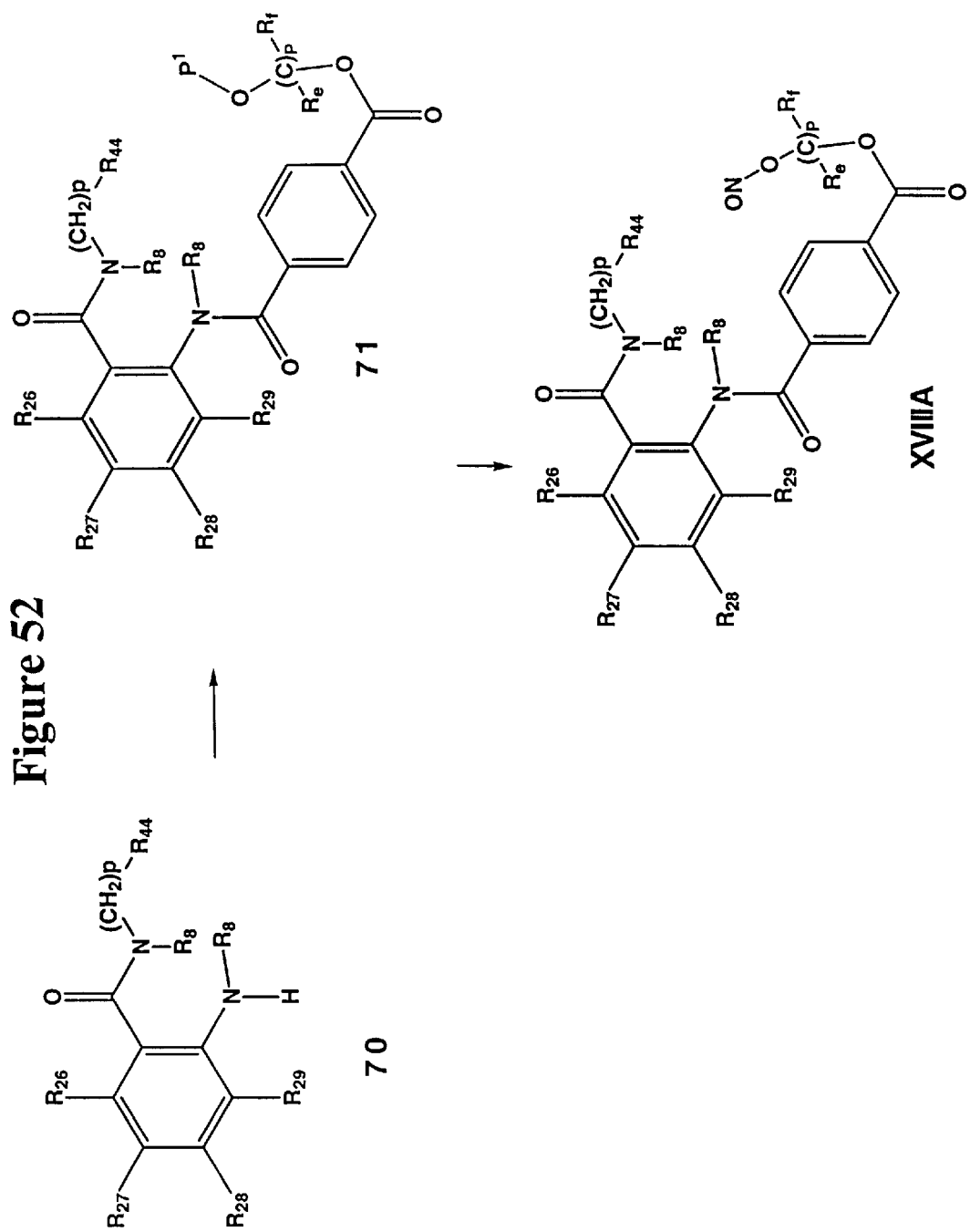
FIG. 52 shows a synthetic scheme for the preparation of nitrite containing substituted 2-aminobenzamide derivatives.

Nitroso compounds of structure (XVIII), wherein $R_e$, $R_f$, $R_8$, $R_{26}$, $R_{27}$, $R_{28}$, $R_{29}$, $R_{44}$ and p are as defined herein, and a nitrite containing ester substituted benzoate is representative of the D group, as defined herein, may be prepared according to FIG. 52. Anthranilic amide of the formula 70 is converted to the N-acylated compound of the formula 71, wherein $P^1$ is as defined herein, by reaction with a hydroxy protected carboxylic ester substituted benzoic acid derivative. Preferred methods for the formation of amides are reacting the amine with the preformed acid chloride or symmetrical anhydride of the carboxylic acid or condensing the amine and carboxylic acid with a dehydrating agent, such as DCC or EDAC.HCl, in the presence of a catalyst, such as DMAP or HOBt. Preferred protecting groups for the alcohol moiety are silyl ethers, such as a trimethylsilyl or a tert-butyldimethylsilyl ether. Deprotection of the hydroxyl moiety (fluoride ion is the preferred method for removing silyl ether protecting groups) followed by reaction with a stoichiometric quantity of a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XVIIIA.

Figure 53:
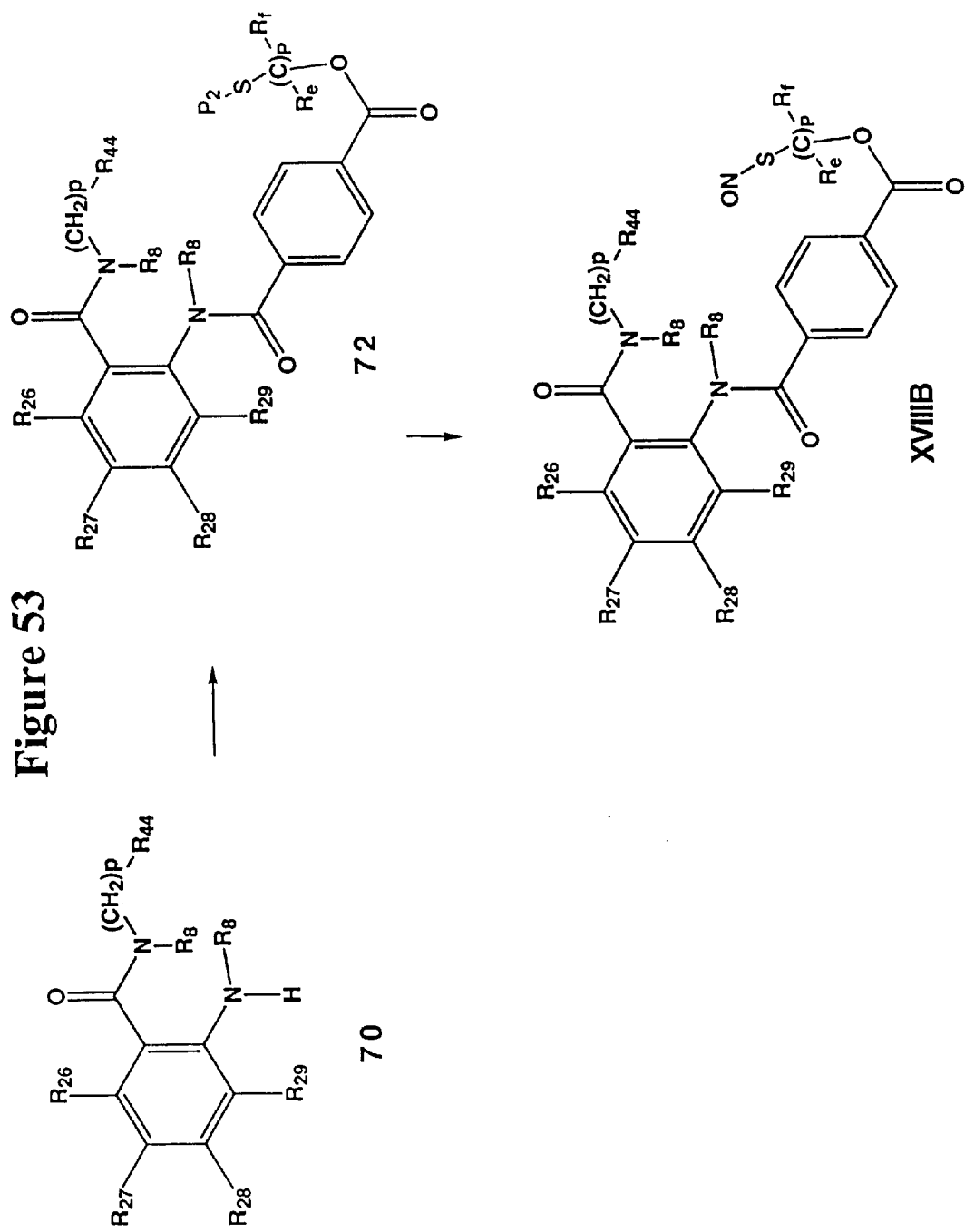
FIG. 53 shows a synthetic scheme for the preparation of nitrosothiol containing substituted 2-aminobenzamide derivatives.

Nitroso compounds of structure (XVIII), wherein $R_e$, $R_f$, $R_8$, $R_{26}$, $R_{27}$, $R_{28}$, $R_{29}$, $R_{44}$ and p are as defined herein, and a nitrosothiol containing ester substituted benzoate is representative of the D group, as defined herein, may be prepared according to FIG. 53. Anthranilic amide of the formula 70 is converted to the N-acylated compound of structure 72, wherein $P^2$ is as defined herein, by reaction with a sulfanyl protected carboxylic ester substituted benzoic acid derivative. Preferred methods for the formation of amides are reacting the amine with the preformed acid chloride or symmetrical anhydride of the carboxylic acid or condensing the amine and carboxylic acid with a dehydrating agent, such as DCC or EDAC.HCl, in the presence of a catalyst, such as DMAP or HOBt. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxy-benzyl thioether, a tetrahydropyranyl thioether or a 2,4,6-trimethoxybenzyl thioether. Deprotection of the sulfanyl moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction with a stoichometric quantity of a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure XVIIIB. Alternatively, treatment of the deprotected thiol derived from compound 72 with a stoichiometric quantity of sodium nitrite in an acidic aqueous or alcoholic solution affords the compound of structure XVIIIB.

Figure 54:
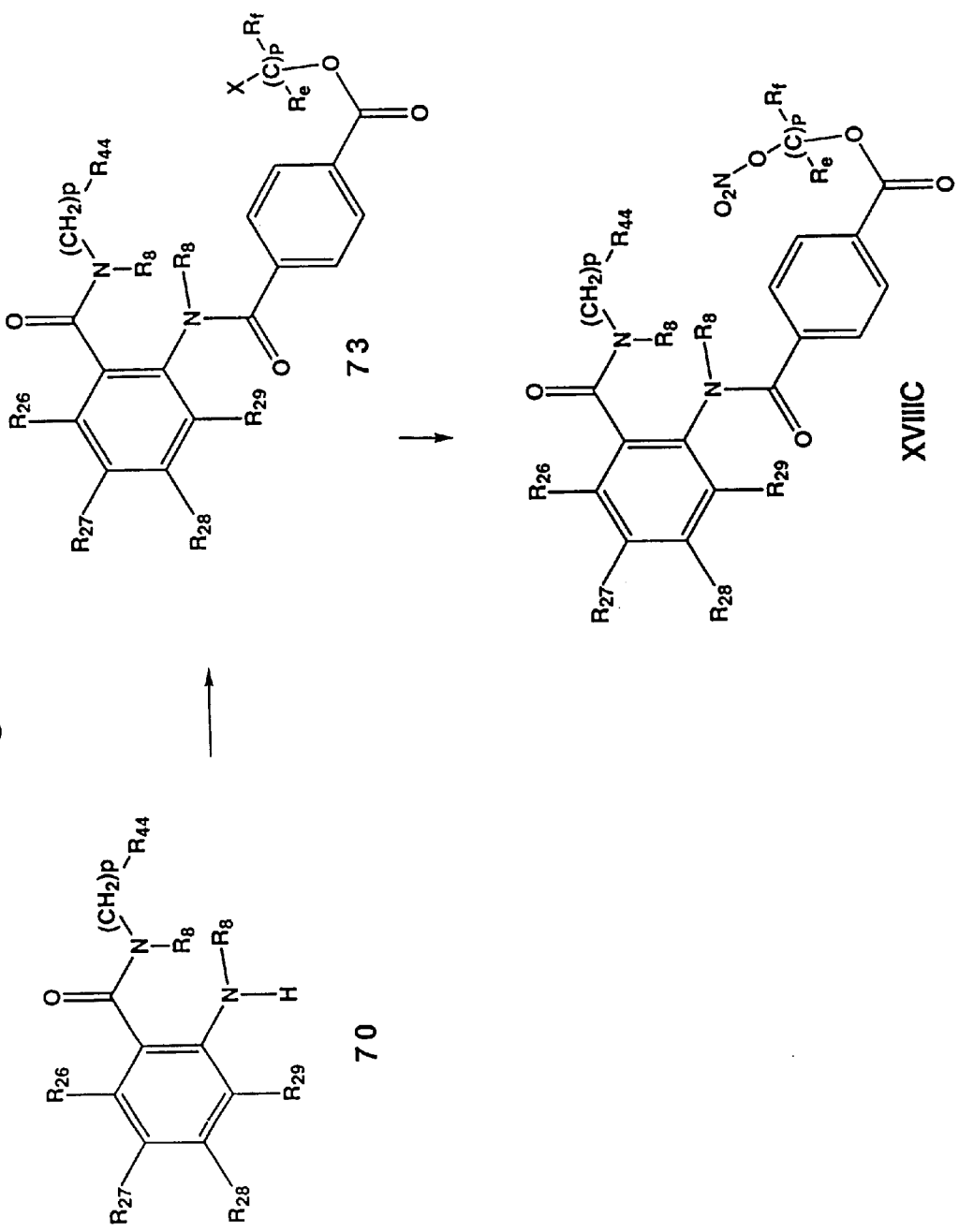
FIG. 54 shows a synthetic scheme for the preparation of nitrate containing substituted 2-aminobenzamide derivatives.

Nitro compounds of structure (XVIII), wherein $R_e$, $R_f$, $R_g$, $R_{26}$, $R_{27}$, $R_{28}$, $R_{29}$, $R_{44}$ and p are as defined herein, and a nitrate containing ester substituted benzoate is representative of the D group, as defined herein, may be prepared according to FIG. 54. Anthranilic amide of the formula 70 is converted to the N-acylated compound of the formula 73, wherein X is as defined herein, by reaction with a halogen containing carboxylic ester substituted benzoic acid derivative. Preferred methods for the formation of amides are reacting the amine with the preformed acid chloride or symmetrical anhydride of the halide containing acid or condensing the amine and halide containing acid derivative with a dehydrating agent, such as DCC or EDAC.HCl in the presence of a catalyst, such as DMAP or HOBt. Preferred halides are bromide and iodide. Reaction of the amide of structure 73 with a suitable nitrating agent, such as silver nitrate in an inert solvent, such as acetonitrile, affords the compound of structure XVIIIC.

Figure 55:
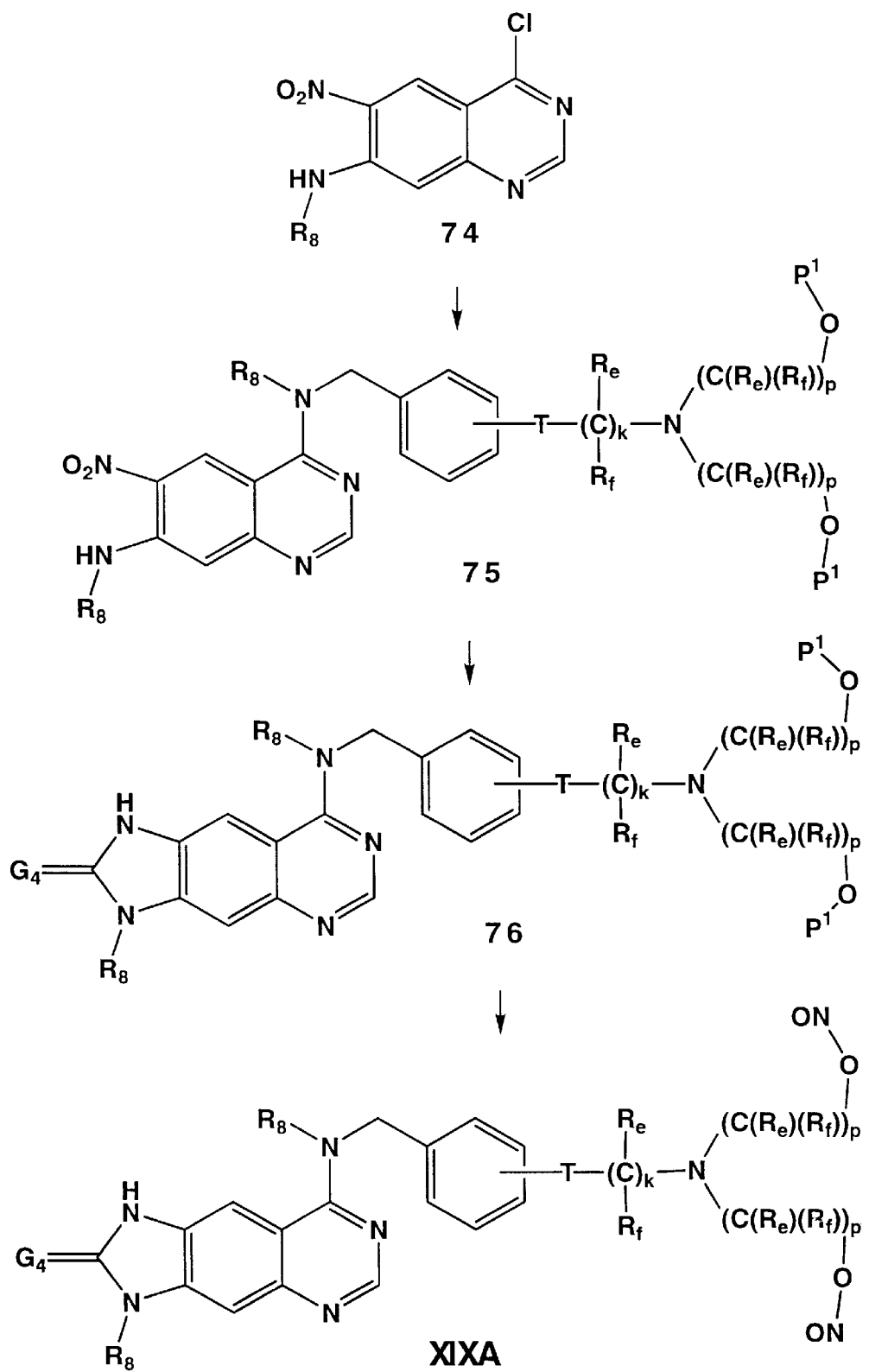
FIG. 55 shows a synthetic scheme for the preparation of nitrite containing substituted imidazoquinazoline derivatives.

Nitroso compounds of structure (XIX), wherein $R_e$, $R_f$, $R_g$, $G_4$, T and p are as defined herein, and nitrite containing substituents are representative of the $R_{46}$ and $R_{47}$ groups, as defined herein, may be prepared according to FIG. 55. Chloroquinazoline of the formula 74 is converted to the compound of structure 75 by reaction with an substituted benzyl amine containing protected hydroxyl groups, wherein $p^1$ is as defined herein. Preferred conditions for the formation of the compound of structure 75 are to heat the amine and the compound of structure 74 at an elevated temperature for several hours in an inert solvent such as isopropanol at reflux. Compound of the formula 75 is then converted into compound of the formula 76 by reduction of the nitro substituent followed by reaction with phosgene, thiophosgene or an equivalent in the presence of a base such as pyridine or triethylamine. Preferred methods for the reduction of nitro groups are to use hydrogen (1-3 atmospheres) in the presence of a palladium catalyst such as palladium on charcoal in an inert solvent such as ethanol at a temperature of 25° C. to 50° C. or iron, tin or zinc metal in aqueous or alcoholic acid. Preferred protecting groups for the alcohol moieties are silyl ethers, such as trimethylsilyl or tert-butyldimethylsilyl ethers. Deprotection of the hydroxyl moieties (fluoride ion is the preferred method for removing silyl ether protecting groups) followed by reaction with a stoichometric quantity of a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of structure XIXA.

Figure 56:
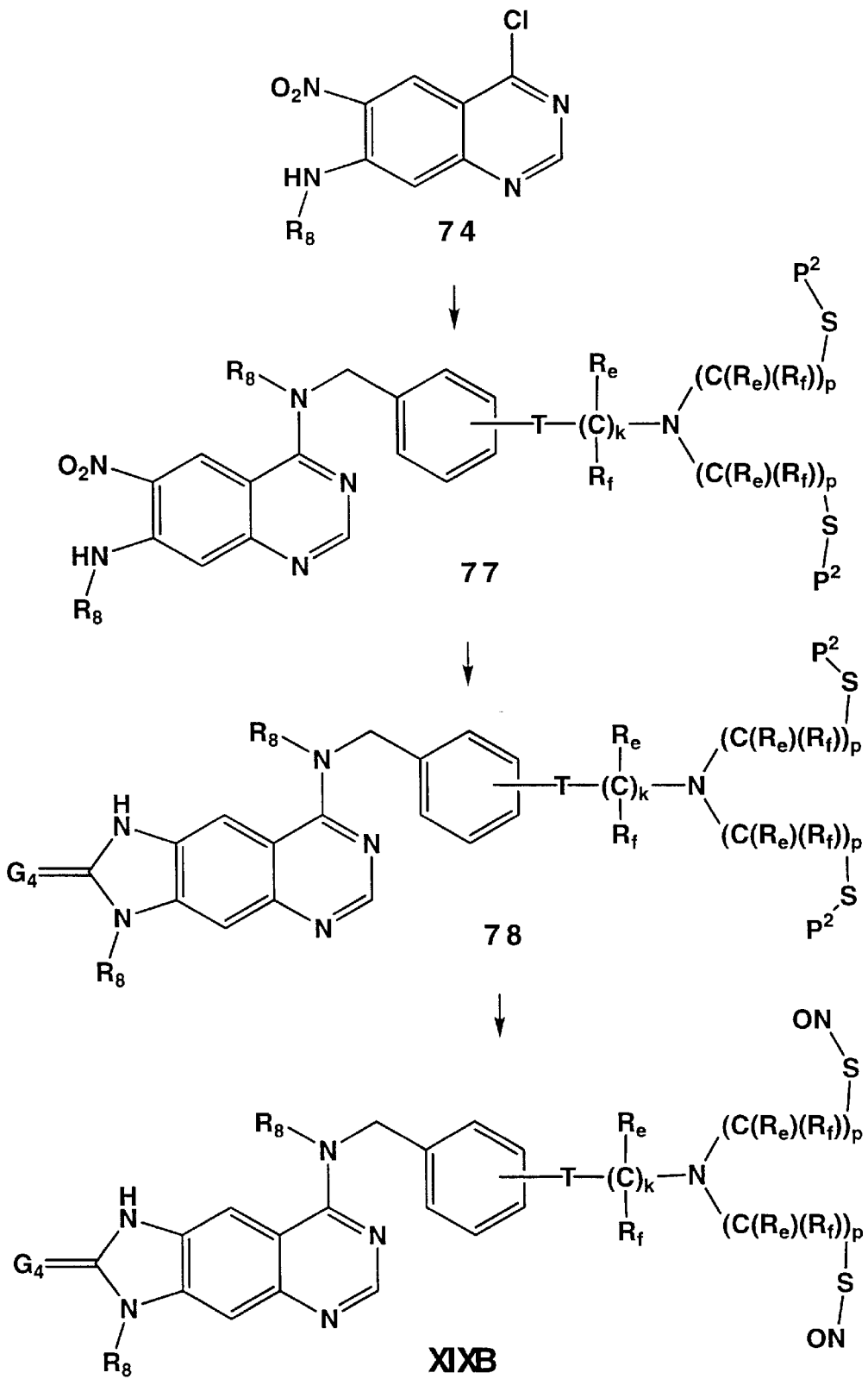
FIG. 56 shows a synthetic scheme for the preparation of nitrosothiol containing substituted imidazoquinazoline derivatives.

Nitroso compounds of structure (XIX), wherein $R_e$, $R_f$, $R_g$, $G_4$, T and p are as defined herein, and nitrosothiol containing substituents are representative of the $R_{46}$ and $R_{47}$ groups, as defined herein, may be prepared according to FIG. 56. Chloroquinazoline of the formula 74 is converted to the compound of structure 77 by reaction with a substituted benzyl amine containing protected thiol groups, wherein $P^2$ is as defined herein. Preferred conditions for the formation of the compound of structure 77 are to heat the amine and the compound of structure 74 for several hours in an inert solvent such as isopropanol at reflux. Compound of the formula 77 is then converted into compound of the formula 78 by reduction of the nitro substituent followed by reaction with phosgene, thiophosgene or an equivalent in the presence of a base such as pyridine or triethylamine. Preferred methods for the reduction of nitro groups are to use hydrogen (1-3 atmospheres) in the presence of a palladium catalyst such as palladium on charcoal in an inert solvent such as ethanol at a temperature of 25° C. to 50° C. or iron, tin or zinc metal in aqueous or alcoholic acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a 2,4,6-trimethoxybenzyl thioether. Deprotection of the sulfanyl moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether, or a 2,4,6-trimethoxybenzyl thioether group) followed by reaction with a stoichometric quantity of a suitable nitrosylating agent such as thionyl chloride nitrite, thionyl dinitrite, a lower alkyl nitrite such as tert-butyl nitrite, or nitrosonium tetrafluoroborate in a suitable anhydrous solvent such as methylene chloride, THF, DMF, or acetonitrile with or without an amine base such as pyridine or triethylamine affords the compound of structure XIXB. Alternatively, treatment of the deprotected thiol derived from compound 78 with a stoichiometric quantity of sodium nitrite in an acidic aqueous or alcoholic solution affords the compound of structure XIXB.

Figure 57:
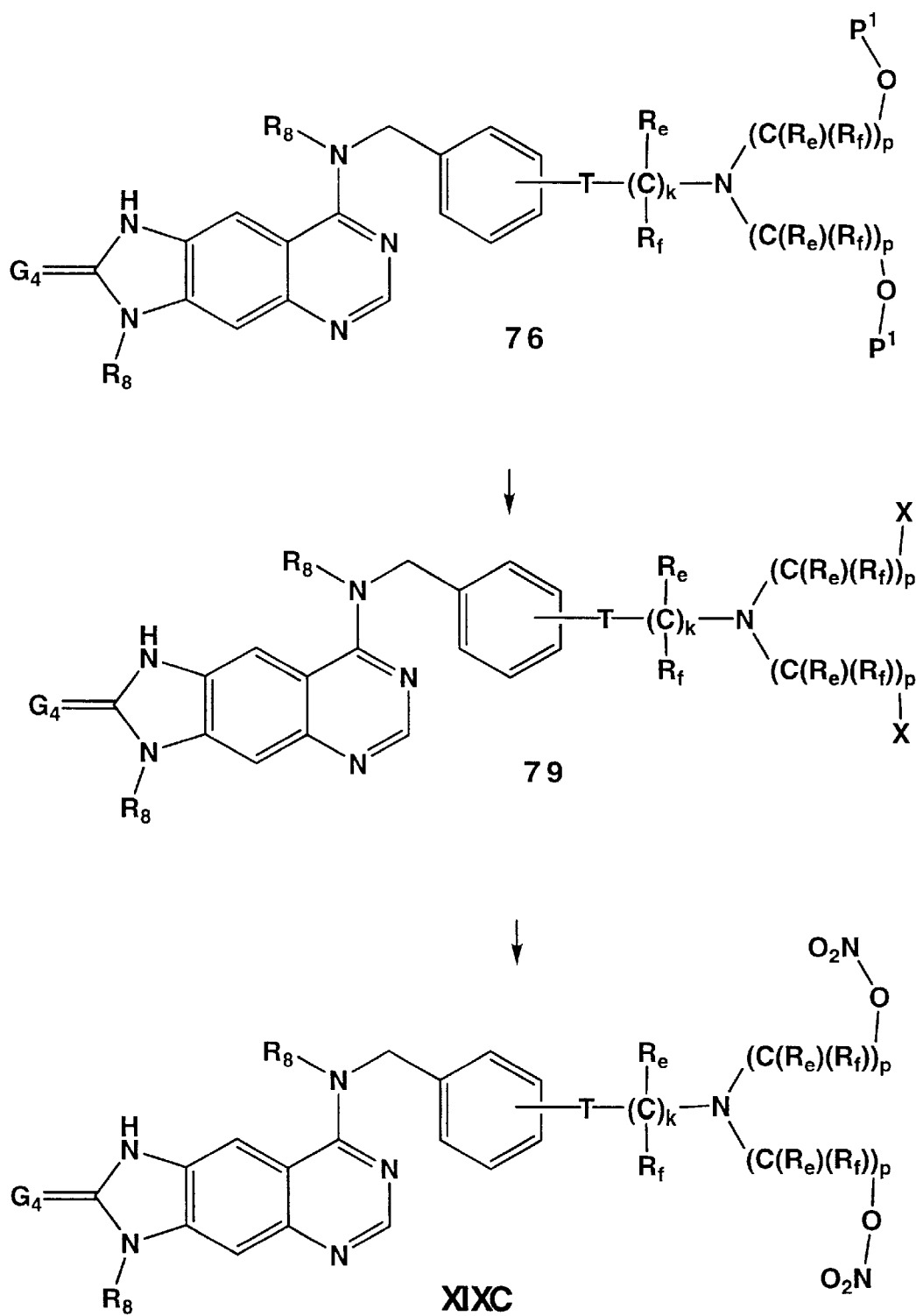
FIG. 57 shows a synthetic scheme for the preparation of nitrate containing substituted imidazoquinazoline derivatives.

Nitro compounds of structure (XIX), wherein $R_e$, $R_f$, $R_g$, $G_4$, T, k and p are as defined herein, and nitrate containing substituents are representative of the $R_{46}$ and $R_{47}$ groups, as defined herein, may be prepared according to FIG. 57. Deprotection of the hydroxyl moiety of the compound of structure 76 (fluoride ion is the preferred method for removing silyl ether protecting groups) followed by activation and nucleophilic displacement of the hydroxyl by a halogen affords the compound of structure 79, wherein X is preferably a bromine or an iodine. Preferred methods for converting a hydroxyl group to a halogen moiety are to first activate it as the mesylate or tosylate by reacting it with methansulfonyl chloride or p-toluesulfonyl chloride in an inert solvent such as methylene chloride or THF in the presence of a base such as triethylamine followed by nucleophilic displacement of the sulfonate moiety with iodide or bromide by reaction with sodium iodide or sodium bromide in refluxing acetone. Reaction of the compound of structure 79 with a suitable nitrating agent such as silver nitrate in an inert solvent such as acetonitrile affords the compound of structure XIXC.

The compounds of the present invention include PDE inhibitors, including those described herein, which have been nitrosated and/or nitrosylated through one or more sites such as oxygen (hydroxyl condensation), sulfur (sulfhydryl condensation), carbon and/or nitrogen. The nitrosated and/or nitrosylated PDE inhibitors of the present invention donate, transfer or release a biologically active form of nitrogen monoxide (nitric oxide).

Nitrogen monoxide can exist in three forms: NO− (nitroxyl), NO• (nitric oxide) and NO$^+$ (nitrosonium). NO• is a highly reactive short-lived species that is potentially toxic to cells. This is critical because the pharmacological efficacy of NO depends upon the form in which it is delivered. In contrast to the nitric oxide radical (NO•), nitrosonium (NO$^+$) does not react with $O_2$ or $O_2-$ species, and functionalities capable of transferring and/or releasing NO$^+$ and NO− are also resistant to decomposition in the presence of many redox metals. Consequently, administration of charged NO equivalents (positive and/or negative) does not result in the generation of toxic by-products or the elimination of the active NO moiety.

Compounds contemplated for use in the present invention (e.g., PDE inhibitors antagonists and/or nitrosated and/or nitrosylated PDE inhibitors) are, optionally, used in combination with nitric oxide and compounds that release nitric oxide or otherwise directly or indirectly deliver or transfer nitric oxide to a site of its activity, such as on a cell membrane in vivo.

The term "nitric oxide" encompasses uncharged nitric oxide (NO•) and charged nitrogen monoxide species, preferably charged nitrogen monoxide species, such as nitrosonium ion (NO$^+$) and nitroxyl ion (NO-). The reactive form of nitric oxide can be provided by gaseous nitric oxide. The nitric oxide releasing, delivering or transferring compounds, have the structure F—NO, wherein F is a nitric oxide releasing, delivering or transferring moiety, include any and all such compounds which provide nitric oxide to its intended site of action in a form active for its intended purpose. The term "NO adducts" encompasses any nitric oxide releasing, delivering or transferring compounds, including, for example, S-nitrosothiols, organic nitrites, organic nitrates, S-nitrothiols, sydnonimines, 2-hydroxy-2-nitrosohydrazines (NONOates), (E)-alkyl-2-[(E)-hydroxyimino]-5-nitro-3-hexene amines or amides, nitrosoamines, furoxanes as well as substrates for the endogenous enzymes which synthesize nitric oxide. The "NO adducts" can be mono-nitrosylated, poly-nitrosylated, mono-nitrosated and/or poly-nitrosated at a variety of naturally susceptible or artificially provided binding sites for nitric oxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) HS[C($R_e$)($R_f$)]$_m$SNO;

(ii) ONS[C($R_e$)($R_f$)]$_m$$R_e$; and (iii) $H_2$N—CH($CO_2$H)—($CH_2$)$_m$—C(O)NH—CH($CH_2$SNO)—C(O)NH—$CH_2$—$CO_2$H;

wherein m is an integer of from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, am alkoxy, a haloalkoxy, an amino, an alkylamino, a dialkylamino, an arylamino, a diarylamino, an alkylarylamino an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or —T—Q; or $R_e$ and $R_f$ taken together are a carbonyl, a methanthial, a heterocyclic ring, a cycloalkyl group or a bridged cycloalkyl group; Q is —NO or —$NO_2$; and T is independently a covalent bond, an oxygen, S(O)$_o$ or N$R_i$, wherein o is an integer from 0 to 2, and $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, carboxamido, —$CH_2$—C(T—Q)($R_e$)($R_f$), or —($N_2O_2$—)M$^+$, wherein M$^+$ in an organic or inorganic cation; with the proviso that when $R_i$ is —$CH_2$—C(T—Q)($R_e$)($R_f$) or —($N_2O_2$—)M$^+$; then "—T—Q" can be a hydrogen, an alkyl group, an alkoxyalkyl group, an aminoalkyl group, a hydroxy group or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O—, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C-heterocyclic compounds.

Another group of NO adducts for use in the present invention include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—N—, $O_2N$—S— or $O_2N$—C— modified and unmodified oligonucleotides (comprising at least 5 nucleotides, preferably 5–200 nucleotides); $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

Another group of NO adducts are N-oxo-N-nitrosoamines that donate, transfer or release nitric oxide and are represented by the formula: $R^1R^2$—N(O—M$^+$)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where M$^+$ is an organic or inorganic cation, such as, for example, an alkyl substituted ammonium cation or a Group I metal cation.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO–) and uncharged nitric oxide (NO•). Compounds where the thiol groups are not sufficiently close to form disulfide bridges generally provide nitric oxide as the NO– form and not as the uncharged NO• form.

The present invention is also directed to agents that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine or glutamine, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. U.S.A*, 84:9265–9269 (1987)).

The present invention is also based on the discovery that the administration of a therapeutically effective amount of the compounds and compositions described herein is effective for treating or preventing sexual dysfunctions or enhancing sexual responses in patients, including males and females. For example, the patient can be administered a therapeutically effective amount of at least one nitrosated and/or nitrosylated PDE inhibitor of the present invention. In another embodiment, the patient can be administered a therapeutically effective amount of at least one PDE inhibitor, optionally substituted with at least one NO and/or $NO_2$ group, and at least one compound that donates, transfers or releases nitric oxide, or elevates levels of endogenous EDRF or nitric oxide, or is a substrate for nitric oxide synthase. In yet another embodiment, the patient can be administered a therapeutically effective amount of at least one PDE inhibitor, optionally substituted with at least one NO and/or $NO_2$ group, and at least one vasoactive agent, and, optionally, at least one compound that donates, transfers or releases nitric oxide, or elevates levels of endogenous EDRF or nitric oxide, or is a substrate for nitric oxide synthase. The compounds can be administered separately or in the form of a composition.

A vasoactive agent is any therapeutic agent capable of relaxing vascular smooth muscle. Suitable vasoactive agents include, but are not limited to, potassium channel activators (such as, for example, nicorandil, pinacidil, cromakalim, minoxidil, aprilkalim, loprazolam and the like); calcium blockers (such as, for example, nifedipine, veraparmil, diltiazem, gallopamil, niludipine, nimodipins, nicardipine, and the like); β-blockers (such as, for example, butixamine, dichloroisoproterenol, propanolol, alprenolol, bunolol, nadolol, oxprenolol, perbutolol, pinodolol, sotalol, timolol, metoprolol, atenolol, acebutolol, bevantolol, pafenolol, tolamodol, and the like); long and short acting α-adrenergic receptor antagonist (such as, for example, phenoxybenzamide, dibenamine, doxazosin, terazosin, phentolamine, tolazoline, prozosin, trimazosin, yohimbine, moxisylyte and the like adenosine, ergot alkaloids (such as, for example, ergotamine, ergotamine analogs, including, for example, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride); vasoactive intestinal peptides (such as, for example, peptide histidine isoleucine, peptide histidine methionine, substance P, calcitonin gene-related peptide, neurokinin A, bradykinin, neurokinin B, and the like); dopamine agonists (such as, for example, apomorphine, bromocriptine, testosterone, cocaine, strychnine, and the like); opioid antagonists (such as, for example, naltrexone, and the like); prostaglandins (such as, for example, alprostadil, prostaglandin $E_2$, prostaglandin $F_2$, misoprostol, enprostil, arbaprostil, unoprostone, trimoprostil, carboprost, limaprost, gemeprost, lantanoprost, ornoprostil, beraprost, sulpostrone, rioprostil, and the like); endothelin antagonists (such as, for example, bosentan, sulfonamide endothelin antagonists, BQ-123, SQ 28608, and the like) and mixtures thereof.

Another embodiment of the present invention provides methods to prevent or treat diseases induced by the increased metabolism of cyclic guanosine 3',5'-monophosphate (cGMP), including, for example, hypertension, pulmonary hypertension, congestive heart failure, renal failure, myocardial infraction, stable, unstable and variant (Prinzmetal) angina, atherosclerosis, cardiac edema, renal insufficiency, nephrotic edema, hepatic edema, stroke, asthma, bronchitis, chronic obstructive pulmonary disease (COPD), cystic fibrosis, dementia, immunodeficiency, premature labor, dysmenorrhoea, benign prostatic hyperplasis (BPH), bladder outlet obstruction, incontinence, conditions of reduced blood vessel patency, e.g., postpercutaneous transluminal coronary angioplasty (post-PTCA), peripheral vascular disease, allergic rhinitis, glucoma and diseases characterized by disorders of gut motility, e.g, irritable bowel syndrome (IBS) by administering to a patient in need thereof a therapeutically effective amount of the compounds and/or compositions described herein. For example, the patient can be administered a therapeutically effective amount of at least one nitrosated and/or nitrosylated PDE inhibitor of the present invention. In another embodiment, the patient can be administered a therapeutically effective amount of at least one PDE inhibitor, optionally substituted with at least one NO and/or $NO_2$ group, and at least one compound that donates, transfers or releases nitric oxide, or elevates levels of endogenous EDRF or nitric oxide or is a substrate for nitric oxide synthase. In yet another embodiment, the patient can be administered a therapeutically effective amount of at least one PDE inhibitor, optionally substituted with at least one NO and/or $NO_2$ group, and at least one vasoactive agent, and, optionally, at least one compound that donates, transfers or releases nitric oxide, or elevates levels of endogenous EDRF or nitric oxide, or is a substrate for nitric oxide synthase. The compounds and compositions of the present invention can also be administered in combination with other medications used for the treatment of these disorders.

When administered in vivo, the compounds and compositions of the present invention can be administered in combination with pharmaceutically acceptable carriers and in dosages described herein. When the compounds and compositions of the present invention are administered as a mixture of at least one nitrosated and/or nitrosylated PDE inhibitor or at least one PDE inhibitor and at least one nitric oxide donor, they can also be used in combination with one or more additional compounds which are known to be effective against the specific disease state targeted for treatment (e.g., vasoactive agents). The nitric oxide donors and/or vasoactive agents can be administered simultaneously with, subsequently to, or prior to administration of the PDE inhibitors, including those that are substituted with one or more NO and/or $NO_2$ groups, and/or other additional compounds.

The compounds and compositions of the present invention can be administered by any available and effective delivery system including, but not limited to, orally, bucally, parenterally, by inhalation spray, by topical application, by injection into the corpus cavernosum tissue, by transurethral drug delivery, transdermally, vaginally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques. Transdermal drug administration, which is known to one skilled in the art, involves the delivery of pharmaceutical agents via percutaneous passage of the drug into the systemic circulation of the patient. Topical administration can also involve transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Dosage forms for topical administration of the compounds and compositions of the present invention can include creams, sprays, lotions, gels, ointments, coatings for condoms and the like. Administration of the cream or gel can be accompanied by use of an applicator or by transurethral drug delivery using a syringe with or without a needle or penile or vaginal insert or device, and is within the skill of the art. Typically a lubricant and/or a local anesthetic for desensitization can also be included in the formulation or provided for use as needed. Lubricants include, for example, K-Y jelly (available from Johnson & Johnson) or a lidocaine jelly, such as Xylocaine 2% jelly (available from Astra Pharmaceutical Products). Local anesthetics include, for example, novocaine, procaine, tetracaine, benzocaine and the like.

The compounds and compositions of the present invention will typically be administered in a pharmaceutical composition containing one or more selected carriers or excipients. Examples of suitable carriers include, for example, water, silicone, waxes, petroleum jelly, polyethylene glycol, propylene glycol, liposomes, sugars, and the like. The compositions can also include one or more permeation enhancers including, for example, dimethylsulfoxide (DMSO), dimethyl formamide (DMF), N,N-dimethylacetamide (DMA), decylmethylsulfoxide (C10MSO), polyethylene glycol monolaurate (PEGML), glyceral monolaurate, lecithin, 1-substituted azacycloheptan-2-ones, particularly 1-N-dodecylcyclazacylcoheptan-2-ones (available under the trademark Azone™ from Nelson Research & Development Co., Irvine, Calif.), alcohols and the like.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compounds and compositions of the present invention can be formulated as pharmaceutically acceptable neutral or acid salt forms. Pharmaceutically acceptable salts include, for example, those formed with free amino groups such as those derived from hydrochloric, hydrobromic, hydroiodide, phosphoric, sulfuric, acetic, citric, benzoic, fumaric, glutamic, lactic, malic, maleic, succinic, tartaric, p-toluenesulfonic, methanesulfonic acids, gluconic acid, and the like, and those formed with free carboxyl groups, such as those derived from sodium, potassium, ammonium, calcium, ferric hydroxides, isopropylamine, triethylamine, 2-ethylamino ethanol, histidine, procaine, and the like.

"Therapeutically effective amount" refers to the amount of the PDE inhibitor, nitrosated and/or nitrosylated PDE inhibitor, nitric oxide donor and/or vasoactive agent that is effective to achieve its intended purpose. While individual patient needs may vary, determination of optimal ranges for effective amounts of each of the compounds and compositions is within the skill of the art. Generally, the dosage required to provide an effective amount of the composition, and which can be adjusted by one of ordinary skill in the art will vary, depending on the age, health, physical condition, sex, weight, extent of the dysfunction of the recipient, frequency of treatment and the nature and scope of the dysfunction.

The amount of a given PDE inhibitor (including nitrosated and/or nitrosylated PDE inhibitors) which will be effective in the prevention or treatment of a particular dysfunction or condition will depend on the nature of the dysfunction or condition, and can be determined by standard clinical techniques, including reference to Goodman and Gilman, supra; The Physician's Desk Reference, supra; Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the dysfunction or disorder, and should be decided by the physician and the patient's circumstances.

The usual doses of PDE inhibitors (including nitrosated and/or nitrosylated PDE inhibitors) are about 0.001 mg to about 100 mg per day, preferably about 0.5 mg to about 50 mg per day. The oral dose of PDE inhibitors (including nitrosated and/or nitrosylated PDE inhibitors) are about 1 mg to about 200 mg per day preferably about 5 mg to about 100 mg per day.

The doses of nitric oxide donors in the pharmaceutical composition can be in amounts of about 0.001 mg to about 20 g and the actual amount administered will be dependent on the specific nitric oxide donor. For example, when L-arginine is the nitric oxide donor, the dose is about 2 g/day to about 6 g/day, preferably about 3 g/day, administered orally at least one hour prior to sexual activity or sexual intercourse. Effective doses can be extrapolated from dose-response curves derived from in vitro or animal model test systems and are in the same ranges or less than as described for the commercially available compounds in the Physician's Desk Reference, supra.

The nitrosated and/or nitrosylated PDE inhibitors of the invention are used at dose ranges and over a course of dose regimen and are administered in the same or substantially equivalent vehicles/carrier by the same or substantially equivalent as their non-nitrosated/nitrosylated counterparts. The nitrosated and/or nitrosylated compounds of the invention can also be used in lower doses and in less extensive regimens of treatment. The amount of active ingredient that can be combined with the carrier materials to produce a single dosage form will vary depending upon the host treated and the particular mode of administration.

The dosage regimen for treating a condition with the compounds and/or compositions of this invention is selected in accordance with a variety of factors, including the type, age, weight, sex, diet and medical condition of the patient, the severity of the dysfunction, the route of administration, pharmacological considerations such as the activity, efficacy, pharmacokinetic and toxicology profiles of the particular compound used, whether a drug delivery system is used, and whether the compound is administered as part of a drug combination. Thus, the dosage regimen actually used can vary widely and therefore may deviate from the preferred dosage regimen set forth herein.

Particularly preferred methods of administration of the contemplated PDE inhibitor compositions (including nitrosated and/or nitrosylated PDE inhibitor compositions) for the treatment of male sexual dysfunction are by oral administration, by transdermal application, by injection into the corpus cavernosum, by transurethral administration or by the use of suppositories. The preferred methods of administration for female sexual dysfunction are by oral administration, topical application, transdermal application or by the use of suppositories.

The present invention also provides pharmaceutical kits comprising one or more containers filled with one or more of the ingredients of the pharmaceutical compounds and/or compositions of the present invention, including, one or more PDE inhibitors, optionally substituted with one or more NO and/or $NO_2$ groups, one or more of the NO donors, and one or more vasoactive agents. Such kits can also include, for example, other compounds and/or compositions (e.g., permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

Example 1

2,6-bis(diethyl(3-methyl-3-(nitrosothio)butyric acid ester)amino)-4,8-dipiperidinopyrimido-[5,4-d]-pyrimidine

1a. 3-Methyl-3(2,4,6-trimethoxyphenylmethylthio)butyric acid

To a solution of 3-mercapto-3-methylbutyric acid (Sweetman et al, *J. Med. Chem.*, 14:868 (1971)) (4.6 g, 34 mmol) in methylene chloride (250 ml) under nitrogen and cooled over ice/salt to 5° C. (internal temperature) was added trifluoroacetic acid (82 g, 0.72 mol). No significant temperature rise was noted during the addition. To this was then added dropwise a solution of 2,4,6-trimethoxybenzyl alcohol (Munson et al, *J. Org. Chem.*, 57:3013 (1992)) (6.45 g. 32 mmol) in methylene chloride (150 ml) such that the reaction temperature does not rise above 5° C. After the addition was complete, the mixture was stirred for an additional 5 minutes at 5° C. and the volatiles were removed in vacuo (toluene or ethyl acetate can be used to assist in the removal of volatile material). The residue was partitioned between diethyl ether and water and the organic phase dried over anhydrous sodium sulfate, filtered and the volatile material removed in vacuo. The residue was treated with activated charcoal and recrystalized from diethyl ether/hexane. The product was isolated as a white solid in 70% yield (7 g); mp 103–105° C. $^1$H NMR (CDCl$_3$) δ6.12 (s, 2 H), 3.80–3.85 (m, 11 H), 2.74 (s, 2 H), 1.47 (s, 6 H). $^{13}$C NMR (CDCl$_3$) δ173.9, 160.6, 158.6, 105.6, 90.5, 55.7, 55.3, 45.9, 43.6, 28.4, 21.0.

1b. 2,6-bis(diethyl-3-methyl-3(2,4,6-trimethoxyphenylmethylthio)butyric acid ester)amino)-4,8-dipiperidinopyrimido-[5,4-d]-pyrimidine Under a nitrogen atmosphere, dipyridamole (1.50 g, 2.97 mmol) was dissolved in anhydrous dimethylformamide (30 ml) and 4-dimethylaminopyridine (1.46 g, 11.9 mmol) was added, followed by the product of Example 1a (3.64 g, 11.9 mmol) and EDAC (2.28 g, 11.9 mmol). The resulting mixture was stirred 44 hours at 50° C. The solvent was evaporated in vacuo, and residue was partitioned between methylene chloride and water, washed with brine and dried over anhydrous sodium sulfate. Volatiles were evaporated and the residue was purified by flash chromatography on silica gel, eluting with hexane/ethyl acetate (2:1) to (1:1) to give the title compound (1.02 g, 23% yield). $^1$H NMR (CDCl$_3$, 300 MHz) δ1.45 (s, 24 H), 1.58–1.69 (m, 12 H), 2.70 (s, 8 H), 3.64–3.88 (m, 52 H), 4.02–4.06 (m, 8 H), 4.25–432 (m, 8 H), 6.10 (s, 8 H).

1c. 2,6-bis(diethyl-3-methyl-3-mercaptobutyric acid ester)amino)-4,8-dipiperidinopyrimido-[5,4-d]-pyrimidine The product of Example 1b (1.00 g, 0.63 mmol) was dissolved in methylene chloride (5.5 ml) and anisole (4.0 ml, 36. 9 mmol), phenol (0.400 g, 4.25 mmol), water (4.0 ml) and trifluoracetic acid (16 ml, 208 mmol) were added. After 1.5 hours of stirring at room temperature, toluene (5 ml) was added and volatiles were evaporated. The residue was purified by flash chromatography on silica gel eluting with hexane/ethyl acetate (5:1) to (3:1) to give the title compound (0.360 g, 59% yield). $^1$H NMR (CDCl$_3$, 300 MHz) δ1.47 (s, 24 H), 1.68–1.72 (m, 12 H), 2.29 (s, 4 H), 2.63 (s, 8 H), 3.85–3.92 (m, 8 H), 3.97–4.03 (m 8 H), 4.28–4.35 (m, 8 H).

1d. 2,6-bis(diethyl(3-methyl-3(nitrosothiol)butyric acid ester)amino)-4,8-dipiperidinopyrimido-[5,4-d]-pyrimidine The product of Example 1c (0.353 g, 0.36 mmol) was dissolved in acetic acid (20 ml) and 1 N solution of hydrochloric acid (3.5 ml) was added, followed by 1 N sodium nitrite solution (2.2 ml). After 30 minutes stirring at room temperature, the reaction mixture was lyophilized, the residue was suspended in methylene chloride and washed with water, brine, and dried over anhydrous sodium sulfate. The solvent was evaporated in vacuo, and the residue was purified by flash chromatography on silica gel eluting methylene chloride/methanol (12:1) to give the title compound (0.144 g, 37% yield). (CDCl$_3$, 300 MHz) δ1.52–1.73 (m, 12 H), 1.98 (s, 24 H), 3.20–3.38 (m, 8 H), 3.39–3.92 (m, 12 H), 3.94–4.35 (m, 12 H).

Example 2

1-(4-{{1,3-benzodioxol-5-methyl)amino)-6-chloro-2-quinazolinyl)-4 piperidine-carboxylic ethyl-(3-methyl-3(nitrosothiol)butyramide) thioester hydrochloride

2a. 3-Methyl-3(thioacetyl)butyric acid

To a solution of 3-mercapto-3-methylbutyric acid (Sweetman et al, *J. Med. Chem.*, 14:868 (1971)) (1.03 g, 7.7 mmol) in pyridine (1.6 ml) was added acetic anhydride (1.57 g, 15.4 mmol) and the reaction mixture was stirred at room temperature over night. The reaction mixture was slowly added to a 0° C. solution of 1 N HCl (20 ml) then water (10 ml) was added and the reaction mixture was stirred at room temperature for 20 hours. The solution was extracted with diethyl ether and the organic phase was washed with brine and then dried over anhydrous sodium sulfate. The solvent was evaporated in vacuo, and the residue was purified by flash chromatography on silica gel eluting with ethyl acetate/hexane (1:4) to give the title compound (0.791 g, 58% yield). (CDCl$_3$, 300 MHz) δ1.55 (s, 6 H), 2.25 (s, 3 H), 2.99 (s, 2 H).

2b. Mercaptoethyl-3-methyl-3(thioacetyl)butyramide

The product of Example 2a (0.556 g, 3.1 mmol) was dissolved in methylene chloride (10 ml) containing a catalytic amount of dimethylforamide (10 μl). Oxalyl chloride (0.556 g, 4.4 mmol) was added and the reaction mixture was stirred at room temperature for 1 hour. The volatile components were then evaporated in vacuo and the residue azeotroped with toluene (2×5 ml). The yellow oil remaining was added to a −78° C. solution of 2-aminoethanethiol hydrochloride (0.341 g, 3.0 mmol), and triethylamine (0.303 g, 3.0 mmol) in dimethylformamide (6 ml). The reaction mixture was stirred at −78° C. for 1 hour and then at room temperature for 2 hours. The reaction was quenched with water (20 ml) and then extracted with ethyl acetate. The organic phase was dried over anhydrous sodium sulfate and then concentrated in vacuo to afford the title compound (0.349 g, 53% yield) which was used without further purification. (CDCl$_3$, 300 MHz) δ1.5 (s, 6 H), 2.3 (s, 3 H), 2.6 (dd, 2 H), 2.8 (s, 2 H), 2.9 (s, 1 H), 3.4 (dd, 2 H), 6.0 (brs, 1 H).

2c. Mercaptoethyl-3-methyl-3(mercapto)butyramide

The product of Example 2b (0.314 g, 1.4 mmol) was dissolved in methanol (10 ml) and solid sodium hydroxide (85 mg, 2.1 mmol) was added. After stirring 5 minutes, the reaction mixture was diluted with ethyl acetate (50 ml) and washed with saturated aqueous sodium bicarbonate, followed by brine, and then dried over anhydrous sodium sulfate. The volatile components were evaporated in vacuo leaving the title compound as a colorless oil (0.188 g, 75% yield) which was used without further purification. (CDCl$_3$, 300 MHz) δ:1.42 (s, 6 H), 1.55 (s, 1 H), 2.17 (s, 1 H), 2.41 (s, 2 H), 2.61 (dd, J=12.5 Hz, k 6.2 Hz, 2 H), 3.39 (dd, J=12.5 Hz, 6.2 Hz, 2 H).

2d. 4-((1,3-benzodioxol-5-ylmethyl)amino)-2,6-dichloro quinazoline

A solution of 2,4,6-trichloroquinazoline (0.186 g, 0.80 mmol) in ethanol (20 ml) was heated to 55° C. and piperonylamine (0.145 g, 0.96 mmol) was added. The resulting mixture was stirred at 55° C. over night. Volatiles were evaporated and the residue was partitioned between methylene chloride and saturated solution of ammonium hydroxide. The organic phase was dried over anhydrous sodium sulfate and concentrated in vacuo to yield 0.268 g (96% yield) of the title compound as a white solid. $^1$H NMR (300 MHz, DMSO) δ4.59–4.63 (d, 2 H), 5.98 (s, 2 H), 6.86 (s, 2 H), 6.86 (s, 2 H), 6.96 (s, 1 H), 7.62–7.66 (d, 1 H), 7.79–7.84 (d, 1 H), 8.46 (s, 1 H), 9.24–9.28 (t, 1 H).

2e. 1-(4-((1,3-benzodioxol-5-ylmethyl)amino)-6-chloro-2-quinazolinyl)-4-piperidine-carboxylic acid ethyl ester The product of Example 2d (0.164 g. 0.47 mmol) and ethyl isonipecotate (0.200 ml, 1.27 mmol) were combined in 5 g of phenol. The resulting mixture was heated at reflux temperature (240° C.) for 5 hours. The mixture was allowed to cool down, dissolved in 20 ml chloroform and washed with 1 N solution of sodium hydroxide (2×40 ml). The organic fraction was dried over anhydrous sodium sulfate and concentrated in vacuo. The residue was purified by flash chromatography on silica gel, eluting with hexane/ethyl acetate (9:1) to (5:1) to give 0.164 g (53% yield) of the title compound as a solid. $^1$H NMR (300 MHz, CDCl$_3$) δ1.24–1.30 (t, 3 H), 1.70–1.79 (m, 2 H), 1.96–2.06 (m, 2 H), 2.54–2.58 (m, 1 H), 3.01–3.10 (t, 2 H), 4.10–4.20 (q, 2 H), 4.66–4.70 (d, 2 H), 4.77–4.84 (d, 2 H), 5.59 (s, 1 H), 5.97 (s, 2 H), 6.77–6.89 (m, 3 H), 7.40–7.45 (m, 3 H).

2f. 1-(4-((1,3-benzodioxol-5-ylmethyl)amino)-6-chloro-2-quinazolinyl)-4-piperidine-carboxylic acid The product of Example 2e (0.100 g, 0.21 mmol) was dissolved in ethanol (1 ml) and water (0.5 ml) was added, followed by sodium hydroxide (0.082 g, 2.05 mmol). The resulting mixture was heated at 100° C. for 20 minutes. The volatiles were evaporated, the residue was diluted with water (2 ml) and 1 N HCl was added until the pH of the reaction mixture registered pH 7. The reaction mixture was then filtered and the precipitate was washed with water (2 ml). Ethanol was added to the precipitate and the volatiles were evaporated to give 0.080 g (86% yield) of the title compound as a pale yellow solid. $^1$H NMR (300 MHz, DMSO) δ1.36–1.45 (m, 2 H), 1.75–1.83 (m, 2 H), 2.92–3.02 (m, 3 H), 4.54–4.60 (m, 4 H), 5.94 (s, 2 H), 6.83 (s, 2 H), 6.93 (s, 1 H), 7.21–7.26 (d, 1 H), 7.44–7.49 (d, 1 H), 8.13 (s, 1 H), 8.51–8.53 (t, 1 H).

2g. 1-(4-((1,3-benzodioxol-5-ylmethyl)amino)-6-chloro-2-quinazolinyl)-4-piperidine-carboxylic ethyl-(3-methyl-3-(thioacetyl)butyramide) thioester Under a nitrogen atmosphere, the product of Example 2f (0.147 g, 0.31 mmol) and triethylamine (0.043 ml, 0.31 mmol) were combined in 3 ml of DMF and heated to 50° C. to dissolve all solid. A solution of Example 2c (0.067 g, 0.38 mmol) in DMF (2 ml) was added, followed by EDAC (0.073 g, 0.38 mmol) and DMAP (0.015 g, 0.12 mmol). The resulting mixture was stirred at room temperature for 5 hours and then at 50° C. overnight. The reaction mixture was diluted with water (20 ml) and extracted with dichloromethane. The combined organic phase was washed with brine and dried over anhydrous sodium sulfate. The volatiles were evaporated and the residue was purified by flash chromatography on silica gel eluting with hexane/ethyl acetate (1:2) to give 0.038 g (21% yield) of the title compound. $^1$H NMR (300 MHz, CDCl$_3$) δ:1.48 (s, 6 H), 1.64–1.75 (m, 2 H), 1.94–2.00 (m, 2 H), 2.04 (s, 1 H), 2.45 (s, 2 H), 2.70–2.77 (m, 1 H), 2.91–2.96 (t, 2 H), 3.01–3.08 (t, 2 H), 3.42–3.48 (t, 2 H), 4.64–4.68 (d, 2 H), 4.87–4.94 (d, 2 H), 5.64–5.68 (m, 1 H), 5.96 (s, 2 H), 6.17–6.20 (m, 1 H), 6.75–6.85 (m, 3 H), 7.38–7.45 (m, 3 H).

2h. 1-(4-{{1,3-benzodioxol-5-methyl)amino)-6-chloro-2-quinazolinyl)-4-piperidine- carboxylic ethyl-(3-methyl-3(nitrosothiol)butyramide) thioester hydrochloride The product of Example 2g (0.034 g, 0.057 mmol) was dissolved in methanol/dichloromethane (1 ml, 1:1) and 4 N HCl in ether (0.100 ml) was added. Concentration in vacuo afforded a white solid. The white solid was then dissolved in a mixture of methylene chloride (3 ml) and methanol (1 ml), and the resulting solution was cooled to 0° C. Tert-butyl nitrite (0.034 ml, 0.29 mmol) was added and the reaction mixture was stirred at 0° C. for 30 minutes. The volatiles were evaporated to give 0.037 g (98% yield) of the title compound as a green solid. $^1$H NMR (300 MHz, CDCl$_3$) δ:1.61–1.76 (m, 4 H), 1.99 (s, 6 H), 2.66–2.85 (m, 1 H), 2.90–3.04 (m, 2 H), 3.18–3.45 (m, 4 H), 3.48 (s, 2 H), 4.59–4.86 (m, 4 H), 5.87 (s, 2 H), 6.62–6.71 (d, 1 H), 6.74 (s, 1 H), 6.80–6.88 (d, 1 H), 6.90 (s, 1 H), 7.48–7.56 (m, 1 H), 7.65–7.76 (m, 1 H), 8.14–8.19 (d, 1 H), 8.43 (s, 1 H).

Example 3

In vitro Comparative Relaxation Responses

Figure 58:
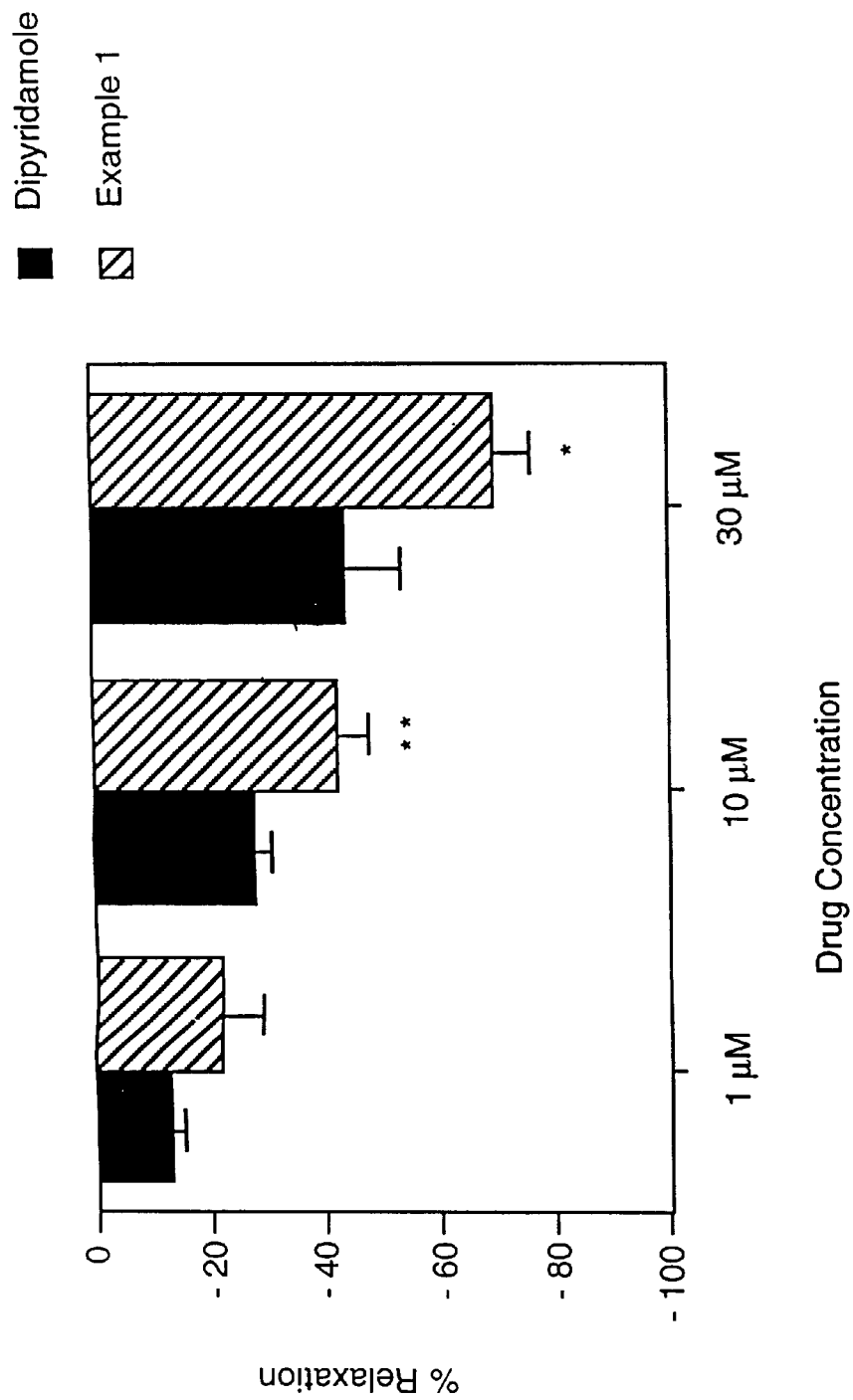
FIG. 58 shows the comparative in vivo relaxation effects of dipyridamole and the compound of Example 1 in phenylephrine-induced contacted human corpus cavernosum tissue.

Human corpus cavernosum tissue biopsies were obtained at the time of penile prosthesis implantation from impotent men. The tissue was maintained in a chilled Krebs-bicarbonate solution prior to assay. The tissue was cut into strips of 0.3×0.3×1 cm and suspended in organ chambers for isometric tension measurement. Tissues were incrementally stretched until optimal isometric tension for contraction was obtained. Once this was achieved, the tissues were contracted with phenylephrine ($7 \times 10^{-7}$ M) and once a stable contraction was achieved, the tissues were exposed to either dipyridamole or the compound of Example 1 ($10^{-6}$ to $3 \times 10^{-5}$ M) by cumulative additions to the chamber. At the end of the experiment, papaverine ($10^{-4}$ M) was added to obtain maximal relaxation. FIG. 58 shows that the compound of Example 1 at doses of 10 μM and 30 μM was more efficacious in relaxing the phenylephrine-induced contraction than was an equimolar dose of the phosphodiesterase inhibitor dipyridamole. Data were expressed as the percent loss in tone from the phenylephrine-induced contraction (0% = phenylephrine contraction; −100% = tone after administration of papaverine).

Example 4

In vivo Comparative Erectile Responses

White New Zealand male rabbits (2.6–3.0 kg) were anesthetized with pentobarbital sodium (30 mg/kg). The femoral artery was exposed and indwelled with PE 50 tubing connected to a transducer for recording systemic arterial blood pressure. The ventral aspect of the penis was then exposed via surgical cut and intracavernosal blood pressure was measured using a 23-gauge needle inserted to the corpus cavernosum. The contralateral corpus cavernosum was implanted with a 23-gauge needle for the administration of drugs.

Following all surgical procedures, rabbits were allowed to rest for 10 minutes during which intracavernosal blood pressure (ICP) and mean arterial blood pressure (MABP) were continuously recorded. All drug treatments were administered after stable intracavernosal and systemic blood pressures were established. If an increase in intracavernosal blood pressure (ICP) was observed, the effect was monitored throughout its entire duration. Animals that did not exhibit an increase in ICP received an injection of a combination of phentolamine (0.2 mg) and papaverine (6.0 mg) to confirm the accuracy of needle implantation and to evaluate the erectile responsiveness of the animal. Animals that did not respond to this combination were disregarded from the analysis.

Sildenafil hydrochloride was prepared as an aqueous solution (injection volume 1 ml) and administered intravenously into the ear vein. S-nitrosoglutathione (SNO-Glu) was prepared as an aqueous solution (200 μg in 200 μL) and injection intracorporally. Following drug injection the tubing was flushed with 100 μL distilled water. The following parameters were obtained from each experimental recording: (i) Maximum ICP (mm Hg), (ii) Duration (minutes), defined as the time in minutes, that the increase in ICP is greater than the 50% difference between baseline and maximum response. Data were analyzed using ANOVA statistical analysis (p<0.05).

Figure 59:
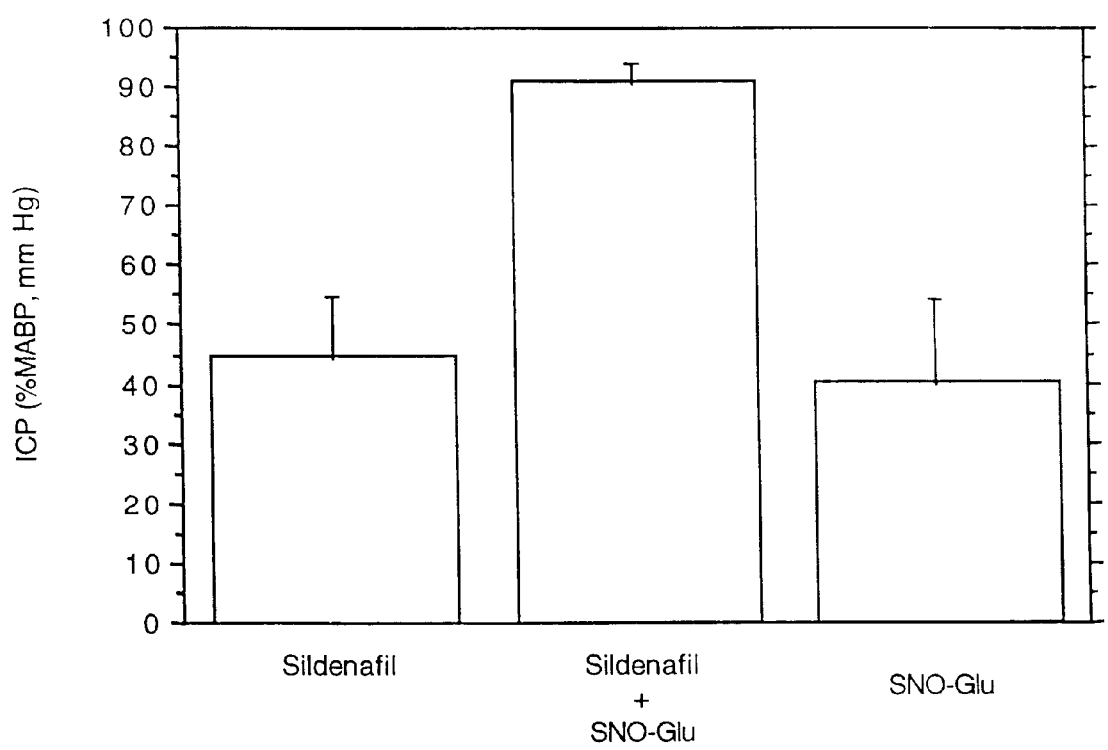
FIG. 59 shows the percent peak erectile response in vivo, expressed as intercavernosal pressure (ICP) as a percent of the mean arterial blood pressure (%MABP) in the anesthetized rabbit following the administration of (i) sildenafil alone (ii) the combination of sildenafil and S-nitrosoglutathione (SNO-Glu) (iii) S-nitrosoglutathione (SNO-Glu) alone. The ordinate is the percent response of intracavernosal pressure and the abscissa indicates the compounds administered.
Figure 60:
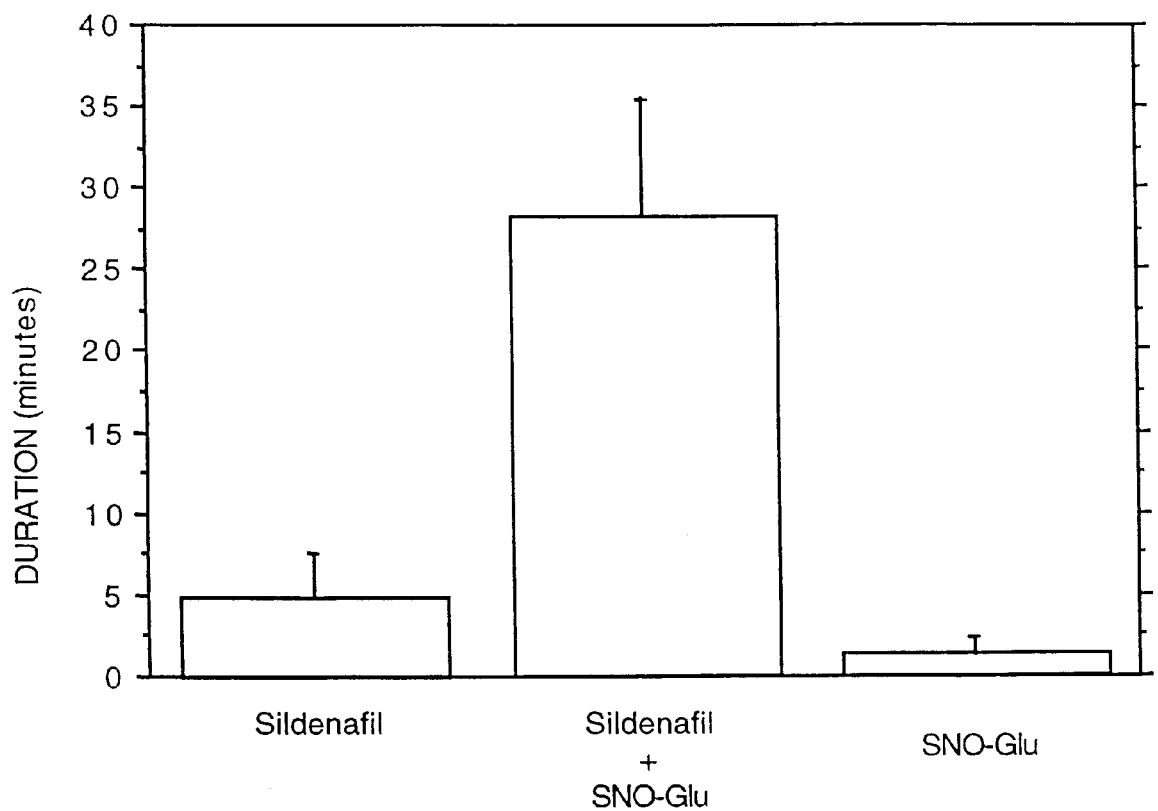
FIG. 60 shows the duration of the erectile response in vivo in the anesthetized rabbit following the administration of (i) sildenafil alone (ii) the combination of sildenafil and S-nitrosoglutathione (SNO-Glu) (iii) S-nitrosoglutathione (SNO-Glu) alone. The ordinate is the duration in minutes and the abscissa indicates the compounds administered.

FIG. 59 shows the peak erectile response in vivo in the anesthetized rabbit following the administration of (i) sildenafil hydrochloride alone (ii) the combination of sildenafil hydrochloride and SNO-Glu (iii) SNO-Glu alone. FIG. 60 shows the duration of the erectile response in vivo in the anesthetized rabbit following the administration of (i) sildenafil hydrochloride alone (ii) the combination of sildenafil hydrochloride and SNO-Glu (iii) SNO-Glu alone. The administration of the combination of sildenafil and SNO-Glu shows an unexpected and superior duration that is greater than the additive effect of sildenafil and SNO-Glu individually.

Each of the publications, patents and patent applications described herein is hereby incorporated by reference herein in their entirety.

Various modifications of the invention, in addition to those described herein, will be apparent to one skilled in the art from the foregoing description. Such modifications are also intended to fall within the scope of the appended claims.

What is claimed is:

1. A compound of formula (XI), formula (XII), formula (XIII), formula (XIV), formula (XV), formula (XVI), formula (XVII), formula (XVIII), formula (XIX), or a pharmaceutically acceptable salt thereof:

wherein the compound of formula (XI) is:

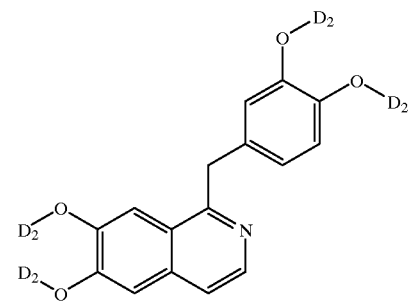

XI wherein
$D_2$ is a hydrogen, a lower alkyl or D;
D is:
  (i) —NO,
  (ii) —NO$_2$,
  (iii) —CH(R$_d$)—O—C(O)—Y—Z—(C(R$_e$)(R$_f$))$_p$—T—Q,
  (iv) —C(O)—Y—Z—(G—(C(R$_e$)(R$_f$))$_b$—T—Q)$_p$;
  (v) —P—Z—(G—(C(R$_e$)(R$_f$))$_b$—T—Q)$_p$;
  (vi) —P$_1$—B$_1$—W—B$_t$—L$_r$—E$_s$—(C(R$_e$)(R$_f$))$_w$—E$_c$—(C(R$_e$)(R$_f$))$_x$—L$_d$—(C(R$_e$)(R$_f$))$_y$—L$_i$—E$_j$—L$_g$—(C(R$_e$)(R$_f$))$_z$—T—Q; or
  (vii) —P$_1$—F'$_n$—L$_r$—E$_s$—(C(R$_e$)(R$_f$))$_w$—E$_c$—(C(R$_e$)(R$_f$))$_x$—L$_d$—(C(R$_e$)(R$_f$))$_y$—L$_i$—E$_j$—L$_g$—(C(R$_e$)(R$_f$))O$_z$—T—Q;

R$_d$ is a hydrogen, a lower alkyl, a cycloalkyl, an aryl or an arylalkyl;

Y is oxygen, S(O)$_o$, lower alkyl or NR$_i$;

o is an integer from 0 to 2;

R$_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, —CH$_2$—C(T—Q)(R$_e$)(R$_f$), or —(N$_2$O$_2^-$)$^-$·M$^+$, wherein M$^+$ in an organic or inorganic cation;

R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, —T—Q, or $(C(R_e)(R_f))_k$—T—Q, or $R_e$ and $R_f$ taken together with the carbon atoms to which they are attached are a carbonyl, a methanthial, a heterocyclic ring, a cycloalkyl group or a bridged cycloalkyl group;

k is an integer from 1 to 3;

p is an integer from 1 to 10;

T is independently a covalent bond, oxygen, $S(O)_o$ or $NR_i$;

Z is a covalent bond, an alkyl, an aryl, an arylalkyl, an alkylaryl, a heteroalkyl, or $(C(R_e)(R_f))_p$;

Q is —NO or —$NO_2$;

G is a covalent bond, —T—C(O)—, —C(O)—T— or T;

b is an integer from 0 to 5;

P is a carbonyl, a phosphoryl or a silyl;

l and t are each independently an integer from 1 to 3;

r, s, c, d, g, i and j are each independently an integer from 0 to 3;

w, x, y and z are each independently an integer from 0 to 10;

$P_1$ is a covalent bond or P;

B at each occurrence is independently an alkyl group, an aryl group, or $(C(R_e)(R_f))_p$;

E at each occurrence is independently —T—, an alkyl group, an aryl group, or —$(CH_2CH_2O)_q$;

q is an integer of from 1 to 5;

L at each occurrence is independently —C(O)—, —C(S)—, —T—, a heterocyclic ring, an aryl group, an alkenyl group, an alkynyl group, an arylheterocyclic ring, or —$(CH_2CH_2O)_q$;

W is oxygen, $S(O)_o$, or $NR_i$;

F' at each occurrence is independently selected from B or carbonyl;

n is an integer from 2 to 5;

with the proviso that when $R_i$ is —$CH_2$—C(T—Q)($R_e$)($R_f$) or —($N_2O_2$)$M^+$, or $R_e$ or $R_f$ are T—Q or $(C(R_e)(R_f))_k$—T—Q, then the "—T—Q" subgroup designated in D can be a hydrogen, an alkyl, an alkoxy, an alkoxyalkyl, an aminoalkyl, a hydroxy, or an aryl; and with the proviso that at least one $D_2$ must be D;

wherein the compound of formula (XII) is:

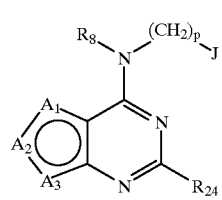

XII wherein, $R_8$ is a hydrogen, a lower alkyl group or a haloalkyl group;

J is:

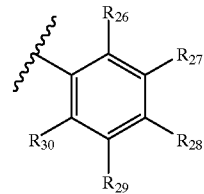

(i)

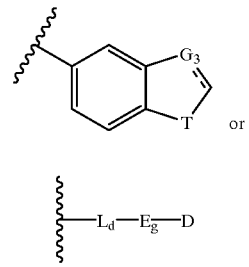 or (ii)

(iii)

$R_{24}$ is hydrogen or K—G—D;

K is:

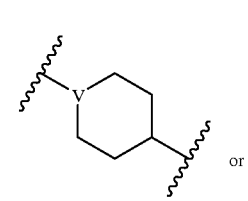

(i)

or

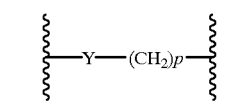

(ii)

$G_3$ is (CH), ($CH_2$), oxygen, sulfur or nitrogen;

V is carbon or nitrogen;

$A_1$, $A_2$ and $A_3$ comprise the other subunits of a 5- or 6-membered monocyclic aromatic ring and each is independently (i) C—$R_{23}$ wherein $R_{23}$ at each occurrence is independently D, a hydrogen, a halogen, an alkoxy, a nitrile, an alkyl, an arylalkyl, an alkylaryl, a carboxamido, a carboxyl, a haloalkyl, an alkoxyalkyl, an alkoxyaryl or a nitro; (ii) sulfur; (iii) oxygen; and (iv) $B_a$=$B_b$ wherein $B_a$ and $B_b$ are each independently nitrogen or C—$R_{23}$ wherein $R_{23}$ at each occurrence is as defined herein; and $R_{26}$, $R_{27}$, $R_{28}$, $R_{29}$, and $R_{30}$ are each independently a hydrogen, a halogen, a hydroxy, a haloalkyl, an alkoxy, an alkoxyalkyl, an alkoxyaryl, an alkoxyhaloalkyl, a nitrile, a nitro, an alkyl, an alkylaryl, an arylalkyl, a hydroxy alkyl, a carboxamido, or a carboxyl;

d, g, p, E, L, G, T, Y and D are as defined herein;

with the proviso that at least one of the variables $A_1$, $A_2$, $A_3$, J or $R_{24}$ must contain the element "—T—Q" or "D";

wherein the compound of formula (XIII) is:

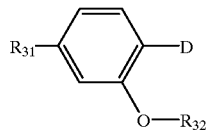

XIII wherein, $R_{31}$ is an alkyl, a halogen, a haloalkyl, or a haloalkoxy;

$R_{32}$ is D, or —C(O)—$R_8$;

$D_1$ is D or hydrogen; and D and $R_8$ are as defined herein;

wherein the compound of formula (XIV) is:

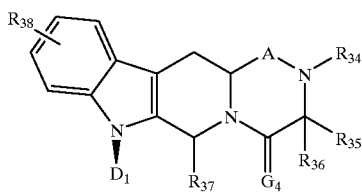

XIV wherein

A is $CH_2$, a carbonyl or a methanethial;

$G_4$ is oxygen or sulfur;

$R_{34}$ is hydrogen, lower alkyl, alkenyl, alkynyl or $L_r$—$E_s$—$(C(R_e)(R_f))_w$—$E_c$—$(C(R_e)(R_f))_x$—$L_d$—$(C(R_e)(R_f))_y$—$L_i$—$L_j$—$E_g$—$(C(R_e)(R_f))_z$—T—Q; $R_{35}$ and $R_{36}$ are each independently a hydrogen, a lower alkyl, an arylalkyl, an alkylaryl, a cycloalkylalkyl, a heterocyclicalkyl, T—Q or $(C(R_e)(R_f))_k$—T—Q; or $R_{35}$ and $R_{36}$ taken together with the carbon to which they are attached are a carbonyl group, a methanethial group, a heterocyclic group or a cycloalkyl group; or $R_{34}$ and $R_{35}$ taken together with the carbon to which they are attached are $(C(R_g)(R_h))_u$ or —$C(R_g)(R_h)$—$C(R_g)$=$C(R_g)$—$(C(R_g)(R_h))_v$ wherein u is an integer of 3 or 4, v is an integer of 1 or 2 and $R_g$ and $R_h$ at each occurrence is independently a hydrogen, an alkyl, T—Q or $(C(R_e)(R_f))_k$—T—Q;

$R_{36}$ is a hydrogen, a halogen or a lower alkyl;

$R_{37}$ is:

(i)

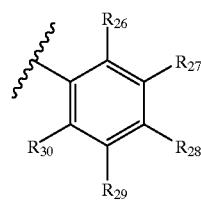

(ii)

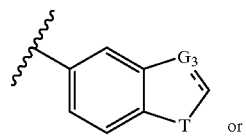

or (iii)

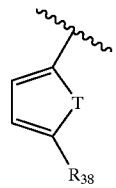

$D_1$ is D or hydrogen;

c, d, g, i, j, k, r, s, w, x, y, z, E, L, $G_3$, T, Q, $R_e$, $R_f$, $R_{26}$, $R_{27}$, $R_{28}$, $R_{29}$, $R_{30}$ and $R_{38}$ are a defined herein;

with the proviso that $D_1$ must be D if $R_{34}$, $R_{35}$, $R_{36}$ or $R_{37}$ do not contain the element "T—Q";

wherein the compound of formula (XV) is:

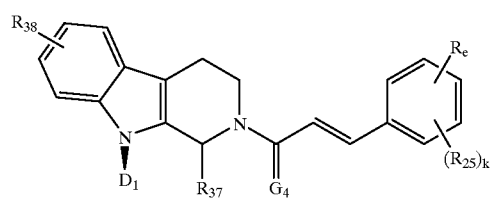

XV wherein $R_{25}$ at each occurrence is independently a hydrogen, an alkyl, a cycloalkoxy, a halogen, a hydroxy, an hydroxyalkyl, an alkoxyalkyl, an arylheterocyclic ring, an alkylaryl, an arylalkoxy, an alkylthio, an arylthio, a cyano, an aminoalkyl, an amino an alkoxy, an aryl, an arylalkyl, a carboxamido, a alkyl carboxamido, an aryl carboxamido, a carboxyl, a carbamoyl, an alkylcarboxylic acid, an arylcarboxylic acid, a carboxylic ester, an alkylcarboxylic ester, an arylcarboxylic ester, a carboxamido, an alkylcarboxamido, an arylcarboxamido, a haloalkoxy, a sulfonamido, a urea, a nitro, or $L_r$—$E_s$—$(C(R_e)(R_f))_w$—$E_c$—$(C(R_e)(R_f))_x$—$L_d$—$(C(R_e)(R_f))_y$—$L_i$—$E_j$—$L_g$—$(C(R_e)(R_f))_z$—T—Q;

c, d, g, i, j, k, r, s, w, x, y, z, $G_4$, $D_1$, E, L, T, Q, $R_e$, $R_f$, $R_{37}$ and $R_{38}$ are as defined herein;

with the proviso that $D_1$ must be D if $R_e$ or $R_{25}$ do not contain the element "T—Q";

wherein the compound of formula (XVI) is:

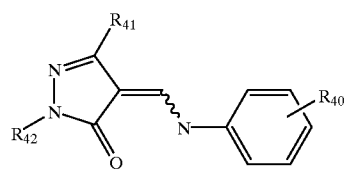

XVI wherein $R_{40}$ is a hydrogen, a lower alkyl, a haloalkyl, a halogen, an alkoxy, an alkenyl, an alkynyl, a carbamoyl, a sulfonamido or $L_r$—$E_s$—$(C(R_e)(R_f))_w$—$E_c$—$(C(R_e)(R_f))_x$—$L_d$—$(C(R_e)(R_f))_y$—$L_i$— $E_j$—$L_g$—$(C(R_e)(R_f))_z$—T—Q;

$R_{41}$ is a lower alkyl, a hydroxyalkyl, an alkylcarboxylic acid, an alkylcarboxylic ester an alkylcarboxamido or $L_r$—$E_s$—$(C(R_e)(R_f))_w$—$E_c$—$(C(R_e)(R_f))_x$—$L_d$—(C$(R_e)(R_f))_y$—$L_i$—$E_j$—$L_g$—$(C(R_e)(R_f))_z$—T—Q; and $R_{42}$ is:

(i)

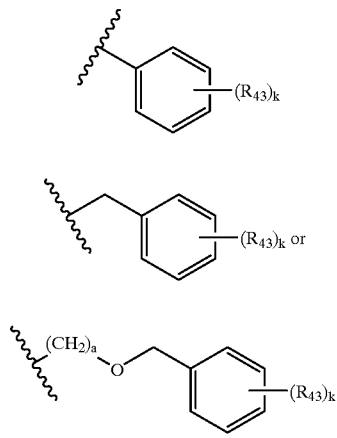

$R_{43}$ at each occurrence is independently an amino, a cyano, a halogen, a nitro group, a carboxyl, a carbamoyl, a sulfonic acid, a sulfonic ester, a sulfonamido, a heterocyclic ring, a carboxamido, a carboxylic ester, an ester, an amidyl, a phosphoryl or $L_r$—$E_s$—$(C(R_e)(R_f))_w$—$E_c$—$(C(R_e)(R_f))_x$—$L_d$—(C$(R_e)(R_f))_y$—$L_i$—$E_j$—$L_g$—$(C(R_e)(R_f))_z$—T—Q; and c, d, g, i, j, k, r, S, w, x, y, z, E, L, T, Q, $R_e$, and $R_f$ are as defined herein;

with the proviso that at least one of $R_{40}$, $R_4$, or $R_{43}$ must contain the element "T—Q";

wherein the compound of formula (XVII) is:

XVII

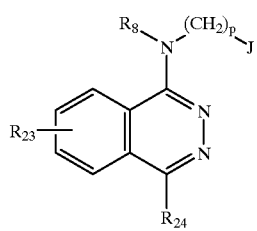

wherein $R_8$, $R_{23}$, $R_{24}$ p and J are as defined herein;

with the proviso that at least one $R_{24}$ or J must contain the element "—T—Q" or wherein the compound of formula (XVIII) is:

XVIII

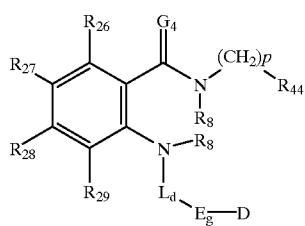

wherein $R_{44}$ is:

(i)

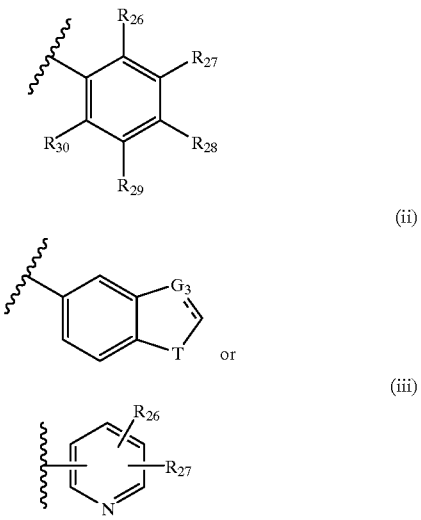

wherein d, g, p, D, E, L, $G_3$, $G_4$, T, $R_8$, $R_{26}$, $R_{27}$, $R_8$, $R_{29}$, and $R_{30}$ are as defined herein;

wherein the compound of formula (XIX) is:

XIX

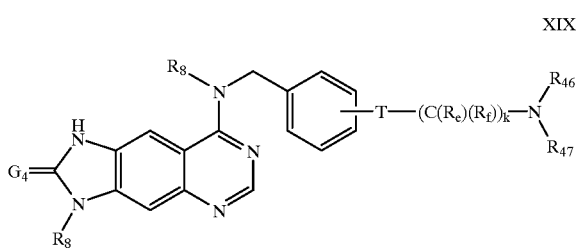

wherein, $R_{46}$ and $R_{47}$ are each independently a lower alkyl, hydroxyalkyl or D, or $R_{46}$ and $R_{47}$ taken together with the nitrogen atom to which they are attached are a heterocyclic ring, $G_4$, T, $R_8$, and k are as defined herein;

with the proviso that at least one of the variables $R_{46}$ or $R_{47}$ must be D or when the variables taken together are a heterocyclic ring, the ring must contain $NR_i$, wherein $R_1$ must contain the element "T—Q".

2. The compound of claim 1, wherein the compound is a nitrosated papaveroline, a nitrosylated papaveroline, a nitrosated and nitrosylated papaveroline, a a nitrosated E 4021, a nitrosated nitrosylated E 4021, a nitrosated and nitrosylated E 4021, a nitrosated thienopyrimidine derivative, a nitrosylated thienopyrimidine derivative, a nitrosated and nitrosylated thienopyrimidine derivative, a nitrosated trifusal, a nitrosylated trifusal, a nitrosated and nitrosylated trifusal, a nitrosated ICOS-351, a nitrosylated ICOS-351, a nitrosated and nitrosylated ICOS 351, a nitrosated tetrahydropiperazino(1,2-b)beta-carboline-1,4-dione derivative, a nitrosylated tetrahydropiperazino(1,2-b)beta-carboline-1,4-dione derivative, a nitrosated and nitrosylated tetrahydropiperazino(1,2-b)beta-carboline-1,4-dione derivative, a nitrosated carboline derivative, a nitrosylated carboline derivative, a nitrosated and nitrosylated carboline derivative, a nitrosated 2-pyrazolin-5-one derivative, a nitrosylated 2-pyrazolin-5-one derivative, a nitrosated and nitrosylated 2-pyrazolin-5-one derivative, a nitrosated fused pyridazine derivative, a nitrosylated fused pyridazine derivative, a nitrosated and nitrosylated fused pyridazine derivative, a nitrosated quinazoline derivative, a nitrosylated quinazoline derivative, a nitrosated and nitrosylated quinazoline derivative, a nitrosated anthranilic acid derivative, a nitrosylated anthranilic acid derivative, a nitrosated and nitrosylated anthranitic acid derivative, a nitrosated imidazoquinazoline derivative, a nitrosylated imidazoquinazoline derivative, or a nitrosated and nitrosylated imidazoquinazoline derivative.

3. A composition comprising the compound of claim 1 and a pharmaceutically acceptable carrier.

4. A method for treating a sexual dysfunction in a patient in need thereof comprising administering a therapeutically effective amount of the composition of claim 3.

5. The method of claim 4, wherein the patient is female.

6. The method of claim 4, wherein the patient is male.

7. The method of claim 4, wherein the composition is administered orally, by intracavernosal injection, by transurethral application, or by transdermal application.

8. A method for treating or preventing a disease induced by the increased metabolism of cyclic guanosine 3',5'-monophosphate in a patient in need thereof comprising administering a therapeutically effective amount of the composition of claim 3.

9. The method of claim 8, wherein the disease induced by the increased metabolism of cyclic guanosine 3',5'-monophosphate is hypertension, pulmonary hypertension, congestive heart failure, renal failure, myocardial infarction, stable, unstable or variant (Prinzmetal) angina, atherosclerosis, cardiac edema, renal insufficiency, nephrotic edema, hepatic edema, stroke, asthma, bronchitis, chronic obstructive pulmonary disease, cystic fibrosis, dementia, immunodeficiency, premature labor, dysmenorrhoea, benign prostatic hyperplasia, bladder outlet obstruction, incontinence, a condition of reduced blood vessel patency, postpercutaneous transluminal coronary angioplasty, peripheral vascular disease, allergic rhinitis, glaucoma, or a disease characterized by a gut motility disorder.

10. The composition of claim 3, further comprising at least one vasoactive agent.

11. The composition of claim 10, wherein the vasoactive agent is a potassium channel activator, a calcium blocker, an α-blocker, a β-blocker, adenosine, an ergot alkaloid, a vasoactive intestinal peptide, a dopamine agonist, an opioid antagonist, a prostaglandin, an endothelin antagonist or a mixture thereof.

12. A method for treating a sexual dysfunction in a patient in need thereof comprising administering a therapeutically effective amount of the composition of claim 10.

13. The method of claim 12, wherein the patient is female.

14. The method of claim 12, wherein the patient is male.

15. The method of claim 12, wherein the composition is administered orally, by intracavernosal injection, by transurethral application or by transdermal application.

16. A method for treating or preventing a disease induced by the increased metabolism of cyclic guanosine 3',5'-monophosphate in a patient in need thereof comprising administering a therapeutically effective amount of the composition of claim 10.

17. The method of claim 16, wherein the disease induced by the increased metabolism of cyclic guanosine 3',5'-monophosphate is hypertension, pulmonary hypertension, congestive heart failure, renal failure, myocardial infarction, stable, unstable or variant (Prinzmetal) angina, atherosclerosis, cardiac edema, renal insufficiency, nephrotic edema, hepatic edema, stroke, asthma, bronchitis, chronic obstructive pulmonary disease, dementia, immunodeficiency, premature labor, dysmenorrhoea, benign prostatic hyperplasia, bladder outlet obstruction, incontinence, a condition of reduced blood vessel patency, postpercutaneous transluminal coronary angioplasty, peripheral vascular disease, allergic rhinitis, cystic fibrosis, glaucoma, or a disease characterized by a gut motility disorder.

18. A composition comprising at least one compound of claim 1 and at least one compound that donates, transfers, or releases nitric oxide, or induces the production of endogenous nitric oxide or endothelium-derived relaxing factor or is a substrate for nitric oxide synthase.

19. The composition of claim 18, wherein the compound that donates, transfers, or releases nitric oxide, or induces the production of endogenous nitric oxide or endothelium-derived relaxing factor or is a substrate for nitric oxide synthase is an S-nitrosothiol.

20. The composition of claim 19, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

21. The composition of claim 19, wherein the S-nitrosothiol is:

(i) $HS(C(R_e)(R_f))_m SNO$;

(ii) $ONS(C(R_e)(R_f))_m R_e$; or (iii) $H_2N-CH(CO_2H)-(CH_2)_m C(O)NH-CH(CH_2SNO)-C(O)NH-CH_2-CO_2H$;

wherein m is an integer of from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, am alkoxy, a haloalkoxy, an amino, an alkylamino, a dialkylamino, an arylamino, a diarylamino, an alkylarylamino an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or —T—Q; or $R_e$ and $R_f$ taken together with the carbon atoms to which they are attached are a carbonyl, a methanthial, a heterocyclic ring, a cycloalkyl group or a bridged cycloalkyl group; Q is —NO or —NO$_2$; and T is independently a covalent bond, an oxygen, $S(O)_o$ or $N_R$, wherein o is an integer from 0 to 2, and $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, carboxamido, —CH$_2$—C(T—Q)($R_e$)($R_f$), or —($N_2O_2^-$)M$^+$, wherein M$^+$ in an organic or inorganic cation; with the proviso that when $R_i$ is —CH$_2$—C(T—Q)($R_e$)($R_f$) or —($N_2O_2^-$)M$^+$; then "—T—Q" can be a hydrogen, an alkyl group, an alkoxyalkyl group, an aminoalkyl group, a hydroxy group or an aryl group.

22. The composition of claim 18, wherein the compound that donates, transfers, or releases nitric oxide, or induces the production of endogenous nitric oxide or endothelium-derived relaxing factor or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, an inhibitor of the enzyme arginase, citrulline, ornithine or glutamine.

23. The composition of claim 18, wherein the compound that donates, transfers, or releases nitric oxide, or induces the production of endogenous nitric oxide or endothelium-derived relaxing factor or is a substrate for nitric oxide synthase is:
  (i) a compound that comprises at least one ON—O—, ON—N— or ON—C— group;
  (ii) a compound that comprises at least one $O_2N$—O—, $O_2N$—N—, $O_2N$—S— or —$O_2N$—C— group;
  (iii) a N-oxo-N-nitrosoamine having the formula: $R^1R^2$—N(O—$M^+$)—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation; or
  (iv) a thionitrate having the formula: $R^1$—(S)—$NO_2$, wherein $R^1$ is a polypeptide, an amino acid, a sugar, an oligonucleotide, a straight or branched, saturated or unsaturated, aliphatic or aromatic, substituted or unsubstituted hydrocarbon, or a heterocyclic group.

24. The composition of claim 23, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

25. The composition of claim 23, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

26. A method for treating a sexual dysfunction in a patient in need thereof comprising administering a therapeutically effective amount of the composition of claim 18.

27. The method of claim 26, wherein the patient is female.

28. The method of claim 26, wherein the patient is male.

29. The method of claim 26, wherein the composition is administered orally, by intracavernosal injection, by transurethral application or by transdermal application.

30. A method for treating or preventing a disease induced by the increased metabolism of cyclic guanosine 3',5'-monophosphate in a patient in need thereof comprising administering a therapeutically effective amount of the composition of claim 18.

31. The method of claim 30, wherein the disease induced by the increased metabolism of cyclic guanosine 3',5'-monophosphate is hypertension, pulmonary hypertension, congestive heart failure, renal failure, myocardial infarction, stable, unstable or variant (Prinzmetal) angina, atherosclerosis, cardiac edema, renal insufficiency, nephrotic edema, hepatic edema, stroke, asthma, bronchitis, chronic obstructive pulmonary disease, dementia, immunodeficiency, premature labor, dysmenorrhoea, benign prostatic hyperplasia, bladder outlet obstruction, incontinence, a condition of reduced blood vessel patency, postpercutaneous transluminal coronary angioplasty, peripheral vascular disease, allergic rhinitis, glaucoma, cystic fibrosis, or a disease characterized by a gut motility disorder.

32. The composition of claim 18, further comprising at least one vasoactive agent.

33. The composition of claim 32, wherein the vasoactive agent is a potassium channel activator, a calcium blocker, an α-blocker, a β-blocker, adenosine, an ergot alkaloid, a vasoactive intestinal peptide, a dopamine agonist, an opioid antagonist, a prostaglandin, an endothelin antagonist or a mixture thereof.

34. A method for treating a sexual dysfunction in a patient in need thereof comprising administering a therapeutically effective amount of the composition of claim 32.

35. The method of claim 34, wherein the patient is female.

36. The method of claim 34, wherein the patient is male.

37. The method of claim 34, wherein the composition is administered orally, by intracavernosal injection, by transurethral application or by transdermal application.

38. A method of treating or preventing a disease induced by the increased metabolism of cyclic guanosine 3',5'-monophosphate in a patient in need thereof comprising administering a therapeutically effective amount of the composition of claim 32.

39. The method of claim 38, wherein the disease induced by the increased metabolism of cyclic guanosine 3',5'-monophosphate is hypertension, pulmonary hypertension, congestive heart failure, renal failure, myocardial infarction, stable, unstable or variant (Prinzmetal) angina, atherosclerosis, cardiac edema, renal insufficiency, nephrotic edema, hepatic edema, stroke, asthma, bronchitis, chronic obstructive pulmonary disease, dementia, immunodeficiency, premature labor, dysmenorrhoea, benign prostatic hyperplasia, bladder outlet obstruction, incontinence, a condition of reduced blood vessel patency, postpercutaneous transluminal coronary angioplasty, peripheral vascular disease, allergic rhinitis, cystic fibrosis, glaucoma, or a disease characterized by a gut motility disorder.

40. A kit comprising the compound of claim 1.

41. The kit of claim 40, further comprising (i) at least one compound that donates, transfers or releases nitrogen monoxide, induces the production of endogenous endothelium-derived relaxing factor, stimulates endogenous synthesis of nitrogen monoxide or is a substrate for nitric oxide synthase, (ii) at least one vasoactive agent or (iii) at least one compound that donates, transfers or releases nitrogen monoxide, induces; the production of endogenous endothelium-derived relaxing factor, stimulates endogenous synthesis of nitrogen monoxide or is a substrate for nitric oxide synthase and at least one vasoactive agent.

42. A kit comprising the composition of claim 1, 18 or 32.

43. A kit comprising at least one compound of claim 1, and (i) at least one compound that donates, transfers or releases nitrogen monoxide, induces the production of endogenous endothelium-derived relaxing factor, stimulates endogenous synthesis of nitrogen monoxide or is a substrate for nitric oxide synthase, (ii) at least one vasoactive agent or (iii) at least one compound that donates, transfers or releases nitrogen monoxide, induces the production of endogenous endothelium-derived relaxing factor, stimulates endogenous synthesis of nitrogen oxide or is a substrate for nitric oxide synthase and at least one vasoactive agent.

44. The kit of claim 43, wherein the compound of claim 1 and the compound that donates, transfers or releases nitrogen monoxide, induces the production of endogenous endothelium-derived relaxing factor, stimulates endogenous synthesis of nitrogen monoxide or is a substrate for nitric oxide synthase or the vasoactive agent are separate components in the kit.

45. The kit of claim 43, wherein the compound of claim 1 and the compound that donates, transfers or releases nitrogen monoxide, induces the production of endogenous endothelium-derived relaxing factor, stimulates endogenous synthesis of nitrogen monoxide or is a substrate for nitric oxide synthase or the vasoactive agent are in the form of a composition in the kit.

46. A compound of formula (I), formula (II), formula (III), formula (IV), formula (V), formula (VI), formula (VII), formula (VIII), formula (IX), formula (X), or a pharmaceutically acceptable salt thereof:

wherein the compound of formula (I) is:

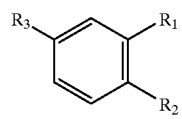

I wherein $R^1$ is an alkoxy, a cycloalkoxy, a halogen, or

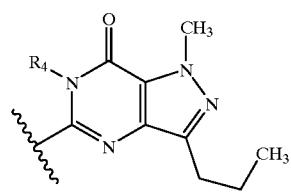

$R_2$ is a hydrogen, an alkoxy, or a haloalkoxy; and $R_3$ is:

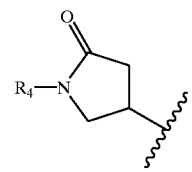 (i)

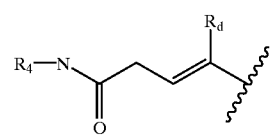 (ii)

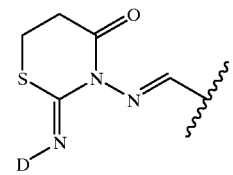 (iii)

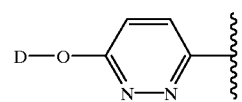 (iv)

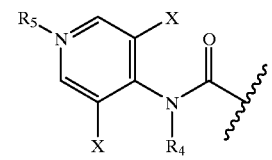 (v)

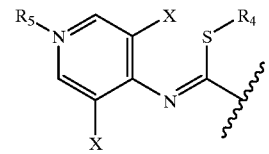 (vi)

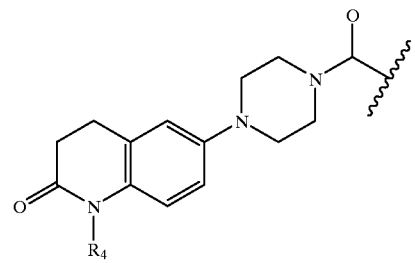 (vii)

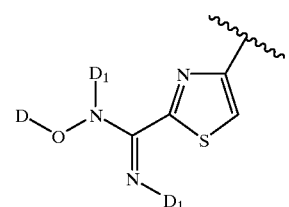 (viii)

-continued

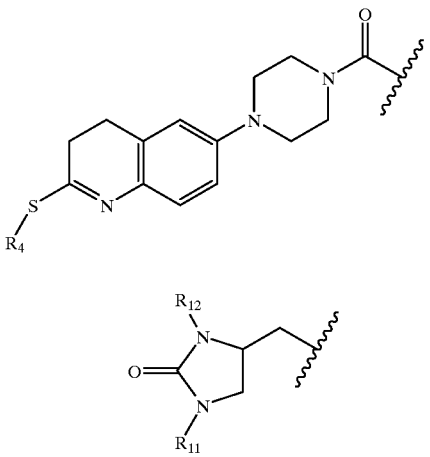

(ix)

or

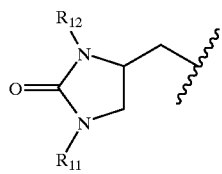

(x)

wherein,

D is:
(i) —P$_1$—B$_1$—W—B$_t$—L$_r$—E$_s$—(C(R$_e$)(R$_f$))$_w$—E$_c$—(C(R$_e$)(R$_f$))$_x$—L$_d$—(C(R$_e$)(R$_f$))$_y$—L$_i$—E$_j$—L$_g$—(C(R$_e$)(R$_f$))$_z$—T—Q or
(ii) —P$_1$—F'$_n$—L$_r$—E$_s$—(C(R$_e$)(R$_f$))$_w$—E$_c$—(C(R$_e$)(R$_f$))$_x$—L$_d$—(C(R$_e$)(R$_f$))$_y$—L$_i$—E$_j$—L$_g$—(C(R$_e$)(R$_f$))$_z$—T—Q wherein, R$_d$ is a hydrogen, a lower alkyl, a cycloalkyl, an aryl or an arylalkyl;

R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, —T—Q , or (C(R$_e$)(R$_f$))$_k$—T—Q, or R$_e$ and R$_f$ taken together with the carbon atoms to which they are attached are a carbonyl, a methanthial, a heterocyclic ring, a cycloalkyl group or a bridged cycloalkyl group;

k is an integer from 1 to 3;

T is independently a covalent bond, oxygen, S(O)$_o$ or NR$_i$;

Q is —NO or —NO$_2$;

P is a carbonyl, a phosphoryl or a silyl;

l and t are each independently an integer from 1 to 3;

r, s, c, d, g, i and j are each independently an integer from 0 to 3;

w, x, y and z are each independently an integer from 0 to 10;

P$_1$ is a covalent bond or P;

B at each occurrence is independently an alkyl group, an aryl group, or (C(R$_e$)(R$_f$))$_p$;

E at each occurrence is independently —T—, an alkyl group, an aryl group, or —(CH$_2$CH$_2$O)$_q$;

q is an integer of from 1 to 5;

L at each occurrence is independently —C(O)—, —C(S)—,—T—, a heterocyclic ring, an aryl group, an alkenyl group, an alkynyl group, an arylheterocyclic ring, or —(CH$_2$CH$_2$O)$_q$;

W is oxygen, S(O)$_o$, or NR$_i$;

o is an integer from 0 to 2;

R$_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, —CH$_2$—C(T—Q)(R$_e$)(R$_f$), or —(N$_2$O$_2$—)$^-$·M$^+$, wherein M$^+$ in an organic or inorganic cation;

F' at each occurrence is independently selected from B or carbonyl;

n is an integer from 2 to 5;

with the proviso that when R$_i$ is —CH$_2$—C(T—Q)(R$_e$)(R$_f$) or —(N$_2$O$_2$)$^-$M$^+$, or R$_e$ or R$_f$ are T—Q or (C(R$_e$)(R$_f$))$_k$—T—Q, then the "—T—Q" subgroup designated in D can be a hydrogen, an alkyl, an alkoxy, an alkoxyalkyl, an aminoalkyl, a hydroxy, or an aryl;

R$_4$ is:
(i) hydrogen;
(ii) —CH(Rd)—O—C(O)—Y—Z—(C(R$_e$)(R$_f$))—T—Q;
(iii) —C(O)—T—(C(R$_e$)(R$_f$))$_p$—T—Q;
(iv) —C(O)—Z—(G—(C(R$_e$)(R$_f$))$_p$—T—Q)$_p$ or
(v) —W$_o$—L$_r$—E$_s$—(C(R$_e$)(R$_f$))$_w$—E—(C(R$_e$)(R$_f$))$_x$—L$_d$—(C(R$_e$)(R$_f$))$_y$—L$_i$—E$_j$—L$_g$—(C(R$_e$)(R$_f$))$_z$—T—Q;

r, s, c, d, g, i, j, o, p, w, x, y, z, R$_d$, R$_e$ R$_f$, E, L, G, T, Q, W, Y, and Z are as defined herein;

R$_5$ is a lone pair of electrons or —CH(R$_d$)—O—C(O)—Y—Z—(C(R$_e$)(R$_f$))$_p$—T—Q;

R$_{11}$ and R$_{12}$ are independently selected from hydrogen or R$_4$;

R$_4$, R$_d$, R$_e$, R$_f$, p, T, Q, Y, and Z are as defined herein;

X is a halogen, and D$_1$ is D or hydrogen, wherein D is as defined herein; with the proviso that if the structure does not contain D, then at least one of the variables R$_4$, R$_5$, R$_{11}$ or R$_{12}$ must contain the element "—T—Q";

wherein the compound of formula (II) is:

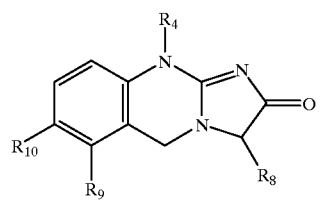

II wherein,

R$_4$ is as defined herein; with the proviso that R$_4$ cannot be hydrogen;

R$_8$ is a hydrogen, a lower alkyl group or a haloalkyl group;

R$_9$ is a hydrogen or a halogen; and

R$_{10}$ is:

(i) hydrogen, (ii)
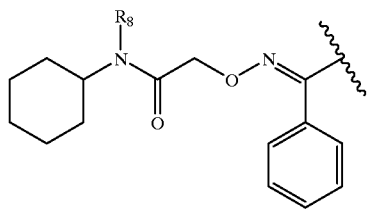

(iii)
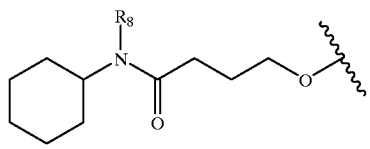

wherein $R_8$ is as defined herein;

wherein the compound of formula (III) is:

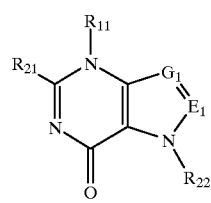

III wherein $E_1$ is nitrogen or —CH—;

$G_1$ is nitrogen or —C($R_8$)—;

$R_{21}$ is:

(i)
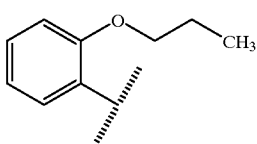

or (ii)
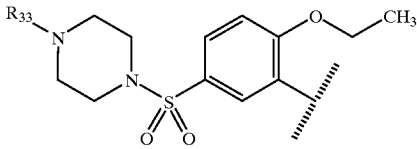

$R_{22}$ is $R_{12}$ or a lower alkyl;

$R_{33}$ is a lower alkyl or $(C(R_e)(R_f))_p$—T—Q; and p, $R_e$, $R_f$, $R_{11}$, $R_{12}$, T and Q are as defined herein;

with the proviso that at least one of the variables $R_{11}$, $R_{12}$, $R_{22}$ or $R_{33}$ must contain the element "T—Q";

wherein the compound of formula (IV) is:

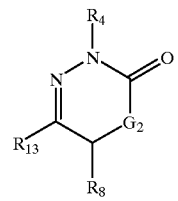

IV wherein, $G_2$ is —CH$_2$— or sulfur;

$R_4$ and $R_8$ are each as defined herein; and $R_{13}$ is:

(i)
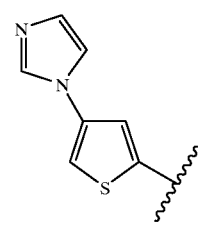

(ii)
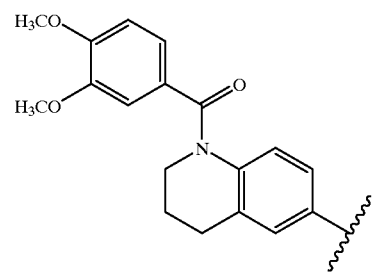

(iii)
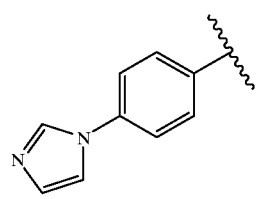

(iv)
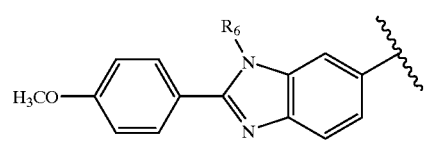

(v)
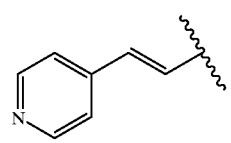

-continued (vi)

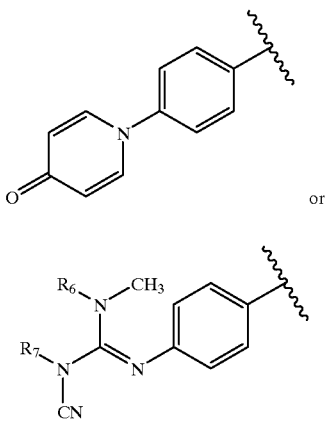

or (vii)

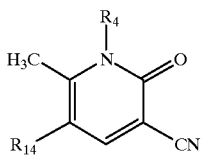

wherein, $R_6$ and $R_7$ are independently selected from $R_4$, wherein $R_4$ is as defined herein; with the proviso that at least one of the variables $R_4$, $R_6$ or $R_7$ must contain the element "T—Q";

wherein the compound of formula (V) is:

V

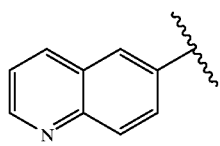

wherein, $R_4$ is as defined herein; and
$R_{14}$ is:

(i)

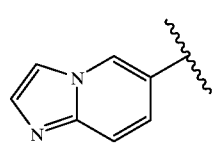

(ii)

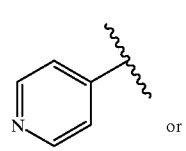

(iii)

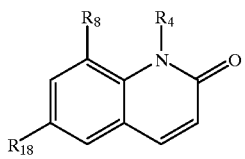

or (iv)

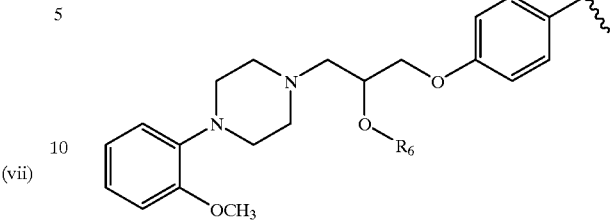

wherein $R_6$ is as defined herein, with the proviso that at least one of the variables $R_4$, or $R_6$ must contain the element "T—Q";

wherein the compound of formula (VI) is:

VI

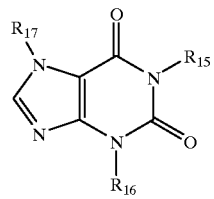

wherein, $R_{15}$ is a hydrogen, a lower alkyl, $R_4$, or —$(CH_2)_4$—C$(CH_3)_2$—O—$D_1$; wherein $R_4$ is as defined herein;

$R_{16}$ is a lower alkyl; and $R_{17}$ is a hydrogen, a lower alkyl, $CH_3$—C(O)—$CH_2$—; $CH_3$—O—$CH_2$—, or D with the proviso that either $R_{15}$ or $R_{17}$ must contain D, wherein D and $D_1$ are as defined herein;

wherein the compound of formula (VII) is:

VII

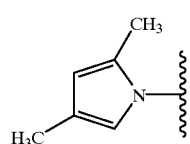

wherein, $R_4$ and $R_8$ are as defined herein; and
$R_{18}$ is:

(i)

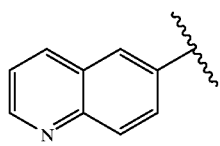

-continued (ii)
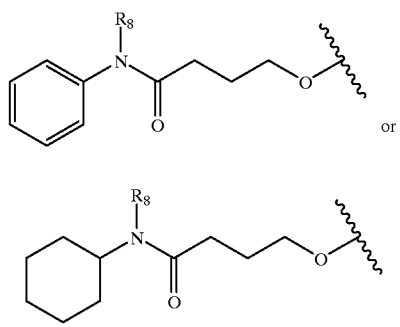
or $R_8$ is as defined herein;
with the proviso that $R_4$ cannot be hydrogen;
wherein the compound of formula (VIII) is:

VIII
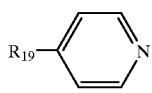

wherein, $R_{19}$ is:

(i)
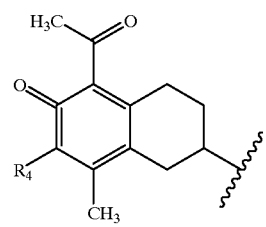

(ii)
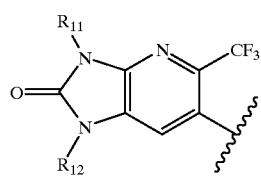

(iii)
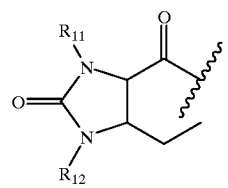

(iv)
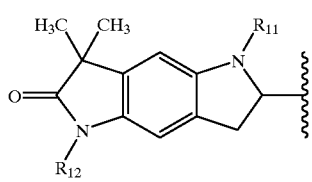

-continued (v)
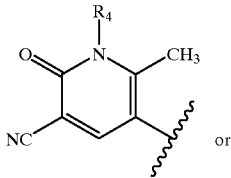
or (vi)
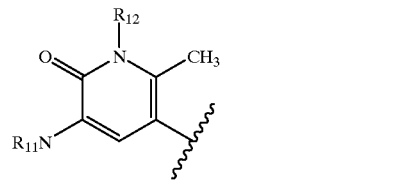

wherein $R_4$, $R_{11}$, and $R_{12}$ are as defined herein; with the proviso that at least one of the variables $R_4$, $R_{11}$ or $R_{12}$ must contain the element "T—Q";

wherein the compound of formula (IX) is:

IX
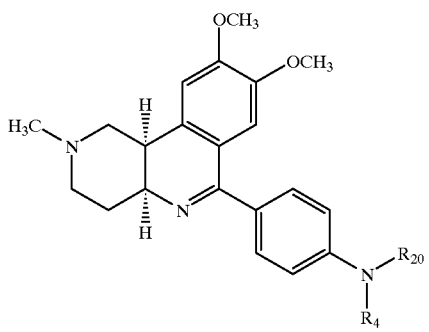

wherein, $R_{20}$ is:

(i)
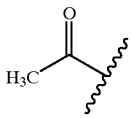

(ii)
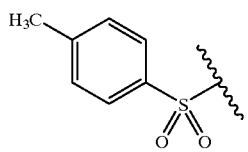

or (iii) —D;
$R_4$ is as defined herein;
with the proviso that when $R_{20}$ is not D, then $R_4$ cannot be hydrogen;

wherein the compound of formula (X) is:

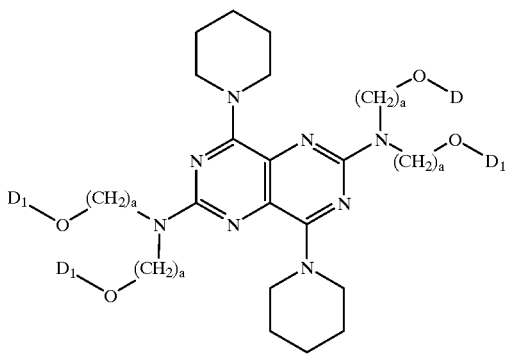

wherein,
a is an integer from 2 to 3 and D and D₁ are as defined herein.

47. The composition of claim 46, wherein the compound of formula I is a nitrosated filaminast, a nitrosylated filaminast, a nitrosated and nitrosylated filaminast, a nitrosated piclamilast, a nitrosylated piclamilast, a nitrosated and nitrosylated piclamilast, a nitrosated rolipram, a nitrosylated rolipram, a nitrosated and nitrosylated rolipram, a nitrosated roflumilast, a nitrosylated roflumilast, a nitrosated and nitrosylated roflumilast, a nitrosated toborinone, a nitrosylated toborinone, a nitrosated and nitrosylated toborinone, a nitrosated MCI-154, a nitrosylated MCI-154, a nitrosated and nitrosylated MCI-154, a nitrosated vesnarinone, a nitrosylated vesnarinone, a nitrosated and nitrosylated vesnarinone, a nitrosated Org 20241, a nitrosylated Org 20241, or a nitrosated and nitrosylated Org 20241; wherein the compound of formula II is a nitrosated posicor, a nitrosylated posicor, a nitrosated and nitrosylated posicor, a nitrosated 6-bromo-1,5-dihydro-imidazo(2,1-b)quinazolin-2(3H)-one, a nitrosylated 6-bromo-1,5-dihydro-imidazo(2,1-b)quinazolin-2(3H)-one, a nitrosated and nitrosylated 6-bromo-1,5-dihydro-imidazo(2,1-b)quinazolin-2(3H)-one, a nitrosated R 79595, a nitrosylated R 79595, a nitrosated and nitrosyalted R 79595, a nitrosated lixazinone, a nitrosylated lixazinone, or a nitrosated and nitrosyalted lixazinone; wherein the compound of formula III is a nitrosated sildenafil, a nitrosylated sildenafil, a nitrosated and nitrosyalted sildenafil, a nitrosated zaprinast, a nitrosylated zaprinast, or a nitrosated and nitrosyalted zaprinast; wherein the compound of formula IV is a nitrosated ICI 153,110, a nitrosylated ICI 153,110, a nitrosated and nitrosylated ICI 153,110, a nitrosated motapizone, a nitrosylated motapizone, a nitrosated and nitrosylated motapizone, a nitrosated pimobenden, a nitrosylated pimobenden, a nitrosated and nitrosylated pimobenden, a nitrosated siguazodan, a nitrosylated siguazodan, a nitrosated and nitrosylated siguazodan, a nitrosated imazodan, a nitrosylated imazodan, a nitrosated and nitrosylated imazodan, a nitrosated CI 930, a nitrosylated CI 930, a nitrosated and nitrosylated CI 930, a nitrosated 4,5-dihydro-5-methyl-6(4-(4-oxo-1(4H)-pyridinyl)phenyl)-3(2H)-pyridazinone, a nitrosylated 4,5-dihydro-5-methyl-6-(4-(4-oxo-1(4H)-pyridinyl)phenyl)-3(2H)-pyridazinone, a nitrosated and nitrosylated 4,5-dihydro-5-methyl-6-(4-(4-oxo-1(4H)-pyridinyl)phenyl)-3(2H)-pyridazinone, a nitrosated EMD 53998, a nitrosylated EMD 53998 or a nitrosated and nitrosylated EMD 53998; wherein the compound of formula V is a nitrosated saterinone, a nitrosylated saterinone, a nitrosated and nitrosylated saterinone, a nitrosated WIN 63291, a nitrosylated WIN 63291, a nitrosated and nitrosylated WIN 63291, a nitrosated milrinone, a nitrosylated milrinone, a nitrosated and nitrosylated milrinone, a nitrosated loprinone, a nitrosylated loprinone, or a nitrosated and nitrosylated loprinone; wherein the compound of formula VI is a nitrosated albifylline, a nitrosylated albifylline, a nitrosated and nitrosylated albifylline, a nitrosated tobrafylline, a nitrosylated tobrafylline, a nitrosated and nitrosylated tobrafylline, a nitrosated denbufylline, a nitrosylated denbufylline, a nitrosated and nitrosylated denbufylline, a nitrosated doxofylline, a nitrosylated doxofylline, a nitrosated and nitrosylated doxofylline, a nitrosated theophylline, a nitrosylated theophylline, a nitrosated and nitrosylated theophylline, a nitrosated pentoxifylline, a nitrosylated pentoxifylline, or a nitrosated and nitrosylated pentoxifylline; wherein the compound of formula VII is a a nitrosated 4-((1,2-dihydro-2-oxo-6-quinolinyl)oxy)-N-ethyl-N-phenyl-butanamide, a nitrosylated 4-((1,2-dihydro-2-oxo-6-quinolinyl)oxy)-N-ethyl-N-phenyl-butanamide, a nitrosated and nitrosylated 4-((1,2-dihydro-2-oxo-6-quinolinyl)oxy)-N-ethyl-N-phenyl-butanamide, a nitrosated 4-((1,2-dihydro-2-oxo-6-quinolinyl)oxy)-N-methyl-N-phenyl-butanamide, a nitrosylated 4-((1,2-dihydro-2-oxo-6-quinolinyl)ox)-N-methyl-N-phenyl-butanamide, a nitrosated and nitrosylated 4-((1,2 -dihydro-2-oxo-6-quinolinyl)oxy)-N-methyl-N-phenyl-butanamide, a nitrosated N-butyl-4-((1,2-dihydro-2-oxo-6-quinolinyl)oxy)-N-phenyl-butanamide, a nitrosylated N-butyl-4-((1,2-dihydro-2-oxo-6-quinolinyl)oxy)-N-phenyl-butanamide, a nitrosated and nitrosylated N-butyl-4-((1,2-dihydro-2-oxo-6-quinolinyl)oxy)-N-phenyl-butanamide, a nitrosated nanterinone, a nitrosylated nanterinone or a nitrosated and nitrosylated nanterinone; wherein the compound of formula VIII is a nitrosated MS 857, a nitrosylated MS 857, a nitrosated and nitrosylated MS 857, a nitrosated WIN 62582, a nitrosylated WIN 62582, a nitrosated and nitrosylated WIN 62582, a nitrosated piroximone, a nitrosylated piroximone, or a nitrosated and nitrosyalted piroximone; wherein the compound of formula IX is a nitrosated tolafentrine, a nitrosylated tolafentrine, a nitrosated and nitrosylated tolafentrine, a nitrosated benafentrine, a nitrosylated benafentrine or a nitrosated and nitrosylated benafentrine; wherein the compounds of formula X is a nitrosated dipyridamole, a nitrosylated dipyridamole, or a nitrosated and nitrosylated dipyridamole.

48. A composition comprising the compound of claim 46 and a pharmaceutically acceptable carrier.

49. A method for treating a sexual dysfunction in a patient in need thereof comprising administering a therapeutically effective amount of the composition of claim 48.

50. The method of claim 49, wherein the patient is female.

51. The method of claim 49, wherein the patient is male.

52. The method of claim 49, wherein the composition is administered orally, by intracavernosal injection, by transurethral application, or by transdermal application.

53. The composition of claim 46, further comprising (i) at least one compound that donates, transfers, or releases nitric oxide, or induces the production of endogenous nitric oxide or endothelium-derived relaxing factor or is a substrate for nitric oxide synthase; (ii) at least one vasoactive agent; or (iii) at least one compound that donates, transfers, or releases nitric oxide, or induces the production of endogenous nitric oxide or endothelium-derived relaxing factor or is a substrate for nitric oxide synthase and at least one vasoactive agent.

54. The composition of claim 53, wherein the vasoactive agent is a potassium channel activator, a calcium blocker, an α-blocker, a β-blocker, adenosine, an ergot alkaloid, a vasoactive intestinal peptide, a dopamine agonist, an opioid antagonist, a prostaglandin, an endothelin antagonist or a mixture thereof.

55. The composition of claim 53, wherein the compound that donates, transfers, or releases nitric oxide, or induces the production of endogenous nitric oxide or endothelium-derived relaxing factor or is a substrate for nitric oxide synthase is an S-nitrosothiol.

56. The composition of claim 55, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

57. The composition of claim 55, wherein the S-nitrosothiol is:
(i) $HS(C(R_e)(R_f))_m SNO$;
(ii) $ONS(C(R_e)(R_f))_m R_e$; or
(iii) $H_2N-CH(CO_2H)-(CH_2)_m-C(O)NH-CH(CH_2SNO)-C(O)NH-CH_2-CO_2H$;

wherein m is an integer of from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, am alkoxy, a haloalkoxy, an amino, an alkylamino, a dialkylamino, an arylamino, a diarylamino, an alkylarylamino an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or —T—Q; or $R_e$ and $R_f$ taken together with the carbon atoms to which they are attached are a carbonyl, a methanthial, a heterocyclic ring, a cycloalkyl group or a bridged cycloalkyl group; Q is —NO or —$NO_2$; and T is independently a covalent bond, an oxygen, $S(O)_o$ or $NR_i$, wherein o is an integer from 0 to 2, and $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, carboxamido, —$CH_2$—C(T—Q)($R_e$)($R_f$), or —($N_2O_2^-$)$M^+$, wherein $M^+$ in an organic or inorganic cation; with the proviso that when $R_i$ is —$CH_2$—C(T—Q)($R_e$)($R_f$) or —($N_2O_2^-$)$M^+$; then "—T—Q" can be a hydrogen, an alkyl group, an alkoxyalkyl group, an aminoalkyl group, a hydroxy group or an aryl group.

58. The composition of claim 53, wherein the compound that donates, transfers, or releases nitric oxide, or induces the production of endogenous nitric oxide or endothelium-derived relaxing factor or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, an inhibitor of the enzyme arginase, citrulline, ornithine or glutamine.

59. The composition of claim 53, wherein the compound that donates, transfers, or releases nitric oxide, or induces the production of endogenous nitric oxide or endothelium-derived relaxing factor or is a substrate for nitric oxide synthase is:

(i) a compound that comprises at least one ON—O—, ON—N— or ON—C— group;
(ii) a compound that comprises at least one $O_2N$—O—, $O_2N$—N—, $O_2N$—S— or —$O_2N$—C— group;
(iii) a N-oxo-N-nitrosoamine having the formula: $R^1 R^2$—N(O—$M^+$)—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation; or
(i) a thionitrate having the formula: $R^1$—(S)—$NO_2$, wherein $R^1$ is a polypeptide, an amino acid, a sugar, an oligonucleotide, a straight or branched, saturated or unsaturated, aliphatic or aromatic, substituted or unsubstituted hydrocarbon, or a heterocyclic group.

60. The composition of claim 59, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

61. The composition of claim 59, wherein the compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

62. A method for treating a sexual dysfunction in a patient in need thereof comprising administering a therapeutically effective amount of the composition of claim 53.

63. The method of claim 62, wherein the patient is female.

64. The method of claim 62, wherein the patient is male.

65. The method of claim 62, wherein the composition is administered orally, by intracavernosal injection, by transurethral application, or by transdermal application.

66. A method for treating or preventing hypertension, congestive heart failure, renal failure, myocardial infraction, stable, unstable and variant (Prinzmetal) angina, atherosclerosis, cardiac edema, renal insufficiency, nephrotic edema, hepatic edema, stroke, dementia, immunodeficiency, premature labor, dysmenorrhoea, benign prostatic hyperplasis, bladder outlet obstruction, incontinence, a condition of reduced blood vessel patency, postpercutaneous transluminal coronary angioplasty, peripheral vascular disease, allergic rhinitis, glucoma, or a disease characterized by a gut motility disorder comprising administering to a patient a therapeutically effective amount of a compound of formula (I), or a pharmaceutically acceptable salt thereof, wherein the compound of formula (I) is:

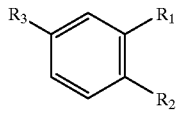

I wherein
R₁ is an alkoxy, a cycloalkoxy, a halogen, or

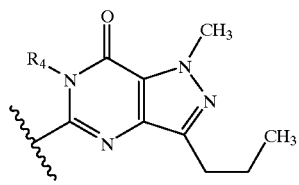

R₂ is a hydrogen, an alkoxy, or a haloalkoxy; and
R₃ is:

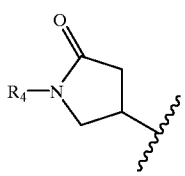

(i)

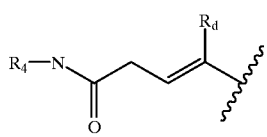

(ii)

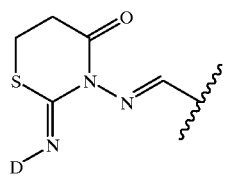

(iii)

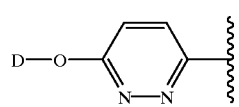

(iv)

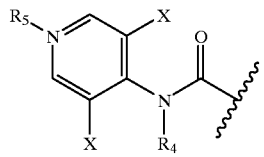

(v)

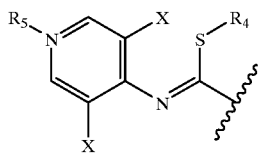

(vi)

D is:
(i) —NO,
(ii) —NO₂,
(iii) —CH(R_d)—O—C(O)—Y—Z—(C(R_e)(R_f))_p—T—Q,
(iv) —C(O)—Y—Z—(G—(C(R_e)(R_f))_b—T—Q)_p;
(v) —P—Z—(G—(C(R_e)(R_f))_b—T—Q)_p;
(vi) —P₁—B₁—W—B_t—L_r—E_s—(C(R_e)(R_f))_w—E_c—(C(R_e)(R_f))_x—L_d—(C(R_e)(R_f))_y—L_i—E_j—L_g—(C(R_e)(R_f))_z—T—Q or
(vii) —P₁—F'_n—L_r—E_s—(C(R_e)(R_f))_x—L_d—(C(R_e)(R_f))_y—L_i—E_j—L_g—(C(R_e)(R_f))_z—T—Q R_d is a hydrogen, a lower alkyl, a cycloalkyl, an aryl or an arylalkyl;

Y is oxygen, S(O)_o, lower alkyl or NR_i;

o is an integer from 0 to 2;

R_i is a hydrogen, an alkyl, an aryl, an alkylcarboxylic acid, an aryl carboxylic acid, an alkylcarboxylic ester, an arylcarboxylic ester, an alkylcaiboxamido, an arylcarboxamido, an alkylaryl, an alkylsulfinyl, an alkylsulfonyl, an arylsulfinyl, an arylsulfonyl, a sulfonarnido, a carboxamido, a carboxylic ester, —CH₂—C(T—Q)(R_e)(R_f), or —(N₂O₂—)⁻·M⁺m, wherein M⁺ in an organic or inorganic cation;

R_e and R_f are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, —T—Q , or (C(R_e)(R_f))_k—T—Q, or R_e and R_f taken together with the carbon atoms to which they are attached are a carbonyl, a methanthial, a heterocyclic ring, a cycloalkyl group or a bridged cycloalkyl group;

k is an integer from 1 to 3;

p is an integer from 1 to 10;

T is independently a covalent bond, oxygen, S(O)_o or NR_i;

Z is a covalent bond, an alkyl, an aryl, an arylalkyl, an alkylaryl, a heteroalkyl, or (C(R_e)(R_f))_p;

Q is —NO or —NO₂;

G is a covalent bond, —T—C(O)—, —C(O)—T— or T;

b is an integer from 0 to 5;

P is a carbonyl, a phosphoryl or a silyl;

l and t are each independently an integer from 1 to 3;

r, s, c, d, g, i and j are each independently an integer from 0 to 3;

w, x, y and z are each independently an integer from 0 to 10;

$P_1$ is a covalent bond or P;

B at each occurrence is independently an alkyl group, an aryl group, or $(C(R_e)(R_f))_p$;

E at each occurrence is independently —T—, an alkyl group, an aryl group, or —$(CH_2CH_2O)_q$;

q is an integer of from 1 to 5;

L at each occurrence is independently —C(O)—, —C(S)—,—T—, a heterocyclic ring, an aryl group, an alkenyl group, an alkynyl group, an arylheterocyclic ring, or —$(CH_2CH_2O)_q$;

W is oxygen, $S(O)_o$, or $NR_i$;

F' at each occurrence is independently selected from B or carbonyl;

n is an integer from 2 to 5;

with the proviso that when $R_i$ is —$CH_2$—$C(T—Q)(R_e)$ $(R_f)$ or —$(N_2O_2)^-M^+$, or $R_e$ or $R_f$ are T—Q or $(C(R_e)(R_f))_k$—T—Q, then the "—T—Q" subgroup designated in D can be a hydrogen, an alkyl, an alkoxy, an alkoxyalkyl, an aminoalkyl, a hydroxy, or an aryl;

$R_4$ is:
(i) hydrogen;
(ii) —$CH(R_d)$—O—C(O)—Y—Z—$(C(R_e)(R_f))_p$—T—Q;
(iii) —C(O)—T—$(C(R_e)(R_f))_p$—T—Q;
(iv) —C(O)—Z—$(G$—$(C(R_e)(R_f))_p$—T—$Q)_p$ or
(v) —$W_o$—$L_r$—$E_s$—$(C(R_e)(R_f))_w$—$E_c$—$(C(R_e)(R_f))_x$—$L_d$—$(C(R_e)(R_f))_y$—$L_i$—$E_j$—$L_g$—$(C(R_e)(R_f))_z$—T—Q;

r, s, c, d, g, i, j, o, p, w, x, y, z, $R_d$, $R_e$ $R_f$, E, L, G, T, Q, W, Y, and Z are as defined herein;

$R_5$ is a lone pair of electrons or —$CH(R_d)$—O—C(O)—Y—Z—$C(R_e)(R_f))_p$—T—Q;

$R_{11}$ and $R_{12}$ are independently selected from hydrogen or $R_4$;

$R_4$, $R_d$, $R_e$, $R_f$, p, T, Q, Y, and Z are as defined herein;

X is a halogen, and $D_1$ is D or hydrogen, wherein D is as defined herein; with the proviso that if the structure does not contain D, then at least one of the variables $R_4$, $R_5$, $R_{11}$ or $R_{12}$ must contain the element "—T—Q".

67. The method of claim 66, wherein the compound of formula I is a nitrosated filaminast, a nitrosylated filaminast, a nitrosated and nitrosylated filaminast, a nitrosated piclamilast, a nitrosylated piclamilast, a nitrosated and nitrosylated piclamilast, a nitrosated rolipram, a nitrosylated rolipram, a nitrosated and nitrosylated rolipram, a nitrosated roflumilast, a nitrosylated roflumilast, a nitrosated and nitrosylated roflumilast, a nitrosated toborinone, a nitrosylated toborinone, a nitrosated and nitrosylated toborinone, a nitrosated MCI-154, a nitrosylated MCI-154, or a nitrosated and nitrosylated MCI-154.

68. The method of claim 66, further comprising administering (i) at least one compound that donates, transfers, or releases nitric oxide, or induces the production of endogenous nitric oxide or endothelium-derived relaxing factor or is a substrate for nitric oxide synthase, (ii) at least one vasoactive agent, or (iii) at least one compound that donates, transfers, or releases nitric oxide, or induces the production of endogenous nitric oxide or endothelium-derived relaxing factor or is a substrate for nitric oxide synthase and at least one vasoactive agent.

69. The method of claim 68, wherein the vasoactive agent is a potassium channel activator, a calcium blocker, an α-blocker, a β-blocker, adenosine, an ergot alkaloid, a vasoactive intestinal peptide, a dopamine agonist, an opioid antagonist, a prostaglandin, an endothelin antagonist or a mixture thereof.

70. The method of claim 68, wherein the compound that donates, transfers, or releases nitric oxide, or induces the production of endogenous nitric oxide or endothelium-derived relaxing factor or is a substrate for nitric oxide synthase is an S-nitrosothiol.

71. The method of claim 70, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

72. The method of claim 71, wherein the S-nitrosothiol is:
(i) $HS(C(R_e)(R_f))_mSNO$;
(ii) $ONS(C(R_e)(R_f))_mR_e$; or
(iii) $H_2N$—$CH(CO_2H)$—$(CH_2)_m$—C(O)NH—CH($CH_2SNO$)—C(O)NH—$CH_2$—$CO_2H$;

wherein m is an integer of from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, am alkoxy, a haloalkoxy, an amino, an alkylamino, a dialkylamino, an arylamino, a diarylamino, an alkylarylamino an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, an alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or —T—Q; or $R_e$ and $R_f$ taken together with the carbon atoms to which they are attached are a carbonyl, a methanthial, a heterocyclic ring, a cycloalkyl group or a bridged cycloalkyl group; Q is —NO or —$NO_2$; and T is independently a covalent bond, an oxygen, $S(O)_o$ or $NR_i$, wherein o is an integer from 0 to 2, and $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, carboxamido, —$CH_2$—$C(T—Q)(R_e)$ $(R_f)$, or —$(N_2O_2^-)M^+$, wherein $M^+$ in an organic or inorganic cation; with the proviso that when $R_i$ is —$CH_2$—$C(T—Q)(R_e)(R_f)$ or —$(N_2O_2^-)M^+$; then "—T—Q" can be a hydrogen, an alkyl group, an alkoxyalkyl group, an aminoalkyl group, a hydroxy group or an aryl group.

73. The method of claim 68, wherein the compound that donates, transfers, or releases nitric oxide, or induces the production of endogenous nitric oxide or endothelium-derived relaxing factor or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, an inhibitor of the enzyme arginase, citrulline, ornithine or glutamine.

74. The method of claim 68, wherein the compound that donates, transfers, or releases nitric oxide, or induces the production of endogenous nitric oxide or endothelium-derived relaxing factor or is a substrate for nitric oxide synthase is:

(i) a compound that comprises at least one ON—O—, ON—N— or ON—C— group;

(ii) a compound that comprises at least one $O_2N$—O—, $O_2N$—N—, $O_2N$—S— or —$O_2N$—C— group;

(iii) a N-oxo-N-nitrosoamine having the formula: $R^1R^2$—N(O—M$^+$)—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation; or (iv) a thionitrate having the formula: $R^1$—(S)—$NO_2$, wherein $R^1$ is a polypeptide, an amino acid, a sugar, an oligonucleotide, a straight or branched, saturated or unsaturated, aliphatic or aromatic, substituted or unsubstituted hydrocarbon, or a heterocyclic group.

75. The method of claim 74, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

76. The method of claim 74, wherein the compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

77. A method for treating or preventing a disease induced by the increased metabolism of cyclic guanosine 3',5'-monophosphate in a patient in need thereof comprising administering to the patient a therapeutically effective amount of a compound of formula (I), formula (II), formula (m), formula (IV), formula (V), formula (VI), formula (VII), formula (VIII), formula (IX), formula (X), or a pharmaceutically acceptable salt thereof, wherein the compound of formula (I) is:

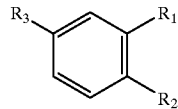

I wherein
$R_1$ is an alkoxy, a cycloalkoxy, a halogcen, or

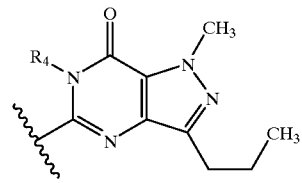

$R_2$ is a hydrogen, an alkoxy, or a haloalkoxy; and
$R_3$ is:

(vii)

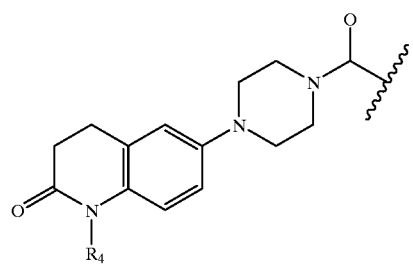

(viii)

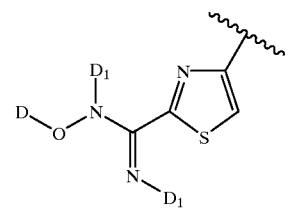

(ix)

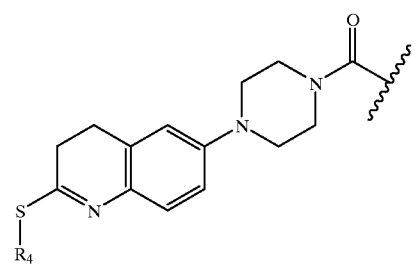

or (x)

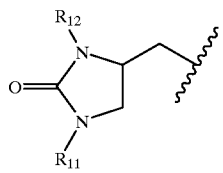

D is:
(i) —NO,
(ii) —$NO_2$, (iii) —CH($R_d$)—O—C(O)—Y—Z—(C($R_e$)($R_f$))$_p$—T—Q, (iv) —C(O)—Y—Z—(G—(C($R_e$)($R_f$))$_b$—T—Q)$_p$;

(v) —P—Z—(G—(C($R_e$)($R_f$))$_b$—T—Q)$_p$;

(vi) —P$_1$—B$_1$—W—B$_t$—L$_T$—E$_s$—(C($R_e$)($R_f$))$_w$—E$_c$—(C($R_e$)($R_f$))$_x$—(C($R_e$)($R_f$))$_y$—L$_i$—E$_j$—L$_g$—(C($R_e$)($R_f$))$_z$—T—Q or (vii) —P$_1$—F'$_n$—L$_r$—E$_s$—(C($R_e$)($R_f$))$_w$—E$_c$—(C($R_e$)($R_f$))$_x$—L$_d$—(C($R_e$)($R_f$))$_y$—L$_i$—E$_j$—L$_g$—(C($R_e$)($R_f$))$_z$—T—Q $R_d$ is a hydrogen, a lower alkyl, a cycloalkyl, an aryl or an arylalkyl;

Y is oxygen, S(O)$_o$, lower alkyl or NR$_i$;

o is an integer from 0 to 2;

$R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, —CH$_2$—C(T—Q)($R_e$)($R_f$), or —(N$_2$O$_2$—)$^-$·M$^+$, wherein M$^+$ in an organic or inorganic cation;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, —T—Q , or (C($R_e$)($R_f$))$_k$—T—Q, or $R_e$ and $R_f$ taken together with the carbon atoms to which they are attached are a carbonyl, a methanthial, a heterocyclic ring, a cycloalkyl group or a bridged cycloalkyl group;

k is an integer from 1 to 3;

p is an integer from 1 to 10;

T is independently a covalent bond, oxygen, S(O)$_o$ or NR$_i$;

Z is a covalent bond, an alkyl, an aryl, an arylalkyl, an alkylaryl, a heteroalkyl, or (C($R_e$)($R_f$))$_p$;

Q is —NO or —NO$_2$;

G is a covalent bond, —T—C(O)—, —C(O)—T—or T;

b is an integer from 0 to 5;

P is a carbonyl, a phosphoryl or a silyl;

L and t are each independently an integer from 1 to 3;

r, s, c, d, g, i and j are each independently an integer from 0 to 3;

w, x, y and z are each independently an integer from 0 to 10;

P$_L$ is a covalent bond or P;

B at each occurrence is independently an alkyl group, an aryl group, or (C($R_e$)($R_f$))$_p$;

E at each occurrence is independently —T—, an alkyl group, an aryl group, or —(CH$_2$CH$_2$O)$_q$;

q is an integer of from 1 to 5;

L at each occurrence is independently —C(O)—, —C(S)—, —T—, a heterocyclic ring, an aryl group, an alkenyl group, an alkynyl group, an arylheterocyclic ring, or —(CH$_2$CH$_2$O)$_q$;

W is oxygen, S(O)$_o$, or NR$_i$;

F' at each occurrence is independently selected from B or carbonyl;

n is an integer from 2 to 5;

with the proviso that when $R_i$ is —CH$_2$—C(T—Q)($R_e$)($R_f$) or —(N$_2$O$_2$)$^-$M$^+$, or $R_e$ or $R_f$ are T—Q or (C($R_e$)($R_f$))$_k$—T—Q, then the "—T—Q" subgroup designated in D can be a hydrogen, an alkyl, an alkoxy, an alkoxyalkyl, an aminoalkyl, a hydroxy, or an aryl;

$R_4$ is:

(i) hydrogen;

(ii) —CH($R_d$)—O—C(O)—Y—Z—(C($R_e$)($R_f$))$_p$—T—Q;

(iii) —C(O)—T—(C($R_e$)($R_f$))$_p$—T—Q;

(iv) —C(O)—Z—(G—(C($R_e$)($R_f$))$_p$—T—Q)$_p$ or (v) —W$_o$—L$_r$—E$_s$—(C($R_e$)($R_f$))$_w$—E$_c$—(C($R_e$)($R_f$))$_x$—L$_d$—(C($R_e$)($R_f$))$_y$—L$_i$—E$_j$—L$_g$—(C($R_e$)($R_f$))$_z$—T—Q;

r, s, c, d, g, i, j, o, p, w, x, y, z, R—W$_o$—L$_r$—E$_s$—(C($R_e$)($R_f$))$_w$—E$_c$—(C($R_e$)($R_f$))$_x$—L$_d$—(C($R_e$)($R_f$))$_y$—L$_i$—E$_j$—L$_g$—(C($R_e$)($R_f$))$_z$—T—Q;

r, s, c, d, g, i, j, o, p, w, x, y, z, $R_d$, $R_e R_f$, E, L, G,T, Q, W, Y, and Z are as defined herein;

$R_5$ is a lone pair of electrons or —CH($R_d$)—O—C(O)—Y—Z—(C($R_e$)($R_f$)$_p$—T—Q;

$R_{11}$ and $R_{12}$ are independently selected from hydrogen or $R_4$; wherein $R_4$, $R_d$, $R_e$, $R_f$, p, T, Q, Y, and Z are as defined herein;

X is a halogen, and $D_1$ is D or hydrogen, wherein D is as defined herein; with the proviso that if the structure does not contain D, then at least one of the variables $R_4$, $R_5$, $R_{11}$ or $R_{12}$ must contain the element "—T—Q";

wherein the compound of formula (II) is:

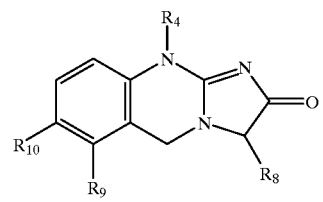

II wherein, $R_4$ is as defined herein; with the proviso that $R_4$ cannot be hydrogen;

$R_8$ is a hydrogen, a lower alkyl group or a haloalkyl group;

$R_9$ is a hydrogen or a halogen; and $R_{10}$ is:

(i) hydrogen, (ii) 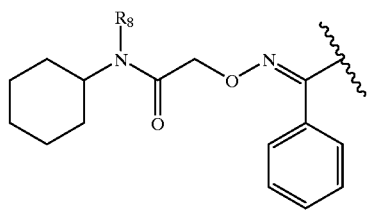

(iii) 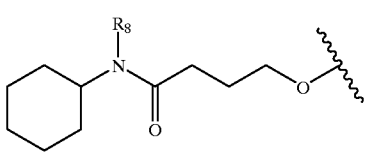

wherein $R_8$ is as defined herein;

wherein the compound of formula (III) is:

III

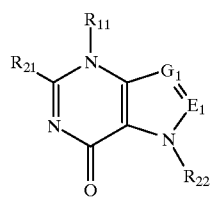

wherein, $E_1$ is nitrogen or —CH—;

$G_1$ is nitrogen or —C($R_8$)—;

$R_{21}$ is:

(i) 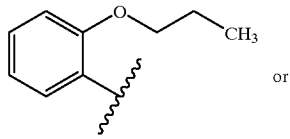

or (ii) 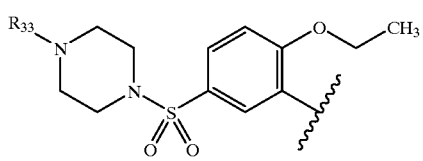

$R_{22}$ is $R_{12}$ or a lower alkyl;

$R_{33}$ is a lower alkyl or $(C(R_e)(R_f))_p$—T—Q; and p, $R_e$, $R_f$, $R_{11}$, $R_{12}$, T and Q are as defined herein; with the proviso that at least one of the variables $R_{11}$, $R_{12}$, $R_{22}$ or $R_{33}$ must contain the element "T—Q";

wherein the compound of formula (IV) is:

IV

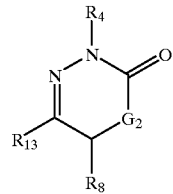

wherein, $G_2$ is —CH$_2$— or sulfur;

$R_4$ and $R_8$ are each as defined herein; and $R_{13}$ is:

(i) 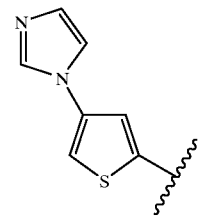

(ii) 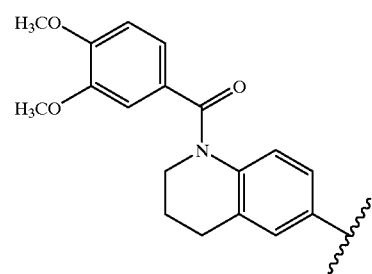

(iii) 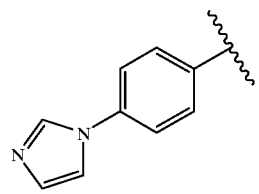

(iv) 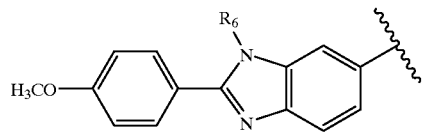

(v) 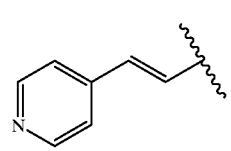

(vi)

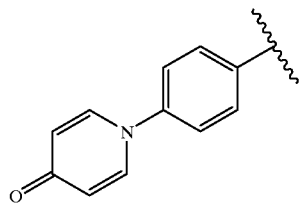

or (vii)

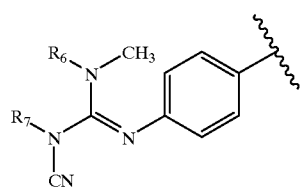

$R_6$ and $R_7$ are independently selected from $R_4$, wherein $R_4$ is as defined herein;

with the proviso that at least one of the variables $R_4$, $R_6$ or $R_7$ must contain the element "T—Q";

wherein the compound of formula (V) is:

V

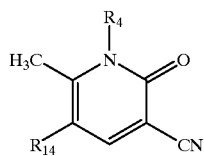

wherein, $R_4$ is as defined herein; and $R_{14}$ is:

(i)

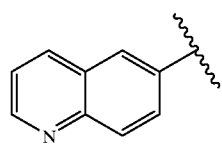

(ii)

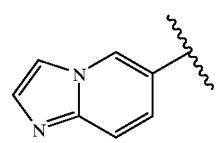

(iii)

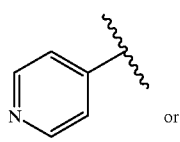

or (iv)

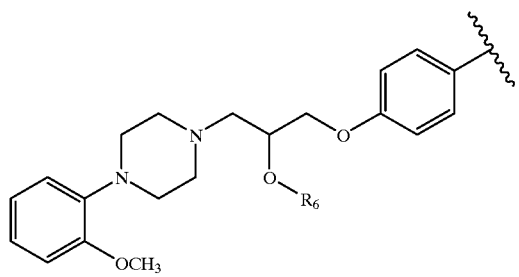

$R_6$ is as defined herein, with the proviso that at least one of the variables $R_4$, or $R_6$ must contain the element "T—Q";

wherein the compound of formula (VI) is:

VI

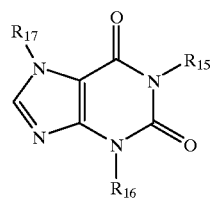

wherein, $R_{15}$ is a hydrogen, a lower alkyl, $R_4$, or —$(CH_2)_4$—C$(CH_3)_2$—O—$D_1$; wherein $R_4$ is as defined herein;

$R_{16}$ is a lower alkyl; and $R_{17}$ is a hydrogen, a lower alkyl, $CH_3$—C(O)—$CH_2$—; $CH_3$—O—$CH_2$—, or D;

with the proviso that either $R_{15}$ or $R_{17}$ must contain D, wherein D and $D_1$ are as defined herein;

wherein the compound of formula (VII) is:

VII

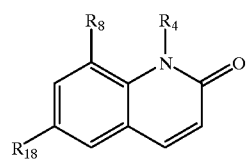

wherein, $R_4$ and $R_8$ are as defined herein; and $R_{18}$ is:

(i)

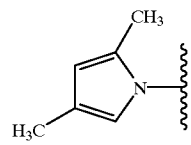

-continued (ii)

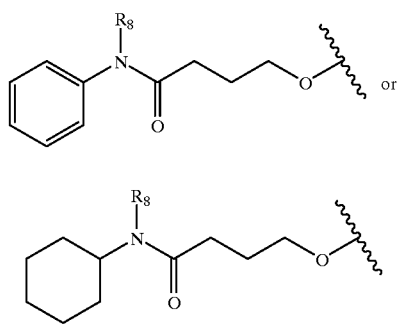 or $R_8$ is as defined herein;
with the proviso that $R_4$ cannot be hydrogen;
wherein the compound of formula (VIII) is:

VIII

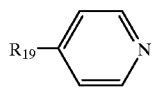

wherein, $R_{19}$ is:

(i)

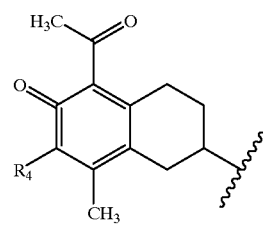

(ii)

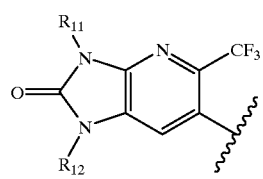

(iii)

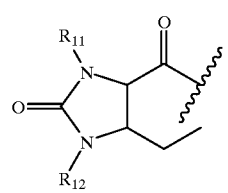

(iv)

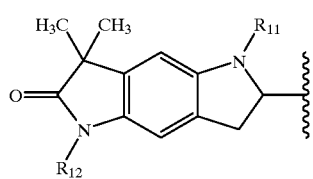

-continued (v)

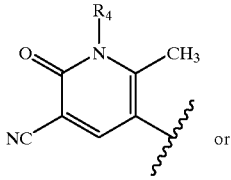 or (vi)

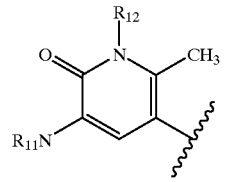

wherein $R_4$, $R_{11}$, and $R_{12}$ are as defined herein; with the proviso that at least one of the variables $R_4$, $R_{11}$ or $R_{12}$ must contain the element "T—Q";

wherein the compound of formula (IX) is:

IX

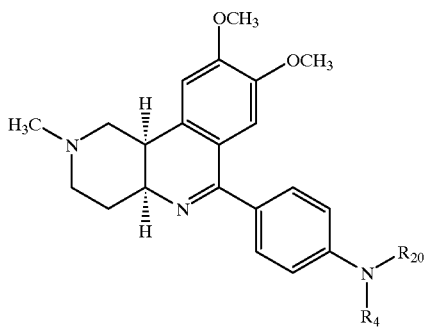

wherein, $R_{20}$ is:

(i)

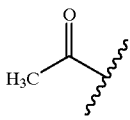

(ii)

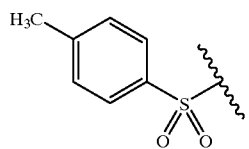

or (iii) —D;

$R_4$ is as defined herein;

with the proviso that when $R_{20}$ is not D, then $R_4$ cannot be hydrogen;

wherein the compound of formula (X) is:

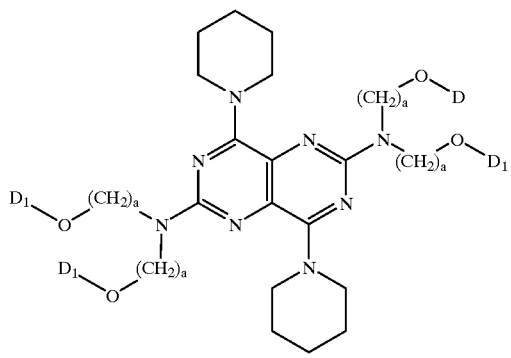

wherein,
a is an integer from 2 to 3 and D and $D_1$ are as defined herein.

78. The method of claim 77, wherein the disease induced by the increased metabolism of cyclic guanosine 3',5'-monophosphate is hypertension, pulmonary hypertension, congestive heart failure, renal failure, myocardial infarction, stable, unstable or variant (Prinzmetal) angina, atherosclerosis, cardiac edema, renal insufficiency, nephrotic edema, hepatic edema, stroke, asthma, bronchitis, chronic obstructive pulmonary disease, cystic fibrosis, dementia, immunodeficiency, premature labor, dysmenorrhoea, benign prostatic hyperplasia, bladder outlet obstruction, incontinence, a condition of reduced blood vessel patency, postpercutaneous transluminal coronary angioplasty, peripheral vascular disease, allergic rhinitis, glaucoma, or a disease characterized by a gut motility disorder.

79. The method of claim 77, wherein the compound of formula I is a nitrosated vesnarinone, a nitrosylated vesnarinone, a nitrosated and nitrosylated vesnarinone, a nitrosated Org 20241, a nitrosylated Org 20241 or a nitrosated and nitrosylated Org 20241; wherein the compound of formula II is a nitrosated posicor, a nitrosylated posicor, a nitrosated and nitrosylated posicor, a nitrosated 6-bromo-1,5-dihydro-.imidazo(2,1-b)quinazolin-2(3H)-one, a nitrosylated 6-bromo-1,5-dihydro-imidazo(2,1-b)quinazolin-2(3H)-one, a nitrosated and nitrosyalted 6-bromo-1,5-dihydro-imidazo(2,1-b)quinazolin-2(3H)-one, a nitrosated R 79595, a nitrosylated R 79595, a nitrosated and nitrosyalted R 79595, a nitrosated lixazinone, a nitrosylated lixazinone, or a nitrosated and nitrosyalted lixazinone; wherein the compound of formula III is a nitrosated sildenafil, a nitrosylated sildenafil, a nitrosated and nitrosyalted sildenafil, a nitrosated zaprinast, a nitrosylated zaprinast, or a nitrosated and nitrosyalted zaprinast; wherein the compound of formula IV is a nitrosated ICI 153,110, a nitrosylated ICI 153,110, a nitrosated and nitrosylated ICI 153,110, a nitrosated motapizone, a nitrosylated motapizone, a nitrosated and nitrosylated motapizone, a nitrosated pimobenden, a nitrosylated pimobenden, a nitrosated and nitrosylated pimobenden, a nitrosated siguazodan, a nitrosylated siguazodan, a nitrosated and nitrosylated siguazodan, a nitrosated imazodan, a nitrosylated imazodan, a nitrosated and nitrosylated imazodan, a nitrosated CI 930, a nitrosylated CI 930, a nitrosated and nitrosylated CI 930, a nitrosated 4,5-dihydro-5-methyl-6-(4-(4-oxo-1 (4H)-pyridinyl)phenyl)-3(2H)-pyridazinone, a nitrosylated 4,5-dihydro-5-methyl-6-(4-(4-oxo-1(4H)-pyridinyl)phenyl)-3(2H)-pyridazinone, a nitrosated and nitrosylated 4,5-dihydro-5-methyl-6-(4-(4-oxo-1(4H)-pyridinyl)phenyl)-3(2H)-pyridazinone, a nitrosated EMD 53998, a nitrosylated EMD 53998 or a nitrosated and nitrosylated EMD 53998; wherein the compound of formula V is a nitrosated saterinone, a nitrosylated saterinone, a nitrosated and nitrosylated saterinone, a nitrosated WIN 63291, a nitrosylated WIN 63291, a nitrosated and nitrosylated WIN 63291, a nitrosated milrinone, a nitrosylated milrinone, a nitrosated and nitrosylated milrinone, a nitrosated loprinone, a nitrosylated loprinone, or a nitrosated and nitrosylated loprinone; wherein the compound of formula VI is a nitrosated albifylline, a nitrosylated albifylline, a nitrosated and nitrosylated albifylline, a nitrosated tobrafylline, a nitrosylated tobrafylline, a nitrosated and nitrosylated tobrafylline, a nitrosated denbufylline, a nitrosylated denbufylline, a nitrosated and nitrosylated denbufylline, a nitrosated doxofylline, a nitrosylated doxofylline, a nitrosated and nitrosylated doxofylline, a nitrosated theophylline, a nitrosylated theophylline, a nitrosated and nitrosylated theophylline, a nitrosated pentoxifylline, a nitrosylated pentoxifylline, a nitrosated and nitrosylated pentoxifylline; wherein the compound of formula VII is a nitrosated 4-((1,2-dihydro-2-oxo-6-quinolinyl)oxy)-N-ethyl-N-phenyl-butanamide, a nitrosylated 4-((1,2-dihydro-2-oxo-6-quinolinyl)oxy)-N-ethyl-N-phenyl-butanamide., a nitrosated and nitrosylated 4-((1,2-dihydro-2-oxo-6-quinolinyl)oxy)-N-ethyl-N-phenyl-butanamide, a nitrosated 4-((1,2-dihydro-2-oxo-6-quinolinyl)oxy)-N-methyl-N-phenyl-butanamide a nitrosylated 4-((1,2-dihydro-2-oxo-6-quinolinyl)oxy)-N-methyl-N-phenyl-butanamide, a nitrosated and nitrosylated 4-((1,2-dihydro-2-oxo-6-quinolinyl)oxy)-N-methyl-N-phenyl-butanamide, a nitrosated N-butyl-4-((1,2-dihydro-2-oxo-6-quinolinyl)oxy)-N-phenyl-butanamide, a nitrosylated N-butyl-4-((1,2-dihydro-2-oxo-6-quinolinyl)oxy)-N-phenyl-butanamide, a nitrosated and nitrosylated N-butyl-4-((1,2-dihydro-2-oxo-6-quinolinyl)oxy)-N-phenyl-butanamide, a nitrosated nanterinone, a nitrosylated nanterinone or a nitrosated and nitrosylated nanterinone; wherein the compound of formula VIII is a nitrosated MS 857, a nitrosylated MS 857, a nitrosated and nitrosylated MS 857, a nitrosated WIN 62582, a nitrosylated WIN 62582, a nitrosated and nitrosylated WIN 62582, a nitrosated piroximone, a nitrosylated piroximone, or a nitrosated and nitrosyalted piroximone; wherein the compound of formula IX is a nitrosated tolafentrine, a nitrosylated tolafentrine, a nitrosated and nitrosylated tolafentrine, a nitrosated benafentrine, a nitrosylated benafentrine or a nitrosated and nitrosylated benafentrine; wherein the compounds of formula X is a nitrosated dipyridamole, a nitrosylated dipyridamole, or a nitrosated and nitrosylated dipyridamole.

80. The method of claim 77, further comprising administering (i) at least one compound that donates, transfers, or releases nitric oxide, or induces the production of endogenous nitric oxide or endothelium-derived relaxing factor or is a substrate for nitric oxide synthase, (ii) at least one vasoactive agent, or (iii) at least one compound that donates, transfers, or releases nitric oxide, or induces the production of endogenous nitric oxide or endothelium-derived relaxing factor or is a substrate for nitric oxide synthase and at least one vasoactive agent.

81. The method of claim 80, wherein the vasoactive agent is a potassium channel activator, a calcium blocker, an α-blocker, a β-blocker, adenosine, an ergot alkaloid, a vasoactive intestinal peptide, a dopamine agonist, an opioid antagonist, a prostaglandin, an endothelin antagonist or a mixture thereof.

82. The method of claim 80, wherein the compound that donates, transfers, or releases nitric oxide, or induces the production of endogenous nitric oxide or endothelium-derived relaxing factor or is a substrate for nitric oxide synthase is an S-nitrosothiol.

83. The method of claim 82, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

84. The method of claim 82, wherein the S-nitrosothiol is:
(i) $HS(C(R_e)(R_f))_nSNO$;
(ii) $ONS(C(R_e)(R_f))_mR_e$; or
(iii) $H_2N-CH(CO_2H)-(CH_2)_m-C(O)NH-CH(CH_2SNO)-C(O)NH-CH_2-CO_2H$;

wherein m is an integer of from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, am alkoxy, a haloalkoxy, an amino, an alkylamino, a dialkylamino, an arylamino, a diarylamino, an alkylarylamino an alkoxyhaloalkyl, a haloalkoxy, a sulfonic acid, an alkylsulfonic acid, an arylsulfonic acid, an alkylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or —T—Q; or $R_e$ and $R_f$ taken together with the carbon atoms to which they are attached are a carbonyl, a methanthial, a heterocyclic ring, a cycloalkyl group or a bridged cycloalkyl group; Q is —NO or —$NO_2$; and T is independently a covalent bond, an oxygen, $S(O)_o$ or $NR_i$, wherein o is an integer from 0 to 2, and $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, carboxamido, —$CH_2$—C(T—Q)($R_e$)($R_f$), or —($N_2O_2^-$)$M^+$, wherein $M^+$ in an organic or inorganic cation; with the proviso that when $R_1$ is —$CH_2$—C(T—Q)($R_e$)($R_f$) or —($N_2O_2^-$)$M^+$; then "—T—Q" can be a hydrogen, an alkyl group, an alkoxyalkyl group, an aminoalkyl group, a hydroxy group or an aryl group.

85. The method of claim 80, wherein the compound that donates, transfers, or releases nitric oxide, or induces the production of endogenous nitric oxide or endothelium-derived relaxing factor or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, an inhibitor of the enzyme arginase, citrulline, ornithine or glutamine.

86. The method of claim 80, wherein the compound that donates, transfers, or releases nitric oxide, or induces the production of endogenous nitric oxide or endothelium-derived relaxing factor or is a substrate for nitric oxide synthase is:
(i) a compound that comprises at least one ON—O—, ON—N— or ON—C— group;
(ii) a compound that comprises at least one $O_2N$—O—, $O_2N$—N—, $O_2N$—S— or —$O_2N$—C— group;
(iii) a N—oxo-N-nitrosoamine having the formula: $R^1R^2$—N(O—$M^+$)—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation; or
(iv) a thionitrate having the formula: $R^1$—(S)—$NO_2$, wherein $R^1$ is a polypeptide, an amino acid, a sugar, an oligonucleotide, a straight or branched, saturated or unsaturated, aliphatic or aromatic, substituted or unsubstituted hydrocarbon, or a heterocyclic group.

87. The method of claim 86, wherein the compound comprising at least one ON—O—, ON—N— or ON—C— group is an ON—O-polypeptide, an ON—N-polypeptide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

88. The method of claim 87, wherein the compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-arnino acid, an $O_2N$—O-sugar, an $O_2N$—N—sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

89. A kit comprising the compound of claim 46.

90. The kit of claim 89, further comprising (i) at least one compound that donates, transfers or releases nitrogen monoxide, induces the production of endogenous endothelium-derived relaxing factor, stimulates endogenous synthesis of nitrogen monoxide or is a substrate for nitric oxide synthase, (ii) at least one vasoactive agent, or (iii) at least one compound that donates, transfers or releases nitrogen monoxide, induces the production of endogenous endothelium-derived relaxing factor, stimulates endogenous synthesis of nitrogen monoxide or is a substrate for nitric oxide synthase and at least one vasoactive agent.

91. A kit comprising the composition of claim 53.

92. A kit comprising at least one compound of claim 46, and (i) at least one compound that donates, transfers or releases nitrogen monoxide, induces the production of endogenous endothelium-derived relaxing factor, stimulates endogenous synthesis of nitrogen monoxide or is a substrate for nitric oxide synthase, (ii) at least one vasoactive agent, or (iii) at least one compound that donates, transfers or releases nitrogen monoxide, induces the production of endogenous endothelium-derived relaxing factor, stimulates endogenous synthesis of nitrogen monoxide or is a substrate for nitric oxide synthase and at least one vasoactive agent.

93. The kit of claim 92, wherein the compound of claim 46 and the compound that donates, transfers or releases nitrogen monoxide, induces the production of endogenous endothelium-derived relaxing factor, stimulates endogenous synthesis of nitrogen monoxide or is a substrate for nitric oxide synthase or the vasoactive agent are separate components in the kit.

94. The kit of claim 92, wherein the compound of claim 46 and the compound that donates, transfers or releases nitrogen monoxide, induces the production of endogenous endothelium-derived relaxing factor, stimulates endogenous synthesis of nitrogen monoxide or is a substrate for nitric oxide synthase or the vasoactive agent are in the form of a composition in the kit.

* * * * *